United States Patent
Mullican et al.

(10) Patent No.: US 12,275,770 B2
(45) Date of Patent: Apr. 15, 2025

(54) GLUCAGON LIKE PEPTIDE 1 (GLP1)-GROWTH DIFFERENTIATION FACTOR 15 (GDF15) FUSION PROTEINS AND USES THEREOF

(71) Applicant: Janssen Sciences Ireland Unlimited Company, Cork (IE)

(72) Inventors: Shannon Mullican, Spring House, PA (US); Matthew M. Rankin, Spring House, PA (US); Xiefan Lin-Schmidt, Spring House, PA (US); Chichi Huang, Spring House, PA (US); Jennifer Furman, San Diego, CA (US); Songmao Zheng, Spring House, PA (US); Shamina Rangwala, Spring House, PA (US); Serena Nelson, San Diego, CA (US)

(73) Assignee: Janssen Sciences Ireland Unlimited Company, Cork (IE)

( * ) Notice: Subject to any disclaimer, the term of this patent is extended or adjusted under 35 U.S.C. 154(b) by 0 days.

(21) Appl. No.: 18/332,690

(22) Filed: Jun. 9, 2023

(65) Prior Publication Data
US 2023/0322888 A1 Oct. 12, 2023

Related U.S. Application Data

(62) Division of application No. 17/309,114, filed as application No. PCT/IB2019/059029 on Oct. 22, 2019, now Pat. No. 11,713,345.

(60) Provisional application No. 62/748,603, filed on Oct. 22, 2018.

(51) Int. Cl.
| | | |
|---|---|---|
| A61K 38/00 | (2006.01) | |
| C07K 14/475 | (2006.01) | |
| C07K 14/605 | (2006.01) | |
| C12N 15/63 | (2006.01) | |

(52) U.S. Cl.
CPC .......... *C07K 14/605* (2013.01); *C07K 14/475* (2013.01); *C12N 15/63* (2013.01); *A61K 38/00* (2013.01)

(58) Field of Classification Search
CPC .... A61K 38/00; A61K 9/0019; C07K 14/475; C07K 14/605; C07K 14/76; C07K 2319/31; C12N 15/62; C12N 15/63; C12N 15/11; A61P 3/04
See application file for complete search history.

(56) References Cited

U.S. PATENT DOCUMENTS

| | | |
|---|---|---|
| 6,420,543 B1 | 7/2002 | Lee et al. |
| 7,919,084 B2 | 4/2011 | Breit et al. |
| 9,161,966 B2 | 10/2015 | Matern et al. |
| 10,336,812 B2 | 7/2019 | Armstrong et al. |
| 11,208,464 B2 | 12/2021 | Armstrong et al. |
| 11,713,345 B2 | 8/2023 | Mullican et al. |
| 2007/0036806 A1 | 2/2007 | Glaesner et al. |
| 2008/0044411 A1 | 2/2008 | O'Neil et al. |
| 2009/0099031 A1 | 4/2009 | Stemmer et al. |
| 2011/0005130 A1 | 1/2011 | Huang et al. |
| 2011/0015130 A1 | 1/2011 | Chuang et al. |
| 2012/0030840 A1 | 2/2012 | Miles |
| 2014/0050725 A1 | 2/2014 | Jenkins et al. |
| 2014/0120090 A1 | 5/2014 | Willemsen |
| 2014/0141000 A1 | 5/2014 | Chiu et al. |
| 2014/0155325 A1 | 6/2014 | Mark et al. |
| 2014/0193427 A1 | 7/2014 | Lerner et al. |
| 2014/0213511 A1 | 7/2014 | Matern et al. |
| 2014/0255401 A1 | 9/2014 | Chi et al. |
| 2014/0349929 A1 | 11/2014 | Camphausen et al. |
| 2014/0378665 A1 | 12/2014 | Xiong et al. |
| 2015/0023960 A1 | 1/2015 | Lindhout et al. |
| 2016/0031960 A1 | 2/2016 | Lindhout et al. |
| 2016/0143998 A1 | 5/2016 | Reedtz-Runge et al. |
| 2016/0168213 A1 | 6/2016 | Xiong et al. |
| 2016/0200787 A1 | 7/2016 | Matern et al. |
| 2017/0204146 A1 | 7/2017 | Upton et al. |
| 2017/0204149 A1 | 7/2017 | Chopra et al. |
| 2017/0327560 A1 | 11/2017 | Armstrong et al. |
| 2018/0282403 A1 | 10/2018 | Blokzijl et al. |
| 2019/0234935 A1 | 8/2019 | Armstrong et al. |
| 2019/0292241 A1 | 9/2019 | Armstrong et al. |
| 2022/0089669 A1 | 3/2022 | Mullican et al. |

FOREIGN PATENT DOCUMENTS

| | | |
|---|---|---|
| CN | 107073130 A | 8/2017 |
| CN | 108367053 A | 8/2018 |
| JP | 2019-523637 A | 8/2019 |

(Continued)

OTHER PUBLICATIONS

NIH—Accessed on Feb. 14, 2024 at https://www.niddk.nih.gov/health-information/kidney-disease#topics (Year: 2024).*

Chen et al. Inflammatory responses and inflammation-associated diseases in organs. Oncotarget, 2018, vol. 9, (No. 6), pp. 7204-7218 (Year: 2018).*

(Continued)

*Primary Examiner* — Aradhana Sasan
*Assistant Examiner* — Mercy H Sabila
(74) *Attorney, Agent, or Firm* — Seed IP Law Group LLP

(57) ABSTRACT

Provided herein are method of using GLP1-GDF15 fusion proteins for reducing food intake, preventing, treating or ameliorating diseases and disorders, such as obesity, type 2 diabetes, the metabolic syndrome, insulin resistance, and dyslipidemia, among others, the fusion protein comprising a GLP1 or GLP1 variant peptide, a first linker peptide, a serum albumin protein, a second linker peptide, and a GDF15 protein.

15 Claims, 22 Drawing Sheets
Specification includes a Sequence Listing.

(56) References Cited

FOREIGN PATENT DOCUMENTS

| WO | 02/46227 A2 | 6/2002 |
|---|---|---|
| WO | WO 2010/048670 A1 | 5/2010 |
| WO | WO 2013/113008 A1 | 8/2013 |
| WO | WO 2013/148117 A1 | 10/2013 |
| WO | WO 2014/120619 A2 | 8/2014 |
| WO | WO 2015/017710 A1 | 2/2015 |
| WO | WO 2015/197446 A1 | 12/2015 |
| WO | WO 2015/198199 A1 | 12/2015 |
| WO | WO 2016/018931 A1 | 2/2016 |
| WO | WO 2016/069921 A1 | 5/2016 |
| WO | WO 2016/069925 A1 | 5/2016 |
| WO | WO 2017/147742 A1 | 9/2017 |
| WO | WO 2017/196647 A1 | 11/2017 |
| WO | WO 2017/202936 A1 | 11/2017 |
| WO | WO 2018/215525 A1 | 11/2018 |
| WO | WO 2020/084496 A1 | 4/2020 |
| WO | WO 2020/104948 A1 | 5/2020 |

OTHER PUBLICATIONS

Pahwa et al. Chronic Inflammation. NCBI Bookshelf. StatPearls Publishing; Jan. 2020 (Year: 2020).*

Dinarello, Grand challenge in inflammation. Frontier in immunology 3:12, 2012 (Year: 2012).*

Stemmler et al. (Int. J. Mol. Sci. 2021, 22(24), 13608). GDF15 Supports the Inflammatory Response of PdL Fibroblasts Stimulated by P. gingivalis LPS and Concurrent Compression (Year: 2021).*

Abulizi et al., "Growth Differentiation Factor-15 Deficiency Augments Inflammatory Response and Exacerbates Septic Heart and Renal Injury Induced by Lipopolysaccharide," *Scientific Reports* 7:1037, 2017. [Published online Apr. 21, 2017] (10 pages).

Baek et al., "Nonsteroidal Anti-Inflammatory Drug-Activated Gene-1 Over Expression in Transgenic Mice Suppresses Intestinal Neoplasia," *Gastroenterology* 131(5):1553-1560, Nov. 2006. (8 pages).

Bazett, "An Analysis of the Time-Relations of Electrocardiograms," *Heart* 7:353-380, 1920 [Also Published as *A.N.E.* 2(2), Apr. 1997]. (18 pages).

Bonaterra et al., "Growth Differentiation Factor-15 Deficiency Inhibits Atheroscleoris Progression by Regulating Interleukin-6-Dependent Inflammatory Response to Vascular Injury," *J. Amer. Heart Assoc.* 1:e002550, Dec. 2012. (14 pages).

Breit et al., "Macrophage inhibitory cytokine-1 (MIC-1/GDF15) and mortality in end-stage renal disease," *Nephrol Dial Transplant* 27:70-75, 2012. [Advance Access publication Sep. 22, 2011] (6 pages).

Breit et al., "The TGF-β superfamily cytokine, MIC-1/GDF15: A pleotrophic cytokine with roles in inflammation, cancer and metabolism," *Growth Factors* 29(5):187-195, Oct. 2011. [Published online Aug. 11, 2011] (10 pages).

Casanovas et al., "The murine growth differentiation factor 15 is not essential for systemic iron homeostasis in phlebotomized mice," *Haematologica* 98(3):444-447, Mar. 2013. (4 pages).

Chang et al., "*Antrodia cinnamomea* reduces obesity and modulates the gut microbiota in high-fat diet-fed mice," *Int. J. Obesity* 42:231-243, Feb. 2018 [Advance Online Publication Aug. 8, 2017]. (13 pages).

Cheang et al., "Glucagon-Like Peptide-1 (GLP-1)-Based Therapeutics: Current Status and Future Opportunities beyond Type 2 Diabetes," *Chem Med Chem* 13:662-671, Apr. 6, 2018. (10 pages).

Chen et al., "Fusion Protein linkers: Property, Design and Functionality," *Adv. Drug Deliv. Rev.* 65:1357-1369, Oct. 2013. (13 pages).

Chen et al., "Inflammatory responses and inflammation-associated diseases in organs," *Oncotarget* 9(6):7204-7218, 2018 [Also Published Dec. 14, 2017]. (15 pages).

Chrysovergis et al., "NAG-1/GDF-15 prevents obesity by increasing thermogenesis, lipolysis and oxidative metabolism," *Int. J. Obes (Lond.)* 38(12):1555-1564, Dec. 2014 (HHS Public Access Author Manuscript, available in PMC Jun. 1, 2015). (19 pages).

Collinson, "The role of cardiac biomarkers in cardiovascular disease risk assessment," *Curr. Opin. Cardiol.* 29(4):366-371, Jul. 2014. (6 pages).

Dinarello, "Grand challenge in inflammation," *Frontiers in Immunology* 3(12), Feb. 2012 [Published online Feb. 14, 2012]. (1 page).

Drucker et al., "Glucagon-like peptide I stimulates insulin gene expression and increases cyclic AMP levels in a rat islet cell line," *PNAS* 84:3434-3438, May 1987. (5 pages).

Drucker, "Mechanisms of Action and Therapeutic Application of Glucagon-like Peptide-1," *Cell Metabolism* 27:740-756, Apr. 3, 2018. (17 pages).

EMA Guidance. EMEA CHMP SWP 28367 07 Rev. 1 (2017), "Guideline on strategies to identify and mitigate risks for first-in-human and early clinical trials with investigational medicinal products," European Medicines Agency; Committee for Medicinal Products for Human Use (CHMP); Jul. 20, 2017. (22 pages).

EMA Guidance. EMEA/CHMP/SWP/28367/07 (2007), "Guideline on Strategies to Identify and Mitigate Risks for First-In-Human Clinical Trials with Investigational Medicinal Products," European Medicines Agency; Committee for Medicinal Products for Human Use (CHMP); Jul. 19, 2007. (12 pages).

Emmerson et al., "The metabolic effects of GDF15 are mediated by the orphan receptor GFRAL," *Nature Medicine* 23(10):1215-1219, Oct. 2017. (9 pages).

EPO Communication for EP Application No. 17796596.9, dated Nov. 15, 2019. (12 pages.).

Expasy MW Calculator entry for FP2 (retrieved from https://web.expasy.org/cgi-bin/compute_pi/pi_tool on Oct. 11, 23) (Year: 2023) (1 page).

FDA Guidance for Industry (2005), "Estimating the Maximum Safe Starting Dose in Initial Clinical Trials for Therapeutics in Adult Healthy Volunteers," US Dep of Health and Human Services. Center for Drug Evaluation and Research (CDER, Jul. 2005). (30 pages).

FDA Guidance for Industry (2007), "Toxicity Grading Scale for Healthy Adult and Adolescent Volunteers Enrolled in Preventive Vaccine Clinical Trials," US Dep of Health and Human Services. Center for Biologics Evaluation and Research (CBER, Sep. 2007). (10 pages).

Fejzo et al., "Placenta and appetite genes GDF15 and IGFBP7 are associated with hyperemesis gravidarum," *Nature Communications* 9:1178-1186, 2018 [Published online Mar. 21, 2018]. (9 pages).

Fisher et al., "Medical and surgical options in the treatment of severe obesity," *Am. J. Surg.* 184:9S-16S, Dec. 2002. (8 pages).

Fryar et al., "Prevalence of Overweight, Obesity, and Extreme Obesity Among Adults: United States, Trends 1960-1962 Through 2009-2010," National Center for Health Statistics, Sep. 2012. (8 pages) Available from http://www.cdc.gov/nchs/data/hestat/obesity_adult_09_10/obesity_adult_09_10.htm Accessed May 23, 2018.

Geneseq, Database accession No. BAQ98634, "Human mature GDF15 monomer encoding DNA, Seq ID 11", retrieved from EBI, Sep. 12, 2013. (1 page).

Geneseq, Database accession No. BBL23018, "Human growth differentiation factor 15 (GDF15) mature protein SEQ: 3", Geneseq, (Sep. 25, 2014), URL: EBI, XP002795264, Sep. 25, 2014. (2 pages).

Geneseq, Database accession No. BBU47607, "Human GDF15 protein fragment, Seq ID 55", Geneseq, (Mar. 26, 2015), URL: EBI, XP002795259, Mar. 26, 2015. (1 page).

Geneseq, Database accession No. BBU47682, "Albumin-linker-GDF15 fusion protein, Seq ID 130", Geneseq, (Mar. 26, 2015), URL: EBI, XP002795260, Mar. 26, 2015. (1 page).

Geneseq, Database accession No. BCK62615, "HSA/MIC-1 fusion protein compound 4", Geneseq, (Feb. 25, 2016), Feb. 25, 2016. (2 pages).

Geneseq, Database accession No. BCK62627, "HSA/MIC-1 fusion protein compound 16", Geneseq, (Feb. 25, 2016), URL: EBI, XP002795262, Dec. 30, 2015. (1 page).

Geneseq, Database accession No. JD590115, "Sequence 111 from Patent WO2015017710", EMBL, (Mar. 21, 2015), URL: EBI, XP002795261, Mar. 21, 2015. (1 page).

Gennemark et al., "Translational Modeling to Guide Study Design and Dose Choice in Obesity Exemplified by AZD1979, a Melanin-

(56) References Cited

OTHER PUBLICATIONS concentrating Hormone Receptor 1 Antagonist," *CPT Pharmacometrics Syst. Pharmacol.* 6:458-468, 2017 [Published online May 27, 2017]. (11 pages).

Gobel et al., "Quantifying Energy Intake Changes during Obesity Pharmacotherapy," *Obesity* 22(10):2105-2108, Oct. 2014 (HHS Public Access Author Manuscript, available in PMC Oct. 1, 2015). (11 pages).

Hall et al., "Quantification of the effect of energy imbalance on bodyweight," *Lancet* 3786(9793), Aug. 27, 2011 (NIH Public Access Author Manuscript, available in PMC Jan. 4, 2014). (23 pages).

Hallbrink et al., "Different domains in the third intracellular loop of the GLP-1 receptor are responsible for $G\alpha_s$ and $G\alpha_i/G\alpha_o$ activation," *Biochimica et Biophysica Acta* 1546:79-86, Mar. 9, 2001. (8 pages).

Ho et al., "Biomarkers of Cardiovascular Stress and Incident Chronic Kidney Disease" *Clin. Chem.* 59(11):1613-1620, Nov. 2013 (NIH Public Access Author Manuscript, available in PMC Apr. 1, 2014). (15 pages).

Hodges et al., "Bazett's QT Correction Reviewed: Evidence that a Linear QT Correction for Heart Rate is Better," *J Am Coll Cardiol* 1(2):694, Mar. 1983. (1 page).

Holz IV et al., "Activation of a cAMP-regulated $Ca^{2+}$-Signaling Pathway in Pancreatic β-Cells by the Insulinotropic Hormone Glucagon-like Peptide-1*," *J Biol Chem.* 270(30):17749-17757, Jul. 28, 1995 (NIH Public Access Author Manuscript, available in PMC Nov. 25, 2012). (31 pages).

Hsu et al., "Non-homeostatic body weight regulation through a brainstem-restricted receptor for GDF15," *Nature* 550(255):255-259, Oct. 12, 2017. (23 pages).

International Conference on Harmonisation of Technical Requirements for Registration of Pharmaceuticals for Human Use, "ICH Harmonised Tripartite Guideline: The Clinical Evaluation of QT/QTc Interval Prolongation and Proarrhythmic Potential for Non-Antiarrhythmic Drugs," ICH, May 12, 2005. (18 pages).

International Search Report and Written Opinion, dated Apr. 2, 2020, for International Application No. PCT/IB19/59029. (17 pages).

International Search Report and Written Opinion, dated May 6, 2020, for International Application No. PCT/IB19/59945. (10 pages).

International Search Report and Written Opinion, dated Sep. 18, 2017, for International Patent Application No. PCT/US2017/031197. (14 pages).

Johnen et al., "Tumor-induced anorexia and weight loss are mediated by the TGF-β superfamily cytokine MIC-1," *Nature Medicine* 13(11):1333-1340, Nov. 2007. [Published online Nov. 4, 2007] (8 pages).

Jones et al., "Supraphysiologic Administration of GDF11 Induces Cachexia in Part by Upregulating GDF15," *Cell Reports* 22:1522-1530, Feb. 6, 2018. (20 pages).

Kempf et al., "GDF-15 is an inhibitor of leukocyte integrin activation required for survival after myocardial infarction in mice," *Nat. Med.* 17(5): 581-589, May 2011. (9 pages).

Kempf et al., "Growth differentiation factor 15 predicts future insulin resistance and impaired glucose control in obese nondiabetic individuals: results from the Xendos trial," European Journal of Endocrinology 167:671-678, Nov. 2012. (8 pages).

Kempf et al., "The Transforming Growth Factor-β Superfamily Member Growth-Differentiation Factor-15 Protects the Heart From Ischemia/Reperfusion Injury," *Circulation Research* 98:351-360, Feb. 17, 2006. (10 pages).

Lim et al., "Glucagon-like Peptide-1 Receptor Agonists and Cardiovascular Events: Class Effects versus Individual Patterns," *Trends Endocrinol Metab* 29(4):238-248, Apr. 2018. (11 pages).

Macia et al., "Macrophage inhibitory Cytokine 1 (MIC-1/GDF15) Decreases Food Intake, Body Weight and Improves Glucose Tolerance in Mice on Normal & Obesogenic Diets," *PLoS One* 7(4):e34868, Apr. 2012. (8 pages).

Mazagova et al., "Genetic deletion of growth differentiation factor 15 augments renal damage in both type 1 and type 2 models of diabetes," *Am J Physiol Renal Physiol* 305:F1249-F1264, 2013. [First published Aug. 28, 2013] (16 pages).

McCurdy et al., "A covalently linked recombinant albumin dimer is more rapidly cleared in vivo than are wild-type and mutant C34A albumin," *J Lab Clin Med* 143(2):115-24, Feb. 2004. (10 pages).

Mensching et al., "Local substitution of GDF-15 improves axonal and sensory recovery after peripheral nerve injury," *Cell Tissue Res.* 350:225-238, 2012. [Published online Sep. 7, 2012] (14 pages).

Montrose-Rafizadeh et al., "Pancreatic Glucagon-Like Peptide-1 Receptor Couples to Multiple G Proteins and Activates Mitogen-Activated Protein Kinase Pathways in Chinese Hamster Ovary Cells," *Endocrinology* 140(3):1132-1140, Mar. 1999. (9 pages).

Mullican et al., "Uniting GDF15 and GFRAL: Therapeutic Opportunities in Obesity and Beyond," *Trends Endocrinol Metab* 29(8):560-570, Aug. 2018. (11 pages).

Mullican et al., "GFRAL is the receptor for GDF15 and the ligand promotes weight loss in mice and nonhuman primates," *Nat. Med.* 23(10):1150-1157, Oct. 2017. (14 pages).

NIH—National Institute of Diabetes and Digestive and Kidney Diseases, "Kidney Disease", Accessed on Feb. 14, 2024 at https://www.niddk.nih.gov/health-information/kidney-disease#topics (Year: 2024). (5 pages).

Pahwa et al., "Chronic Inflammation," NCI Bookshelf, StatPearls Publishing, Jan. 2020. (10 pages).

Rueda-Clausen et al., "Health Benefits of Long-Term Weight-Loss Maintenance," *Annu. Rev. Nutr.* 35:475-516, 2015 [Published Online May 13, 2015]. (45 pages).

Sagie et al., "An Improved Method for Adjusting the QT Interval for Heart Rate (the Framingham Heart Study)," *Am J Cardiol.* 70:797-801, Sep. 15, 1992. (5 pages).

Spahr et al., "O-glycosylation of glycine-serine linkers in recombinant Fc-fusion proteins: Attachment of glycosaminoglycans and other intermediates with phosphorylation at the xylose sugar subunit," *mAbs* 6(4):904-914, Jul./Aug. 2014 [Published Online Apr. 16, 2014]. (11 pages).

Stemmler et al., "GDF15 Supports the Inflammatory Response of PdL Fibroblasts Stimulated by P. gingivalis LPS and Concurrent Compression," *International Journal of Molecular Sciences* 22:13608, 2021 [Published Dec. 19, 2021]. (13 pages).

Strelau et al., "Progressive Postnatal Motoneuron Loss in Mice Lacking GDF-15," *J. Neurosci.* 29(43):13640-13648, Oct. 28, 2009. (9 pages).

Sugulle et al., "Circulating and Placental Growth-Differentiation Factor 15 in Preeclampsia and in Pregnancy Complicated by Diabetes Mellitus," *Hypertension* 54:106-112, Jul. 2009. (7 pages).

Taverna et al., "Specific antioxidant properties of human serum albumin," *Annals of Intensive Care* 3:4, 2013 [Published online Feb. 15, 2013]. (7 pages).

The GBD 2013 Obesity Collaboration, "Global, regional and national prevalence of overweight and obesity in children and adults 1980-2013: a systematic analysis," *Lancet.* 384(9945):766-781, Aug. 30, 2014 (Europe PMC Funders Group Author Manuscript, available in PMC Oct. 2, 20158). (33 pages).

Thorens et al., "Cloning and Functional Expression of the Human Islet GLP-1 Receptor," *Diabetes* 42:1678-1682, Nov. 1993. (5 pages).

Tsai et al., "Anorexia/cachexia of chronic diseases: a role for the TGF-β family cytokine MIC-1/GDF15," *J. Cachexia Sarcopenia Muscle* 3:239-243, 2012. [Published online Aug. 31, 2012] (5 pages).

Tsai et al., "Serum Levels of Human MIC-1/GDF15 Vary in a Diurnal Pattern, Do Not Display a Profile Suggestive of a Satiety Factor and Are Related to BMI," *PLos One* 10(7):e0133362, Jul. 24, 2015. (15 pages).

Tsai et al., "TGF-b Superfamily Cytokine MIC-1/GDF15 Is a Physiological Appetite and Body Weight Regulator," *PLoS One* 8(2):e55174, Feb. 2013. (10 pages).

Vila et al., "The Relationship between Insulin Resistance and the Cardiovascular Biomarker Growth Differentiation Factor-15 in Obese Patients," *Clin. Chem.* 57(2):309-316, Feb. 2011. (8 pages).

Wang et al., "hNAG-1 increases lifespan by regulating energy metabolism and insulin/IGF-1/mTOR signaling," *Aging* 6(8):690-700, Aug. 2014. (w/ Supplementary Data) (15 pages).

(56) References Cited

OTHER PUBLICATIONS

Wheeler et al., "Functional Expression of the Rat Glucagon-Like Peptide-I Receptor, Evidence for Coupling to both Adenylyl Cyclase and Phospholipase-C," *Endocrinology* 133(1):57-62, Jul. 1993. (6 pages).

Wolfe et al., "Treatment of Obesity: Weight Loss and Bariatric Surgery," *Circ Res.* 118(11):1844-1855, May 27, 2016 (HHS Public Access Author Manuscript, available in PMC May 27, 2017). (23 pages).

World Health Organization (2012), Blood Donor Selection, "Guidelines on Assessing Donor Suitability for Blood Donation," Geneva. Available from: https://www.ncbi.nlm.nih.gov/books/NBK138212/ Accessed Jun. 21, 2018. (126 pages).

Xiong et al., "Long-acting MIC-1/GDF15 molecules to treat obesity: Evidence from mice to monkeys," *Sci. Trans. Med.* 9:eaan8732, Oct. 18, 2017. (12 pages).

Xu et al., "GDF15/MIC-1 Functions as a Protective and Antihypertrophic Factor Released From the Myocardium in Association With SMAD Protein Activation," *Circ Res.* 98:342-350, Feb. 17, 2006. (9 pages).

Yang et al., "GFRAL is the receptor for GDF15 and is required for the anti-obesity effects of the ligand," *Nat. Med.* 23(10):1158-1166, Oct. 2017. (16 pages).

Yanovski et al., "The Questionnaire on Eating and Weight Patterns-5 (QEWP-5): An Updated Screening Instrument for Binge Eating Disorder," *Int J Eat Disord.* 48(3): 259-261, Apr. 2015 (HHS Public Access Author Manuscript, available in PMC Apr. 1, 2016). (5 pages).

Zhao et al., "Elimination of the free sulfhydryl group in the human serum albumin (HSA) moiety of human interferon-α2b and HSA fusion protein increases its stability against mechanical and thermal stresses," *European Journal of Pharmaceutics and Biopharmaceutics* 72:405-411, 2009. [Available online Jan. 27, 2009] (7 pages).

Zimmers et al., "Growth Differentiation Factor-15/Macrophage Inhibitory Cytokine-1 Induction After Kidney and Lung Injury," *Shock* 23(6):543-548, Jun. 2005. (6 pages).

\* cited by examiner

Vehicle shown for reference only

Vehicle shown for reference only

SEQUENCE LISTING

```
Sequence total quantity: 84
SEQ ID NO: 1            moltype = AA  length = 30
FEATURE                 Location/Qualifiers
REGION                  1..30
                        note = (A8S, A30E) GLP-1(7-36)
source                  1..30
                        mol_type = protein
                        organism = synthetic construct
SEQUENCE: 1
HSEGTFTSDV SSYLEGQAAK EFIEWLVKGR                                    30

SEQ ID NO: 2            moltype = AA  length = 30
FEATURE                 Location/Qualifiers
REGION                  1..30
                        note = (A8G, G22E, R36G) GLP1(7-36)
source                  1..30
```

```
                          mol_type = protein
                          organism = synthetic construct
SEQUENCE: 2
HGEGTFTSDV SSYLEEQAAK EFIAWLVKGG                                                30

SEQ ID NO: 3              moltype = AA  length = 39
FEATURE                   Location/Qualifiers
REGION                    1..39
                          note = Exendin 4 (1-39)
source                    1..39
                          mol_type = protein
                          organism = synthetic construct
SEQUENCE: 3
HGEGTFTSDL SKQMEEEAVR LFIEWLKNGG PSSGAPPPS                                      39

SEQ ID NO: 4              moltype = AA  length = 28
FEATURE                   Location/Qualifiers
REGION                    1..28
                          note = Exendin 4 (1-28)
source                    1..28
                          mol_type = protein
                          organism = synthetic construct
SEQUENCE: 4
HGEGTFTSDL SKQMEEEAVR LFIEWLKN                                                  28

SEQ ID NO: 5              moltype = AA  length = 10
FEATURE                   Location/Qualifiers
REGION                    1..10
                          note = First linker peptide 1-1
source                    1..10
                          mol_type = protein
                          organism = synthetic construct
SEQUENCE: 5
APAPAPAPAP                                                                      10

SEQ ID NO: 6              moltype = AA  length = 20
FEATURE                   Location/Qualifiers
REGION                    1..20
                          note = First linker peptide 1-2
source                    1..20
                          mol_type = protein
                          organism = synthetic construct
SEQUENCE: 6
APAPAPAPAP APAPAPAPAP                                                           20

SEQ ID NO: 7              moltype = AA  length = 30
FEATURE                   Location/Qualifiers
REGION                    1..30
                          note = First linker peptide 1-3
source                    1..30
                          mol_type = protein
                          organism = synthetic construct
SEQUENCE: 7
APAPAPAPAP APAPAPAPAP APAPAPAPAP                                                30

SEQ ID NO: 8              moltype = AA  length = 40
FEATURE                   Location/Qualifiers
REGION                    1..40
                          note = First linker peptide 1-4
source                    1..40
                          mol_type = protein
                          organism = synthetic construct
SEQUENCE: 8
APAPAPAPAP APAPAPAPAP APAPAPAPAP APAPAPAPAP                                     40

SEQ ID NO: 9              moltype = AA  length = 50
FEATURE                   Location/Qualifiers
REGION                    1..50
                          note = First linker peptide 1-5
source                    1..50
                          mol_type = protein
                          organism = synthetic construct
SEQUENCE: 9
APAPAPAPAP APAPAPAPAP APAPAPAPAP APAPAPAPAP APAPAPAPAP                          50

SEQ ID NO: 10             moltype = AA  length = 24
FEATURE                   Location/Qualifiers
REGION                    1..24
                          note = First linker peptide 1-6
```

```
source                     1..24
                           mol_type = protein
                           organism = synthetic construct
SEQUENCE: 10
ASAPAPAPAP APAPAPAPAP APGS                                              24

SEQ ID NO: 11              moltype = AA  length = 14
FEATURE                    Location/Qualifiers
REGION                     1..14
                           note = First linker peptide 1-7
source                     1..14
                           mol_type = protein
                           organism = synthetic construct
SEQUENCE: 11
ASAPAPAPAP APGS                                                         14

SEQ ID NO: 12              moltype = AA  length = 12
FEATURE                    Location/Qualifiers
REGION                     1..12
                           note = First linker peptide 1-8
source                     1..12
                           mol_type = protein
                           organism = synthetic construct
SEQUENCE: 12
ASGGGGSGGG GS                                                           12

SEQ ID NO: 13              moltype = AA  length = 42
FEATURE                    Location/Qualifiers
REGION                     1..42
                           note = First linker peptide 1-9
source                     1..42
                           mol_type = protein
                           organism = synthetic construct
SEQUENCE: 13
ASGGGGSGGG GSGGGGSGGG GSGGGGSGGG GS                                     42

SEQ ID NO: 14              moltype = AA  length = 12
FEATURE                    Location/Qualifiers
REGION                     1..12
                           note = First linker peptide 1-10
source                     1..12
                           mol_type = protein
                           organism = synthetic construct
SEQUENCE: 14
GAGGGGAGGG GA                                                           12

SEQ ID NO: 15              moltype = AA  length = 42
FEATURE                    Location/Qualifiers
REGION                     1..42
                           note = First linker peptide 1-11
source                     1..42
                           mol_type = protein
                           organism = synthetic construct
SEQUENCE: 15
GAGGGGAGGG GAGGGGAGGG GAGGGGAGGG GAGGGGAGGG GA                          42

SEQ ID NO: 16              moltype = AA  length = 15
FEATURE                    Location/Qualifiers
REGION                     1..15
                           note = First linker peptide 1-12
source                     1..15
                           mol_type = protein
                           organism = synthetic construct
SEQUENCE: 16
GGGGAGGGGA GGGGA                                                        15

SEQ ID NO: 17              moltype = AA  length = 20
FEATURE                    Location/Qualifiers
REGION                     1..20
                           note = First linker peptide 1-13
source                     1..20
                           mol_type = protein
                           organism = synthetic construct
SEQUENCE: 17
GGGGAGGGGA GGGGAGGGGA                                                   20

SEQ ID NO: 18              moltype = AA  length = 25
FEATURE                    Location/Qualifiers
REGION                     1..25
```

```
                        note = First linker peptide 1-14
source                  1..25
                        mol_type = protein
                        organism = synthetic construct
SEQUENCE: 18
GGGGAGGGGA GGGGAGGGGA GGGGA                                              25

SEQ ID NO: 19           moltype = AA   length = 30
FEATURE                 Location/Qualifiers
REGION                  1..30
                        note = First linker peptide 1-15
source                  1..30
                        mol_type = protein
                        organism = synthetic construct
SEQUENCE: 19
GGGGAGGGGA GGGGAGGGGA GGGGAGGGGA                                         30

SEQ ID NO: 20           moltype = AA   length = 40
FEATURE                 Location/Qualifiers
REGION                  1..40
                        note = First linker peptide 1-16
source                  1..40
                        mol_type = protein
                        organism = synthetic construct
SEQUENCE: 20
GGGGAGGGGA GGGGAGGGGA GGGGAGGGGA GGGGAGGGGA                              40

SEQ ID NO: 21           moltype = AA   length = 20
FEATURE                 Location/Qualifiers
REGION                  1..20
                        note = First linker peptide 1-17
source                  1..20
                        mol_type = protein
                        organism = synthetic construct
SEQUENCE: 21
GGGGGGGGGG GGGGGGGGGG                                                    20

SEQ ID NO: 22           moltype = AA   length = 25
FEATURE                 Location/Qualifiers
REGION                  1..25
                        note = First linker peptide 1-18
source                  1..25
                        mol_type = protein
                        organism = synthetic construct
SEQUENCE: 22
GGGGGGGGGG GGGGGGGGGG GGGGG                                              25

SEQ ID NO: 23           moltype = AA   length = 15
FEATURE                 Location/Qualifiers
REGION                  1..15
                        note = First linker peptide 1-19
source                  1..15
                        mol_type = protein
                        organism = synthetic construct
SEQUENCE: 23
GGGGSGGGGS GGGGS                                                         15

SEQ ID NO: 24           moltype = AA   length = 25
FEATURE                 Location/Qualifiers
REGION                  1..25
                        note = First linker peptide 1-20
source                  1..25
                        mol_type = protein
                        organism = synthetic construct
SEQUENCE: 24
GGGGSGGGGS GGGGSGGGGS GGGGS                                              25

SEQ ID NO: 25           moltype = AA   length = 30
FEATURE                 Location/Qualifiers
REGION                  1..30
                        note = First linker peptide 1-21
source                  1..30
                        mol_type = protein
                        organism = synthetic construct
SEQUENCE: 25
GGGGSGGGGS GGGGSGGGGS GGGGSGGGGS                                         30

SEQ ID NO: 26           moltype = AA   length = 585
FEATURE                 Location/Qualifiers
```

```
REGION                   1..585
                         note = HSA(C34S)
source                   1..585
                         mol_type = protein
                         organism = synthetic construct
SEQUENCE: 26
DAHKSEVAHR FKDLGEENFK ALVLIAFAQY LQQSPFEDHV KLVNEVTEFA KTCVADESAE  60
NCDKSLHTLF GDKLCTVATL RETYGEMADC CAKQEPERNE CFLQHKDDNP NLPRLVRPEV 120
DVMCTAFHDN EETFLKKYLY EIARRHPYFY APELLFFAKR YKAAFTECCQ AADKAACLLP 180
KLDELRDEGK ASSAKQRLKC ASLQKFGERA FKAWAVARLS QRFPKAEFAE VSKLVTDLTK 240
VHTECCHGDL LECADDRADL AKYICENQDS ISSKLKECCE KPLLEKSHCI AEVENDEMPA 300
DLPSLAADFV ESKDVCKNYA EAKDVFLGMF LYEYARRHPD YSVVLLLRLA KTYETTLEKC 360
CAAADPHECY AKVFDEFKPL VEEPQNLIKQ NCELFEQLGE YKFQNALLVR YTKKVPQVST 420
PTLVEVSRNL GKVGSKCCKH PEAKRMPCAE DYLSVVLNQL CVLHEKTPVS DRVTKCCTES 480
LVNRRPCFSA LEVDETYVPK EFNAETFTFH ADICTLSEKE RQIKKQTALV ELVKHKPKAT 540
KEQLKAVMDD FAAFVEKCCK ADDKETCFAE EGKKLVAASQ AALGL              585

SEQ ID NO: 27            moltype = AA  length = 585
FEATURE                  Location/Qualifiers
REGION                   1..585
                         note = GSA(C34S)
source                   1..585
                         mol_type = protein
                         organism = synthetic construct
SEQUENCE: 27
DAHKSEVAHR FKDLGEETFK ALVLVAFAQY LQQSPFEDHV KLVNEVTEFA KTCVADESAE  60
NCDKSLHTLF GDKLCTVATL RETYGEMADC CAKQEPERNE CFLQHKDDNP NLPRLVRPEV 120
DVMCTAFHDN EETFLKKYLY EIARRHPYFY APELLFFAAR YKAAFTECCQ AADKAACLLP 180
KLDELRDEGK ASSAKQRLKC ASLQKFGERA FKAWAVARLS QRFPKAEFAE VSKLVTDLTK 240
VHTECCHGDL LECADDRADL AKYICENQDS ISSKLKECCE KPLLEKSHCL AEVENDEMPA 300
DLPSLAADFV ESKDVCKNYA EAKDVFLGMF LYEYARRHPD YSVVLLLRLA KTYETTLEKC 360
CAAADPHECY AKVFDEFKPL VEEPQNLIKQ NCELFEQLGE YKFQNALLVR YTKKVPQVST 420
PTLVEVSRNL GKVGSKCCKH PEAKRMPCAE DYLSVVLNQL CVLHEKTPVS DRVTKCCTES 480
LVNRRPCFSA LEVDETYVPK EFNAETFTFH ADICTLSEKE RQIKKQTALA ELVKHKPKAT 540
KEQLKTVMDD FAAFVEKCCK ADDKETCFAE EGKKLVAASQ AALGL              585

SEQ ID NO: 28            moltype = AA  length = 20
FEATURE                  Location/Qualifiers
REGION                   1..20
                         note = Second linker peptide 2-1
source                   1..20
                         mol_type = protein
                         organism = synthetic construct
SEQUENCE: 28
APAPAPAPAP APAPAPAPAP                                           20

SEQ ID NO: 29            moltype = AA  length = 42
FEATURE                  Location/Qualifiers
REGION                   1..42
                         note = Second linker peptide 2-2
source                   1..42
                         mol_type = protein
                         organism = synthetic construct
SEQUENCE: 29
GAGGGGAGGG GAGGGGAGGG GAGGGGAGGG GAGGGGAGGG GA                  42

SEQ ID NO: 30            moltype = AA  length = 42
FEATURE                  Location/Qualifiers
REGION                   1..42
                         note = Second linker peptide 2-3
source                   1..42
                         mol_type = protein
                         organism = synthetic construct
SEQUENCE: 30
GSGGGGSGGG GSGGGGSGGG GSGGGGSGGG GSGGGGSGGG GS                  42

SEQ ID NO: 31            moltype = AA  length = 108
FEATURE                  Location/Qualifiers
REGION                   1..108
                         note = GDF15 variant 1
source                   1..108
                         mol_type = protein
                         organism = synthetic construct
SEQUENCE: 31
DHCPLGPGRC CRLHTVRASL EDLGWADWVL SPREVQVTMC IGACPSQFRA ANMHAQIKTS  60
LHRLKPDTVP APCCVPASYN PMVLIQKTDT GVSLQTYDDL LAKDCHCI            108

SEQ ID NO: 32            moltype = AA  length = 112
FEATURE                  Location/Qualifiers
```

```
REGION                      1..112
                            note = GDF15 WT mature
source                      1..112
                            mol_type = protein
                            organism = synthetic construct
SEQUENCE: 32
ARNGDHCPLG PGRCCRLHTV RASLEDLGWA DWVLSPREVQ VTMCIGACPS QFRAANMHAQ    60
IKTSLHRLKP DTVPAPCCVP ASYNPMVLIQ KTDTGVSLQT YDDLLAKDCH CI           112

SEQ ID NO: 33               moltype = AA  length = 768
FEATURE                     Location/Qualifiers
REGION                      1..768
                            note = GLP1-GDF15 Fusion Protein 1
source                      1..768
                            mol_type = protein
                            organism = synthetic construct
SEQUENCE: 33
HGEGTFTSDV SSYLEEQAAK EFIAWLVKGG GGGGAGGGGA GGGGAGGGGA GGGGADAHKS    60
EVAHRFKDLG EENFKALVLI AFAQYLQQSP FEDHVKLVNE VTEFAKTCVA DESAENCDKS   120
LHTLFGDKLC TVATLRETYG EMADCCAKQE PERNECFLQH KDDNPNLPRL VRPEVDVMCT   180
AFHDNEETFL KKYLYEIARR HPYFYAPELL FFAKRYKAAF TECCQAADKA ACLLPKLDEL   240
RDEGKASSAK QRLKCASLQK FGERAFKAWA VARLSQRFPK AEFAEVSKLV TDLTKVHTEC   300
CHGDLLECAD DRADLAKYIC ENQDSISSKL KECCEKPLLE KSHCIAEVEN DEMPADLPSL   360
AADFVESKDV CKNYAEAKDV FLGMFLYEYA RRHPDYSVVL LLRLAKTYET TLEKCCAAAD   420
PHECYAKVFD EFKPLVEEPQ NLIKQNCELF EQLGEYKFQN ALLVRYTKKV PQVSTPTLVE   480
VSRNLGKVGS KCCKHPEAKR MPCAEDYLSV VLNQLCVLHE KTPVSDRVTK CCTESLVNRR   540
PCFSALEVDE TYVPKEFNAE TFTFHADICT LSEKERQIKK QTALVELVKH KPKATKEQLK   600
AVMDDFAAFV EKCCKADDKE TCFAEEGKKL VAASQAALGL APAPAPAPAP APAPAPAPAP   660
DHCPLGPGRC CRLHTVRASL EDLGWADWVL SPREVQVTMC IGACPSQFRA ANMHAQIKTS   720
LHRLKPDTVP APCCVPASYN PMVLIQKTDT GVSLQTYDDL LAKDCHCI                768

SEQ ID NO: 34               moltype = AA  length = 758
FEATURE                     Location/Qualifiers
REGION                      1..758
                            note = GLP1-GDF15 Fusion Protein 2
source                      1..758
                            mol_type = protein
                            organism = synthetic construct
SEQUENCE: 34
HGEGTFTSDV SSYLEEQAAK EFIAWLVKGG GGGGAGGGGA GGGGADAHKS EVAHRFKDLG    60
EENFKALVLI AFAQYLQQSP FEDHVKLVNE VTEFAKTCVA DESAENCDKS LHTLFGDKLC   120
TVATLRETYG EMADCCAKQE PERNECFLQH KDDNPNLPRL VRPEVDVMCT AFHDNEETFL   180
KKYLYEIARR HPYFYAPELL FFAKRYKAAF TECCQAADKA ACLLPKLDEL RDEGKASSAK   240
QRLKCASLQK FGERAFKAWA VARLSQRFPK AEFAEVSKLV TDLTKVHTEC CHGDLLECAD   300
DRADLAKYIC ENQDSISSKL KECCEKPLLE KSHCIAEVEN DEMPADLPSL AADFVESKDV   360
CKNYAEAKDV FLGMFLYEYA RRHPDYSVVL LLRLAKTYET TLEKCCAAAD PHECYAKVFD   420
EFKPLVEEPQ NLIKQNCELF EQLGEYKFQN ALLVRYTKKV PQVSTPTLVE VSRNLGKVGS   480
KCCKHPEAKR MPCAEDYLSV VLNQLCVLHE KTPVSDRVTK CCTESLVNRR PCFSALEVDE   540
TYVPKEFNAE TFTFHADICT LSEKERQIKK QTALVELVKH KPKATKEQLK AVMDDFAAFV   600
EKCCKADDKE TCFAEEGKKL VAASQAALGL APAPAPAPAP APAPAPAPAP DHCPLGPGRC   660
CRLHTVRASL EDLGWADWVL SPREVQVTMC IGACPSQFRA ANMHAQIKTS LHRLKPDTVP   720
APCCVPASYN PMVLIQKTDT GVSLQTYDDL LAKDCHCI                           758

SEQ ID NO: 35               moltype = AA  length = 793
FEATURE                     Location/Qualifiers
REGION                      1..793
                            note = GLP1-GDF15 Fusion Protein 3
source                      1..793
                            mol_type = protein
                            organism = synthetic construct
SEQUENCE: 35
HGEGTFTSDV SSYLEEQAAK EFIAWLVKGG APAPAPAPAP APAPAPAPAP APAPAPAPAP    60
APAPAPAPAP DAHKSEVAHR FKDLGEENFK ALVLIAFAQY LQQSPFEDHV KLVNEVTEFA   120
KTCVADESAE NCDKSLHTLF GDKLCTVATL RETYGEMADC CAKQEPERNE CFLQHKDDNP   180
NLPRLVRPEV DVMCTAFHDN EETFLKKYLY EIARRHPYFY APELLFFAKR YKAAFTECCQ   240
AADKAACLLP KLDELRDEGK ASSAKQRLKC ASLQKFGERA FKAWAVARLS QRFPKAEFAE   300
VSKLVTDLTK VHTECCHGDL LECADDRADL AKYICENQDS ISSKLKECCE KPLLEKSHCI   360
AEVENDEMPA DLPSLAADFV ESKDVCKNYA EAKDVFLGMF LYEYARRHPD YSVVLLLRLA   420
KTYETTLEKC CAAADPHECY AKVFDEFKPL VEEPQNLIKQ NCELFEQLGE YKFQNALLVR   480
YTKKVPQVST PTLVEVSRNL GKVGSKCCKH PEAKRMPCAE DYLSVVLNQL CVLHEKTPVS   540
DRVTKCCTES LVNRRPCFSA LEVDETYVPK EFNAETFTFH ADICTLSEKE RQIKKQTALV   600
ELVKHKPKAT KEQLKAVMDD FAAFVEKCCK ADDKETCFAE EGKKLVAASQ AALGLAPAPA   660
PAPAPAPAPA PAPAPAPAPA PAPADHCPLG PGRCCRLHT VRASLEDLGW ADWVLSPREV    720
QVTMCIGACP SQFRAANMHA QIKTSLHRLK PDTVPAPCCV PASYNPMVLI QKTDTGVSLQ   780
TYDDLLAKDC HCI                                                     793

SEQ ID NO: 36               moltype = AA  length = 783
FEATURE                     Location/Qualifiers
REGION                      1..783
```

```
                        note = GLP1-GDF15 Fusion Protein 4
source                  1..783
                        mol_type = protein
                        organism = synthetic construct
SEQUENCE: 36
HGEGTFTSDV SSYLEEQAAK EFIAWLVKGG APAPAPAPAP APAPAPAPAP APAPAPAPAP    60
APAPAPAPAP DAHKSEVAHR FKDLGEENFK ALVLIAFAQY LQQSPFEDHV KLVNEVTEFA   120
KTCVADESAE NCDKSLHTLF GDKLCTVATL RETYGEMADC CAKQEPERNE CFLQHKDDNP   180
NLPRLVRPEV DVMCTAFHDN EETFLKKYLY EIARRHPYFY APELLFFAKR YKAAFTECCQ   240
AADKAACLLP KLDELRDEGK ASSAKQRLKC ASLQKFGERA FKAWAVARLS QRFPKAEFAE   300
VSKLVTDLTK VHTECCHGDL LECADDRADL AKYICENQDS ISSKLKECCE KPLLEKSHCI   360
AEVENDEMPA DLPSLAADFV ESKDVCKNYA EAKDVFLGMF LYEYARRHPD YSVVLLLRLA   420
KTYETTLEKC CAAADPHECY AKVFDEFKPL VEEPQNLIKQ NCELFEQLGE YKFQNALLVR   480
YTKKVPQVST PTLVEVSRNL GKVGSKCCKH PEAKRMPCAE DYLSVVLNQL CVLHEKTPVS   540
DRVTKCCTES LVNRRPCFSA LEVDETYVPK EFNAETFTFH ADICTLSEKE RQIKKQTALV   600
ELVKHKPKAT KEQLKAVMDD FAAFVEKCCK ADDKETCFAE EGKKLVAASQ AALGLAPAPA   660
PAPAPAPAPA PAPAPDHCPL GPGRCCRLHT VRASLEDLGW ADWVLSPREV QVTMCIGACP   720
SQFRAANMHA QIKTSLHRLK PDTVPAPCCV PASYNPMVLI QKTDTGVSLQ TYDDLLAKDC   780
HCI                                                                783

SEQ ID NO: 37           moltype = AA  length = 773
FEATURE                 Location/Qualifiers
REGION                  1..773
                        note = GLP1-GDF15 Fusion Protein 5
source                  1..773
                        mol_type = protein
                        organism = synthetic construct
SEQUENCE: 37
HGEGTFTSDV SSYLEEQAAK EFIAWLVKGG APAPAPAPAP APAPAPAPAP APAPAPAPAP    60
DAHKSEVAHR FKDLGEENFK ALVLIAFAQY LQQSPFEDHV KLVNEVTEFA KTCVADESAE   120
NCDKSLHTLF GDKLCTVATL RETYGEMADC CAKQEPERNE CFLQHKDDNP NLPRLVRPEV   180
DVMCTAFHDN EETFLKKYLY EIARRHPYFY APELLFFAKR YKAAFTECCQ AADKAACLLP   240
KLDELRDEGK ASSAKQRLKC ASLQKFGERA FKAWAVARLS QRFPKAEFAE VSKLVTDLTK   300
VHTECCHGDL LECADDRADL AKYICENQDS ISSKLKECCE KPLLEKSHCI AEVENDEMPA   360
DLPSLAADFV ESKDVCKNYA EAKDVFLGMF LYEYARRHPD YSVVLLLRLA KTYETTLEKC   420
CAAADPHECY AKVFDEFKPL VEEPQNLIKQ NCELFEQLGE YKFQNALLVR YTKKVPQVST   480
PTLVEVSRNL GKVGSKCCKH PEAKRMPCAE DYLSVVLNQL CVLHEKTPVS DRVTKCCTES   540
LVNRRPCFSA LEVDETYVPK EFNAETFTFH ADICTLSEKE RQIKKQTALV ELVKHKPKAT   600
KEQLKAVMDD FAAFVEKCCK ADDKETCFAE EGKKLVAASQ AALGLAPAPA PAPAPAPAPA   660
PAPAPDHCPL GPGRCCRLHT VRASLEDLGW ADWVLSPREV QVTMCIGACP SQFRAANMHA   720
QIKTSLHRLK PDTVPAPCCV PASYNPMVLI QKTDTGVSLQ TYDDLLAKDC HCI          773

SEQ ID NO: 38           moltype = AA  length = 783
FEATURE                 Location/Qualifiers
REGION                  1..783
                        note = GLP1-GDF15 Fusion Protein 6
source                  1..783
                        mol_type = protein
                        organism = synthetic construct
SEQUENCE: 38
HGEGTFTSDV SSYLEEQAAK EFIAWLVKGG GGGGAGGGGA GGGGAGGGGA GGGGAGGGGA    60
GGGGAGGGGA DAHKSEVAHR FKDLGEENFK ALVLIAFAQY LQQSPFEDHV KLVNEVTEFA   120
KTCVADESAE NCDKSLHTLF GDKLCTVATL RETYGEMADC CAKQEPERNE CFLQHKDDNP   180
NLPRLVRPEV DVMCTAFHDN EETFLKKYLY EIARRHPYFY APELLFFAKR YKAAFTECCQ   240
AADKAACLLP KLDELRDEGK ASSAKQRLKC ASLQKFGERA FKAWAVARLS QRFPKAEFAE   300
VSKLVTDLTK VHTECCHGDL LECADDRADL AKYICENQDS ISSKLKECCE KPLLEKSHCI   360
AEVENDEMPA DLPSLAADFV ESKDVCKNYA EAKDVFLGMF LYEYARRHPD YSVVLLLRLA   420
KTYETTLEKC CAAADPHECY AKVFDEFKPL VEEPQNLIKQ NCELFEQLGE YKFQNALLVR   480
YTKKVPQVST PTLVEVSRNL GKVGSKCCKH PEAKRMPCAE DYLSVVLNQL CVLHEKTPVS   540
DRVTKCCTES LVNRRPCFSA LEVDETYVPK EFNAETFTFH ADICTLSEKE RQIKKQTALV   600
ELVKHKPKAT KEQLKAVMDD FAAFVEKCCK ADDKETCFAE EGKKLVAASQ AALGLAPAPA   660
PAPAPAPAPA PAPAPDHCPL GPGRCCRLHT VRASLEDLGW ADWVLSPREV QVTMCIGACP   720
SQFRAANMHA QIKTSLHRLK PDTVPAPCCV PASYNPMVLI QKTDTGVSLQ TYDDLLAKDC   780
HCI                                                                783

SEQ ID NO: 39           moltype = AA  length = 802
FEATURE                 Location/Qualifiers
REGION                  1..802
                        note = GLP1-GDF15 Fusion Protein 7
source                  1..802
                        mol_type = protein
                        organism = synthetic construct
SEQUENCE: 39
HGEGTFTSDL SKQMEEEAVR LFIEWLKNGG PSSGAPPPSA PAPAPAPAPA PAPAPAPAPA    60
PAPAPAPAPA PAPAPAPAPA PAPAPAPAPD AHKSEVAHRF KDLGEENFKA LVLIAFAQYL   120
QQSPFEDHVK LVNEVTEFAK TCVADESAEN CDKSLHTLFG DKLCTVATLR ETYGEMADCC   180
AKQEPERNEC FLQHKDDNPN LPRLVRPEVD VMCTAFHDNE ETFLKKYLYE IARRHPYFYA   240
PELLFFAKRY KAAFTECCQA ADKAACLLPK LDELRDEGKA SSAKQRLKCA SLQKFGERAF   300
KAWAVARLSQ RFPKAEFAEV SKLVTDLTKV HTECCHGDLL ECADDRADLA KYICENQDSI   360
```

```
SSKLKECCEK PLLEKSHCIA EVENDEMPAD LPSLAADFVE SKDVCKNYAE AKDVFLGMFL  420
YEYARRHPDY SVVLLLRLAK TYETTLEKCC AAADPHECYA KVFDEFKPLV EEPQNLIKQN  480
CELFEQLGEY KFQNALLVRY TKKVPQVSTP TLVEVSRNLG KVGSKCCKHP EAKRMPCAED  540
YLSVVLNQLC VLHEKTPVSD RVTKCCTESL VNRRPCFSAL EVDETYVPKE FNAETFTFHA  600
DICTLSEKER QIKKQTALVE LVKHKPKATK EQLKAVMDDF AAFVEKCCKA DDKETCFAEE  660
GKKLVAASQA ALGLAPAPAP APAPAPAPAP APAPDHCPLG PGRCCRLHTV RASLEDLGWA  720
DWVLSPREVQ VTMCIGACPS QFRAANMHAQ IKTSLHRLKP DTVPAPCCVP ASYNPMVLIQ  780
KTDTGVSLQT YDDLLAKDCH CI                                          802

SEQ ID NO: 40          moltype = AA  length = 782
FEATURE                Location/Qualifiers
REGION                 1..782
                       note = GLP1-GDF15 Fusion Protein 8
source                 1..782
                       mol_type = protein
                       organism = synthetic construct
SEQUENCE: 40
HGEGTFTSDL SKQMEEEAVR LFIEWLKNGG PSSGAPPPSA PAPAPAPAPA PAPAPAPAPA   60
PAPAPAPAPD AHKSEVAHRF KDLGEENFKA LVLIAFAQYL QQSPFEDHVK LVNEVTEFAK  120
TCVADESAEN CDKSLHTLFG DKLCTVATLR ETYGEMADCC AKQEPERNEC FLQHKDDNPN  180
LPRLVRPEVD VMCTAFHDNE ETFLKKYLYE IARRHPYFYA PELLFFAKRY KAAFTECCQA  240
ADKAACLLPK LDELRDEGKA SSAKQRLKCA SLQKFGERAF KAWAVARLSQ RFPKAEFAEV  300
SKLVTDLTKV HTECCHGDLL ECADDRADLA KYICENQDSI SSKLKECCEK PLLEKSHCIA  360
EVENDEMPAD LPSLAADFVE SKDVCKNYAE AKDVFLGMFL YEYARRHPDY SVVLLLRLAK  420
TYETTLEKCC AAADPHECYA KVFDEFKPLV EEPQNLIKQN CELFEQLGEY KFQNALLVRY  480
TKKVPQVSTP TLVEVSRNLG KVGSKCCKHP EAKRMPCAED YLSVVLNQLC VLHEKTPVSD  540
RVTKCCTESL VNRRPCFSAL EVDETYVPKE FNAETFTFHA DICTLSEKER QIKKQTALVE  600
LVKHKPKATK EQLKAVMDDF AAFVEKCCKA DDKETCFAEE GKKLVAASQA ALGLAPAPAP  660
APAPAPAPAP APAPDHCPLG PGRCCRLHTV RASLEDLGWA DWVLSPREVQ VTMCIGACPS  720
QFRAANMHAQ IKTSLHRLKP DTVPAPCCVP ASYNPMVLIQ KTDTGVSLQT YDDLLAKDCH  780
CI                                                                782

SEQ ID NO: 41          moltype = AA  length = 772
FEATURE                Location/Qualifiers
REGION                 1..772
                       note = GLP1-GDF15 Fusion Protein 9
source                 1..772
                       mol_type = protein
                       organism = synthetic construct
SEQUENCE: 41
HGEGTFTSDL SKQMEEEAVR LFIEWLKNGG PSSGAPPPSA PAPAPAPAPA PAPAPAPAPD   60
AHKSEVAHRF KDLGEENFKA LVLIAFAQYL QQSPFEDHVK LVNEVTEFAK TCVADESAEN  120
CDKSLHTLFG DKLCTVATLR ETYGEMADCC AKQEPERNEC FLQHKDDNPN LPRLVRPEVD  180
VMCTAFHDNE ETFLKKYLYE IARRHPYFYA PELLFFAKRY KAAFTECCQA ADKAACLLPK  240
LDELRDEGKA SSAKQRLKCA SLQKFGERAF KAWAVARLSQ RFPKAEFAEV SKLVTDLTKV  300
HTECCHGDLL ECADDRADLA KYICENQDSI SSKLKECCEK PLLEKSHCIA EVENDEMPAD  360
LPSLAADFVE SKDVCKNYAE AKDVFLGMFL YEYARRHPDY SVVLLLRLAK TYETTLEKCC  420
AAADPHECYA KVFDEFKPLV EEPQNLIKQN CELFEQLGEY KFQNALLVRY TKKVPQVSTP  480
TLVEVSRNLG KVGSKCCKHP EAKRMPCAED YLSVVLNQLC VLHEKTPVSD RVTKCCTESL  540
VNRRPCFSAL EVDETYVPKE FNAETFTFHA DICTLSEKER QIKKQTALVE LVKHKPKATK  600
EQLKAVMDDF AAFVEKCCKA DDKETCFAEE GKKLVAASQA ALGLAPAPAP APAPAPAPAP  660
APAPDHCPLG PGRCCRLHTV RASLEDLGWA DWVLSPREVQ VTMCIGACPS QFRAANMHAQ  720
IKTSLHRLKP DTVPAPCCVP ASYNPMVLIQ KTDTGVSLQT YDDLLAKDCH CI          772

SEQ ID NO: 42          moltype = AA  length = 792
FEATURE                Location/Qualifiers
REGION                 1..792
                       note = GLP1-GDF15 Fusion Protein 10
source                 1..792
                       mol_type = protein
                       organism = synthetic construct
SEQUENCE: 42
HGEGTFTSDL SKQMEEEAVR LFIEWLKNGG PSSGAPPPSG GGGAGGGGAG GGGAGGGGAG   60
GGGAGGGGAG GGGAGGGGAD AHKSEVAHRF KDLGEENFKA LVLIAFAQYL QQSPFEDHVK  120
LVNEVTEFAK TCVADESAEN CDKSLHTLFG DKLCTVATLR ETYGEMADCC AKQEPERNEC  180
FLQHKDDNPN LPRLVRPEVD VMCTAFHDNE ETFLKKYLYE IARRHPYFYA PELLFFAKRY  240
KAAFTECCQA ADKAACLLPK LDELRDEGKA SSAKQRLKCA SLQKFGERAF KAWAVARLSQ  300
RFPKAEFAEV SKLVTDLTKV HTECCHGDLL ECADDRADLA KYICENQDSI SSKLKECCEK  360
PLLEKSHCIA EVENDEMPAD LPSLAADFVE SKDVCKNYAE AKDVFLGMFL YEYARRHPDY  420
SVVLLLRLAK TYETTLEKCC AAADPHECYA KVFDEFKPLV EEPQNLIKQN CELFEQLGEY  480
KFQNALLVRY TKKVPQVSTP TLVEVSRNLG KVGSKCCKHP EAKRMPCAED YLSVVLNQLC  540
VLHEKTPVSD RVTKCCTESL VNRRPCFSAL EVDETYVPKE FNAETFTFHA DICTLSEKER  600
QIKKQTALVE LVKHKPKATK EQLKAVMDDF AAFVEKCCKA DDKETCFAEE GKKLVAASQA  660
ALGLAPAPAP APAPAPAPAP APAPDHCPLG PGRCCRLHTV RASLEDLGWA DWVLSPREVQ  720
VTMCIGACPS QFRAANMHAQ IKTSLHRLKP DTVPAPCCVP ASYNPMVLIQ KTDTGVSLQT  780
YDDLLAKDCH CI                                                     792

SEQ ID NO: 43          moltype = AA  length = 777
FEATURE                Location/Qualifiers
```

| | | |
|---|---|---|
| REGION | 1..777 | |
| | note = GLP1-GDF15 Fusion Protein 11 | |
| source | 1..777 | |
| | mol_type = protein | |
| | organism = synthetic construct | |

SEQUENCE: 43

```
HGEGTFTSDL SKQMEEEAVR LFIEWLKNGG PSSGAPPPSG GGGAGGGGAG GGGAGGGGAG      60
GGGADAHKSE VAHRFKDLGE ENFKALVLIA FAQYLQQSPF EDHVKLVNEV TEFAKTCVAD     120
ESAENCDKSL HTLFGDKLCT VATLRETYGE MADCCAKQEP ERNECFLQHK DDNPNLPRLV     180
RPEVDVMCTA FHDNEETFLK KYLYEIARRH PYFYAPELLF FAKRYKAAFT ECCQAADKAA     240
CLLPKLDELR DEGKASSAKQ RLKCASLQKF GERAFKAWAV ARLSQRFPKA EFAEVSKLVT     300
DLTKVHTECC HGDLLECADD RADLAKYICE NQDSISSKLK ECCEKPLLEK SHCIAEVEND     360
EMPADLPSLA ADFVESKDVC KNYAEAKDVF LGMFLYEYAR RHPDYSVVLL LRLAKTYETT     420
LEKCCAAADP HECYAKVFDE FKPLVEEPQN LIKQNCELFE QLGEYKFQNA LLVRYTKKVP     480
QVSTPTLVEV SRNLGKVGSK CCKHPEAKRM PCAEDYLSVV LNQLCVLHEK TPVSDRVTKC     540
CTESLVNRRP CFSALEVDET YVPKEFNAET FTFHADICTL SEKERQIKKQ TALVELVKHK     600
PKATKEQLKA VMDDFAAFVE KCCKADDKET CFAEEGKKLV AASQAALGLA PAPAPAPAPA     660
PAPAPAPAPD HCPLGPGRCC RLHTVRASLE DLGWADWVLS PREVQVTMCI GACPSQFRAA     720
NMHAQIKTSL HRLKPDTVPA PCCVPASYNP MVLIQKTDTG VSLQTYDDLL AKDCHCI       777
```

| | | |
|---|---|---|
| SEQ ID NO: 44 | moltype = AA  length = 762 | |
| FEATURE | Location/Qualifiers | |
| REGION | 1..762 | |
| | note = GLP1-GDF15 Fusion Protein 12 | |
| source | 1..762 | |
| | mol_type = protein | |
| | organism = synthetic construct | |

SEQUENCE: 44

```
HGEGTFTSDL SKQMEEEAVR LFIEWLKNGG PSSGAPPPSA PAPAPAPAPD AHKSEVAHRF      60
KDLGEENFKA LVLIAFAQYL QQSPFEDHVK LVNEVTEFAK TCVADESAEN CDKSLHTLFG     120
DKLCTVATLR ETYGEMADCC AKQEPERNEC FLQHKDDNPN LPRLVRPEVD VMCTAFHDNE     180
ETFLKKYLYE IARRHPYFYA PELLFFAKRY KAAFTECCQA ADKAACLLPK LDELRDEGKA     240
SSAKQRLKCA SLQKFGERAF KAWAVARLSQ RFPKAEFAEV SKLVTDLTKV HTECCHGDLL     300
ECADDRADLA KYICENQDSI SSKLKECCEK PLLEKSHCIA EVENDEMPAD LPSLAADFVE     360
SKDVCKNYAE AKDVFLGMFL YEYARRHPDY SVVLLLRLAK TYETTLEKCC AAADPHECYA     420
KVFDEFKPLV EEPQNLIKQN CELFEQLGEY KFQNALLVRY TKKVPQVSTP TLVEVSRNLG     480
KVGSKCCKHP EAKRMPCAED YLSVVLNQLC VLHEKTPVSD RVTKCCTESL VNRRPCFSAL     540
EVDETYVPKE FNAETFTFHA DICTLSEKER QIKKQTALVE LVKHKPKATK EQLKAVMDDF     600
AAFVEKCCKA DDKETCFAEE GKKLVAASQA ALGLAPAPAP APAPAPAPAP APAPDHCPLG     660
PGRCCRLHTV RASLEDLGWA DWVLSPREVQ VTMCIGACPS QFRAANMHAQ IKTSLHRLKP     720
DTVPAPCCVP ASYNPMVLIQ KTDTGVSLQT YDDLLAKDCH CI                       762
```

| | | |
|---|---|---|
| SEQ ID NO: 45 | moltype = AA  length = 763 | |
| FEATURE | Location/Qualifiers | |
| REGION | 1..763 | |
| | note = GLP1-GDF15 Fusion Protein 13 | |
| source | 1..763 | |
| | mol_type = protein | |
| | organism = synthetic construct | |

SEQUENCE: 45

```
HGEGTFTSDV SSYLEEQAAK EFIAWLVKGG APAPAPAPAP APAPAPAPAP DAHKSEVAHR      60
FKDLGEENFK ALVLIAFAQY LQQSPFEDHV KLVNEVTEFA KTCVADESAE NCDKSLHTLF     120
GDKLCTVATL RETYGEMADC CAKQEPERNE CFLQHKDDNP NLPRLVRPEV DVMCTAFHDN     180
EETFLKKYLY EIARRHPYFY APELLFFAKR YKAAFTECCQ AADKAACLLP KLDELRDEGK     240
ASSAKQRLKC ASLQKFGERA FKAWAVARLS QRFPKAEFAE VSKLVTDLTK VHTECCHGDL     300
LECADDRADL AKYICENQDS ISSKLKECCE KPLLEKSHCI AEVENDEMPA DLPSLAADFV     360
ESKDVCKNYA EAKDVFLGMF LYEYARRHPD YSVVLLLRLA KTYETTLEKC CAAADPHECY     420
AKVFDEFKPL VEEPQNLIKQ NCELFEQLGE YKFQNALLVR YTKKVPQVST PTLVEVSRNL     480
GKVGSKCCKH PEAKRMPCAE DYLSVVLNQL CVLHEKTPVS DRVTKCCTES LVNRRPCFSA     540
LEVDETYVPK EFNAETFTFH ADICTLSEKE RQIKKQTALV ELVKHKPKAT KEQLKAVMDD     600
FAAFVEKCCK ADDKETCFAE EGKKLVAASQ AALGLAPAPA PAPAPAPAPA PAPAPDHCPL     660
GPGRCCRLHT VRASLEDLGW ADWVLSPREV QVTMCIGACP SQFRAANMHA QIKTSLHRLK     720
PDTVPAPCCV PASYNPMVLI QKTDTGVSLQ TYDDLLAKDC HCI                      763
```

| | | |
|---|---|---|
| SEQ ID NO: 46 | moltype = AA  length = 784 | |
| FEATURE | Location/Qualifiers | |
| REGION | 1..784 | |
| | note = GLP1-GDF15 Fusion Protein 14 | |
| source | 1..784 | |
| | mol_type = protein | |
| | organism = synthetic construct | |

SEQUENCE: 46

```
HGEGTFTSDL SKQMEEEAVR LFIEWLKNGG PSSGAPPPSA PAPAPAPAPD AHKSEVAHRF      60
KDLGEENFKA LVLIAFAQYL QQSPFEDHVK LVNEVTEFAK TCVADESAEN CDKSLHTLFG     120
DKLCTVATLR ETYGEMADCC AKQEPERNEC FLQHKDDNPN LPRLVRPEVD VMCTAFHDNE     180
ETFLKKYLYE IARRHPYFYA PELLFFAKRY KAAFTECCQA ADKAACLLPK LDELRDEGKA     240
SSAKQRLKCA SLQKFGERAF KAWAVARLSQ RFPKAEFAEV SKLVTDLTKV HTECCHGDLL     300
ECADDRADLA KYICENQDSI SSKLKECCEK PLLEKSHCIA EVENDEMPAD LPSLAADFVE     360
SKDVCKNYAE AKDVFLGMFL YEYARRHPDY SVVLLLRLAK TYETTLEKCC AAADPHECYA     420
```

```
KVFDEFKPLV EEPQNLIKQN CELFEQLGEY KFQNALLVRY TKKVPQVSTP TLVEVSRNLG    480
KVGSKCCKHP EAKRMPCAED YLSVVLNQLC VLHEKTPVSD RVTKCCTESL VNRRPCFSAL    540
EVDETYVPKE FNAETFTFHA DICTLSEKER QIKKQTALVE LVKHKPKATK EQLKAVMDDF    600
AAFVEKCCKA DDKETCFAEE GKKLVAASQA ALGLGAGGGG AGGGGAGGGG AGGGGAGGGG    660
AGGGGAGGGG AGGGGADHCP LGPGRCCRLH TVRASLEDLG WADWVLSPRE VQVTMCIGAC    720
PSQFRAANMH AQIKTSLHRL KPDTVPAPCC VPASYNPMVL IQKTDTGVSL QTYDDLLAKD    780
CHCI                                                                784

SEQ ID NO: 47           moltype = AA   length = 790
FEATURE                 Location/Qualifiers
REGION                  1..790
                        note = GLP1-GDF15 Fusion Protein 15
source                  1..790
                        mol_type = protein
                        organism = synthetic construct
SEQUENCE: 47
HGEGTFTSDV SSYLEEQAAK EFIAWLVKGG GGGGGGGGG GGGGGGGGGG GGGGDAHKS    60
EVAHRFKDLG EENFKALVLI AFAQYLQQSP FEDHVKLVNE VTEFAKTCVA DESAENCDKS   120
LHTLFGDKLC TVATLRETYG EMADCCAKQE PERNECFLQH KDDNPNLPRL VRPEVDVMCT   180
APHDNEETFL KKYLYEIARR HPYFYAPELL FFAKRYKAAF TECCQAADKA ACLLPKLDEL   240
RDEGKASSAK QRLKCASLQK FGERAFKAWA VARLSQRFPK AEFAEVSKLV TDLTKVHTEC   300
CHGDLLECAD DRADLAKYIC ENQDSISSKL KECCEKPLLE KSHCIAEVEN DEMPADLPSL   360
AADFVESKDV CKNYAEAKDV FLGMFLYEYA RRHPDYSVVL LLRLAKTYET TLEKCCAAAD   420
PHECYAKVFD EFKPLVEEPQ NLIKQNCELF EQLGEYKFQN ALLVRYTKKV PQVSTPTLVE   480
VSRNLGKVGS KCCKHPEAKR MPCAEDYLSV VLNQLCVLHE KTPVSDRVTK CCTESLVNRR   540
PCFSALEVDE TYVPKEFNAE TFTFHADICT LSEKERQIKK QTALVELVKH KPKATKEQLK   600
AVMDDFAAFV EKCCKADDKE TCFAEEGKKL VAASQAALGL GAGGGGAGGG GAGGGGAGGG   660
GAGGGGAGGG GAGGGGAGGG GADHCPLGPG RCCRLHTVRA SLEDLGWADW VLSPREVQVT   720
MCIGACPSQF RAANMHAQIK TSLHRLKPDT VPAPCCVPAS YNPMVLIQKT DTGVSLQTYD   780
DLLAKDCHCI                                                          790

SEQ ID NO: 48           moltype = AA   length = 785
FEATURE                 Location/Qualifiers
REGION                  1..785
                        note = GLP1-GDF15 Fusion Protein 16
source                  1..785
                        mol_type = protein
                        organism = synthetic construct
SEQUENCE: 48
HGEGTFTSDV SSYLEEQAAK EFIAWLVKGG GGGGGGGGG GGGGGGGGGG DAHKSEVAHR    60
FKDLGEENFK ALVLIAFAQY LQQSPFEDHV KLVNEVTEFA KTCVADESAE NCDKSLHTLF   120
GDKLCTVATL RETYGEMADC CAKQEPERNE CFLQHKDDNP NLPRLVRPEV DVMCTAFHDN   180
EETFLKKYLY EIARRHPYFY APELLFFAKR YKAAFTECCQ AADKAACLLP KLDELRDEGK   240
ASSAKQRLKC ASLQKFGERA FKAWAVARLS QRFPKAEFAE VSKLVTDLTK VHTECCHGDL   300
LECADDRADL AKYICENQDS ISSKLKECCE KPLLEKSHCI AEVENDEMPA DLPSLAADFV   360
ESKDVCKNYA EAKDVFLGMF LYEYARRHPD YSVVLLLRLA KTYETTLEKC CAAADPHECY   420
AKVFDEFKPL VEEPQNLIKQ NCELFEQLGE YKFQNALLVR YTKKVPQVST PTLVEVSRNL   480
GKVGSKCCKH PEAKRMPCAE DYLSVVLNQL CVLHEKTPVS DRVTKCCTES LVNRRPCFSA   540
LEVDETYVPK EFNAETFTFH ADICTLSEKE RQIKKQTALV ELVKHKPKAT KEQLKAVMDD   600
FAAFVEKCCK ADDKETCFAE EGKKLVAASQ AALGLGAGGG GAGGGGAGGG GAGGGGAGGG   660
GAGGGGAGGG GAGGGGADHC PLGPGRCCRL HTVRASLEDL GWADWVLSPR EVQVTMCIGA   720
CPSQFRAANM HAQIKTSLHR LKPDTVPAPC CVPASYNPMV LIQKTDTGVS LQTYDDLLAK   780
DCHCI                                                               785

SEQ ID NO: 49           moltype = AA   length = 785
FEATURE                 Location/Qualifiers
REGION                  1..785
                        note = GLP1-GDF15 Fusion Protein 17
source                  1..785
                        mol_type = protein
                        organism = synthetic construct
SEQUENCE: 49
HGEGTFTSDV SSYLEEQAAK EFIAWLVKGG GGGAGGGGA GGGAGGGGA DAHKSEVAHR    60
FKDLGEENFK ALVLIAFAQY LQQSPFEDHV KLVNEVTEFA KTCVADESAE NCDKSLHTLF   120
GDKLCTVATL RETYGEMADC CAKQEPERNE CFLQHKDDNP NLPRLVRPEV DVMCTAFHDN   180
EETFLKKYLY EIARRHPYFY APELLFFAKR YKAAFTECCQ AADKAACLLP KLDELRDEGK   240
ASSAKQRLKC ASLQKFGERA FKAWAVARLS QRFPKAEFAE VSKLVTDLTK VHTECCHGDL   300
LECADDRADL AKYICENQDS ISSKLKECCE KPLLEKSHCI AEVENDEMPA DLPSLAADFV   360
ESKDVCKNYA EAKDVFLGMF LYEYARRHPD YSVVLLLRLA KTYETTLEKC CAAADPHECY   420
AKVFDEFKPL VEEPQNLIKQ NCELFEQLGE YKFQNALLVR YTKKVPQVST PTLVEVSRNL   480
GKVGSKCCKH PEAKRMPCAE DYLSVVLNQL CVLHEKTPVS DRVTKCCTES LVNRRPCFSA   540
LEVDETYVPK EFNAETFTFH ADICTLSEKE RQIKKQTALV ELVKHKPKAT KEQLKAVMDD   600
FAAFVEKCCK ADDKETCFAE EGKKLVAASQ AALGLGAGGG GAGGGGAGGG GAGGGGAGGG   660
GAGGGGAGGG GAGGGGADHC PLGPGRCCRL HTVRASLEDL GWADWVLSPR EVQVTMCIGA   720
CPSQFRAANM HAQIKTSLHR LKPDTVPAPC CVPASYNPMV LIQKTDTGVS LQTYDDLLAK   780
DCHCI                                                               785

SEQ ID NO: 50           moltype = AA   length = 790
FEATURE                 Location/Qualifiers
```

```
REGION                  1..790
                        note = GLP1-GDF15 Fusion Protein 18
source                  1..790
                        mol_type = protein
                        organism = synthetic construct
SEQUENCE: 50
HGEGTFTSDV SSYLEEQAAK EFIAWLVKGG GGGGAGGGGA GGGGAGGGGA GGGGADAHKS   60
EVAHRFKDLG EENFKALVLI AFAQYLQQSP FEDHVKLVNE VTEFAKTCVA DESAENCDKS  120
LHTLFGDKLC TVATLRETYG EMADCCAKQE PERNECFLQH KDDNPNLPRL VRPEVDVMCT  180
AFHDNEETFL KKYLYEIARR HPYFYAPELL FFAKRYKAAF TECCQAADKA ACLLPKLDEL  240
RDEGKASSAK QRLKCASLQK FGERAFKAWA VARLSQRFPK AEFAEVSKLV TDLTKVHTEC  300
CHGDLLECAD DRADLAKYIC ENQDSISSKL KECCEKPLLE KSHCIAEVEN DEMPADLPSL  360
AADFVESKDV CKNYAEAKDV FLGMFLYEYA RRHPDYSVVL LLRLAKTYET TLEKCCAAAD  420
PHECYAKVFD EFKPLVEEPQ NLIKQNCELF EQLGEYKFQN ALLVRYTKKV PQVSTPTLVE  480
VSRNLGKVGS KCCKHPEAKR MPCAEDYLSV VLNQLCVLHE KTPVSDRVTK CCTESLVNRR  540
PCFSALEVDE TYVPKEFNAE TFTFHADICT LSEKERQIKK QTALVELVKH KPKATKEQLK  600
AVMDDFAAFV EKCCKADDKE TCFAEEGKKL VAASQAALGL GAGGGGAGGG GAGGGGAGGG  660
GAGGGGAGGG GAGGGGAGGG GADHCPLGPG RCCRLHTVRA SLEDLGWADW VLSPREVQVT  720
MCIGACPSQF RAANMHAQIK TSLHRLKPDT VPAPCCVPAS YNPMVLIQKT DTGVSLQTYD  780
DLLAKDCHCI                                                         790

SEQ ID NO: 51           moltype = AA  length = 807
FEATURE                 Location/Qualifiers
REGION                  1..807
                        note = GLP1-GDF15 Fusion Protein 19
source                  1..807
                        mol_type = protein
                        organism = synthetic construct
SEQUENCE: 51
HGEGTFTSDV SSYLEEQAAK EFIAWLVKGG GAGGGGAGGG GAGGGGAGGG GAGGGGAGGG   60
GAGGGGAGGG GADAHKSEVA HRFKDLGEEN FKALVLIAFA QYLQQSPFED HVKLVNEVTE  120
FAKTCVADES AENCDKSLHT LFGDKLCTVA TLRETYGEMA DCCAKQEPER NECFLQHKDD  180
NPNLPRLVRP EVDVMCTAFH DNEETFLKKY LYEIARRHPY FYAPELLFFA KRYKAAFTEC  240
CQAADKAACL LPKLDELRDE GKASSAKQRL KCASLQKFGE RAFKAWAVAR LSQRFPKAEF  300
AEVSKLVTDL TKVHTECCHG DLLECADDRA DLAKYICENQ DSISSKLKEC CEKPLLEKSH  360
CIAEVENDEM PADLPSLAAD FVESKDVCKN YAEAKDVFLG MFLYEYARRH PDYSVVLLLR  420
LAKTYETTLE KCCAAADPHE CYAKVFDEFK PLVEEPQNLI KQNCELFEQL GEYKFQNALL  480
VRYTKKVPQV STPTLVEVSR NLGKVGSKCC KHPEAKRMPC AEDYLSVVLN QLCVLHEKTP  540
VSDRVTKCCT ESLVNRRPCF SALEVDETYV PKEFNAETFT FHADICTLSE KERQIKKQTA  600
LVELVKHKPK ATKEQLKAVM DDFAAFVEKC CKADDKETCF AEEGKKLVAA SQAALGLGSG  660
GGGSGGGGSG GGGSGGGGSG GGGSGGGGSG GGGSGGGGSD HCPLGPGRCC RLHTVRASLE  720
DLGWADWVLS PREVQVTMCI GACPSQFRAA NMHAQIKTSL HRLKPDTVPA PCCVPASYNP  780
MVLIQKTDTG VSLQTYDDLL AKDCHCI                                      807

SEQ ID NO: 52           moltype = AA  length = 786
FEATURE                 Location/Qualifiers
REGION                  1..786
                        note = GLP1-GDF15 Fusion Protein 20
source                  1..786
                        mol_type = protein
                        organism = synthetic construct
SEQUENCE: 52
HGEGTFTSDL SKQMEEEAVR LFIEWLKNGG PSSGAPPPSG AGGGGAGGGG ADAHKSEVAH   60
RFKDLGEENF KALVLIAFAQ YLQQSPFEDH VKLVNEVTEF AKTCVADESA ENCDKSLHTL  120
FGDKLCTVAT LRETYGEMAD CCAKQEPERN ECFLQHKDDN PNLPRLVRPE VDVMCTAFHD  180
NEETFLKKYL YEIARRHPYF YAPELLFFAK RYKAAFTECC QAADKAACLL PKLDELRDEG  240
KASSAKQRLK CASLQKFGER AFKAWAVARL SQRFPKAEFA EVSKLVTDLT KVHTECCHGD  300
LLECADDRAD LAKYICENQD SISSKLKECC EKPLLEKSHC IAEVENDEMP ADLPSLAADF  360
VESKDVCKNY AEAKDVFLGM FLYEYARRHP DYSVVLLLRL AKTYETTLEK CCAAADPHEC  420
YAKVFDEFKP LVEEPQNLIK QNCELFEQLG EYKFQNALLV RYTKKVPQVS TPTLVEVSRN  480
LGKVGSKCCK HPEAKRMPCA EDYLSVVLNQ LCVLHEKTPV SDRVTKCCTE SLVNRRPCFS  540
ALEVDETYVP KEFNAETFTF HADICTLSEK ERQIKKQTAL VELVKHKPKA TKEQLKAVMD  600
DFAAFVEKCC KADDKETCFA EEGKKLVAAS QAALGLGSGG GGSGGGGSGG GGSGGGGSGG  660
GGSGGGGSGG GGSGGGGSDH CPLGPGRCCR LHTVRASLED LGWADWVLSP REVQVTMCIG  720
ACPSQFRAAN MHAQIKTSLH RLKPDTVPAP CCVPASYNPM VLIQKTDTGV SLQTYDDLLA  780
KDCHCI                                                             786

SEQ ID NO: 53           moltype = AA  length = 795
FEATURE                 Location/Qualifiers
REGION                  1..795
                        note = GLP1-GDF15 Fusion Protein 21
source                  1..795
                        mol_type = protein
                        organism = synthetic construct
SEQUENCE: 53
HGEGTFTSDV SSYLEEQAAK EFIAWLVKGG GGGGAGGGGA GGGGAGGGGA GGGGAGGGGA   60
DAHKSEVAHR FKDLGEENFK ALVLIAFAQY LQQSPFEDHV KLVNEVTEFA KTCVADESAE  120
NCDKSLHTLF GDKLCTVATL RETYGEMADC CAKQEPERNE CFLQHKDDNP NLPRLVRPEV  180
DVMCTAFHDN EETFLKKYLY EIARRHPYFY APELLFFAKR YKAAFTECCQ AADKAACLLP  240
```

```
KLDELRDEGK  ASSAKQRLKC  ASLQKFGERA  FKAWAVARLS  QRFPKAEFAE  VSKLVTDLTK   300
VHTECCHGDL  LECADDRADL  AKYICENQDS  ISSKLKECCE  KPLLEKSHCI  AEVENDEMPA   360
DLPSLAADFV  ESKDVCKNYA  EAKDVFLGMF  LYEYARRHPD  YSVVLLLRLA  KTYETTLEKC   420
CAAADPHECY  AKVFDEFKPL  VEEPQNLIKQ  NCELFEQLGE  YKFQNALLVR  YTKKVPQVST   480
PTLVEVSRNL  GKVGSKCCKH  PEAKRMPCAE  DYLSVVLNQL  CVLHEKTPVS  DRVTKCCTES   540
LVNRRPCFSA  LEVDETYVPK  EFNAETFTFH  ADICTLSEKE  RQIKKQTALV  ELVKHKPKAT   600
KEQLKAVMDD  FAAFVEKCCK  ADDKETCFAE  EGKKLVAASQ  AALGLSGGG   GSGGGGSGGG   660
GSGGGGSGGG  GSGGGGSGGG  GSGGGGSDHC  PLGPGRCCRL  HTVRASLEDL  GWADWVLSPR   720
EVQVTMCIGA  CPSQFRAANM  HAQIKTSLHR  LKPDTVPAPC  CVPASYNPMV  LIQKTDTGVS   780
LQTYDDLLAK  DCHCI                                                       795

SEQ ID NO: 54           moltype = AA  length = 790
FEATURE                 Location/Qualifiers
REGION                  1..790
                        note = GLP1-GDF15 Fusion Protein 22
source                  1..790
                        mol_type = protein
                        organism = synthetic construct
SEQUENCE: 54
HGEGTFTSDV  SSYLEEQAAK  EFIAWLVKGG  GGGGAGGGGA  GGGGAGGGGA  GGGGADAHKS    60
EVAHRFKDLG  EENFKALVLI  AFAQYLQQSP  FEDHVKLVNE  VTEFAKTCVA  DESAENCDKS   120
LHTLFGDKLC  TVATLRETYG  EMADCCAKQE  PERNECFLQH  KDDNPNLPRL  VRPEVDVMCT   180
AFHDNEETFL  KKYLYEIARR  HPYFYAPELL  FFAKRYKAAF  TECCQAADKA  ACLLPKLDEL   240
RDEGKASSAK  QRLKCASLQK  FGERAFKAWA  VARLSQRFPK  AEFAEVSKLV  TDLTKVHTEC   300
CHGDLLECAD  DRADLAKYIC  ENQDSISSKL  KECCEKPLLE  KSHCIAEVEN  DEMPADLPSL   360
AADFVESKDV  CKNYAEAKDV  FLGMFLYEYA  RRHPDYSVVL  LLRLAKTYET  TLEKCCAAAD   420
PHECYAKVFD  EFKPLVEEPQ  NLIKQNCELF  EQLGEYKFQN  ALLVRYTKKV  PQVSTPTLVE   480
VSRNLGKVGS  KCCKHPEAKR  MPCAEDYLSV  VLNQLCVLHE  KTPVSDRVTK  CCTESLVNRR   540
PCFSALEVDE  TYVPKEFNAE  TFTFHADICT  LSEKERQIKK  QTALVELVKH  KPKATKEQLK   600
AVMDDFAAFV  EKCCKADDKE  TCFAEEGKKL  VAASQAALGL  GSGGGGSGGG  GSGGGGSGGG   660
GSGGGGSGGG  GSGGGGSGGG  GSDHCPLGPG  RCCRLHTVRA  SLEDLGWADW  VLSPREVQVT   720
MCIGACPSQF  RAANMHAQIK  TSLHRLKPDT  VPAPCCVPAS  YNPMVLIQKT  DTGVSLQTYD   780
DLLAKDCHCI                                                              790

SEQ ID NO: 55           moltype = AA  length = 795
FEATURE                 Location/Qualifiers
REGION                  1..795
                        note = GLP1-GDF15 Fusion Protein 23
source                  1..795
                        mol_type = protein
                        organism = synthetic construct
SEQUENCE: 55
HGEGTFTSDV  SSYLEEQAAK  EFIAWLVKGG  GGGSGGGGS   GGGGSGGGGS  GGGGSGGGGS    60
DAHKSEVAHR  FKDLGEENFK  ALVLIAFAQY  LQQSPFEDHV  KLVNEVTEFA  KTCVADESAE   120
NCDKSLHTLF  GDKLCTVATL  RETYGEMADC  CAKQEPERNE  CFLQHKDDNP  NLPRLVRPEV   180
DVMCTAFHDN  EETFLKKYLY  EIARRHPYFY  APELLFFAKR  YKAAFTECCQ  AADKAACLLP   240
KLDELRDEGK  ASSAKQRLKC  ASLQKFGERA  FKAWAVARLS  QRFPKAEFAE  VSKLVTDLTK   300
VHTECCHGDL  LECADDRADL  AKYICENQDS  ISSKLKECCE  KPLLEKSHCI  AEVENDEMPA   360
DLPSLAADFV  ESKDVCKNYA  EAKDVFLGMF  LYEYARRHPD  YSVVLLLRLA  KTYETTLEKC   420
CAAADPHECY  AKVFDEFKPL  VEEPQNLIKQ  NCELFEQLGE  YKFQNALLVR  YTKKVPQVST   480
PTLVEVSRNL  GKVGSKCCKH  PEAKRMPCAE  DYLSVVLNQL  CVLHEKTPVS  DRVTKCCTES   540
LVNRRPCFSA  LEVDETYVPK  EFNAETFTFH  ADICTLSEKE  RQIKKQTALV  ELVKHKPKAT   600
KEQLKAVMDD  FAAFVEKCCK  ADDKETCFAE  EGKKLVAASQ  AALGLSGGG   GSGGGGSGGG   660
GSGGGGSGGG  GSGGGGSGGG  GSGGGGSDHC  PLGPGRCCRL  HTVRASLEDL  GWADWVLSPR   720
EVQVTMCIGA  CPSQFRAANM  HAQIKTSLHR  LKPDTVPAPC  CVPASYNPMV  LIQKTDTGVS   780
LQTYDDLLAK  DCHCI                                                       795

SEQ ID NO: 56           moltype = AA  length = 790
FEATURE                 Location/Qualifiers
REGION                  1..790
                        note = GLP1-GDF15 Fusion Protein 24
source                  1..790
                        mol_type = protein
                        organism = synthetic construct
SEQUENCE: 56
HGEGTFTSDV  SSYLEEQAAK  EFIAWLVKGG  GGGSGGGGS   GGGGSGGGGS  GGGGSDAHKS    60
EVAHRFKDLG  EENFKALVLI  AFAQYLQQSP  FEDHVKLVNE  VTEFAKTCVA  DESAENCDKS   120
LHTLFGDKLC  TVATLRETYG  EMADCCAKQE  PERNECFLQH  KDDNPNLPRL  VRPEVDVMCT   180
AFHDNEETFL  KKYLYEIARR  HPYFYAPELL  FFAKRYKAAF  TECCQAADKA  ACLLPKLDEL   240
RDEGKASSAK  QRLKCASLQK  FGERAFKAWA  VARLSQRFPK  AEFAEVSKLV  TDLTKVHTEC   300
CHGDLLECAD  DRADLAKYIC  ENQDSISSKL  KECCEKPLLE  KSHCIAEVEN  DEMPADLPSL   360
AADFVESKDV  CKNYAEAKDV  FLGMFLYEYA  RRHPDYSVVL  LLRLAKTYET  TLEKCCAAAD   420
PHECYAKVFD  EFKPLVEEPQ  NLIKQNCELF  EQLGEYKFQN  ALLVRYTKKV  PQVSTPTLVE   480
VSRNLGKVGS  KCCKHPEAKR  MPCAEDYLSV  VLNQLCVLHE  KTPVSDRVTK  CCTESLVNRR   540
PCFSALEVDE  TYVPKEFNAE  TFTFHADICT  LSEKERQIKK  QTALVELVKH  KPKATKEQLK   600
AVMDDFAAFV  EKCCKADDKE  TCFAEEGKKL  VAASQAALGL  GSGGGGSGGG  GSGGGGSGGG   660
GSGGGGSGGG  GSGGGGSGGG  GSDHCPLGPG  RCCRLHTVRA  SLEDLGWADW  VLSPREVQVT   720
MCIGACPSQF  RAANMHAQIK  TSLHRLKPDT  VPAPCCVPAS  YNPMVLIQKT  DTGVSLQTYD   780
DLLAKDCHCI                                                              790
```

```
SEQ ID NO: 57           moltype = AA  length = 789
FEATURE                 Location/Qualifiers
REGION                  1..789
                        note = GLP1-GDF15 Fusion Protein 25
source                  1..789
                        mol_type = protein
                        organism = synthetic construct
SEQUENCE: 57
HGEGTFTSDV SSYLEEQAAK EFIAWLVKGG ASAPAPAPAP APAPAPAPAP APGSDAHKSE    60
VAHRFKDLGE ENFKALVLIA FAQYLQQSPF EDHVKLVNEV TEFAKTCVAD ESAENCDKSL   120
HTLFGDKLCT VATLRETYGE MADCCAKQEP ERNECFLQHK DDNPNLPRLV RPEVDVMCTA   180
FHDNEETFLK KYLYEIARRH PYFYAPELLF FAKRYKAAFT ECCQAADKAA CLLPKLDELR   240
DEGKASSAKQ RLKCASLQKF GERAFKAWAV ARLSQRFPKA EFAEVSKLVT DLTKVHTECC   300
HGDLLECADD RADLAKYICE NQDSISSKLK ECCEKPLLEK SHCIAEVEND EMPADLPSLA   360
ADFVESKDVC KNYAEAKDVF LGMFLYEYAR RHPDYSVVLL LRLAKTYETT LEKCCAAADP   420
HECYAKVFDE FKPLVEEPQN LIKQNCELFE QLGEYKFQNA LLVRYTKKVP QVSTPTLVEV   480
SRNLGKVGSK CCKHPEAKRM PCAEDYLSVV LNQLCVLHEK TPVSDRVTKC CTESLVNRRP   540
CFSALEVDET YVPKEFNAET FTFHADICTL SEKERQIKKQ TALVELVKHK PKATKEQLKA   600
VMDDFAAFVE KCCKADDKET CFAEEGKKLV AASQAALGLG SGGGGSGGGG SGGGGSGGGG   660
SGGGGSGGGG SGGGGSGGGG SDHCPLGPGR CCRLHTVRAS LEDLGWADWV LSPREVQVTM   720
CIGACPSQFR AANMHAQIKT SLHRLKPDTV PAPCCVPASY NPMVLIQKTD TGVSLQTYDD   780
LLAKDCHCI                                                          789

SEQ ID NO: 58           moltype = AA  length = 807
FEATURE                 Location/Qualifiers
REGION                  1..807
                        note = GLP1-GDF15 Fusion Protein 26
source                  1..807
                        mol_type = protein
                        organism = synthetic construct
SEQUENCE: 58
HGEGTFTSDV SSYLEEQAAK EFIAWLVKGG ASGGGGSGGG GSGGGGSGGG GSGGGGSGGG    60
GSGGGGSGGG GSDAHKSEVA HRFKDLGEEN FKALVLIAFA QYLQQSPFED HVKLVNEVTE   120
FAKTCVADES AENCDKSLHT LFGDKLCTVA TLRETYGEMA DCCAKQEPER NECFLQHKDD   180
NPNLPRLVRP EVDVMCTAFH DNEETFLKKY LYEIARRHPY FYAPELLFFA KRYKAAFTEC   240
CQAADKAACL LPKLDELRDE GKASSAKQRL KCASLQKFGE RAFKAWAVAR LSQRFPKAEF   300
AEVSKLVTDL TKVHTECCHG DLLECADDRA DLAKYICENQ DSISSKLKEC EKPLLEKSH   360
CIAEVENDEM PADLPSLAAD FVESKDVCKN YAEAKDVFLQ MFLYEYARRH PDYSVVLLLR   420
LAKTYETTLE KCCAAADPHE CYAKVFDEFK PLVEEPQNLI KQNCELFEQL GEYKFQNALL   480
VRYTKKVPQV STPTLVEVSR NLGKVGSKCC KHPEAKRMPC AEDYLSVVLN QLCVLHEKTP   540
VSDRVTKCCT ESLVNRRPCF SALEVDETYV PKEFNAETFT FHADICTLSE KERQIKKQTA   600
LVELVKHKPK ATKEQLKAVM DDFAAFVEKC CKADDKETCF AEEGKKLVAA SQAALGLGSG   660
GGGSGGGGSG GGGSGGGGSG GGGSGGGGSD HCPLGPGRCC RLHTVRASLE            720
DLGWADWVLS PREVQVTMCI GACPSQFRAA NMHAQIKTSL HRLKPDTVPA PCCVPASYNP   780
MVLIQKTDTG VSLQTYDDLL AKDCHCI                                      807

SEQ ID NO: 59           moltype = AA  length = 816
FEATURE                 Location/Qualifiers
REGION                  1..816
                        note = GLP1-GDF15 Fusion Protein 27
source                  1..816
                        mol_type = protein
                        organism = synthetic construct
SEQUENCE: 59
HGEGTFTSDL SKQMEEEAVR LFIEWLKNGG PSSGAPPPSA SGGGGSGGGG SGGGGSGGGG    60
SGGGGSGGGG SGGGGSGGGG SDAHKSEVAH RFKDLGEENF KALVLIAFAQ YLQQSPFEDH   120
VKLVNEVTEF AKTCVADESA ENCDKSLHTL FGDKLCTVAT LRETYGEMAD CCAKQEPERN   180
ECFLQHKDDN PNLPRLVRPE VDVMCTAFHD NEETFLKKYL YEIARRHPYF YAPELLFFAK   240
RYKAAFTECC QAADKAACLL PKLDELRDEG KASSAKQRLK CASLQKFGER AFKAWAVARL   300
SQRFPKAEFA EVSKLVTDLT KVHTECCHGD LLECADDRAD LAKYICENQD SISSKLKECC   360
EKPLLEKSHC IAEVENDEMP ADLPSLAADF VESKDVCKNY AEAKDVFLGM FLYEYARRHP   420
DYSVVLLLRL AKTYETTLEK CCAAADPHEC YAKVFDEFKP LVEEPQNLIK QNCELFEQLG   480
EYKFQNALLV RYTKKVPQVS TPTLVEVSRN LGKVGSKCCK HPEAKRMPCA EDYLSVVLNQ   540
LCVLHEKTPV SDRVTKCCTE SLVNRRPCFS ALEVDETYVP KEFNAETFTF HADICTLSEK   600
ERQIKKQTAL VELVKHKPKA TKEQLKAVMD DFAAFVEKCC KADDKETCFA EEGKKLVAAS   660
QAALGLGSGG GGSGGGGSGG GGSGGGGSGG GGSGGGGSGG GGSGGGGSDH CPLGPGRCCR   720
LHTVRASLED LGWADWVLSP REVQVTMCIG ACPSQFRAAN MHAQIKTSLH RLKPDTVPAP   780
CCVPASYNPM VLIQKTDTGV SLQTYDDLLA KDCHCI                            816

SEQ ID NO: 60           moltype = AA  length = 798
FEATURE                 Location/Qualifiers
REGION                  1..798
                        note = GLP1-GDF15 Fusion Protein 28
source                  1..798
                        mol_type = protein
                        organism = synthetic construct
SEQUENCE: 60
HGEGTFTSDL SKQMEEEAVR LFIEWLKNGG PSSGAPPPSA SAPAPAPAPA PAPAPAPAPA    60
```

```
PGSDAHKSEV AHRFKDLGEE NFKALVLIAF AQYLQQSPFE DHVKLVNEVT EFAKTCVADE   120
SAENCDKSLH TLFGDKLCTV ATLRETYGEM ADCCAKQEPE RNECFLQHKD DNPNLPRLVR   180
PEVDVMCTAF HDNEETFLKK YLYEIARRHP YFYAPELLFF AKRYKAAFTE CCQAADKAAC   240
LLPKLDELRD EGKASSAKQR LKCASLQKFG ERAFKAWAVA RLSQRFPKAE FAEVSKLVTD   300
LTKVHTECCH GDLLECADDR ADLAKYICEN QDSISSKLKE CCEKPLLEKS HCIAEVENDE   360
MPADLPSLAA DFVESKDVCK NYAEAKDVFL GMFLYEYARR HPDYSVVLLL RLAKTYETTL   420
EKCCAAADPH ECYAKVFDEF KPLVEEPQNL IKQNCELFEQ LGEYKFQNAL LVRYTKKVPQ   480
VSTPTLVEVS RNLGKVGSKC CKHPEAKRMP CAEDYLSVVL NQLCVLHEKT PVSDRVTKCC   540
TESLVNRRPC FSALEVDETY VPKEFNAETF TFHADICTLS EKERQIKKQT ALVELVKHKP   600
KATKEQLKAV MDDFAAFVEK CCKADDKETC FAEEGKKLVA ASQAALGLGS GGGGSGGGGS   660
GGGGSGGGGS GGGGSGGGGS GGGGSGGGGS DHCPLGPGRC CRLHTVRASL EDLGWADWVL   720
SPREVQVTMC IGACPSQFRA ANMHAQIKTS LHRLKPDTVP APCCVPASYN PMVLIQKTDT   780
GVSLQTYDDL LAKDCHCI                                                798

SEQ ID NO: 61          moltype = AA   length = 789
FEATURE                Location/Qualifiers
REGION                 1..789
                       note = GLP1-GDF15 Fusion Protein 29
source                 1..789
                       mol_type = protein
                       organism = synthetic construct
SEQUENCE: 61
HSEGTFTSDV SSYLEGQAAK EFIEWLVKGR ASAPAPAPAP APAPAPAPAP APGSDAHKSE    60
VAHRFKDLGE ENFKALVLIA FAQYLQQSPF EDHVKLVNEV TEFAKTCVAD ESAENCDKSL   120
HTLFGDKLCT VATLRETYGE MADCCAKQEP ERNECFLQHK DDNPNLPRLV RPEVDVMCTA   180
FHDNEETFLK KYLYEIARRH PYFYAPELLF FAKRYKAAFT ECCQAADKAA CLLPKLDELR   240
DEGKASSAKQ RLKCASLQKF GERAFKAWAV ARLSQRFPKA EFAEVSKLVT DLTKVHTECC   300
HGDLLECADD RADLAKYICE NQDSISSKLK ECCEKPLLEK SHCIAEVEND EMPADLPSLA   360
ADFVESKDVC KNYAEAKDVF LGMFLYEYAR RHPDYSVVLL LRLAKTYETT LEKCCAAADP   420
HECYAKVFDE FKPLVEEPQN LIKQNCELFE QLGEYKFQNA LLVRYTKKVP QVSTPTLVEV   480
SRNLGKVGSK CCKHPEAKRM PCAEDYLSVV LNQLCVLHEK TPVSDRVTKC CTESLVNRRP   540
CFSALEVDET YVPKEFNAET FTFHADICTL SEKERQIKKQ TALVELVKHK PKATKEQLKA   600
VMDDFAAFVE KCCKADDKET CFAEEGKKLV AASQAALGLG SGGGGSGGGG SGGGGSGGGG   660
SGGGGSGGGG GGGGGSGGGG SDHCPLGPGR CCRLHTVRAS LEDLGWADWV LSPREVQVTM   720
CIGACPSQFR AANMHAQIKT SLHRLKPDTV PAPCCVPASY NPMVLIQKTD TGVSLQTYDD   780
LLAKDCHCI                                                          789

SEQ ID NO: 62          moltype = AA   length = 807
FEATURE                Location/Qualifiers
REGION                 1..807
                       note = GLP1-GDF15 Fusion Protein 30
source                 1..807
                       mol_type = protein
                       organism = synthetic construct
SEQUENCE: 62
HSEGTFTSDV SSYLEGQAAK EFIEWLVKGR ASGGGGSGGG GSGGGGSGGG GSGGGGSGGG    60
GSGGGGSGGG GSDAHKSEVA HRFKDLGEEN FKALVLIAFA QYLQQSPFED HVKLVNEVTE   120
FAKTCVADES AENCDKSLHT LFGDKLCTVA TLRETYGEMA DCCAKQEPER NECFLQHKDD   180
NPNLPRLVRP EVDVMCTAFH DNEETFLKKY LYEIARRHPY FYAPELLFFA KRYKAAFTEC   240
CQAADKAACL LPKLDELRDE GKASSAKQRL KCASLQKFGE RAFKAWAVAR LSQRFPKAEF   300
AEVSKLVTDL TKVHTECCHG DLLECADDRA DLAKYICENQ DSISSKLKEC CEKPLLEKSH   360
CIAEVENDEM PADLPSLAAD FVESKDVCKN YAEAKDVFLG MFLYEYARRH PDYSVVLLLR   420
LAKTYETTLE KCCAAADPHE CYAKVFDEFK PLVEEPQNLI KQNCELFEQL GEYKFQNALL   480
VRYTKKVPQV STPTLVEVSR NLGKVGSKCC KHPEAKRMPC AEDYLSVVLN QLCVLHEKTP   540
VSDRVTKCCT ESLVNRRPCF SALEVDETYV PKEFNAETFT FHADICTLSE KERQIKKQTA   600
LVELVKHKPK ATKEQLKAVM DDFAAFVEKC CKADDKETCF AEEGKKLVAA SQAALGLGSG   660
GGGSGGGGSG GGGSGGGGSG GGGSGGGGSD HCPLGPGRCC RLHTVRASLE   720
DLGWADWVLS PREVQVTMCI GACPSQFRAA NMHAQIKTSL HRLKPDTVPA PCCVPASYNP   780
MVLIQKTDTG VSLQTYDDLL AKDCHCI                                      807

SEQ ID NO: 63          moltype = AA   length = 780
FEATURE                Location/Qualifiers
REGION                 1..780
                       note = GLP1-GDF15 Fusion Protein 31
source                 1..780
                       mol_type = protein
                       organism = synthetic construct
SEQUENCE: 63
HGEGTFTSDV SSYLEEQAAK EFIAWLVKGG GGGGSGGGGS GGGGSDAHKS EVAHRFKDLG    60
EENFKALVLI AFAQYLQQSP FEDHVKLVNE VTEFAKTCVA DESAENCDKS LHTLFGDKLC   120
TVATLRETYG EMADCCAKQE PERNECFLQH KDDNPNLPRL VRPEVDVMCT AFHDNEETFL   180
KKYLYEIARR HPYFYAPELL FFAKRYKAAF TECCQAADKA ACLLPKLDEL RDEGKASSAK   240
QRLKCASLQK FGERAFKAWA VARLSQRFPK AEFAEVSKLV TDLTKVHTEC CHGDLLECAD   300
DRADLAKYIC ENQDSISSKL KECCEKPLLE KSHCIAEVEN DEMPADLPSL AADFVESKDV   360
CKNYAEAKDV FLGMFLYEYA RRHPDYSVVL LLRLAKTYET TLEKCCAAAD PHECYAKVFD   420
EFKPLVEEPQ NLIKQNCELF EQLGEYKFQN ALLVRYTKKV PQVSTPTLVE VSRNLGKVGS   480
KCCKHPEAKR MPCAEDYLSV VLNQLCVLHE KTPVSDRVTK CCTESLVNRR PCFSALEVDE   540
TYVPKEFNAE TFTFHADICT LSEKERQIKK QTALVELVKH KPKATKEQLK AVMDDFAAFV   600
EKCCKADDKE TCFAEEGKKL VAASQAALGL GSGGGGSGGG GSGGGGSGGG GSGGGGSGGG   660
```

```
GSGGGGSGGG GSDHCPLGPG RCCRLHTVRA SLEDLGWADW VLSPREVQVT MCIGACPSQF    720
RAANMHAQIK TSLHRLKPDT VPAPCCVPAS YNPMVLIQKT DTGVSLQTYD DLLAKDCHCI    780

SEQ ID NO: 64           moltype = AA  length = 789
FEATURE                 Location/Qualifiers
REGION                  1..789
                        note = GLP1-GDF15 Fusion Protein 32
source                  1..789
                        mol_type = protein
                        organism = synthetic construct
SEQUENCE: 64
HGEGTFTSDL SKQMEEEAVR LFIEWLKNGG PSSGAPPPSG GGGSGGGGSG GGGSDAHKSE     60
VAHRFKDLGE ENFKALVLIA FAQYLQQSPF EDHVKLVNEV TEFAKTCVAD ESAENCDKSL    120
HTLFGDKLCT VATLRETYGE MADCCAKQEP ERNECFLQHK DDNPNLPRLV RPEVDVMCTA    180
FHDNEETFLK KYLYEIARRH PYFYAPELLF FAKRYKAAFT ECCQAADKAA CLLPKLDELR    240
DEGKASSAKQ RLKCASLQKF GERAFKAWAV ARLSQRFPKA EFAEVSKLVT DLTKVHTECC    300
HGDLLECADD RADLAKYICE NQDSISSKLK ECCEKPLLEK SHCIAEVEND EMPADLPSLA    360
ADFVESKDVC KNYAEAKDVF LGMFLYEYAR RHPDYSVVLL LRLAKTYETT LEKCCAAADP    420
HECYAKVFDE FKPLVEEPQN LIKQNCELFE QLGEYKFQNA LLVRYTKKVP QVSTPTLVEV    480
SRNLGKVGSK CCKHPEAKRM PCAEDYLSVV LNQLCVLHEK TPVSDRVTKC CTESLVNRRP    540
CFSALEVDET YVPKEFNAET FTFHADICTL SEKERQIKKQ TALVELVKHK PKATKEQLKA    600
VMDDFAAFVE KCCKADDKET CFAEEGKKLV AASQAALGLG SGGGGSGGGG SGGGGSGGGG    660
SGGGGSGGGG SGGGGSGGGG SDHCPLGPGR CCRLHTVRAS LEDLGWADWV LSPREVQVTM    720
CIGACPSQFR AANMHAQIKT SLHRLKPDTV PAPCCVPASY NPMVLIQKTD TGVSLQTYDD    780
LLAKDCHCI                                                           789

SEQ ID NO: 65           moltype = AA  length = 777
FEATURE                 Location/Qualifiers
REGION                  1..777
                        note = GLP1-GDF15 Fusion Protein 33
source                  1..777
                        mol_type = protein
                        organism = synthetic construct
SEQUENCE: 65
HSEGTFTSDV SSYLEGQAAK EFIEWLVKGR ASGGGGSGGG GSDAHKSEVA HRFKDLGEEN     60
FKALVLIAFA QYLQQSPFED HVKLVNEVTE FAKTCVADES AENCDKSLHT LFGDKLCTVA    120
TLRETYGEMA DCCAKQEPER NECFLQHKDD NPNLPRLVRP EVDVMCTAFH DNEETFLKKY    180
LYEIARRHPY FYAPELLFFA KRYKAAFTEC CQAADKAACL LPKLDELRDE GKASSAKQRL    240
KCASLQKFGE RAFKAWAVAR LSQRFPKAEF AEVSKLVTDL TKVHTECCHG DLLECADDRA    300
DLAKYICENQ DSISSKLKEC CEKPLLEKSH CIAEVENDEM PADLPSLAAD FVESKDVCKN    360
YAEAKDVFLG MFLYEYARRH PDYSVVLLLR LAKTYETTLE KCCAAADPHE CYAKVFDEFK    420
PLVEEPQNLI KQNCELFEQL GEYKFQNALL VRYTKKVPQV STPTLVEVSR NLGKVGSKCC    480
KHPEAKRMPC AEDYLSVVLN QLCVLHEKTP VSDRVTKCCT ESLVNRRPCF SALEVDETYV    540
PKEFNAETFT FHADICTLSE KERQIKKQTA LVELVKHKPK ATKEQLKAVM DDFAAFVEKC    600
CKADDKETCF AEEGKKLVAA SQAALGLGSG GGGSGGGGSG GGGSGGGGSG GGGSGGGGSG    660
GGGSGGGGSD HCPLGPGRCC RLHTVRASLE DLGWADWVLS PREVQVTMCI GACPSQFRAA    720
NMHAQIKTSL HRLKPDTVPA PCCVPASYNP MVLIQKTDTG VSLQTYDDLL AKDCHCI      777

SEQ ID NO: 66           moltype = AA  length = 779
FEATURE                 Location/Qualifiers
REGION                  1..779
                        note = GLP1-GDF15 Fusion Protein 34
source                  1..779
                        mol_type = protein
                        organism = synthetic construct
SEQUENCE: 66
HSEGTFTSDV SSYLEGQAAK EFIEWLVKGR ASAPAPAPAP APGSDAHKSE VAHRFKDLGE     60
ENFKALVLIA FAQYLQQSPF EDHVKLVNEV TEFAKTCVAD ESAENCDKSL HTLFGDKLCT    120
VATLRETYGE MADCCAKQEP ERNECFLQHK DDNPNLPRLV RPEVDVMCTA FHDNEETFLK    180
KYLYEIARRH PYFYAPELLF FAKRYKAAFT ECCQAADKAA CLLPKLDELR DEGKASSAKQ    240
RLKCASLQKF GERAFKAWAV ARLSQRFPKA EFAEVSKLVT DLTKVHTECC HGDLLECADD    300
RADLAKYICE NQDSISSKLK ECCEKPLLEK SHCIAEVEND EMPADLPSLA ADFVESKDVC    360
KNYAEAKDVF LGMFLYEYAR RHPDYSVVLL LRLAKTYETT LEKCCAAADP HECYAKVFDE    420
FKPLVEEPQN LIKQNCELFE QLGEYKFQNA LLVRYTKKVP QVSTPTLVEV SRNLGKVGSK    480
CCKHPEAKRM PCAEDYLSVV LNQLCVLHEK TPVSDRVTKC CTESLVNRRP CFSALEVDET    540
YVPKEFNAET FTFHADICTL SEKERQIKKQ TALVELVKHK PKATKEQLKA VMDDFAAFVE    600
KCCKADDKET CFAEEGKKLV AASQAALGLG SGGGGSGGGG SGGGGSGGGG SGGGGSGGGG    660
SGGGGSGGGG SDHCPLGPGR CCRLHTVRAS LEDLGWADWV LSPREVQVTM CIGACPSQFR    720
AANMHAQIKT SLHRLKPDTV PAPCCVPASY NPMVLIQKTD TGVSLQTYDD LLAKDCHCI    779

SEQ ID NO: 67           moltype = AA  length = 786
FEATURE                 Location/Qualifiers
REGION                  1..786
                        note = GLP1-GDF15 Fusion Protein 35
source                  1..786
                        mol_type = protein
                        organism = synthetic construct
SEQUENCE: 67
HGEGTFTSDL SKQMEEEAVR LFIEWLKNGG PSSGAPPPSA SGGGGSGGGG SDAHKSEVAH     60
```

```
RFKDLGEENF KALVLIAFAQ YLQQSPFEDH VKLVNEVTEF AKTCVADESA ENCDKSLHTL   120
FGDKLCTVAT LRETYGEMAD CCAKQEPERN ECFLQHKDDN PNLPRLVRPE VDVMCTAFHD   180
NEETFLKKYL YEIARRHPYF YAPELLFFAK RYKAAFTECC QAADKAACLL PKLDELRDEG   240
KASSAKQRLK CASLQKFGER AFKAWAVARL SQRFPKAEFA EVSKLVTDLT KVHTECCHGD   300
LLECADDRAD LAKYICENQD SISSKLKECC EKPLLEKSHC IAEVENDEMP ADLPSLAADF   360
VESKDVCKNY AEAKDVFLGM FLYEYARRHP DYSVVLLLRL AKTYETTLEK CCAAADPHEC   420
YAKVFDEFKP LVEEPQNLIK QNCELFEQLG EYKFQNALLV RYTKKVPQVS TPTLVEVSRN   480
LGKVGSKCCK HPEAKRMPCA EDYLSVVLNQ LCVLHEKTPV SDRVTKCCTE SLVNRRPCFS   540
ALEVDETYVP KEFNAETFTF HADICTLSEK ERQIKKQTAL VELVKHKPKA TKEQLKAVMD   600
DFAAFVEKCC KADDDKETCFA EEGKKLVAAS QAALGLGSGG GGSGGGGSGG GGSGGGGSGG   660
GGSGGGGSGG GGSGGGGSDH CPLGPGRCCR LHTVRASLED LGWADVVLSP REVQVTMCIG   720
ACPSQFRAAN MHAQIKTSLH RLKPDTVPAP CCVPASYNPM VLIQKTDTGV SLQTYDDLLA   780
KDCHCI                                                              786

SEQ ID NO: 68           moltype = AA  length = 788
FEATURE                 Location/Qualifiers
REGION                  1..788
                        note = GLP1-GDF15 Fusion Protein 36
source                  1..788
                        mol_type = protein
                        organism = synthetic construct
SEQUENCE: 68
HGEGTFTSDL SKQMEEEAVR LFIEWLKNGG PSSGAPPPSA SAPAPAPAPA PGSDAHKSEV    60
AHRFKDLGEE NFKALVLIAF AQYLQQSPFE DHVKLVNEVT EFAKTCVADE SAENCDKSLH   120
TLFGDKLCTV ATLRETYGEM ADCCAKQEPE RNECFLQHKD DNPNLPRLVR PEVDVMCTAF   180
HDNEETFLKK YLYEIARRHP YFYAPELLFF AKRYKAAFTE CCQAADKAAC LLPKLDELRD   240
EGKASSAKQR LKCASLQKFG ERAFKAWAVA RLSQRFPKAE FAEVSKLVTD LTKVHTECCH   300
GDLLECADDR ADLAKYICEN QDSISSKLKE CCEKPLLEKS HCIAEVENDE MPADLPSLAA   360
DFVESKDVCK NYAEAKDVFL GMFLYEYARR HPDYSVVLLL RLAKTYETTL EKCCAAADPH   420
ECYAKVFDEF KPLVEEPQNL IKQNCELFEQ LGEYKFQNAL LVRYTKKVPQ VSTPTLVEVS   480
RNLGKVGSKC CKHPEAKRMP CAEDYLSVVL NQLCVLHEKT PVSDRVTKCC TESLVNRRPC   540
FSALEVDETY VPKEFNAETF TFHADICTLS EKERQIKKQT ALVELVKHKP KATKEQLKAV   600
MDDFAAFVEK CCKADDKETC FAEEGKKLVA ASQAALGLGS GGGGSGGGGS GGGGSGGGGS   660
GGGGSGGGGS GGGGSGGGGS DHCPLGPGRC CRLHTVRASL EDLGWADVVL SPREVQVTMC   720
IGACPSQFRA ANMHAQIKTS LHRLKPDTVP APCCVPASYN PMVLIQKTDT GVSLQTYDDL   780
LAKDCHCI                                                            788

SEQ ID NO: 69           moltype = AA  length = 777
FEATURE                 Location/Qualifiers
REGION                  1..777
                        note = GLP1-GDF15 Fusion Protein 37
source                  1..777
                        mol_type = protein
                        organism = synthetic construct
SEQUENCE: 69
HGEGTFTSDV SSYLEEQAAK EFIAWLVKGG ASGGGGSGGG GSDAHKSEVA HRFKDLGEEN    60
FKALVLIAFA QYLQQSPFED HVKLVNEVTE FAKTCVADES AENCDKSLHT LFGDKLCTVA   120
TLRETYGEMA DCCAKQEPER NECFLQHKDD NPNLPRLVRP EVDVMCTAFH DNEETFLKKY   180
LYEIARRHPY FYAPELLFFA KRYKAAFTEC CQAADKAACL LPKLDELRDE GKASSAKQRL   240
KCASLQKFGE RAFKAWAVAR LSQRFPKAEF AEVSKLVTDL TKVHTECCHG DLLECADDRA   300
DLAKYICENQ DSISSKLKEC CEKPLLEKSH CIAEVENDEM PADLPSLAAD FVESKDVCKN   360
YAEAKDVFLG MFLYEYARRH PDYSVVLLLR LAKTYETTLE KCCAAADPHE CYAKVFDEFK   420
PLVEEPQNLI KQNCELFEQL GEYKFQNALL VRYTKKVPQV STPTLVEVSR NLGKVGSKCC   480
KHPEAKRMPC AEDYLSVVLN QLCVLHEKTP VSDRVTKCCT ESLVNRRPCF SALEVDETYV   540
PKEFNAETFT FHADICTLSE KERQIKKQTA LVELVKHKPK ATKEQLKAVM DDFAAFVEKC   600
CKADDKETCF AEEGKKLVAA SQAALGLGSG GGGSGGGGSG GGGSGGGGSG GGGSGGGGSG   660
GGGSGGGGSD HCPLGPGRCC RLHTVRASLE DLGWADVVLS PREVQVTMCI GACPSQFRAA   720
NMHAQIKTSL HRLKPDTVPA PCCVPASYNP MVLIQKTDTG VSLQTYDDLL AKDCHCI      777

SEQ ID NO: 70           moltype = AA  length = 779
FEATURE                 Location/Qualifiers
REGION                  1..779
                        note = GLP1-GDF15 Fusion Protein 38
source                  1..779
                        mol_type = protein
                        organism = synthetic construct
SEQUENCE: 70
HGEGTFTSDV SSYLEEQAAK EFIAWLVKGG ASAPAPAPAP APGSDAHKSE VAHRFKDLGE    60
ENFKALVLIA FAQYLQQSPF EDHVKLVNEV TEFAKTCVAD ESAENCDKSL HTLFGDKLCT   120
VATLRETYGE MADCCAKQEP ERNECFLQHK DDNPNLPRLV RPEVDVMCTA FHDNEETFLK   180
KYLYEIARRH PYFYAPELLF FAKRYKAAFT ECCQAADKAA CLLPKLDELR DEGKASSAKQ   240
RLKCASLQKF GERAFKAWAV ARLSQRFPKA EFAEVSKLVT DLTKVHTECC HGDLLECADD   300
RADLAKYICE NQDSISSKLK ECCEKPLLEK SHCIAEVEND EMPADLPSLA ADFVESKDVC   360
KNYAEAKDVF LGMFLYEYAR RHPDYSVVLL LRLAKTYETT LEKCCAAADP HECYAKVFDE   420
FKPLVEEPQN LIKQNCELFE QLGEYKFQNA LLVRYTKKVP QVSTPTLVEV SRNLGKVGSK   480
CCKHPEAKRM PCAEDYLSVV LNQLCVLHEK TPVSDRVTKC CTESLVNRRP CFSALEVDET   540
YVPKEFNAET FTFHADICTL SEKERQIKKQ TALVELVKHK PKATKEQLKA VMDDFAAFVE   600
KCCKADDKET CFAEEGKKLV AASQAALGLG SGGGGSGGGG SGGGGSGGGG SGGGGSGGGG   660
SGGGGSGGGG SDHCPLGPGR CCRLHTVRAS LEDLGWADVV LSPREVQVTM CIGACPSQFR   720
```

```
AANMHAQIKT SLHRLKPDTV PAPCCVPASY NPMVLIQKTD TGVSLQTYDD LLAKDCHCI   779

SEQ ID NO: 71           moltype = AA  length = 780
FEATURE                 Location/Qualifiers
REGION                  1..780
                        note = GLP1-GDF15 Fusion Protein 39
source                  1..780
                        mol_type = protein
                        organism = synthetic construct
SEQUENCE: 71
HSEGTFTSDV SSYLEGQAAK EFIEWLVKGR GGGGSGGGGS GGGGSDAHKS EVAHRFKDLG   60
EENFKALVLI AFAQYLQQSP FEDHVKLVNE VTEFAKTCVA DESAENCDKS LHTLFGDKLC  120
TVATLRETYG EMADCCAKQE PERNECFLQH KDDNPNLPRL VRPEVDVMCT AFHDNEETFL  180
KKYLYEIARR HPYFYAPELL FFAKRYKAAF TECCQAADKA ACLLPKLDEL RDEGKASSAK  240
QRLKCASLQK FGERAFKAWA VARLSQRFPK AEFAEVSKLV TDLTKVHTEC CHGDLLECAD  300
DRADLAKYIC ENQDSISSKL KECCEKPLLE KSHCIAEVEN DEMPADLPSL AADFVESKDV  360
CKNYAEAKDV FLGMFLYEYA RRHPDYSVVL LLRLAKTYET TLEKCCAAAD PHECYAKVFD  420
EFKPLVEEPQ NLIKQNCELF EQLGEYKFQN ALLVRYTKKV PQVSTPTLVE VSRNLGKVGS  480
KCCKHPEAKR MPCAEDYLSV VLNQLCVLHE KTPVSDRVTK CCTESLVNRR PCFSALEVDE  540
TYVPKEFNAE TFTFHADICT LSEKERQIKK QTALVELVKH KPKATKEQLK AVMDDFAAFV  600
EKCCFAEEGKKL TCFAEEGKKL VAASQAALGL GSGGGGSGGG GSGGGGSGGG GSGGGGSGGG  660
GSGGGGSGGG GSDHCPLGPG RCCRLHTVRA SLEDLGWADW VLSPREVQVT MCIGACPSQF  720
RAANMHAQIK TSLHRLKPDT VPAPCCVPAS YNPMVLIQKT DTGVSLQTYD DLLAKDCHCI  780

SEQ ID NO: 72           moltype = AA  length = 780
FEATURE                 Location/Qualifiers
REGION                  1..780
                        note = GLP1-GDF15 Fusion Protein 40
source                  1..780
                        mol_type = protein
                        organism = synthetic construct
SEQUENCE: 72
HGEGTFTSDV SSYLEEQAAK EFIAWLVKGG GGGGSGGGGS GGGGSDAHKS EVAHRFKDLG   60
EETFKALVLV AFAQYLQQSP FEDHVKLVNE VTEFAKTCVA DESAENCDKS LHTLFGDKLC  120
TVATLRETYG EMADCCAKQE PERNECFLQH KDDNPNLPRL VRPEVDVMCT AFHDNEETFL  180
KKYLYEIARR HPYFYAPELL FFAARYKAAF TECCQAADKA ACLLPKLDEL RDEGKASSAK  240
QRLKCASLQK FGERAFKAWA VARLSQRFPK AEFAEVSKLV TDLTKVHTEC CHGDLLECAD  300
DRADLAKYIC ENQDSISSKL KECCEKPLLE KSHCLAEVEN DEMPADLPSL AADFVESKDV  360
CKNYAEAKDV FLGMFLYEYA RRHPDYSVVL LLRLAKTYET TLEKCCAAAD PHECYAKVFD  420
EFKPLVEEPQ NLIKQNCELF EQLGEYKFQN ALLVRYTKKV PQVSTPTLVE VSRNLGKVGS  480
KCCKHPEAKR MPCAEDYLSV VLNQLCVLHE KTPVSDRVTK CCTESLVNRR PCFSALEVDE  540
TYVPKEFNAE TFTFHADICT LSEKERQIKK QTALAELVKH KPKATKEQLK TVMDDFAAFV  600
EKCCKADDKE TCFAEEGKKL VAASQAALGL GSGGGGSGGG GSGGGGSGGG GSGGGGSGGG  660
GSGGGGSGGG GSDHCPLGPG RCCRLHTVRA SLEDLGWADW VLSPREVQVT MCIGACPSQF  720
RAANMHAQIK TSLHRLKPDT VPAPCCVPAS YNPMVLIQKT DTGVSLQTYD DLLAKDCHCI  780

SEQ ID NO: 73           moltype = AA  length = 780
FEATURE                 Location/Qualifiers
REGION                  1..780
                        note = GLP1-GDF15 Fusion Protein 41
source                  1..780
                        mol_type = protein
                        organism = synthetic construct
SEQUENCE: 73
HGEGTFTSDV SSYLEEQAAK EFIAWLVKGG GGGGSGGGGS GGGGSDAHKS EVAHRFKDLG   60
EETFKALVLV AFAQYLQQSP FEDHVKLVNE VTEFAKTCVA DESAENCDKS LHTLFGDKLC  120
TVATLRETYG EMADCCAKQE PERNECFLQH KDDNPNLPRL VRPEVDVMCT AFHDNEETFL  180
KKYLYEIARR HPYFYAPELL FFAARYKAAF TECCQAADKA ACLLPKLDEL RDEGKASSAK  240
QRLKCASLQK FGERAFKAWA VARLSQRFPK AEFAEVSKLV TDLTKVHTEC CHGDLLECAD  300
DRADLAKYIC ENQDSISSKL KECCEKPLLE KSHCLAEVEN DEMPADLPSL AADFVESKDV  360
CKNYAEAKDV FLGMFLYEYA RRHPDYSVVL LLRLAKTYET TLEKCCAAAD PHECYAKVFD  420
EFKPLVEEPQ NLIKQNCELF EQLGEYKFQN ALLVRYTKKV PQVSTPTLVE VSRNLGKVGS  480
KCCKHPEAKR MPCAEDYLSV VLNQLCVLHE KTPVSDRVTK CCTESLVNRR PCFSALEVDE  540
TYVPKEFNAE TFTFHADICT LSEKERQIKK QTALAELVKH KPKATKEQLK TVMDDFAAFV  600
EKCCKADDKE TCFAEEGKKL VAASQAALGL GSGGGGSGGG GSGGGGSGGG GSGGGGSGGG  660
GSGGGGSGGG GSDHCPLGPG RCCRLHTVRA SLEDLGWADW VLSPREVQVT MCIGACPSQF  720
RAANMHAQIK TSLHRLKPDT VPAPCCVPAS YNPMVLRQKT DTGVSLQTYD DLLAKDCHCI  780

SEQ ID NO: 74           moltype = AA  length = 778
FEATURE                 Location/Qualifiers
REGION                  1..778
                        note = GLP1-GDF15 Fusion Protein 42
source                  1..778
                        mol_type = protein
                        organism = synthetic construct
SEQUENCE: 74
EGTFTSDVSS YLEEQAAKEF IAWLVKGGGG GGSGGGGSGG GGSDAHKSEV AHRFKDLGEE   60
TFKALVLVAF AQYLQQSPFE DHVKLVNEVT EFAKTCVADE SAENCDKSLH TLFGDKLCTV  120
ATLRETYGEM ADCCAKQEPE RNECFLQHKD DNPNLPRLVR PEVDVMCTAF HDNEETFLKK  180
```

```
YLYEIARRHP YFYAPELLFF AARYKAAFTE CCQAADKAAC LLPKLDELRD EGKASSAKQR   240
LKCASLQKFG ERAFKAWAVA RLSQRFPKAE FAEVSKLVTD LTKVHTECCH GDLLECADDR   300
ADLAKYICEN QDSISSKLKE CCEKPLLEKS HCLAEVENDE MPADLPSLAA DFVESKDVCK   360
NYAEAKDVFL GMFLYEYARR HPDYSVVLLL RLAKTYETTL EKCCAAADPH ECYAKVFDEF   420
KPLVEEPQNL IKQNCELFEQ LGEYKFQNAL LVRYTKKVPQ VSTPTLVEVS RNLGKVGSKC   480
CKHPEAKRMP CAEDYLSVVL NQLCVLHEKT PVSDRVTKCC TESLVNRRPC FSALEVDETY   540
VPKEFNAETF TFHADICTLS EKERQIKKQT ALAELVKHKP KATKEQLKTV MDDFAAFVEK   600
CCKADDKETC FAEEGKKLVA ASQAALGLGS GGGGSGGGGS GGGGSGGGGS GGGGSGGGGS   660
GGGGSGGGGS DHCPLGPGRC CRLHTVRASL EDLGWADWVL SPREVQVTMC IGACPSQFRA   720
ANMHAQIKTS LHRLKPDTVP APCCVPASYN PMVLIQKTDT GVSLQTYDDL LAKDCHCI    778

SEQ ID NO: 75            moltype = AA   length = 735
FEATURE                  Location/Qualifiers
REGION                   1..735
                         note = GSA-GDF15 fusion protein
source                   1..735
                         mol_type = protein
                         organism = synthetic construct
SEQUENCE: 75
DAHKSEVAHR FKDLGEETFK ALVLVAFAQY LQQSPFEDHV KLVNEVTEFA KTCVADESAE    60
NCDKSLHTLF GDKLCTVATL RETYGEMADC CAKQEPERNE CFLQHKDDNP NLPRLVRPEV   120
DVMCTAFHDN EETFLKKYLY EIARRHPYFY APELLFFAAR YKAAFTECCQ AADKAACLLP   180
KLDELRDEGK ASSAKQRLKC ASLQKFGERA FKAWAVARLS QRFPKAEFAE VSKLVTDLTK   240
VHTECCHGDL LECADDRADL AKYICENQDS ISSKLKECCE KPLLEKSHCL AEVENDEMPA   300
DLPSLAADFV ESKDVCKNYA EAKDVFLGMF LYEYARRHPD YSVVLLLRLA KTYETTLEKC   360
CAAADPHECY AKVFDEFKPL VEEPQNLIKQ NCELFEQLGE YKFQNALLVR YTKKVPQVST   420
PTLVEVSRNL GKVGSKCCKH PEAKRMPCAE DYLSVVLNQL CVLHEKTPVS DRVTKCCTES   480
LVNRRPCFSA LEVDETYVPK EFNAETFTFH ADICTLSEKE RQIKKQTALA ELVKHKPKAT   540
KEQLKTVMDD FAAFVEKCCK ADDKETCFAE EGKKLVAASQ AALGLGSGGG GSGGGGSGGG   600
GSGGGGSGGG GSGGGGSGGG GSGGGGSDHC PLGPGRCCRL HTVRASLEDL GWADWVLSPR   660
EVQVTMCIGA CPSQFRAANM HAQIKTSLHR LKPDTVPAPC CVPASYNPMV LIQKTDTGVS   720
LQTYDDLLAK DCHCI                                                   735

SEQ ID NO: 76            moltype = AA   length = 20
FEATURE                  Location/Qualifiers
REGION                   1..20
                         note = HSE peptide
source                   1..20
                         mol_type = protein
                         organism = synthetic construct
SEQUENCE: 76
HSEGTFTSDV SSYLEGQAAK                                                20

SEQ ID NO: 77            moltype = AA   length = 20
FEATURE                  Location/Qualifiers
REGION                   1..20
                         note = HGE-1 peptide
source                   1..20
                         mol_type = protein
                         organism = synthetic construct
SEQUENCE: 77
HGEGTFTSDV SSYLEEQAAK                                                20

SEQ ID NO: 78            moltype = AA   length = 12
FEATURE                  Location/Qualifiers
REGION                   1..12
                         note = HGE-2 peptide
source                   1..12
                         mol_type = protein
                         organism = synthetic construct
SEQUENCE: 78
HGEGTFTSDL SK                                                        12

SEQ ID NO: 79            moltype = AA   length = 21
FEATURE                  Location/Qualifiers
REGION                   1..21
                         note = ALV peptide
source                   1..21
                         mol_type = protein
                         organism = synthetic construct
SEQUENCE: 79
ALVLIAFAQY LQQSPFEDHV K                                              21

SEQ ID NO: 80            moltype = AA   length = 16
FEATURE                  Location/Qualifiers
REGION                   1..16
                         note = TDT peptide
source                   1..16
                         mol_type = protein
```

```
                         organism = synthetic construct
SEQUENCE: 80
TDTGVSLQTY DDLLAK                                                    16

SEQ ID NO: 81            moltype = AA   length = 727
FEATURE                  Location/Qualifiers
REGION                   1..727
                         note = HSA-GDF15 fusion protein
source                   1..727
                         mol_type = protein
                         organism = synthetic construct
SEQUENCE: 81
EPHHHHHHDA HKSEVAHRFK DLGEENFKAL VLIAFAQYLQ QSPFEDHVKL VNEVTEFAKT    60
CVADESAENC DKSLHTLFGD KLCTVATLRE TYGEMADCCA KQEPERNECF LQHKDDNPNL   120
PRLVRPEVDV MCTAFHDNEE TFLKKYLYEI ARRHPYFYAP ELLFFAKRYK AAFTECCQAA   180
DKAACLLPKL DELRDEGKAS SAKQRLKCAS LQKFGERAFK AWAVARLSQR FPKAEFAEVS   240
KLVTDLTKVH TECCHGDLLE CADDRADLAK YICENQDSIS SKLKECCEKP LLEKSHCIAE   300
VENDEMPADL PSLAADFVES KDVCKNYAEA KDVFLGMFLY EYARRHPDYS VVLLLRLAKT   360
YETTLEKCCA AADPHECYAK VFDEFKPLVE EPQNLIKQNC ELFEQLGEYK FQNALLVRYT   420
KKVPQVSTPT LVEVSRNLGK VGSKCCKHPE AKRMPCAEDY LSVVLNQLCV LHEKTPVSDR   480
VTKCCTESLV NRRPCFSALE VDETYVPKEF NAETFTFHAD ICTLSEKERQ IKKQTALVEL   540
VKHKPKATKE QLKAVMDDFA AFVEKCCKAD DKETCFAEEG KKLVAASQAA LGLGSGGGGS   600
GGGGSGGGGS GGGGSARNGD HCPLGPGRCC RLHTVRASLE DLGWADWVLS PREVQVTMCI   660
GACPSQFRAA NMHAQIKTSL HRLKPDTVPA PCCVPASYNP MVLIQKTDTG VSLQTYDDLL   720
AKDCHCI                                                            727

SEQ ID NO: 82            moltype = AA   length = 16
FEATURE                  Location/Qualifiers
REGION                   1..16
                         note = VVS peptide
source                   1..16
                         mol_type = protein
                         organism = synthetic construct
SEQUENCE: 82
VVSVLTVLHQ DWLNGK                                                    16

SEQ ID NO: 83            moltype = AA   length = 713
FEATURE                  Location/Qualifiers
REGION                   1..713
                         note = HSA-GDF15 fusion peptide
source                   1..713
                         mol_type = protein
                         organism = synthetic construct
SEQUENCE: 83
DAHKSEVAHR FKDLGEENFK ALVLIAFAQY LQQSPFEDHV KLVNEVTEFA KTCVADESAE    60
NCDKSLHTLF GDKLCTVATL RETYGEMADC CAKQEPERNE CFLQHKDDNP NLPRLVRPEV   120
DVMCTAFHDN EETFLKKYLY EIARRHPYFY APELLFFAKR YKAAFTECCQ AADKAACLLP   180
KLDELRDEGK ASSAKQRLKC ASLQKFGERA FKAWAVARLS QRFPKAEFAE VSKLVTDLTK   240
VHTECCHGDL LECADDRADL AKYICENQDS ISSKLKECCE KPLLEKSHCI AEVENDEMPA   300
DLPSLAADFV ESKDVCKNYA EAKDVFLGMF LYEYARRHPD YSVVLLLRLA KTYETTLEKC   360
CAAADPHECY AKVFDEFKPL VEEPQNLIKQ NCELFEQLGE YKFQNALLVR YTKKVPQVST   420
PTLVEVSRNL GKVGSKCCKH PEAKRMPCAE DYLSVVLNQL CVLHEKTPVS DRVTKCCTES   480
LVNRRPCFSA LEVDETYVPK EFNAETFTFH ADICTLSEKE RQIKKQTALV ELVKHKPKAT   540
KEQLKAVMDD FAAFVEKCCK ADDKETCFAE EGKKLVAASQ AALGLAPAPA PAPAPAPAPA   600
PAPAPDHCPL GPGRCCRLHT VRASLEDLGW ADWVLSPREV QVTMCIGACP SQFRAANMHA   660
QIKTSLHRLK PDTVPAPCCV PASYNPMVLI QKTDTGVSLQ TYDDLLAKDC HCI          713

SEQ ID NO: 84            moltype = AA   length = 762
FEATURE                  Location/Qualifiers
REGION                   1..762
                         note = GLP1-GDF15 (I89R) fusion peptide
source                   1..762
                         mol_type = protein
                         organism = synthetic construct
SEQUENCE: 84
HGEGTFTSDL SKQMEEEAVR LFIEWLKNGG PSSGAPPPSA PAPAPAPAPD AHKSEVAHRF    60
KDLGEENFKA LVLIAFAQYL QQSPFEDHVK LVNEVTEFAK TCVADESAEN CDKSLHTLFG   120
DKLCTVATLR ETYGEMADCC AKQEPERNEC FLQHKDDNPN LPRLVRPEVD VMCTAFHDNE   180
ETFLKKYLYE IARRHPYFYA PELLFFAKRY KAAFTECCQA ADKAACLLPK LDELRDEGKA   240
SSAKQRLKCA SLQKFGERAF KAWAVARLSQ RFPKAEFAEV SKLVTDLTKV HTECCHGDLL   300
ECADDRADLA KYICENQDSI SSKLKECCEK PLLEKSHCIA EVENDEMPAD LPSLAADFVE   360
SKDVCKNYAE AKDVFLGMFL YEYARRHPDY SVVLLLRLAK TYETTLEKCC AAADPHECYA   420
KVFDEFKPLV EEPQNLIKQN CELFEQLGEY KFQNALLVRY TKKVPQVSTP TLVEVSRNLG   480
KVGSKCCKHP EAKRMPCAED YLSVVLNQLC VLHEKTPVSD RVTKCCTESL VNRRPCFSAL   540
EVDETYVPKE FNAETFTFHA DICTLSEKER QIKKQTALVE LVKHKPKATK EQLKAVMDDF   600
AAFVEKCCKA DDKETCFAEE GKKLVAASQA ALGLAPAPAP APAPAPAPAP APAPDHCPLG   660
PGRCCRLHTV RASLEDLGWA DWVLSPREVQ VTMCIGACPS QFRAANMHAQ IKTSLHRLKP   720
DTVPAPCCVP ASYNPMVLRQ KTDTGVSLQT YDDLLAKDCH CI                      762
```

GLUCAGON LIKE PEPTIDE 1 (GLP1)-GROWTH DIFFERENTIATION FACTOR 15 (GDF15) FUSION PROTEINS AND USES THEREOF

FIELD OF THE INVENTION

The present invention is directed generally to novel glucagon like peptide-1 (GLP1)-growth differentiation factor 15 (GDF15) fusion proteins. The GLP1-GDF15 fusion proteins modulate the GLP1R and/or the GDF15R. The invention also relates to pharmaceutical compositions and methods for use thereof. The novel GLP1-GDF15 fusion proteins are useful for preventing, treating or ameliorating diseases and disorders, such as obesity, type 2 diabetes, the metabolic syndrome, insulin resistance, and dyslipidemia, among others.

CROSS REFERENCE TO RELATED APPLICATIONS

This application is a Divisional application of U.S. patent application Ser. No. 17/309,114, filed Apr. 26, 2021, which is a Section 371 of International Application No. PCT/IB2019/059029, filed on Oct. 22, 2019, which was published in the English language on Apr. 30, 2020, under International Publication No. WO 2020/084496 A1, which claims priority to U.S. Provisional Application No. 62/748,603, filed Oct. 22, 2018. Each disclosure is incorporated herein by reference in its entirety.

REFERENCE TO AN ELECTRONIC SEQUENCE LISTING

The contents of the electronic sequence listing (200310_405D1_SeqListing.xml; Size: 141 kilobytes; and Date of Creation: Jun. 9, 2023) is herein incorporated by reference in its entirety.

BACKGROUND OF THE INVENTION

GDF15, a member of the TGFβ family, is a secreted protein that circulates in plasma as a 25 kDa homodimer and elicits its biological function through interaction with the brainstem expressed receptor GFRAL (Mullican et al., Nat Med. 23:1150-7 (2017), Yang et al., Nat Med. 23:1158-66 (2017), Hsu et al., Nature 550:255-9 (2017), Emmerson et al., Nat Med 23:1215-9 (2017)). Plasma levels of GDF15 range between 150 and 1150 pg/ml in most individuals (Tsai et al., J Cachexia Sarcopenia Muscle 3:239-43 (2012)). Elevated plasma levels of GDF15 are associated with weight loss due to anorexia and cachexia in cancer, and in renal and heart failure. Furthermore, GDF15 is increased in patients experiencing weight loss after Roux-en-Y gastric bypass (RYGB) surgery (Vila et al., Clin Chem 57:309-16 (2011)).

The correlation between weight loss and GDF15 is conserved in rodents. Overexpression of GDF15 results in decreased food intake, lower body weight and protects mice from obesity, liver steatosis and glucose intolerance upon high fat diet feeding (Baek et al., Gastroenterology 131: 1553-60 (2006), Johnen et al., Nat Med 13:1333-40 (2007), Chrysovergis et al., Int J Obesity 38:1555-64 (2014), Macia et al., PloS One 7:e34868 (2012), Jones et al., Cell Reports 22:1522-30 (2018), Xiong et al., Sci Trans Med 9:412 (2017)). Xenografts of prostate tumor cells transfected with GDF15 also decrease food intake and body weight (Johnen et al., Nat Med 13:1333-40 (2007)). Conversely, numerous investigators have reported that mice lacking GDF15 gain more weight and have greater fat mass than wildtype animals (Strelau et al., J Neurosci 29:13640-8 (2009), Casanovas et al., Haematologica 98:444-7 (2013), Bonaterra et al., J Amer Heart Assoc 1:e002550 (2012), Tsai et al., PloS one. 8:e55174 (2013)).

The potential of pharmacologically administered GDF15 to decrease energy intake and thereby elicit weight loss has been demonstrated in mice, rats and monkeys. Lean mice treated with recombinant GDF15 eat less and lose weight (Johnen et al., Nat Med 13:1333-40 (2007), Hsu et al., Nature 550:255-9 (2017), Mullican et al., Nat Med 23:1150-7 (2017), Tsai et al., Int J Obesity 42:561-71 (2018)). Decreased food intake and body weight is also observed in genetic and diet induced rat and mouse models of obesity after administration of GDF15 (Johnen et al., Nat Med 13:1333-40 (2007), Hsu et al., Nature 550:255-9 (2017), Mullican et al., Nat Med 23:1150-7 (2017), Yang et al., Nat Med 23:1158-66 (2017), Tsai et al., Int J Obesity 42:561-71 (2018), Xiong et al., Sci Trans Med 9:412 (2017)). GDF15 treatment mediated weight loss in diet induced obese mice leads to metabolic improvements including enhanced glucose homeostasis and lower plasma triglycerides and cholesterol. These effects translate to higher species as a six-week daily treatment regimen with recombinant human GDF15 in spontaneously obese non-human primates reduced food intake, body weight, and plasma triglyceride concentrations and improved glucose tolerance (Xiong et al., Sci Trans Med 9:412 (2017)). Furthermore, the half-life of recombinant GDF15 was previously demonstrated to be extended by fusion to human serum albumin (HSA) and is predicted to be a therapeutic suitable for once-weekly dosing in human (Mullican et al., Nat Med 23:1150-7 (2017) and U.S. Patent Publication No. 2017/0327560.

GLP1 is a peptide hormone derived from the enteroendocrine cells of the gut that also reduces food intake leading to weight loss. This function is mediated by interaction with the GLP1 receptor (GLP1R) within the central nervous system and this ligand/receptor interaction in peripheral tissues has additional biological effects including enhancement of glucose stimulated insulin secretion, suppression of glucagon release and slowing of gastric emptying (Druker et al. Cell Met 27:740-56 (2018)). Harnessing all of these biological effects, GLP1R agonists improve glucose homeostasis and drive weight loss in humans. In addition, treatment with GLP1R agonists is reported to significantly improve cardiovascular outcomes in diabetic patients although the exact mechanism is yet to be determined (Lim et al. Trends Endocrinol Metab. 29:238-48 (2018)). GLP1R agonist therapeutics are peptide sequences based on either native human GLP1 or exendin-4 (a peptide isolated from the saliva of the Gila monster lizard) with modifications to prevent enzymatic cleavage. The GLP1R agonists can be delivered via platforms that extend half-life such as lipidation, antibody Fc or human serum albumin (HSA) (Cheang and Moyle, Chem Med Chem 13:662-71 (2018)).

Thus, it is desirable to obtain a GLP1 analogue or derivative thereof and/or a GDF15 analogue or derivative thereof with an improved metabolic stability and pharmacokinetic profile relative to GLP1 or GDF15, respectively. Such derivatives would provide GLP1 receptor and GDF15 receptor modulation with greater duration of action, making them suitable as therapeutic agents for subjects in need of such modulation.

The foregoing discussion is presented solely to provide a better understanding of the nature of the problems confronting the art and should not be construed in any way as an admission that such reference constitutes "prior art" to the instant application.

SUMMARY OF THE INVENTION

In one general aspect, the invention relates to novel glucagon-like peptide-1 (GLP1)-growth differentiation factor 15 (GDF15) fusion proteins. The GLP1-GDF15 fusion proteins modulate the GLP1R and/or the GDF15R (GFRAL).

Provided herein are glucagon-like peptide-1 (GLP1)-growth differentiation factor 15 (GDF15) fusion proteins. The GLP1-GDF15 fusion proteins comprise a GLP1 peptide, a first linker peptide, a serum albumin protein, a second linker peptide, and a GDF15 protein.

In certain embodiments, GLP1 peptide comprises an amino acid sequence selected from the group consisting of SEQ ID NOs:1-4.

In certain embodiments, the first linker peptide comprises an amino acid sequence selected from the group consisting of SEQ ID NOs:5-25.

In certain embodiments, the serum albumin protein comprises an amino acid sequence selected from SEQ ID NO:26 or SEQ ID NO:27.

In certain embodiments, the second linker peptide comprises an amino acid sequence selected from the group consisting of SEQ ID NOs:28-30.

In certain embodiments, the GDF15 protein comprises an amino acid sequence selected from SEQ ID NO:31 or SEQ ID NO:32.

In certain embodiments, the GLP1-GDF15 fusion protein comprises an amino acid sequence selected from the group consisting of SEQ ID NOs:33-74 and 84.

Also provided are isolated nucleic acids encoding the GLP1-GDF15 fusion proteins of the invention. Also provided are vectors comprising the isolated nucleic acids of the invention. Also provided are host cells comprising the isolated nucleic acids of the invention or the vectors of the invention.

Also provided are pharmaceutical compositions comprising the GLP1-GDF15 fusion proteins of the invention and a pharmaceutically acceptable carrier.

Also provided are methods for treating or preventing a disease or disorder in a subject in need thereof, wherein said disease or disorder is selected from the group consisting of obesity, type I or type II diabetes, metabolic syndrome, insulin resistance, impaired glucose tolerance, hyperglycemia, hyperinsulinemia, hypertriglyceridemia, hypoglycemia due to congenital hyperinsulinism (CHI), dyslipidemia, atherosclerosis, diabetic nephropathy, and other cardiovascular risk factors such as hypertension and cardiovascular risk factors related to unmanaged cholesterol and/or lipid levels, osteoporosis, inflammation, non-alcoholic fatty liver disease (NAFLD), non-alcoholic steatohepatitis (NASH), renal disease, and eczema, the method comprising administering to the subject in need thereof an effective amount of the pharmaceutical composition of the invention.

Also provided are methods of reducing food intake in a subject in need thereof, the method comprising administering to the subject in need thereof an effective amount of the pharmaceutical composition of the invention.

Also provided are methods of modulating GLP1 receptor activity in a subject in need thereof, the method comprising administering to the subject in need thereof an effective amount of the pharmaceutical composition of the invention.

Also provided are methods of modulating GDF15 receptor (GFRAL) activity in a subject in need thereof, the method comprising administering to the subject in need thereof an effective amount of the pharmaceutical composition of the invention.

In certain embodiments, the pharmaceutical composition is administered via an injection.

Also provided are kits comprising the GLP1-GDF15 fusion proteins of the invention, the isolated nucleic acids of the invention, and/or the vectors of the invention. The kit can, for example, further comprise a device for injection.

Also provided are methods of producing a pharmaceutical composition comprising the GLP1-GDF15 fusion proteins of the invention. The methods comprise combining the GLP1-GDF15 fusion proteins with a pharmaceutically acceptable carrier to obtain the pharmaceutical composition.

Also provided are methods of producing the GLP1-GDF15 fusion proteins of the invention. The methods comprise culturing a cell comprising a nucleic acid encoding the GLP1-GDF15 fusion protein under conditions to produce the GLP1-GDF15 fusion protein and recovering the GLP1-GDF15 fusion protein from the cell or culture.

BRIEF DESCRIPTION OF THE DRAWINGS

The foregoing summary, as well as the following detailed description of preferred embodiments of the present application, will be better understood when read in conjunction with the appended drawings. It should be understood, however, that the application is not limited to the precise embodiments shown in the drawings.

DETAILED DESCRIPTION OF THE INVENTION

Figure 1:
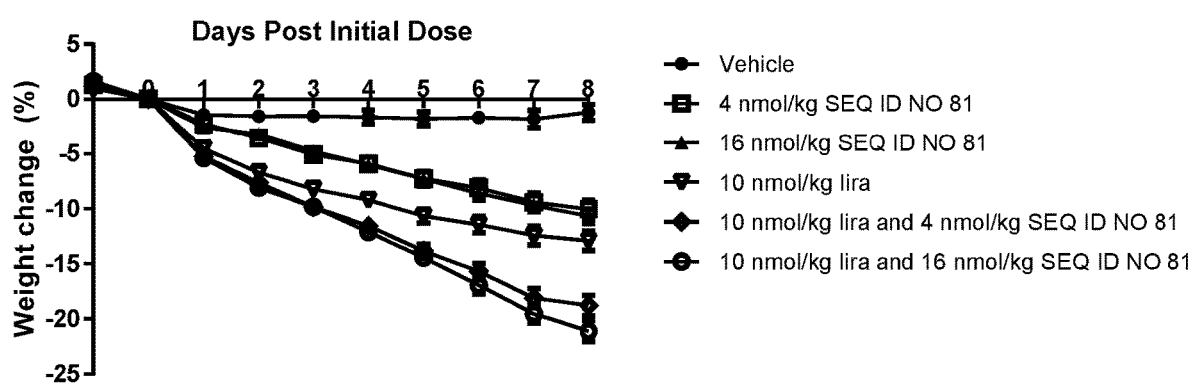
FIG. 1 shows a graph demonstrating percent weight change (from day 0) in DIO mice receiving daily administration of liraglutide (lira) and/or every other day administration of HSA-GDF15 (SEQ ID NO:81).

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification.

It must be noted that as used herein and in the appended claims, the singular forms "a," "an," and "the" include plural reference unless the context clearly dictates otherwise.

Unless otherwise stated, any numerical values, such as a concentration or a concentration range described herein, are to be understood as being modified in all instances by the term "about." Thus, a numerical value typically includes ±10% of the recited value. For example, a concentration of 1 mg/mL includes 0.9 mg/mL to 1.1 mg/mL. Likewise, a concentration range of 1% to 10% (w/v) includes 0.9% (w/v) to 11% (w/v). As used herein, the use of a numerical range expressly includes all possible subranges, all individual numerical values within that range, including integers within such ranges and fractions of the values unless the context clearly indicates otherwise.

Unless otherwise indicated, the term "at least" preceding a series of elements is to be understood to refer to every element in the series. Those skilled in the art will recognize or be able to ascertain using no more than routine experimentation, many equivalents to the specific embodiments of the invention described herein. Such equivalents are intended to be encompassed by the invention.

As used herein, the terms "comprises," "comprising," "includes," "including," "has," "having," "contains" or "containing," or any other variation thereof, will be understood to imply the inclusion of a stated integer or group of integers but not the exclusion of any other integer or group of integers and are intended to be non-exclusive or open-ended. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the conjunctive term "and/or" between multiple recited elements is understood as encompassing both individual and combined options. For instance, where two elements are conjoined by "and/or," a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

It should also be understood that the terms "about," "approximately," "generally," "substantially" and like terms, used herein when referring to a dimension or characteristic of a component of the preferred invention, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

The terms "identical" or percent "identity," in the context of two or more nucleic acids or polypeptide sequences (e.g., GLP1 peptide, linker peptides, serum albumin proteins, GDF15 proteins and polynucleotides that encode the peptides), refer to two or more sequences or subsequences that are the same or have a specified percentage of amino acid residues or nucleotides that are the same, when compared and aligned for maximum correspondence, as measured using one of the following sequence comparison algorithms or by visual inspection using methods known in the art in view of the present disclosure.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, WI), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) J. Mol. Biol. 215: 403-410 and Altschul et al. (1997) Nucleic Acids Res. 25: 3389-3402, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased.

In addition to calculating percent sequence identity, the BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions.

As used herein, "subject" means any animal, preferably a mammal, most preferably a human. The term "mammal" as used herein, encompasses any mammal. Examples of mammals include, but are not limited to, cows, horses, sheep, pigs, cats, dogs, mice, rats, rabbits, guinea pigs, monkeys, humans, etc., more preferably a human.

The term "administering" with respect to the methods of the invention, means a method for therapeutically or prophylactically preventing, treating or ameliorating a syndrome, disorder or disease as described herein by using a conjugate or compound of the invention or a form, composition or medicament thereof. Such methods include administering an effective amount of said conjugate, compound, a form, composition or medicament thereof at different times during the course of a therapy or concurrently in a combination form. The methods of the invention are to be understood as embracing all known therapeutic treatment regimens.

The term "effective amount" means that amount of active conjugate, compound or pharmaceutical agent that elicits the biological or medicinal response in a tissue system, animal or human, that is being sought by a researcher, veterinarian, medical doctor, or other clinician, which includes preventing, treating or ameliorating a syndrome, disorder, or disease being treated, or the symptoms of a syndrome, disorder or disease being treated.

As used herein, the term "composition" is intended to encompass a product comprising the specified ingredients in the specified amounts, as well as any product which results, directly or indirectly, from combinations of the specified ingredients in the specified amounts.

The term "isolated" can refer to a nucleic acid or polypeptide that is substantially free of cellular material, bacterial material, viral material, or culture medium (when produced by recombinant DNA techniques) of their source of origin, or chemical precursors or other chemicals (when chemically synthesized). Moreover, an isolated polypeptide refers to one that can be administered to a subject as an isolated polypeptide; in other words, the polypeptide may not simply be considered "isolated" if it is adhered to a column or embedded in a gel. Moreover, an "isolated nucleic acid fragment" or "isolated peptide" is a nucleic acid or protein fragment that is not naturally occurring as a fragment and/or is not typically in the functional state.

As used herein, the term "polynucleotide," synonymously referred to as "nucleic acid molecule," "nucleotides" or "nucleic acids," refers to any polyribonucleotide or polydeoxyribonucleotide, which can be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications can be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short nucleic acid chains, often referred to as oligonucleotides.

The term "expression" as used herein, refers to the biosynthesis of a gene product. The term encompasses the transcription of a gene into RNA. The term also encompasses translation of RNA into one or more polypeptides, and further encompasses all naturally occurring post-transcriptional and post-translational modifications. The expressed polypeptide can be within the cytoplasm of a host cell, into the extracellular milieu such as the growth medium of a cell culture or anchored to the cell membrane.

As used herein, the terms "peptide," "polypeptide," or "protein" can refer to a molecule comprised of amino acids and can be recognized as a protein by those of skill in the art. The convention one-letter or three-letter code for amino acid residues is used herein. The terms "peptide," "polypeptide," and "protein" can be used interchangeably herein to refer to polymers of amino acids of any length, including those comprising linked (e.g., fused) peptides/polypeptide (e.g., fusion proteins). The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

The peptide sequences described herein are written according to the usual convention whereby the N-terminal region of the peptide is on the left and the C-terminal region is on the right. Although isomeric forms of the amino acids are known, it is the L-form of the amino acid that is represented unless otherwise expressly indicated.

Glucagon-Like Peptide-1 (GLP1)-Growth Differentiation Factor 15 (GDF15) Fusion Proteins Although both GDF15 and GLP1 signaling can reduce food intake, these effects appear to be independent of one another. For example, GDF15 effects are maintained in the absence of GLP1R in mice and conversely, GLP1 treatment still leads to food intake effects in the absence of GFRAL (Hsu et al., Nature 550:255-9 (2017), Mullican et al., Nat Med 23:1150-7 (2017)). Therefore, it is hypothesized that targeting both mechanisms simultaneously could lead to greater food intake reductions and weight loss than either mechanism alone. Combining the independent yet complementary pharmacology of GDF15 and GLP1 agonists through fusion to human serum albumin will deliver benefits on weight loss, insulin sensitivity, insulin secretion and cardiovascular outcomes with a single fully recombinant molecule suitable for once-weekly administration. A major challenge to this approach will be to deliver each agonist within the molecule in a balanced manner that engages the corresponding receptor at the desired level, enough to achieve all desired effects but that avoids on-target adverse effects. This balance can be fine-tuned by adjusting potency and/or pharmacokinetic properties of either agonist arm of the molecule.

In one general aspect, the invention relates to glucagon-like peptide-1 (GLP1)-growth differentiation factor 15 (GDF15) fusion proteins. The GLP1-GDF15 fusion proteins comprise a GLP1 or GLP1 variant peptide, a first linker peptide (e.g., an amino (N)-terminal linker), a human serum albumin (HSA) protein, a second linker peptide (e.g., a carboxy (C)-terminal linker), and a GDF15 or GDF15 variant protein.

Glucagon-Like Peptide-1 (GLP1) or GLP1 Variant Peptide

Glucagon-like peptide 1 (GLP1) is an insulin secretagogue synthesized in the intestine and released in response to the intake of food. It is secreted primarily in two forms, GLP1-(7-37) and GLP1-(7-36)$NH_2$, both of which bind to a specific GLP1 receptor (GLP1R) found in many tissues including the pancreatic beta-cell where it augments glucose-stimulated insulin secretion and in the brainstem where it controls satiety and meal size.

Numerous GLP1 analogs and derivatives are known and can be referred to herein as "GLP1 variants." These GLP1 variant peptides can include the Exendins, which are peptides found in the venom of the Gila monster. These Exendins have sequence homology to native GLP1 and can bind the GLP1 receptor and initiate the signal transduction cascade response.

GLP1 and GLP1 variant peptides have been shown to act in a variety of manners, which can include, but are not limited to, decreasing food intake, stimulating insulin release, lowering glucagon secretion, inhibiting gastric emptying, and enhancing glucose utilization.

GLP1R belongs to the class B family of 7-transmembrane-spanning, heterotrimeric G-protein-coupled receptors and is expressed in a wide range of tissues including, but not limited to, α-, β-, and δ-cells of the pancreatic islets, heart, kidney, stomach, intestine, nodose ganglion neurons of the vagus nerve, and several regions of the central nervous system (CNS) including the hypothalamus and brainstem. The GLP1R can couple to $G\alpha_s$, $G\alpha_q$, $G\alpha_i$, and $G\alpha_o$ (Montrose-Rafizadeh et al., Endocrinology 140:1132-40 (1999); Hallbrink et al., Biochim Biophys Acta 1546:79-86 (2001)) leading to increases in intracellular calcium, adenylate cyclase, and phospholipase C, and activation of PKA, PKC, PI-3K, Epac2, and MAPK signal transduction pathways (Drucker et al., PNAS 84:3434-8 (1987); Wheeler et al., Endrocrinology 133:57-62 (1993); and Holz et al., JBC 270:17749-57 (1995)).

Provided herein are GLP1-GDF15 fusion proteins that comprise a first component, wherein the first component is a GLP1 or GLP1 variant peptide. As used herein, the terms "GLP1 peptide," "GLP1 variant peptide," "GLP1 peptide variant," and "GLP1 or GLP1 variant peptide" are used interchangeably. The GLP1 or GLP1 variant peptide can comprise one of the sequences provided in Table 1. The GLP1 or GLP1 variant peptide can comprise at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to one of the sequences provided in Table 1. The GLP1 or GLP1 variant peptide sequence can be chosen based on at least one of the following criteria: (i) expression yield and purity, (ii) in vitro stability, (iii) in vitro potency, (iv) the retention of in vitro potency in combination with the GDF15 or GDF15 variant protein, (v) lack of serine xylosylation or potential for serine xylosylation, and (vi) properties of the GLP1-GDF15 fusion proteins (e.g., in vivo stability, in vivo potency (i.e., whether the GLP1 or GLP1 variant peptide and GDF15 or GDF15 variant protein are capable of having agonist activity on GLP1R and GDF15R (GFRAL) receptor, respectively)).

The GLP1 or GLP1 variant peptides that make up the first component of the GLP1 fusion peptide are intended to encompass peptides that have sufficient homology and functionality to the native GLP1. The GLP1 or GLP1 variant peptides are designed to be capable of binding to the GLP1 receptor in tissues including the pancreas and brainstem resulting in the same signaling pathway and exhibiting the same or similar physiological activity as when the native GLP1 binds the GLP1 receptor in these tissues.

TABLE 1

Glucagon-like peptide-1 and variants thereof

| GLP1 or GLP1 Variant Peptide | Peptide Sequence | SEQ ID NO: |
|---|---|---|
| (A8S, A30E) GLP1(7-36) | HSEGTFTSDVSSYLEG QAAKEFIEWLVKGR | 1 |
| (A8G, G22E, R36G) GLP1 (7-36) | HGEGTFTSDVSSYLEE QAAKEFIAWLVKGG | 2 |
| Exendin 4 (1-39) | HGEGTFTSDLSKQMEE EAVRLFIEWLKNGGPS SGAPPPS | 3 |
| Exendin 4 (1-28) | HGEGTFTSDLSKQMEE EAVRLFIEWLKN | 4 |

First Linker Peptide: Amino-Terminal Liker (N-Terminal Linker)

Provided herein are GLP1-GDF15 fusion proteins that comprise a second component, wherein the second component is a first linker peptide (i.e., an amino-terminal linker peptide). The first linker peptide can comprise one of the sequences provided in Table 2. The first linker peptide can comprise at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to one of the sequences provided in Table 2.

The first linker peptide can, for example, comprise about 5 to about 60 amino acid residues, about 10 to about 50 amino acid residues, about 10 to about 60 amino acid residues, about 5 to about 50 amino acid residues, about 15 to about 40 amino acid residues, about 12 to about 30 amino acid residues, about 12 to about 42 amino acid residues, about 20 to about 25 amino acid residues, about 8 to about 48 amino acid residues, about 10 to about 46 amino acid residues, about 12 to about 44 amino acid residues, about 14 to about 42 amino acid residues, about 16 to about 40 amino acid residues, about 18 to about 38 amino acid residues, about 20 to about 36 amino acid residues, about 20 to about 42 amino acid residues, about 22 to about 34 amino acid residues, about 24 to about 32 amino acid residues, about 26 to about 30 amino acid residues, or any value in between. The first linker peptide can comprise 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 amino acid residues.

In certain embodiments, the first linker peptide can contain an alanine-proline repeat (i.e., an AP repeat), wherein an AP dipeptide can be referred to as an AP unit. The AP repeat can comprise 2, 3, 4, 5, 6, 7, 8, 9, 10, 11, 12, 13, 14, 15, 16, 17, 18, 19, 20, 21, 22, 23, 24, 25, 26, or 27 AP units. In certain embodiments, the first linker peptide can, for example, comprise 2 to 25 AP units, 5 to 25 units, 4 to 23 AP units, 6 to 21 AP units, 8 to 19 AP units, 10 to 17 AP units, 12 to 15 AP units, 5 to 10 AP units, 5 to 15 AP units, 10 to 25 AP units, 15 to 25 AP units, 20 to 25 AP units, or any value in between. In certain embodiments, the AP repeat can be internal to an alanine-serine dipeptide (i.e., an AS unit) and a glycine-serine dipeptide (i.e., a GS unit). The AS unit can, for example, be at the amino terminal end of the first linker peptide. The GS unit can, for example, be at the carboxyl terminal end of the first linker peptide.

In certain embodiments, the first linker peptide can contain a glycine-glycine-glycine-glycine-serine repeat (i.e., a G$_4$S repeat), wherein a G$_4$S pentapeptide can be referred to as a G$_4$S unit. The G$_4$S repeat can comprise 2, 3, 4, 5, 6, 7, 8, 9, 10, 11, 12, 13, 14, or 15 G$_4$S units. In certain embodiments, the first linker peptide can, for example, comprise 2 to 15 G$_4$S units, 4 to 13 G$_4$S units, 6 to 11 G$_4$S units, 8 to 9 G$_4$S units, 2 to 8 G$_4$S units, 2 to 6 G$_4$S units, 6 to 8 G$_4$S units, 7 to 8 G$_4$S units, 7 to 9 G$_4$S units, 7 to 10 G$_4$S units, or any value in between. In certain embodiments, an AS or a GS unit can, for example be at the amino terminal end of the first linker peptide.

In certain embodiments, the first linker peptide can contain a glycine-glycine-glycine-glycine-alanine repeat (i.e., a G$_4$A repeat), wherein a G$_4$A pentapeptide can be referred to as a G$_4$A unit. The G$_4$A repeat can comprise 2, 3, 4, 5, 6, 7, 8, 9, 10, 11, 12, 13, 14, or 15 G$_4$A units. In certain embodiments, the first linker peptide can, for example, comprise 2 to 15 G$_4$A units, 4 to 13 G$_4$A units, 6 to 11 G$_4$A units, 8 to 9 G$_4$A units, 2 to 8 G$_4$A units, 2 to 4 G$_4$A units, 2 to 6 G$_4$A units, 4 to 6 G$_4$A units, 4 to 8 G$_4$A units, 6 to 8 G$_4$A units, 6 to 9 G$_4$A units, 6 to 10 G$_4$A units or any value in between. In certain embodiments, a glycine-alanine dipeptide (i.e., a GA unit) unit can, for example be at the amino terminal end of the first linker peptide.

In certain embodiments, the first linker peptide can be a poly-glycine peptide. The poly-glycine peptide can comprise about 6 to about 50 glycine residues, about 10 to about 45 glycine residues, about 15 to about 40 glycine residues, about 20 to about 35 glycine residues, about 25 to about 30 glycine residues, about 20 to about 25 glycine residues, or any number in between. The poly-glycine first linker peptide can comprise 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 glycine residues.

The first linker peptide sequence can be chosen based on at least one of the following criteria: (i) expression yield and purity, (ii) in vitro potency, (iii) in vitro stability, (iv) lack of serine xylosylation or potential for serine xylosylation, and (v) properties of the GLP1-GDF15 fusion protein (e.g., in vivo stability, in vivo potency (i.e., whether GLP1 or GLP1 variant peptide and GDF15 or GDF15 variant protein are capable of having agonist activity on GLP1R and GDF15R (GFRAL), respectively)).

TABLE 2

First linker peptides (N-terminal linker peptide)

| First Linker Peptide | Peptide Sequence | SEQ ID NO: |
|---|---|---|
| 1-1 | APAPAPAPAP | 5 |
| 1-2 | APAPAPAPAPAPAPAPAP | 6 |
| 1-3 | APAPAPAPAPAPAPAPAPAPAPAPAP | 7 |
| 1-4 | APAPAPAPAPAPAPAPAPAPAPAPAPAPAPAPAP | 8 |
| 1-5 | APAPAPAPAPAPAPAPAPAPAPAPAPAPAPAPAPAPAPAPAP | 9 |
| 1-6 | ASAPAPAPAPAPAPAPAPAPGS | 10 |
| 1-7 | ASAPAPAPAPAPGS | 11 |
| 1-8 | ASGGGGSGGGGS | 12 |
| 1-9 | ASGGGGSGGGGSGGGGSGGGGSGGGGSGGGGSGGGGS | 13 |

TABLE 2-continued

First linker peptides (N-terminal linker peptide)

| First Linker Peptide | Peptide Sequence | SEQ ID NO: |
|---|---|---|
| 1-10 | GAGGGGAGGGGA | 14 |
| 1-11 | GAGGGGAGGGGAGGGGAGGGGAGGGGAGGGGAGGGGAGGGGA | 15 |
| 1-12 | GGGGAGGGGAGGGGA | 16 |
| 1-13 | GGGGAGGGGAGGGGAGGGGA | 17 |
| 1-14 | GGGGAGGGGAGGGGAGGGGAGGGGA | 18 |
| 1-15 | GGGGAGGGGAGGGGAGGGGAGGGGAGGGGA | 19 |
| 1-16 | GGGGAGGGGAGGGGAGGGGAGGGGAGGGGAGGGGAGGGGA | 20 |
| 1-17 | GGGGGGGGGGGGGGGGGG | 21 |
| 1-18 | GGGGGGGGGGGGGGGGGGGGGGGGG | 22 |
| 1-19 | GGGGSGGGSGGGGS | 23 |
| 1-20 | GGGGSGGGGSGGGGSGGGGSGGGGS | 24 |
| 1-21 | GGGGSGGGGSGGGGSGGGGSGGGGSGGGGSGGGGS | 25 |

Serum Albumin Protein

Provided herein are GLP1-GDF15 fusion proteins that comprise a third component, wherein the third component is a serum albumin protein (e.g., a human serum albumin (HSA) protein or a gorilla serum albumin (GSA) protein). Native human serum albumin protein contains 35 cysteine (Cys, C) residues that form 17 disulfide bonds, with the Cys-34 residue being the only free cysteine in the molecule. This free Cys-34 has been shown to function as a free radical scavenger, by trapping multiple reactive oxygen species (ROS) and reactive nitrogen species (RNS) (Taverna et al., Ann. Intensive Care 3:4 (2013)). This free Cys was mutated to serine (Ser) to minimize the risk of heterogeneity due to oxidation.

The serum albumin protein can comprise one of the sequences provided in Table 3. The serum albumin protein can comprise at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to one of the sequences provided in Table 3. The serum albumin protein sequence can be chosen based on at least one of the following criteria: (i) in vitro stability, (ii) in vitro potency, and (iii) properties of the GLP1-GDF15 fusion protein (e.g., in vivo stability and in vivo potency (i.e., whether the GLP1 or GLP1 variant peptide and GDF15 or GDF15 variant protein are capable of having agonist activity on GLP1R and GDF15R, respectively)).

TABLE 3

Serum Albumin protein

| Half-life extension protein | Protein Sequence | SEQ ID NO: |
|---|---|---|
| HSA (C34S) | DAHKSEVAHRFKDLGEENFKALVLIAFAQY LQQSPFEDHVKLVNEVTEFAKTCVADESAE NCDKSLHTLFGDKLCTVATLRETYGEMADC CAKQEPERNECFLQHKDDNPNLPRLVRPEV | 26 |

TABLE 3-continued

Serum Albumin protein

| Half-life extension protein | Protein Sequence | SEQ ID NO: |
|---|---|---|
| | DVMCTAFHDNEETFLKKYLYEIARRHPYFY APELLFFAKRYKAAFTECCQAADKAACLLP KLDELRDEGKASSAKQRLKCASLQKFGERA FKAWAVARLSQRFPKAEFAEVSKLVTDLTK VHTECCHGDLLECADDRADLAKYICENQDS ISSKLKECCEKPLLEKSHCIAEVENDEMPA DLPSLAADFVESKDVCKNYAEAKDVFLGMF LYEYARRHPDYSVVLLLRLAKTYETTLEKC CAAADPHECYAKVFDEFKPLVEEPQNLIKQ NCELFEQLGEYKFQNALLVRYTKKVPQVST PTLVEVSRNLGKVGSKCCKHPEAKRMPCAE DYLSVVLNQLCVLHEKTPVSDRVTKCCTES LVNRRPCFSALEVDETYVPKEFNAETFTFH ADICTLSEKERQIKKQTALVELVKHKPKAT KEQLKAVMDDFAAFVEKCCKADDKETCFAE EGKKLVAASQAALGL | |
| GSA (C34S) | DAHKSEVAHRFKDLGEETFKALVLVAFAQY LQQSPFEDHVKLVNEVTEFAKTCVADESAE NCDKSLHTLFGDKLCTVATLRETYGEMADC CAKQEPERNECFLQHKDDNPNLPRLVRPEV DVMCTAFHDNEETFLKKYLYEIARRHPYFY APELLFFAARYKAAFTECCQAADKAACLLP KLDELRDEGKASSAKQRLKCASLQKFGERA FKAWAVARLSQRFPKAEFAEVSKLVTDLTK VHTECCHGDLLECADDRADLAKYICENQDS ISSKLKECCEKPLLEKSHCIAEVENDEMPA DLPSLAADFVESKDVCKNYAEAKDVFLGMF LYEYARRHPDYSVVLLLRLAKTYETTLEKC CAAADPHECYAKVFDEFKPLVEEPQNLIKQ NCELFEQLGEYKFQNALLVRYTKKVPQVST PTLVEVSRNLGKVGSKCCKHPEAKRMPCAE DYLSVVLNQLCVLHEKTPVSDRVTKCCTES LVNRRPCFSALEVDETYVPKEFNAETFTFH ADICTLSEKERQIKKQTALAELVKHKPKAT KEQLKTVMDDFAAFVEKCCKADDKETCFAE EGKKLVAASQAALGL | 27 |

Second Linker Peptide: Carboxy-Terminal Linker (C-Terminal Linker)

Provided herein are GLP1-GDF15 fusion proteins that comprise a fourth component, wherein the fourth component is a second linker peptide (i.e., a carboxy-terminal linker peptide). The second linker peptide can comprise one of the sequences provided in Table 4. The second linker peptide can comprise at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to one of the sequences provided in Table 4.

The second linker peptide can, for example, comprise about 5 to about 60 amino acid residues, about 10 to about 50 amino acid residues, about 10 to about 60 amino acid residues, about 5 to about 50 amino acid residues, about 15 to about 40 amino acid residues, about 12 to about 30 amino acid residues, about 12 to about 42 amino acid residues, about 20 to about 25 amino acid residues, about 8 to about 48 amino acid residues, about 10 to about 46 amino acid residues, about 12 to about 44 amino acid residues, about 14 to about 42 amino acid residues, about 16 to about 40 amino acid residues, about 18 to about 38 amino acid residues, about 20 to about 36 amino acid residues, about 20 to about 42 amino acid residues, about 22 to about 34 amino acid residues, about 24 to about 32 amino acid residues, about 26 to about 30 amino acid residues, or any value in between. The second linker peptide can comprise 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 amino acid residues.

In certain embodiments, the second linker peptide can contain an alanine-proline repeat (i.e., an AP repeat), wherein an AP dipeptide can be referred to as an AP unit. The AP repeat can comprise 2, 3, 4, 5, 6, 7, 8, 9, 10, 11, 12, 13, 14, 15, 16, 17, 18, 19, 20, 21, 22, 23, 24, 25, 26 or 27 AP units. In certain embodiments, the second linker peptide can, for example, comprise 2 to 25 AP units, 5 to 25 units, 4 to 23 AP units, 6 to 21 AP units, 8 to 19 AP units, 10 to 17 AP units, 12 to 15 AP units, 5 to 10 units, 5 to 15 units, 10 to 25 units, 15 to 25 units, 20 to 25 units, or any value in between. In certain embodiments, the AP repeat can be internal to an alanine-serine dipeptide (i.e., an AS unit) and a glycine-serine dipeptide (i.e., a GS unit). The AS unit can, for example, be at the amino terminal end of the second linker peptide. The GS unit can, for example, be at the carboxyl terminal end of the second linker peptide.

In certain embodiments, the second linker peptide can contain a glycine-glycine-glycine-glycine-serine repeat (i.e., a $G_4S$ repeat), wherein a $G_4S$ pentapeptide can be referred to as a $G_4S$ unit. The $G_4S$ repeat can comprise 2, 3, 4, 5, 6, 7, 8, 9, 10, 11, 12, 13, 14, or 15 $G_4S$ units. In certain embodiments, the second linker peptide can, for example, comprise 2 to 15 $G_4S$ units, 4 to 13 $G_4S$ units, 6 to 11 $G_4S$ units, 8 to 9 $G_4S$ units, 2 to 8 $G_4S$ units, 2 to 6 $G_4S$ units, 6 to 8 $G_4S$ units, 7 to 8 $G_4S$ units, 7 to 9 $G_4S$ units, 7 to 10 $G_4S$ units, or any value in between. In certain embodiments, an AS or a GS unit can, for example be at the amino terminal end of the second linker peptide.

In certain embodiments, the second linker peptide can contain a glycine-glycine-glycine-glycine-alanine repeat (i.e., a $G_4A$ repeat), wherein a $G_4A$ pentapeptide can be referred to as a $G_4A$ unit. The $G_4A$ repeat can comprise 2, 3, 4, 5, 6, 7, 8, 9, 10, 11, 12, 13, 14, or 15 $G_4A$ units. In certain embodiments, the second linker peptide can, for example, comprise 2 to 15 $G_4A$ units, 4 to 13 $G_4A$ units, 6 to 11 $G_4A$ units, 8 to 9 $G_4A$ units, 2 to 8 $G_4A$ units, 2 to 4 $G_4A$ units, 2 to 6 $G_4A$ units, 4 to 6 $G_4A$ units, 4 to 8 $G_4A$ units, 6 to 8 $G_4A$ units, 6 to 9 $G_4A$ units, 6 to 10 $G_4A$ units, or any value in between. In certain embodiments, a glycine-alanine dipeptide (i.e., a GA unit) unit can, for example be at the amino terminal end of the second linker peptide.

In certain embodiments, the second linker peptide can be a poly-glycine peptide. The poly-glycine peptide can comprise about 6 to about 50 glycine residues, about 10 to about 45 glycine residues, about 15 to about 40 glycine residues, about 20 to about 35 glycine residues, about 25 to about 30 glycine residues, about 20 to about 25 glycine residues, or any number in between. The poly-glycine second linker peptide can comprise 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 glycine residues.

The second linker peptide sequence can be chosen based on at least one of the following criteria: (i) expression yield and purity, (ii) in vitro potency, (iii) in vitro stability, (iv) lack of serine xylosylation or potential for serine xylosylation, and (v) properties of the GLP1-GDF15 fusion protein (e.g., in vivo stability, in vivo potency (i.e., whether the GLP1 or GLP1 variant peptide and GDF15 or GDF15 variant protein are capable of having agonist activity of GLP1R and GDF15R (GFRAL), respectively)).

TABLE 4

Second linker peptide
(C-terminal linker peptide)

| Second linker peptide | Peptide Sequence | SEQ ID NO: |
|---|---|---|
| 2-1 | APAPAPAPAPAPAPAPAPAP | 28 |
| 2-2 | GAGGGGAGGGGAGGGGAGGGG AGGGGAGGGGAGGGGAGGGGA | 29 |
| 2-3 | GSGGGGSGGGGSGGGGSGGGG SGGGGSGGGGSGGGGSGGGGS | 30 |

GDF15 or GDF15 Variant Protein

Growth differentiation factor 15 (GDF15) is a protein belonging to the transforming growth factor beta (TGF-β) superfamily. GDF15 is a secreted protein that circulates as a 25-kDa dimer. GDF15 is also referred to as prostate derived factor (PDF), macrophage inhibitory cytokine-1 (MIC-1), NSAID (nonsteroidal anti-inflammatory drugs)-activated gene (NAG-1) and placental TGF-beta (PTGFβ).

GDF15 function has yet to be fully elucidated, but has been implicated in multiple biological processes including, but not limited to, energy homeostasis, body weight regulation, and cachexia driven by cancer and chronic disease. The potential of pharmacologically administered GDF15 to decrease energy intake and thereby elicit weight loss has been demonstrated in mice, rats and monkeys. (Johnen et al., Nat Med 13:1333-40 (2007), Hsu et al., Nature 550:255-9 (2017), Mullican et al., Nat Med 23:1150-7 (2017), Tsai et al., Int J Obesity 42:561-71 (2018)). GDF15 treatment mediated weight loss leads to metabolic improvements including enhanced glucose homeostasis and lower plasma triglycerides and cholesterol (Xiong et al., Sci Trans Med 9:412 (2017)).

GDF15 binds to GDNF Family Receptor Alpha Like (GFRAL), a transmembrane receptor exclusively located in neurons in the brainstem (Mullican et al., Hsu et al, Yang et al., Emmerson et al.). Upon GDF15 binding, GFRAL complexes with RET, a tyrosine kinase that stimulates a downstream intracellular phosphorylation cascade including the post-translational modification of AKT, ERK and PLCγ. While the additional molecular and cellular components of this cascade remain to be elucidated, the ultimate effect of GDF15/GFRAL signaling is decreased food intake and weight loss (Mullican and Rangwala, 2018).

Provided herein are GLP1-GDF15 fusion proteins that comprise a fifth component, wherein the fifth component is a GDF15 or GDF15 variant protein. The GDF15 protein can comprise the sequence provided in Table 5, and a GDF15 variant protein can comprise a variant of the sequence provided in Table 5. The GDF15 or GDF15 variant protein can comprise at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to one of the sequences provided in Table 5. The GDF15 and/or GDF15 variant protein sequence can be chosen based on at least one of the following criteria: (i) expression yield and purity, (ii) in vitro stability, (iii) in vitro potency, (iv) the retention of in vitro potency in combination with the GLP1 or GLP1 variant protein, (v) lack of serine xylosylation or potential for serine xylosylation, and (vi) properties of the GLP1-GDF15 fusion protein (e.g., in vivo stability, in vivo potency (i.e., whether GLP1 or GLP1 variant peptide and GDF15 or GDF15 variant protein are capable of having agonist activity on GLP1R and/or GDF15R (GFRAL) receptor, respectively)).

The GDF15 or GDF15 variant proteins that make up the fifth component of the GLP1-GDF15 fusion proteins are intended to encompass proteins that have sufficient homology and functionality to activate the native GDF15R (GFRAL). The GDF15 or GDF15 variant proteins are designed to be capable of binding to GFRAL in the brainstem resulting in the same signaling pathway and exhibiting the same impact on food intake as when the native GDF15 binds GFRAL in these neurons.

TABLE 5

| GDF15 or GDF15 variant protein | Protein Sequence | SEQ ID NO: |
|---|---|---|
| GDF15 variant 1 | DHCPLGPGRCCRLHTVRASLEDLGW ADWVLSPREVQVTMCIGACPSQFRA ANMHAQIKTSLHRLKPDTVPAPCCV PASYNPMVLIQKTDTGVSLQTYD DLLAKDCHCI | 31 |
| GDF15 WT mature | ARNGDHCPLGPGRCCRLHTVRASLED LGWADWVLSPREVQVTMCIGACPSQF RAANMHAQIKTSLHRLKPDTVPAPCC VPASYNPMVLIQKTDTGVSLQ TYDDLLAKDCHCI | 32 |

GLP1-GDF15 Fusion Proteins

Provided herein are GLP1-GDF15 fusion proteins that comprise a first, a second, a third, a fourth, and a fifth component as described previously. The first component is a GLP1 or GLP1 variant peptide, the second component is a first linker peptide, the third component is a serum albumin protein, the fourth component is a second linker peptide, and the fifth component is a GDF15 or GDF15 variant protein. The GLP1-GDF15 fusion proteins can comprise one of the sequences provided in Table 6. The GLP1-GDF15 fusion protein can comprise at least 85%, 86%, 87%, 88%, 89%, 90%, 91%, 92%, 93%, 94%, 95%, 96%, 97%, 98%, or 99% identity to one of the sequences provided in Table 6. The GLP1-GDF15 fusion protein can be chosen based on at least one of the following criteria: (i) expression yield and purity, (ii) in vitro potency, (iii) in vitro stability, (iv) lack of serine xylosylation, and (v) physical properties of the GLP1-GDF15 fusion protein (e.g., in vivo stability, in vivo potency (i.e., whether the GLP1 or GLP1 variant peptide and GDF15 or GDF15 variant protein are capable of having agonist activity on GLP1R and GDF15R, respectively)), and (vi) desired balance of dual agonism pharmacology in vivo.

For a fusion protein therapeutic that delivers dual pharmacology in one molecule, it is important to properly adjust the pharmacokinetic/pharmacodynamic (PK/PD) properties of each moiety so that both agonists are in the therapeutic range with the intended dosing. Extensive investigation of various glucagon-like peptide-1 (GLP1)-growth differentiation factor 15 (GDF15) fusion proteins comprising various combinations of a GLP1 peptide or GLP1 variant peptide sequence, a first linker peptide sequence, a serum albumin protein sequence, a second linker peptide sequence, and a GDF15 or GDF15 variant protein sequence resulted in the discovery of novel molecules possessing the unique property of delivering optimal balanced doses of both GLP1 and GDF15 agonists. These novel GLP1-GDF15 fusion proteins were demonstrated to be as efficacious in engaging the GDF15R (GFRAL) in vivo as HSA-GDF15, when used at a specific dose range (see Example 11). Furthermore, the GLP1-GDF15 fusion proteins, used at the same dose range (see Example 11), were unexpectedly as efficacious in engaging the GLP1R as dulaglutide (GLP1-Fc), and without adverse side effects, despite having a GLP1 moiety exposure 10-30 times greater than that in dulaglutide. The delivery of GLP1 peptides as fusions with HSA-GDF15 unexpectedly altered the in vivo potency of the GLP1 moiety yet enabled novel glucagon-like peptide-1 (GLP1)-growth differentiation factor 15 (GDF15) fusion proteins to have an optimal balance of both agonists.

TABLE 6

GLP1-GDF15 fusion proteins

| GLP1-GDF15 fusion proteins | Protein Sequence | SEQ ID NO: |
|---|---|---|
| 1 | HGEGTFTSDVSSYLEEQAAKEFIAW LVKGGGGGAGGGGAGGGGAGGGGA GGGGADAHKSEVAHRFKDLGEENFK ALVLIAFAQYLQQSPFEDHVKLVNE VTEFAKTCVADESAENCDKSLHTLF GDKLCTVATLRETYGEMADCCAKQE PERNECFLQHKDDNPNLPRLVRPEV DVMCTAFHDNEETFLKKYLYEIARR HPYFYAPELLFFAKRYKAAFTECCQ AADKAACLLPKLDELRDEGKASSAK QRLKCASLQKFGERAFKAWAVARLS QRFPKAEFAEVSKLVTDLTKVHTEC CHGDLLECADDRADLAKYICENQDS ISSKLKECCEKPLLEKSHCIAEVEN DEMPADLPSLAADFVESKDVCKNYA EAKDVFLGMFLYEYARRHPDYSVVL LLRLAKTYETTLEKCCAAADPHECY AKVFDEFKPLVEEPQNLIKQNCELF EQLGEYKFQNALLVRYTKKVPQVST PTLVEVSRNLGKVGSKCCKHPEAKRM PCAEDYLSVVLNQLCVLHEKTPVSDR VTKCCTESLVNRRPCFSALEVDETY VPKEFNAETFTFHADICTLSEKERQ IKKQTALVELVKHKPKATKEQLKAV MDDFAAFVEKCCKADDKETCFAEEG KKLVAASQAALGLAPAPAPAPAPAP APAPAPAPDHCPLGPGRCCRLHTVR ASLEDLGWADWVLSPREVQVTMCIG ACPSQFRAANMHAQIKTSLHRLKPD TVPAPCCVPASYNPMVLIQKTDTGV SLQTYDDLLAKDCHCI | 33 |
| 2 | HGEGTFTSDVSSYLEEQAAKEFIAW LVKGGGGGAGGGGAGGGGADAHKS EVAHRFKDLGEENFKALVLIAFAQY LQQSPFEDHVKLVNEVTEFAKTCVA DESAENCDKSLHTLFGDKLCTVATL RETYGEMADCCAKQEPERNECFLQH KDDNPNLPRLVRPEVDVMCTAFHDN EETFLKKYLYEIARRHPYFYAPELL FFAKRYKAAFTECCQAADKAACLLP KLDELRDEGKASSAKQRLKCASLQK FGERAFKAWAVARLSQRFPKAEFAE VSKLVTDLTKVHTECCHGDLLECAD DRADLAKYICENQDSISSKLKECCE KPLLEKSHCIAEVENDEMPADLPSL AADFVESKDVCKNYAEAKDVFLGMF LYEYARRHPDYSVVLLLRLAKTYET TLEKCCAAADPHECYAKVFDEFKPL VEEPQNLIKQNCELFEQLGEYKFQN ALLVRYTKKVPQVSTPTLVEVSRNL GKVGSKCCKHPEAKRMPCAEDYLSV VLNQLCVLHEKTPVSDRVTKCCTES LVNRRPCFSALEVDETYVPKEFNAE TFTFHADICTLSEKERQIKKQTALV ELVKHKPKATKEQLKAVMDDFAAFV EKCCKADDKETCFAEEGKKLVAASQ AALGLAPAPAPAPAPAPAPAPAPAP DHCPLGPGRCCRLHTVRASLEDLGW ADWVLSPREVQVTMCIGACPSQFRA ANMHAQIKTSLHRLKPDTVPAPCCV PASYNPMVLIQKTDTGVSLQTYDDL LAKDCHCI | 34 |
| 3 | HGEGTFTSDVSSYLEEQAAKEFIAW LVKGGAPAPAPAPAPAPAPAPAPAP APAPAPAPAPAPAPAPAPAPAPAPA PAPAPDAHKSEVAHRFKDLGEENFK ALVLIAFAQYLQQSPFEDHVKLVNE VTEFAKTCVADESAENCDKSLHTLF GDKLCTVATLRETYGEMADCCAKQE PERNECFLQHKDDNPNLPRLVRPEV DVMCTAFHDNEETFLKKYLYEIARR HPYFYAPELLFFAKRYKAAFTECCQ AADKAACLLPKLDELRDEGKASSAK QRLKCASLQKFGERAFKAWAVARLS QRFPKAEFAEVSKLVTDLTKVHTEC CHGDLLECADDRADLAKYICENQDS ISSKLKECCEKPLLEKSHCIAEVEN DEMPADLPSLAADFVESKDVCKNYA EAKDVFLGMFLYEYARRHPDYSVVL LLRLAKTYETTLEKCCAAADPHECY AKVFDEFKPLVEEPQNLIKQNCELF EQLGEYKFQNALLVRYTKKVPQVST PTLVEVSRNLGKVGSKCCKHPEAKR MPCAEDYLSVVLNQLCVLHEKTPVS DRVTKCCTESLVNRRPCFSALEVDE TYVPKEFNAETFTFHADICTLSEKE RQIKKQTALVELVKHKPKATKEQLK AVMDDFAAFVEKCCKADDKETCFAE EGKKLVAASQAALGLAPAPAPAPAP APAPAPAPAPDHCPLGPGRCCRLHT VRASLEDLGWADWVLSPREVQVTMC IGACPSQFRAANMHAQIKTSLHRLK PDTVPAPCCVPASYNPMVLIQKTDT GVSLQTYDDLLAKDCHCI | 35 |
| 4 | HGEGTFTSDVSSYLEEQAAKEFIAW LVKGGAPAPAPAPAPAPAPAPAPAP APAPAPAPAPAPAPAPAPDAHKS EVAHRFKDLGEENFKALVLIAFAQY LQQSPFEDHVKLVNEVTEFAKTCVA DESAENCDKSLHTLFGDKLCTVATL RETYGEMADCCAKQEPERNECFLQH KDDNPNLPRLVRPEVDVMCTAFHDN EETFLKKYLYEIARRHPYFYAPELL FFAKRYKAAFTECCQAADKAACLLP KLDELRDEGKASSAKQRLKCASLQK FGERAFKAWAVARLSQRFPKAEFAE VSKLVTDLTKVHTECCHGDLLECAD DRADLAKYICENQDSISSKLKECCE KPLLEKSHCIAEVENDEMPADLPSL AADFVESKDVCKNYAEAKDVFLGMF LYEYARRHPDYSVVLLLRLAKTYET TLEKCCAAADPHECYAKVFDEFKPL VEEPQNLIKQNCELFEQLGEYKFQN ALLVRYTKKVPQVSTPTLVEVSRNL GKVGSKCCKHPEAKRMPCAEDYLSV VLNQLCVLHEKTPVSDRVTKCCTES LVNRRPCFSALEVDETYVPKEFNAE TFTFHADICTLSEKERQIKKQTALV ELVKHKPKATKEQLKAVMDDFAAFV EKCCKADDKETCFAEEGKKLVAASQ AALGLAPAPAPAPAPAPAPAPAPAP DHCPLGPGRCCRLHTVRASLEDLGW ADWVLSPREVQVTMCIGACPSQFRA ANMHAQIKTSLHRLKPDTVPAPCCV PASYNPMVLIQKTDTGVSLQTYDDL LAKDCHCI | 36 |

TABLE 6-continued

GLP1-GDF15 fusion proteins

| GLP1-GDF15 fusion proteins | Protein Sequence | SEQ ID NO: |
|---|---|---|
| 5 | HGEGTFTSDVSSYLEEQAAKEFIAW LVKGGAPAPAPAPAPAPAPAPAP APAPAPAPDAHKSEVAHRFKDLG EENFKALVLIAFAQYLQQSPFEDHV KLVNEVTEFAKTCVADESAENCDKS LHTLFGDKLCTVATLRETYGEMADC CAKQEPERNECFLQHKDDNPNLPRL VRPEVDVMCTAFHDNEETFLKKYLY EIARRHPYFYAPELLFFAKRYKAAF TECCQAADKAACLLPKLDELRDEGK ASSAKQRLKCASLQKFGERAFKAWA VARLSQRFPKAEFAEVSKLVTDLTK VHTECCHGDLLECADDRADLAKYIC ENQDSISSKLKECCEKPLLEKSHCI AEVENDEMPADLPSLAADFVESKDV CKNYAEAKDVFLGMFLYEYARRHPD YSVVLLLRLAKTYETTLEKCCAAAD PHECYAKVFDEFKPLVEEPQNLIKQ NCELFEQLGEYKFQNALLVRYTKKV PQVSTPTLVEVSRNLGKVGSKCCKH PEAKRMPCAEDYLSVVLNQLCVLHE KTPVSDRVTKCCTESLVNRRPCFSA LEVDETYVPKEFNAETFTFHADICT LSEKERQIKKQTALVELVKHKPKAT KEQLKAVMDDFAAFVEKCCKADDKE TCFAEEGKKLVAASQAALGLAPAPA PAPAPAPAPAPAPDHCPLGPGRC CRLHTVRASLEDLGWADWVLSPREV QVTMCIGACPSQFRAANMHAQIKTS LHRLKPDTVPAPCCVPASYNPMVLI QKTDTGVSLQTYDDLLAKDCHCI | 37 |
| 6 | HGEGTFTSDVSSYLEEQAAKEFIAW LVKGGGGGGAGGGGAGGGGAGGGGA GGGGAGGGGAGGGGAGGGGADAHKS EVAHRFKDLGEENFKALVLIAFAQY LQQSPFEDHVKLVNEVTEFAKTCVA DESAENCDKSLHTLFGDKLCTVATL RETYGEMADCCAKQEPERNECFLQH KDDNPNLPRLVRPEVDVMCTAFHDN EETFLKKYLYEIARRHPYFYAPELL FFAKRYKAAFTECCQAADKAACLLP KLDELRDEGKASSAKQRLKCASLQK FGERAFKAWAVARLSQRFPKAEFAE VSKLVTDLTKVHTECCHGDLLECAD DRADLAKYICENQDSISSKLKECCE KPLLEKSHCIAEVENDEMPADLPSL AADFVESKDVCKNYAEAKDVFLGMF LYEYARRHPDYSVVLLLRLAKTYET TLEKCCAAADPHECYAKVFDEFKPL VEEPQNLIKQNCELFEQLGEYKFQN ALLVRYTKKVPQVSTPTLVEVSRNL GKVGSKCCKHPEAKRMPCAEDYLSV VLNQLCVLHEKTPVSDRVTKCCTES LVNRRPCFSALEVDETYVPKEFNAE TFTFHADICTLSEKERQIKKQTALV ELVKHKPKATKEQLKAVMDDFAAFV EKCCKADDKETCFAEEGKKLVAASQ AALGLAPAPAPAPAPAPAPAPAP DHCPLGPGRCCRLHTVRASLEDLGW ADWVLSPREVQVTMCIGACPSQFRA ANMHAQIKTSLHRLKPDTVPAPCCV PASYNPMVLIQKTDTGVSLQTYDDL LAKDCHCI | 38 |
| 7 | HGEGTFTSDLSKQMEEEAVRLFIEW LKNGGPSSGAPPPSAPAPAPAPA PAPAPAPAPAPAPAPAPAPAPAP APAPAPAPAPAPAPDAHKSEVAHRF KDLGEENFKALVLIAFAQYLQQSPF EDHVKLVNEVTEFAKTCVADESAEN CDKSLHTLFGDKLCTVATLRETYGE | 39 |
| | MADCCAKQEPERNECFLQHKDDNPN LPRLVRPEVDVMCTAFHDNEETFLK KYLYEIARRHPYFYAPELLFFAKRY KAAFTECCQAADKAACLLPKLDELR DEGKASSAKQRLKCASLQKFGERAF KAWAVARLSQRFPKAEFAEVSKLVT DLTKVHTECCHGDLLECADDRADLA KYICENQDSISSKLKECCEKPLLEK SHCIAEVENDEMPADLPSLAADFVE SKDVCKNYAEAKDVFLGMFLYEYAR RHPDYSVVLLLRLAKTYETTLEKCC AAADPHECYAKVFDEFKPLVEEPQN LIKQNCELFEQLGEYKFQNALLVRY TKKVPQVSTPTLVEVSRNLGKVGSK CCKHPEAKRMPCAEDYLSVVLNQLC VLHEKTPVSDRVTKCCTESLVNRRP CFSALEVDETYVPKEFNAETFTFHA DICTLSEKERQIKKQTALVELVKHK PKATKEQLKAVMDDFAAFVEKCCKA DDKETCFAEEGKKLVAASQAALGLA PAPAPAPAPAPAPAPAPAPDHCPLG PGRCCRLHTVRASLEDLGWADWVLS PREVQVTMCIGACPSQFRAANMHAQ IKTSLHRLKPDTVPAPCCVPASYNP MVLIQKTDTGVSLQTYDDLLAKDCH CI | |
| 8 | HGEGTFTSDLSKQMEEEAVRLFIEW LKNGGPSSGAPPPSAPAPAPAPAPA PAPAPAPAPAPAPAPAPDAHKSE VAHRFKDLGEENFKALVLIAFAQYL QQSPFEDHVKLVNEVTEFAKTCVAD ESAENCDKSLHTLFGDKLCTVATLR ETYGEMADCCAKQEPERNECFLQHK DDNPNLPRLVRPEVDVMCTAFHDNE ETFLKKYLYEIARRHPYFYAPELLF FAKRYKAAFTECCQAADKAACLLPK LDELRDEGKASSAKQRLKCASLQKF GERAFKAWAVARLSQRFPKAEFAEV SKLVTDLTKVHTECCHGDLLECADD RADLAKYICENQDSISSKLKECCEK PLLEKSHCIAEVENDEMPADLPSLA ADFVESKDVCKNYAEAKDVFLGMFL YEYARRHPDYSVVLLLRLAKTYETT LEKCCAAADPHECYAKVFDEFKPLV EEPQNLIKQNCELFEQLGEYKFQNA LLVRYTKKVPQVSTPTLVEVSRNLG KVGSKCCKHPEAKRMPCAEDYLSVV LNQLCVLHEKTPVSDRVTKCCTESL VNRRPCFSALEVDETYVPKEFNAET FTFHADICTLSEKERQIKKQTALVE LVKHKPKATKEQLKAVMDDFAAFVE KCCKADDKETCFAEEGKKLVAASQA ALGLAPAPAPAPAPAPAPAPAPD HCPLGPGRCCRLHTVRASLEDLGWA DWVLSPREVQVTMCIGACPSQFRAA NMHAQIKTSLHRLKPDTVPAPCCVP ASYNPMVLIQKTDTGVSLQTYDDLL AKDCHCI | 40 |
| 9 | HGEGTFTSDLSKQMEEEAVRLFIEW LKNGGPSSGAPPPSAPAPAPAPAPA PAPAPAPDAHKSEVAHRFKDLGE ENFKALVLIAFAQYLQQSPFEDHVK LVNEVTEFAKTCVADESAENCDKSL HTLFGDKLCTVATLRETYGEMADCC AKQEPERNECFLQHKDDNPNLPRLV RPEVDVMCTAFHDNEETFLKKYLYE IARRHPYFYAPELLFFAKRYKAAFT ECCQAADKAACLLPKLDELRDEGKA SSAKQRLKCASLQKFGERAFKAWAV ARLSQRFPKAEFAEVSKLVTDLTKV HTECCHGDLLECADDRADLAKYICE | 41 |

TABLE 6-continued

GLP1-GDF15 fusion proteins

| GLP1-GDF15 fusion proteins | Protein Sequence | SEQ ID NO: |
|---|---|---|
| | NQDSISSKLKECCEKPLLEKSHCIA EVENDEMPADLPSLAADFVESKDVC KNYAEAKDVFLGMFLYEYARRHPDY SVVLLLRLAKTYETTLEKCCAAADP HECYAKVFDEFKPLVEEPQNLIKQN CELFEQLGEYKFQNALLVRYTKKVP QVSTPTLVEVSRNLGKVGSKCCKHP EAKRMPCAEDYLSVVLNQLCVLHEK TPVSDRVTKCCTESLVNRRPCFSAL EVDETYVPKEFNAETFTFHADICTL SEKERQIKKQTALVELVKHKPKATK EQLKAVMDDFAAFVEKCCKADDKET CFAEEGKKLVAASQAALGLAPAPAP APAPAPAPAPAPDHCPLGPGRCC RLHTVRASLEDLGWADWVLSPREVQ VTMCIGACPSQFRAANMHAQIKTSL HRLKPDTVPAPCCVPASYNPMVLIQ KTDTGVSLQTYDDLLAKDCHCI | |
| 10 | HGEGTFTSDLSKQMEEEAVRLFIEW LKNGGPSSGAPPPSGGGGAGGGGAG GGGAGGGGAGGGGAGGGGAGGGGAG GGGADAHKSEVAHRFKDLGEENFKA LVLIAFAQYLQQSPFEDHVKLVNEV TEFAKTCVADESAENCDKSLHTLFG DKLCTVATLRETYGEMADCCAKQEP ERNECFLQHKDDNPNLPRLVRPEVD VMCTAFHDNEETFLKKYLYEIARRH PYFYAPELLFFAKRYKAAFTECCQA ADKAACLLPKLDELRDEGKASSAKQ RLKCASLQKFGERAFKAWAVARLSQ RFPKAEFAEVSKLVTDLTKVHTECC HGDLLECADDRADLAKYICENQDSI SSKLKECCEKPLLEKSHCIAEVEND EMPADLPSLAADFVESKDVCKNYAE AKDVFLGMFLYEYARRHPDYSVVLL LRLAKTYETTLEKCCAAADPHECYA KVFDEFKPLVEEPQNLIKQNCELFE QLGEYKFQNALLVRYTKKVPQVSTP TLVEVSRNLGKVGSKCCKHPEAKRM PCAEDYLSVVLNQLCVLHEKTPVSD RVTKCCTESLVNRRPCFSALEVDET YVPKEFNAETFTFHADICTLSEKER QIKKQTALVELVKHKPKATKEQLKA VMDDFAAFVEKCCKADDKETCFAEE GKKLVAASQAALGLAPAPAPAPAPA PAPAPAPDHCPLGPGRCCRLHTV RASLEDLGWADWVLSPREVQVTMCI GACPSQFRAANMHAQIKTSLHRLKP DTVPAPCCVPASYNPMVLIQKTDTG VSLQTYDDLLAKDCHCI | 42 |
| 11 | HGEGTFTSDLSKQMEEEAVRLFIEW LKNGGPSSGAPPPSGGGGAGGGGAG GGGAGGGGADAHKSEVAHRF KDLGEENFKALVLIAFAQYLQQSPF EDHVKLVNEVTEFAKTCVADESAEN CDKSLHTLFGDKLCTVATLRETYGE MADCCAKQEPERNECFLQHKDDNPN LPRLVRPEVDVMCTAFHDNEETFLK KYLYEIARRHPYFYAPELLFFAKRY KAAFTECCQAADKAACLLPKLDELR DEGKASSAKQRLKCASLQKFGERAF KAWAVARLSQRFPKAEFAEVSKLVT DLTKVHTECCHGDLLECADDRADLA KYICENQDSISSKLKECCEKPLLEK SHCIAEVENDEMPADLPSLAADFVE SKDVCKNYAEAKDVFLGMFLYEYAR RHPDYSVVLLLRLAKTYETTLEKCC AAADPHECYAKVFDEFKPLVEEPQN LIKQNCELFEQLGEYKFQNALLVRY TKKVPQVSTPTLVEVSRNLGKVGSK CCKHPEAKRMPCAEDYLSVVLNQLC | 43 |
| | VLHEKTPVSDRVTKCCTESLVNRRP CFSALEVDETYVPKEFNAETFTFHA DICTLSEKERQIKKQTALVELVKHK PKATKEQLKAVMDDFAAFVEKCCKA DDKETCFAEEGKKLVAASQAALGLA PAPAPAPAPAPAPAPDHCPLG PGRCCRLHTVRASLEDLGWADWVLS PREVQVTMCIGACPSQFRAANMHAQ IKTSLHRLKPDTVPAPCCVPASYNP MVLIQKTDTGVSLQTYDDLLAKDCH CI | |
| 12 | HGEGTFTSDLSKQMEEEAVRLFIEW LKNGGPSSGAPPPSAPAPAPAPAPD AHKSEVAHRFKDLGEENFKALVLIA FAQYLQQSPFEDHVKLVNEVTEFAK TCVADESAENCDKSLHTLFGDKLCT VATLRETYGEMADCCAKQEPERNEC FLQHKDDNPNLPRLVRPEVDVMCTA FHDNEETFLKKYLYEIARRHPYFYA PELLFFAKRYKAAFTECCQAADKAA CLLPKLDELRDEGKASSAKQRLKCA SLQKFGERAFKAWAVARLSQRFPKA EFAEVSKLVTDLTKVHTECCHGDLL ECADDRADLAKYICENQDSISSKLK ECCEKPLLEKSHCIAEVENDEMPAD LPSLAADFVESKDVCKNYAEAKDVF LGMFLYEYARRHPDYSVVLLLRLAK TYETTLEKCCAAADPHECYAKVFDE FKPLVEEPQNLIKQNCELFEQLGEY KFQNALLVRYTKKVPQVSTPTLVEV SRNLGKVGSKCCKHPEAKRMPCAED YLSVVLNQLCVLHEKTPVSDRVTKC CTESLVNRRPCFSALEVDETYVPKE FNAETFTFHADICTLSEKERQIKKQ TALVELVKHKPKATKEQLKAVMDDF AAFVEKCCKADDKETCFAEEGKKLV AASQAALGLAPAPAPAPAPAPAPAP APAPDHCPLGPGRCCRLHTVRASLE DLGWADWVLSPREVQVTMCIGACPS QFRAANMHAQIKTSLHRLKPDTVPA PCCVPASYNPMVLIQKTDTGVSLQT YDDLLAKDCHCI | 44 |
| 13 | HGEGTFTSDVSSYLEEQAAKEFIAW LVKGGAPAPAPAPAPAPAPAPAPAP DAHKSEVAHRFKDLGEENFKALVLI AFAQYLQQSPFEDHVKLVNEVTEFA KTCVADESAENCDKSLHTLFGDKLC TVATLRETYGEMADCCAKQEPERNE CFLQHKDDNPNLPRLVRPEVDVMCT AFHDNEETFLKKYLYEIARRHPYFY APELLFFAKRYKAAFTECCQAADKA ACLLPKLDELRDEGKASSAKQRLKC ASLQKFGERAFKAWAVARLSQRFPK AEFAEVSKLVTDLTKVHTECCHGDL LECADDRADLAKYICENQDSISSKL KECCEKPLLEKSHCIAEVENDEMPA DLPSLAADFVESKDVCKNYAEAKDV FLGMFLYEYARRHPDYSVVLLLRLA KTYETTLEKCCAAADPHECYAKVFD EFKPLVEEPQNLIKQNCELFEQLGE YKFQNALLVRYTKKVPQVSTPTLVE VSRNLGKVGSKCCKHPEAKRMPCAE DYLSVVLNQLCVLHEKTPVSDRVTK CCTESLVNRRPCFSALEVDETYVPK EFNAETFTFHADICTLSEKERQIKK QTALVELVKHKPKATKEQLKAVMDD FAAFVEKCCKADDKETCFAEEGKKL VAASQAALGLAPAPAPAPAPAPAPA PAPAPDHCPLGPGRCCRLHTVRASL EDLGWADWVLSPREVQVTMCIGACP SQFRAANMHAQIKTSLHRLKPDTVP | 45 |

TABLE 6-continued

GLP1-GDF15 fusion proteins

| GLP1-GDF15 fusion proteins | Protein Sequence | SEQ ID NO: |
|---|---|---|
| | APCCVPASYNPMVLIQKTDTGVSLQTYDDLLAKDCHCI | |
| 14 | HGEGTFTSDLSKQMEEEAVRLFIEWLKNGGPSSGAPPPSAPAPAPAPAPDAHKSEVAHRFKDLGEENFKALVLIAFAQYLQQSPFEDHVKLVNEVTEFAKTCVADESAENCDKSLHTLFGDKLCTVATLRETYGEMADCCAKQEPERNECFLQHKDDNPNLPRLVRPEVDVMCTAFHDNEETFLKKYLYEIARRHPYFYAPELLFFAKRYKAAFTECCQAADKAACLLPKLDELRDEGKASSAKQRLKCASLQKFGERAFKAWAVARLSQRFPKAEFAEVSKLVTDLTKVHTECCHGDLLECADDRADLAKYICENQDSISSKLKECCEKPLLEKSHCIAEVENDEMPADLPSLAADFVESKDVCKNYAEAKDVFLGMFLYEYARRHPDYSVVLLLRLAKTYETTLEKCCAAADPHECYAKVFDEFKPLVEEPQNLIKQNCELFEQLGEYKFQNALLVRYTKKVPQVSTPTLVEVSRNLGKVGSKCCKHPEAKRMPCAEDYLSVVLNQLCVLHEKTPVSDRVTKCCTESLVNRRPCFSALEVDETYVPKEFNAETFTFHADICTLSEKERQIKKQTALVELVKHKPKATKEQLKAVMDDFAAFVEKCCKADDKETCFAEEGKKLVAASQAALGLGAGGGGAGGGGAGGGGAGGGGAGGGGAGGGGAGGGGAGGGGADHCPLGPGRCCRLHTVRASLEDLGWADWVLSPREVQVTMCIGACPSQFRAANMHAQIKTSLHRLKPDTVPAPCCVPASYNPMVLIQKTDTGVSLQTYDDLLAKDCHCI | 46 |
| 15 | HGEGTFTSDVSSYLEEQAAKEFIAWLVKGGGGGGGGGGGGGGGGGGGGGGGGDAHKSEVAHRFKDLGEENFKALVLIAFAQYLQQSPFEDHVKLVNEVTEFAKTCVADESAENCDKSLHTLFGDKLCTVATLRETYGEMADCCAKQEPERNECFLQHKDDNPNLPRLVRPEVDVMCTAFHDNEETFLKKYLYEIARRHPYFYAPELLFFAKRYKAAFTECCQAADKAACLLPKLDELRDEGKASSAKQRLKCASLQKFGERAFKAWAVARLSQRFPKAEFAEVSKLVTDLTKVHTECCHGDLLECADDRADLAKYICENQDSISSKLKECCEKPLLEKSHCIAEVENDEMPADLPSLAADFVESKDVCKNYAEAKDVFLGMFLYEYARRHPDYSVVLLLRLAKTYETTLEKCCAAADPHECYAKVFDEFKPLVEEPQNLIKQNCELFEQLGEYKFQNALLVRYTKKVPQVSTPTLVEVSRNLGKVGSKCCKHPEAKRMPCAEDYLSVVLNQLCVLHEKTPVSDRVTKCCTESLVNRRPCFSALEVDETYVPKEFNAETFTFHADICTLSEKERQIKKQTALVELVKHKPKATKEQLKAVMDDFAAFVEKCCKADDKETCFAEEGKKLVAASQAALGLGAGGGGAGGGGAGGGGAGGGGAGGGGAGGGGADHCPLGPGRCCRLHTVRASLEDLGWADWVLSPREVQVTMCIGACPSQFRAANMHAQIKTSLHRLKPDTVPAPCCVPASYNPMVLIQKTDTGVSLQTYDDLLAKDCHCI | 47 |
| 16 | HGEGTFTSDVSSYLEEQAAKEFIAWLVKGGGGGGGGGGGGGGGGGGGGGGGGDAHKSEVAHRFKDLGEENFKALVLIAFAQYLQQSPFEDHVKLVNEVTEFA | 18 |
| | KTCVADESAENCDKSLHTLFGDKLCTVATLRETYGEMADCCAKQEPERNECFLQHKDDNPNLPRLVRPEVDVMCTAFHDNEETFLKKYLYEIARRHPYFYAPELLFFAKRYKAAFTECCQAADKAACLLPKLDELRDEGKASSAKQRLKCASLQKFGERAFKAWAVARLSQRFPKAEFAEVSKLVTDLTKVHTECCHGDLLECADDRADLAKYICENQDSISSKLKECCEKPLLEKSHCIAEVENDEMPADLPSLAADFVESKDVCKNYAEAKDVFLGMFLYEYARRHPDYSVVLLLRLAKTYETTLEKCCAAADPHECYAKVFDEFKPLVEEPQNLIKQNCELFEQLGEYKFQNALLVRYTKKVPQVSTPTLVEVSRNLGKVGSKCCKHPEAKRMPCAEDYLSVVLNQLCVLHEKTPVSDRVTKCCTESLVNRRPCFSALEVDETYVPKEFNAETFTFHADICTLSEKERQIKKQTALVELVKHKPKATKEQLKAVMDDFAAFVEKCCKADDKETCFAEEGKKLVAASQAALGLGAGGGGAGGGGAGGGGAGGGGAGGGGAGGGGADHCPLGPGRCCRLHTVRASLEDLGWADWVLSPREVQVTMCIGACPSQFRAANMHAQIKTSLHRLKPDTVPAPCCVPASYNPMVLIQKTDTGVSLQTYDDLLAKDCHCI | |
| 17 | HGEGTFTSDVSSYLEEQAAKEFIAWLVKGGGGGGAGGGGAGGGGAGGGGADAHKSEVAHRFKDLGEENFKALVLIAFAQYLQQSPFEDHVKLVNEVTEFAKTCVADESAENCDKSLHTLFGDKLCTVATLRETYGEMADCCAKQEPERNECFLQHKDDNPNLPRLVRPEVDVMCTAFHDNEETFLKKYLYEIARRHPYFYAPELLFFAKRYKAAFTECCQAADKAACLLPKLDELRDEGKASSAKQRLKCASLQKFGERAFKAWAVARLSQRFPKAEFAEVSKLVTDLTKVHTECCHGDLLECADDRADLAKYICENQDSISSKLKECCEKPLLEKSHCIAEVENDEMPADLPSLAADFVESKDVCKNYAEAKDVFLGMFLYEYARRHPDYSVVLLLRLAKTYETTLEKCCAAADPHECYAKVFDEFKPLVEEPQNLIKQNCELFEQLGEYKFQNALLVRYTKKVPQVSTPTLVEVSRNLGKVGSKCCKHPEAKRMPCAEDYLSVVLNQLCVLHEKTPVSDRVTKCCTESLVNRRPCFSALEVDETYVPKEFNAETFTFHADICTLSEKERQIKKQTALVELVKHKPKATKEQLKAVMDDFAAFVEKCCKADDKETCFAEEGKKLVAASQAALGLGAGGGGAGGGGAGGGGAGGGGAGGGGAGGGGADHCPLGPGRCCRLHTVRASLEDLGWADWVLSPREVQVTMCIGACPSQFRAANMHAQIKTSLHRLKPDTVPAPCCVPASYNPMVLIQKTDTGVSLQTYDDLLAKDCHCI | 49 |
| 18 | HGEGTFTSDVSSYLEEQAAKEFIAWLVKGGGGGGAGGGGAGGGGAGGGGAGGGGADAHKSEVAHRFKDLGEENFKALVLIAFAQYLQQSPFEDHVKLVNEVTEFAKTCVADESAENCDKSLHTLFGDKLCTVATLRETYGEMADCCAKQEPERNECFLQHKDDNPNLPRLVRPEVDVMCTAFHDNEETFLKKYLYEIARRHPYFYAPELLFFAKRYKAAFTECCQAADKAACLLPKLDELRDEGKASSAKQRLKCASLQKFGERAFKAWAVARLS | 50 |

TABLE 6-continued

GLP1-GDF15 fusion proteins

| GLP1-GDF15 fusion proteins | Protein Sequence | SEQ ID NO: |
|---|---|---|
| | QRFPKAEFAEVSKLVTDLTKVHTEC CHGDLLECADDRADLAKYICENQDS ISSKLKECCEKPLLEKSHCIAEVEN DEMPADLPSLAADFVESKDVCKNYA EAKDVFLGMFLYEYARRHPDYSVVL LLRLAKTYETTLEKCCAAADPHECY AKVFDEFKPLVEEPQNLIKQNCELF EQLGEYKFQNALLVRYTKKVPQVST PTLVEVSRNLGKVGSKCCKHPEAKR MPCAEDYLSVVLNQLCVLHEKTPVS DRVTKCCTESLVNRRPCFSALEVDE TYVPKEFNAETFTFHADICTLSEKE RQIKKQTALVELVKHKPKATKEQLK AVMDDFAAFVEKCCKADDKETCFAE EGKKLVAASQAALGLGAGGGGAGGG GAGGGGAGGGGAGGGGAGGGGAGGG GAGGGGADHCPLGPGRCCRLHTVRA SLEDLGWADWVLSPREVQVTMCIGA CPSQFRAANMHAQIKTSLHRLKPDT VPAPCCVPASYNPMVLIQKTDTGVS LQTYDDLLAKDCHCI | |
| 19 | HGEGTFTSDVSSYLEEQAAKEFIAW LVKGGGAGGGGAGGGGAGGGGAGGG GAGGGGAGGGGAGGGGAGGGGADAH KSEVAHRFKDLGEENFKALVLIAFA QYLQQSPFEDHVKLVNEVTEFAKTC VADESAENCDKSLHTLFGDKLCTVA TLRETYGEMADCCAKQEPERNECFL QHKDDNPNLPRLVRPEVDVMCTAFH DNEETFLKKYLYEIARRHPYFYAPE LLFFAKRYKAAFTECCQAADKAACL LPKLDELRDEGKASSAKQRLKCASL QKFGERAFKAWAVARLSQRFPKAEF AEVSKLVTDLTKVHTECCHGDLLEC ADDRADLAKYICENQDSISSKLKEC CEKPLLEKSHCIAEVENDEMPADLP SLAADFVESKDVCKNYAEAKDVFLG MFLYEYARRHPDYSVVLLLRLAKTY ETTLEKCCAAADPHECYAKVFDEFK PLVEEPQNLIKQNCELFEQLGEYKF QNALLVRYTKKVPQVSTPTLVEVSR NLGKVGSKCCKHPEAKRMPCAEDYL SVVLNQLCVLHEKTPVSDRVTKCCT ESLVNRRPCFSALEVDETYVPKEFN AETFTFHADICTLSEKERQIKKQTA LVELVKHKPKATKEQLKAVMDDFAA FVEKCCKADDKETCFAEEGKKLVAA SQAALGLGSGGGGSGGGGSGGGGSG GGGSGGGGSGGGGSGGGGSGGGGSD HCPLGPGRCCRLHTVRASLEDLGWA DWVLSPREVQVTMCIGACPSQFRAA NMHAQIKTSLHRLKPDTVPAPCCVP ASYNPMVLIQKTDTGVSLQTYDDLL AKDCHCI | 51 |
| 20 | HGEGTFTSDLSKQMEEEAVRLFIEW LKNGGPSSGAPPPSGAGGGGAGGGG ADAHKSEVAHRFKDLGEENFKALVL IAFAQYLQQSPFEDHVKLVNEVTEF AKTCVADESAENCDKSLHTLFGDKL CTVATLRETYGEMADCCAKQEPERN ECFLQHKDDNPNLPRLVRPEVDVMC TAFHDNEETFLKKYLYEIARRHPYF YAPELLFFAKRYKAAFTECCQAADK AACLLPKLDELRDEGKASSAKQRLK CASLQKFGERAFKAWAVARLSQRFP KAEFAEVSKLVTDLTKVHTECCHGD LLECADDRADLAKYICENQDSISSK LKECCEKPLLEKSHCIAEVENDEMP ADLPSLAADFVESKDVCKNYAEAKD VFLGMFLYEYARRHPDYSVVLLLRL AKTYETTLEKCCAAADPHECYAKVF | 52 |
| | DEFKPLVEEPQNLIKQNCELFEQLG EYKFQNALLVRYTKKVPQVSTPTLV EVSRNLGKVGSKCCKHPEAKRMPCA EDYLSVVLNQLCVLHEKTPVSDRVT KCCTESLVNRRPCFSALEVDETYVP KEFNAETFTFHADICTLSEKERQIK KQTALVELVKHKPKATKEQLKAVMD DFAAFVEKCCKADDKETCFAEEGKK LVAASQAALGLGSGGGGSGGGGSGG GGSGGGGSGGGGSGGGGSGGGGSGG GGSGGGGSDHCPLGPGRCCRLHTVR ASLEDLGWADWVLSPREVQVTMCIG ACPSQFRAANMHAQIKTSLHRLKPD TVPAPCCVPASYNPMVLIQKTDTGV SLQTYDDLLAKDCHCI | |
| 21 | HGEGTFTSDVSSYLEEQAAKEFIAW LVKGGGGGAGGGGAGGGGAGGGGGA GGGGAGGGGADAHKSEVAHRFKDLG EENFKALVLIAFAQYLQQSPFEDHV KLVNEVTEFAKTCVADESAENCDKS LHTLFGDKLCTVATLRETYGEMADC CAKQEPERNECFLQHKDDNPNLPRL VRPEVDVMCTAFHDNEETFLKKYLY EIARRHPYFYAPELLFFAKRYKAAF TECCQAADKAACLLPKLDELRDEGK ASSAKQRLKCASLQKFGERAFKAWA VARLSQRFPKAEFAEVSKLVTDLTK VHTECCHGDLLECADDRADLAKYIC ENQDSISSKLKECCEKPLLEKSHCI AEVENDEMPADLPSLAADFVESKDV CKNYAEAKDVFLGMFLYEYARRHPD YSVVLLLRLAKTYETTLEKCCAAAD PHECYAKVFDEFKPLVEEPQNLIKQ NCELFEQLGEYKFQNALLVRYTKKV PQVSTPTLVEVSRNLGKVGSKCCKH PEAKRMPCAEDYLSVVLNQLCVLHE KTPVSDRVTKCCTESLVNRRPCFSA LEVDETYVPKEFNAETFTFHADICT LSEKERQIKKQTALVELVKHKPKAT KEQLKAVMDDFAAFVEKCCKADDKE TCFAEEGKKLVAASQAALGLGSGGG GSGGGGSGGGGSGGGGSGGGGSGGG GSGGGGSGGGGSDHCPLGPGRCCRL HTVRASLEDLGWADWVLSPREVQVT MCIGACPSQFRAANMHAQIKTSLHR LKPDTVPAPCCVPASYNPMVLIQKT DTGVSLQTYDDLLAKDCHCI | 53 |
| 22 | HGEGTFTSDVSSYLEEQAAKEFIAW LVKGGGGGAGGGGAGGGGAGGGGGA GGGGADAHKSEVAHRFKDLGEENFK ALVLIAFAQYLQQSPFEDHVKLVNE VTEFAKTCVADESAENCDKSLHTLF GDKLCTVATLRETYGEMADCCAKQE PERNECFLQHKDDNPNLPRLVRPEV DVMCTAFHDNEETFLKKYLYEIARR HPYFYAPELLFFAKRYKAAFTECCQ AADKAACLLPKLDELRDEGKASSAK QRLKCASLQKFGERAFKAWAVARLS QRFPKAEFAEVSKLVTDLTKVHTEC CHGDLLECADDRADLAKYICENQDS ISSKLKECCEKPLLEKSHCIAEVEN DEMPADLPSLAADFVESKDVCKNYA EAKDVFLGMFLYEYARRHPDYSVVL LLRLAKTYETTLEKCCAAADPHECY AKVFDEFKPLVEEPQNLIKQNCELF EQLGEYKFQNALLVRYTKKVPQVST PTLVEVSRNLGKVGSKCCKHPEAKR MPCAEDYLSVVLNQLCVLHEKTPVS DRVTKCCTESLVNRRPCFSALEVDE TYVPKEFNAETFTFHADICTLSEKE RQIKKQTALVELVKHKPKATKEQLK | 54 |

TABLE 6-continued

GLP1-GDF15 fusion proteins

| GLP1-GDF15 fusion proteins | Protein Sequence | SEQ ID NO: |
|---|---|---|
| | AVMDDFAAFVEKCCKADDKETCFAE EGKKLVAASQAALGLGSGGGGSGGG GSGGGGSGGGGSGGGGSGGGGSGGG GSGGGGGSDHCPLGPGRCCRLHTVRA SLEDLGWADWVLSPREVQVTMCIGA CPSQFRAANMHAQIKTSLHRLKPDT VPAPCCVPASYNPMVLIQKTDTGVS LQTYDDLLAKDCHCI | |
| 23 | HGEGTFTSDVSSYLEEQAAKEFIAW LVKGGGGGGSGGGGSGGGGSGGGGS GGGGSGGGGSDAHKSEVAHRFKDLG EENFKALVLIAFAQYLQQSPFEDHV KLVNEVTEFAKTCVADESAENCDKS LHTLFGDKLCTVATLRETYGEMADC CAKQEPERNECFLQHKDDNPNLPRL VRPEVDVMCTAFHDNEETFLKKYLY EIARRHPYFYAPELLFFAKRYKAAF TECCQAADKAACLLPKLDELRDEGK ASSAKQRLKCASLQKFGERAFKAWA VARLSQRFPKAEFAEVSKLVTDLTK VHTECCHGDLLECADDRADLAKYIC ENQDSISSKLKECCEKPLLEKSHCI AEVENDEMPADLPSLAADFVESKDV CKNYAEAKDVFLGMFLYEYARRHPD YSVVLLLRLAKTYETTLEKCCAAAD PHECYAKVFDEFKPLVEEPQNLIKQ NCELFEQLGEYKFQNALLVRYTKKV PQVSTPTLVEVSRNLGKVGSKCCKH PEAKRMPCAEDYLSVVLNQLCVLHE KTPVSDRVTKCCTESLVNRRPCFSA LEVDETYVPKEFNAETFTFHADICT LSEKERQIKKQTALVELVKHKPKAT KEQLKAVMDDFAAFVEKCCKADDKE TCFAEEGKKLVAASQAALGLGSGGG GSGGGGSGGGGSGGGGSGGGGSGGG GSGGGGSGGGGSDHCPLGPGRCCRL HTVRASLEDLGWADWVLSPREVQVT MCIGACPSQFRAANMHAQIKTSLHR LKPDTVPAPCCVPASYNPMVLIQKT DTGVSLQTYDDLLAKDCHCI | 55 |
| 24 | HGEGTFTSDVSSYLEEQAAKEFIAW LVKGGGGGGSGGGGSGGGGSGGGGS GGGGSDAHKSEVAHRFKDLGEENFK ALVLIAFAQYLQQSPFEDHVKLVNE VTEFAKTCVADESAENCDKSLHTLF GDKLCTVATLRETYGEMADCCAKQE PERNECFLQHKDDNPNLPRLVRPEV DVMCTAFHDNEETFLKKYLYEIARR HPYFYAPELLFFAKRYKAAFTECCQ AADKAACLLPKLDELRDEGKASSAK QRLKCASLQKFGERAFKAWAVARLS QRFPKAEFAEVSKLVTDLTKVHTEC CHGDLLECADDRADLAKYICENQDS ISSKLKECCEKPLLEKSHCIAEVEN DEMPADLPSLAADFVESKDVCKNYA EAKDVFLGMFLYEYARRHPDYSVVL LLRLAKTYETTLEKCCAAADPHECY AKVFDEFKPLVEEPQNLIKQNCELF EQLGEYKFQNALLVRYTKKVPQVST PTLVEVSRNLGKVGSKCCKHPEAKR MPCAEDYLSVVLNQLCVLHEKTPVS DRVTKCCTESLVNRRPCFSALEVDE TYVPKEFNAETFTFHADICTLSEKE RQIKKQTALVELVKHKPKATKEQLK AVMDDFAAFVEKCCKADDKETCFAE EGKKLVAASQAALGLGSGGGGSGGG GSGGGGSGGGGSGGGGSGGGGSGGG GSGGGGSDHCPLGPGRCCRLHTVRA SLEDLGWADWVLSPREVQVTMCIGA CPSQFRAANMHAQIKTSLHRLKPDT | 56 |
| | VPAPCCVPASYNPMVLIQKTDTGVS LQTYDDLLAKDCHCI | |
| 25 | HGEGTFTSDVSSYLEEQAAKEFIAW LVKGGASAPAPAPAPAPAPAPAPAP APGSDAHKSEVAHRFKDLGEENFKA LVLIAFAQYLQQSPFEDHVKLVNEV TEFAKTCVADESAENCDKSLHTLFG DKLCTVATLRETYGEMADCCAKQEP ERNECFLQHKDDNPNLPRLVRPEVD VMCTAFHDNEETFLKKYLYEIARRH PYFYAPELLFFAKRYKAAFTECCQA ADKAACLLPKLDELRDEGKASSAKQ RLKCASLQKFGERAFKAWAVARLSQ RFPKAEFAEVSKLVTDLTKVHTECC HGDLLECADDRADLAKYICENQDSI SSKLKECCEKPLLEKSHCIAEVEND EMPADLPSLAADFVESKDVCKNYAE AKDVFLGMFLYEYARRHPDYSVVLL LRLAKTYETTLEKCCAAADPHECYA KVFDEFKPLVEEPQNLIKQNCELFE QLGEYKFQNALLVRYTKKVPQVSTP TLVEVSRNLGKVGSKCCKHPEAKRM PCAEDYLSVVLNQLCVLHEKTPVSD RVTKCCTESLVNRRPCFSALEVDET YVPKEFNAETFTFHADICTLSEKER QIKKQTALVELVKHKPKATKEQLKA VMDDFAAFVEKCCKADDKETCFAEE GKKLVAASQAALGLGSGGGGSGGGG SGGGGSGGGGSGGGGSGGGGSGGGG SGGGGSDHCPLGPGRCCRLHTVRAS LEDLGWADWVLSPREVQVTMCIGAC PSQFRAANMHAQIKTSLHRLKPDTV PAPCCVPASYNPMVLIQKTDTGVSL QTYDDLLAKDCHCI | 57 |
| 26 | HGEGTFTSDVSSYLEEQAAKEFIAW LVKGGASGGGGSGGGGSGGGGSGGG GSGGGGSGGGGSGGGGSGGGGSDAH KSEVAHRFKDLGEENFKALVLIAFA QYLQQSPFEDHVKLVNEVTEFAKTC VADESAENCDKSLHTLFGDKLCTVA TLRETYGEMADCCAKQEPLLFFAKR YKAAFTECCQAADKAACLLPKLDEL RDEGKASSAKQRLKCASLQKFGERA FKAWAVARLSQRFPKAEFAEVSKLV TDLTKVHTECCHGDLLECADDRADL AKYICENQDSISSKLKECCEKPLLE KSHCIAEVENDEMPADLPSLAADFV ESKDVCKNYAEAKDVFLGMFLYEYA RRHPDYSVVLLLRLAKTYETTLEKC CAAADPHECYAKVFDEFKPLVEEPQ NLIKQNCELFEQLGEYKFQNALLVR YTKKVPQVSTPTLVEVSRNLGKVGS KCCKHPEAKRMPCAEDYLSVVLNQL CVLHEKTPVSDRVTKCCTESLVNRR PCFSALEVDETYVPKEFNAETFTFH ADICTLSEKERQIKKQTALVELVKH KPKATKEQLKAVMDDFAAFVEKCCK ADDKETCFAEEGKKLVAASQAALGL GSGGGGSGGGGSGGGGSGGGGSGGG GSGGGGSGGGGSGGGGSDHCPLGPG RCCRLHTVRASLEDLGWADWVLSPR EVQVTMCIGACPSQFRAANMHAQIK TSLHRLKPDTVPAPCCVPASYNPMV LIQKTDTGVSLQTYDDLLAKDCHCI | 58 |
| 27 | HGEGTFTSDLSKQMEEEAVRLFIEW LKNGGPSSGAPPPSASGGGGSGGGG SGGGGSGGGGSGGGGSGGGGSGGGG SGGGGSDAHKSEVAHRFKDLGEENF KALVLIAFAQYLQQSPFEDHVKLVN EVTEFAKTCVADESAENCDKSLHTL | 59 |

TABLE 6-continued

GLP1-GDF15 fusion proteins

| GLP1-GDF15 fusion proteins | Protein Sequence | SEQ ID NO: |
|---|---|---|
| | FGDKLCTVATLRETYGEMADCCAKQ EPERNECFLQHKDDNPNLPRLVRPE VDVMCTAFHDNEETFLKKYLYEIAR RHPYFYAPELLFFAKRYKAAFTECC QAADKAACLLPKLDELRDEGKASSA KQRLKCASLQKFGERAFKAWAVARL SQRFPKAEFAEVSKLVTDLTKVHTE CCHGDLLECADDRADLAKYICENQD SISSKLKECCEKPLLEKSHCIAEVE NDEMPADLPSLAADFVESKDVCKNY AEAKDVFLGMFLYEYARRHPDYSVV LLLRLAKTYETTLEKCCAAADPHEC YAKVFDEFKPLVEEPQNLIKQNCEL FEQLGEYKFQNALLVRYTKKVPQVS TPTLVEVSRNLGKVGSKCCKHPEAK RMPCAEDYLSVVLNQLCVLHEKTPV SDRVTKCCTESLVNRRPCFSALEVD ETYVPKEFNAETFTFHADICTLSEK ERQIKKQTALVELVKHKPKATKEQL KAVMDDFAAFVEKCCKADDKETCFA EEGKKLVAASQAALGLGSGGGGSGG GGSGGGGSGGGGSGGGGSGGGGSGG GGSGGGGSDHCPLGPGRCCRLHTVR ASLEDLGWADWVLSPREVQVTMCIG ACPSQFRAANMHAQIKTSLHRLKPD TVPAPCCVPASYNPMVLIQKTDTGV SLQTYDDLLAKDCHCI | |
| 28 | HGEGTFTSDLSKQMEEEAVRLFIEW LKNGGPSSGAPPPSASAPAPAPAPA PAPAPAPAPGSDAHKSEVAHRFKDL GEENFKALVLIAFAQYLQQSPFEDH VKLVNEVTEFAKTCVADESAENCDK SLHTLFGDKLCTVATLRETYGEMAD CCAKQEPERNECFLQHKDDNPNLPR LVRPEVDVMCTAFHDNEETFLKKYL YEIARRHPYFYAPELLFFAKRYKAA FTECCQAADKAACLLPKLDELRDEG KASSAKQRLKCASLQKFGERAFKAW AVARLSQRFPKAEFAEVSKLVTDLT KVHTECCHGDLLECADDRADLAKYI CENQDSISSKLKECCEKPLLEKSHC IAEVENDEMPADLPSLAADFVESKD VCKNYAEAKDVFLGMFLYEYARRHP DYSVVLLLRLAKTYETTLEKCCAAA DPHECYAKVFDEFKPLVEEPQNLIK QNCELFEQLGEYKFQNALLVRYTKK VPQVSTPTLVEVSRNLGKVGSKCCK HPEAKRMPCAEDYLSVVLNQLCVLH EKTPVSDRVTKCCTESLVNRRPCFS ALEVDETYVPKEFNAETFTFHADIC TLSEKERQIKKQTALVELVKHKPKA TKEQLKAVMDDFAAFVEKCCKADDK ETCFAEEGKKLVAASQAALGLGSGG GGSGGGGSGGGGSGGGGSGGGGSGG GGSGGGGSDHCPLGPGRCCRLHTVR ASLEDLGWADWVLSPREVQVTMCIG ACPSQFRAANMHAQIKTSLHRLKPD TVPAPCCVPASYNPMVLIQKTDTGV SLQTYDDLLAKDCHCI | 60 |
| 29 | HSEGTFTSDVSSYLEGQAAKEFIEW LVKGRASAPAPAPAPAPAPAPAPAP APGSDAHKSEVAHRFKDLGEENFKA LVLIAFAQYLQQSPFEDHVKLVNEV TEFAKTCVADESAENCDKSLHTLFG DKLCTVATLRETYGEMADCCAKQEP ERNECFLQHKDDNPNLPRLVRPEVD VMCTAFHDNEETFLKKYLYEIARRH PYFYAPELLFFAKRYKAAFTECCQA ADKAACLLPKLDELRDEGKASSAKQ RLKCASLQKFGERAFKAWAVARLSQ RFPKAEFAEVSKLVTDLTKVHTECC | 61 |

TABLE 6-continued

GLP1-GDF15 fusion proteins

| GLP1-GDF15 fusion proteins | Protein Sequence | SEQ ID NO: |
|---|---|---|
| | HGDLLECADDRADLAKYICENQDSI SSKLKECCEKPLLEKSHCIAEVEND EMPADLPSLAADFVESKDVCKNYAE AKDVFLGMFLYEYARRHPDYSVVLL LRLAKTYETTLEKCCAAADPHECYA KVFDEFKPLVEEPQNLIKQNCELFE QLGEYKFQNALLVRYTKKVPQVSTP TLVEVSRNLGKVGSKCCKHPEAKRM PCAEDYLSVVLNQLCVLHEKTPVSD RVTKCCTESLVNRRPCFSALEVDET YVPKEFNAETFTFHADICTLSEKER QIKKQTALVELVKHKPKATKEQLKA VMDDFAAFVEKCCKADDKETCFAEE GKKLVAASQAALGLGSGGGGSGGGG SGGGGSGGGGSGGGGSGGGGSGGGG SGGGGSDHCPLGPGRCCRLHTVRAS LEDLGWADWVLSPREVQVTMCIGAC PSQFRAANMHAQIKTSLHRLKPDTV PAPCCVPASYNPMVLIQKTDTGVSL QTYDDLLAKDCHCI | |
| 30 | HSEGTFTSDVSSYLEGQAAKEFIEW LVKGRASGGGGSGGGGSGGGGSGGG GSGGGGSGGGGSGGGGSGGGGSDAH KSEVAHRFKDLGEENFKALVLIAFA QYLQQSPFEDHVKLVNEVTEFAKTC VADESAENCDKSLHTLFGDKLCTVA TLRETYGEMADCCAKQEPERNECFL QHKDDNPNLPRLVRPEVDVMCTAFH DNEETFLKKYLYEIARRHPYFYAPE LLFFAKRYKAAFTECCQAADKAACL LPKLDELRDEGKASSAKQRLKCASL QKFGERAFKAWAVARLSQRFPKAEF AEVSKLVTDLTKVHTECCHGDLLEC ADDRADLAKYICENQDSISSKLKEC CEKPLLEKSHCIAEVENDEMPADLP SLAADFVESKDVCKNYAEAKDVFLG MFLYEYARRHPDYSVVLLLRLAKTY ETTLEKCCAAADPHECYAKVFDEFK PLVEEPQNLIKQNCELFEQLGEYKF QNALLVRYTKKVPQVSTPTLVEVSR NLGKVGSKCCKHPEAKRMPCAEDYL SVVLNQLCVLHEKTPVSDRVTKCCT ESLVNRRPCFSALEVDETYVPKEFN AETFTFHADICTLSEKERQIKKQTA LVELVKHKPKATKEQLKAVMDDFAA FVEKCCKADDKETCFAEEGKKLVAA SQAALGLGSGGGGSGGGGSGGGGSG GGGSGGGGSGGGGSGGGGSGGGGSD HCPLGPGRCCRLHTVRASLEDLGWA DWVLSPREVQVTMCIGACPSQFRAA NMHAQIKTSLHRLKPDTVPAPCCVP ASYNPMVLIQKTDTGVSLQTYDDLL AKDCHCI | 62 |
| 31 | HGEGTFTSDVSSYLEEQAAKEFIAW LVKGGGGGSGGGGSGGGGSDAHKS EVAHRFKDLGEENFKALVLIAFAQY LQQSPFEDHVKLVNEVTEFAKTCVA DESAENCDKSLHTLFGDKLCTVATL RETYGEMADCCAKQEPERNECFLQH KDDNPNLPRLVRPEVDVMCTAFHDN EETFLKKYLYEIARRHPYFYAPELL FFAKRYKAAFTECCQAADKAACLLP KLDELRDEGKASSAKQRLKCASLQK FGERAFKAWAVARLSQRFPKAEFAE VSKLVTDLTKVHTECCHGDLLECAD DRADLAKYICENQDSISSKLKECCE KPLLEKSHCIAEVENDEMPADLPSL AADFVESKDVCKNYAEAKDVFLGMF LYEYARRHPDYSVVLLLRLAKTYET TLEKCCAAADPHECYAKVFDEFKPL VEEPQNLIKQNCELFEQLGEYKFQN | 63 |

TABLE 6-continued

GLP1-GDF15 fusion proteins

| GLP1-GDF15 fusion proteins | Protein Sequence | SEQ ID NO: |
|---|---|---|
| | ALLVRYTKKVPQVSTPTLVEVSRNL GKVGSKCCKHPEAKRMPCAEDYLSV VLNQLCVLHEKTPVSDRVTKCCTES LVNRRPCFSALEVDETYVPKEFNAE TFTFHADICTLSEKERQIKKQTALV ELVKHHKPKATKEQLKAVMDDFAAFV EKCCKADDKETCFAEEGKKLVAASQ AALGLGSGGGGSGGGGSGGGGSGGG GSGGGGSGGGGSGGGGSGGGGSDHC PLGPGRCCRLHTVRASLEDLGWADW VLSPREVQVTMCIGACPSQFRAANM HAQIKTSLHRLKPDTVPAPCCVPAS YNPMVLIQKTDTGVSLQTYDDLLAK DCHCI | |
| 32 | HGEGTFTSDLSKQMEEEAVRLFIEW LKNGGPSSGAPPPSGGGGSGGGGSG GGGSDAHKSEVAHRFKDLGEENFKA LVLIAFAQYLQQSPFEDHVKLVNEV TEFAKTCVADESAENCDKSLHTLFG DKLCTVATLRETYGEMADCCAKQEP ERNECFLQHKDDNPNLPRLVRPEVD VMCTAFHDNEETFLKKYLYEIARRH PYFYAPELLFFAKRYKAAFTECCQA ADKAACLLPKLDELRDEGKASSAKQ RLKCASLQKFGERAFKAWAVARLSQ RFPKAEFAEVSKLVTDLTKVHTECC HGDLLECADDRADLAKYICENQDSI SSKLKECCEKPLLEKSHCIAEVEND EMPADLPSLAADFVESKDVCKNYAE AKDVFLGMFLYEYARRHPDYSVVLL LRLAKTYETTLEKCCAAADPHECYA KVFDEFKPLVEEPQNLIKQNCELFE QLGEYKFQNALLVRYTKKVPQVSTP TLVEVSRNLGKVGSKCCKHPEAKRM PCAEDYLSVVLNQLCVLHEKTPVSD RVTKCCTESLVNRRPCFSALEVDET YVPKEFNAETFTFHADICTLSEKER QIKKQTALVELVKHKPKATKEQLKA VMDDFAAFVEKCCKADDKETCFAEE GKKLVAASQAALGLGSGGGGSGGGG SGGGGSGGGGSGGGGSGGGGSGGGG SGGGGSDHCPLGPGRCCRLHTVRAS LEDLGWADWVLSPREVQVTMCIGAC PSQFRAANMHAQIKTSLHRLKPDTV PAPCCVPASYNPMVLIQKTDTGVSL QTYDDLLAKDCHCI | 64 |
| 33 | HSEGTFTSDVSSYLEGQAAKEFIEW LVKGRASGGGGSGGGGSDAHKSEVA HRFKDLGEENFKALVLIAFAQYLQQ SPFEDHVKLVNEVTEFAKTCVADES AENCDKSLHTLFGDKLCTVATLRET YGEMADCCAKQEPERNECFLQHKDD NPNLPRLVRPEVDVMCTAFHDNEET FLKKYLYEIARRHPYFYAPELLFFA KRYKAAFTECCQAADKAACLLPKLD ELRDEGKASSAKQRLKCASLQKFGE RAFKAWAVARLSQRFPKAEFAEVSK LVTDLTKVHTECCHGDLLECADDRA DLAKYICENQDSISSKLKECCEKPL LEKSHCIAEVENDEMPADLPSLAAD FVESKDVCKNYAEAKDVFLGMFLYE YARRHPDYSVVLLLRLAKTYETTLE KCCAAADPHECYAKVFDEFKPLVEE PQNLIKQNCELFEQLGEYKFQNALL VRYTKKVPQVSTPTLVEVSRNLGKV GSKCCKHPEAKRMPCAEDYLSVVLN QLCVLHEKTPVSDRVTKCCTESLVN RRPCFSALEVDETYVPKEFNAETFT FHADICTLSEKERQIKKQTALVELV KHKPKATKEQLKAVMDDFAAFVEKC CKADDKETCFAEEGKKLVAASQAAL | 65 |
| | GLGSGGGGSGGGGSGGGGSGGGGSG GGGSGGGGSGGGGSGGGGSGGGGSG GGGSGGGGSGGGGSGGGGSDHCPLG PGRCCRLHTVRASLEDLGWADWVLS PREVQVTMCIGACPSQFRAANMHAQ IKTSLHRLKPDTVPAPCCVPASYNP MVLIQKTDTGVSLQTYDDLLAKDCH CI | |
| 34 | HSEGTFTSDVSSYLEGQAAKEFIEW LVKGRASAPAPAPAPAPGSDAHKSE VAHRFKDLGEENFKALVLIAFAQYL QQSPFEDHVKLVNEVTEFAKTCVAD ESAENCDKSLHTLFGDKLCTVATLR ETYGEMADCCAKQEPERNECFLQHK DDNPNLPRLVRPEVDVMCTAFHDNE ETFLKKYLYEIARRHPYFYAPELLF FAKRYKAAFTECCQAADKAACLLPK LDELRDEGKASSAKQRLKCASLQKF GERAFKAWAVARLSQRFPKAEFAEV SKLVTDLTKVHTECCHGDLLECADD RADLAKYICENQDSISSKLKECCEK PLLEKSHCIAEVENDEMPADLPSLA ADFVESKDVCKNYAEAKDVFLGMFL YEYARRHPDYSVVLLLRLAKTYETT LEKCCAAADPHECYAKVFDEFKPLV EEPQNLIKQNCELFEQLGEYKFQNA LLVRYTKKVPQVSTPTLVEVSRNLG KVGSKCCKHPEAKRMPCAEDYLSVV LNQLCVLHEKTPVSDRVTKCCTESL VNRRPCFSALEVDETYVPKEFNAET FTFHADICTLSEKERQIKKQTALVE LVKHKPKATKEQLKAVMDDFAAFVE KCCKADDKETCFAEEGKKLVAASQA ALGLGSGGGGSGGGGSGGGGSGGGG SGGGGSGGGGSGGGGSGGGGSDHCP LGPGRCCRLHTVRASLEDLGWADWV LSPREVQVTMCIGACPSQFRAANMH AQIKTSLHRLKPDTVPAPCCVPASY NPMVLIQKTDTGVSLQTYDDLLAKD CHCI | 66 |
| 35 | HGEGTFTSDLSKQMEEEAVRLFIEW LKNGGPSSGAPPPSASGGGGSGGGG SDAHKSEVAHRFKDLGEENFKALVL IAFAQYLQQSPFEDHVKLVNEVTEF AKTCVADESAENCDKSLHTLFGDKL CTVATLRETYGEMADCCAKQEPERN ECFLQHKDDNPNLPRLVRPEVDVMC TAFHDNEETFLKKYLYEIARRHPYF YAPELLFFAKRYKAAFTECCQAADK AACLLPKLDELRDEGKASSAKQRLK CASLQKFGERAFKAWAVARLSQRFP KAEFAEVSKLVTDLTKVHTECCHGD LLECADDRADLAKYICENQDSISSK LKECCEKPLLEKSHCIAEVENDEMP ADLPSLAADFVESKDVCKNYAEAKD VFLGMFLYEYARRHPDYSVVLLLRL AKTYETTLEKCCAAADPHECYAKVF DEFKPLVEEPQNLIKQNCELFEQLG EYKFQNALLVRYTKKVPQVSTPTLV EVSRNLGKVGSKCCKHPEAKRMPCA EDYLSVVLNQLCVLHEKTPVSDRVT KCCTESLVNRRPCFSALEVDETYVP KEFNAETFTFHADICTLSEKERQIK KQTALVELVKHKPKATKEQLKAVMD DFAAFVEKCCKADDKETCFAEEGKK LVAASQAALGLGSGGGGSGGGGSGG GGSGGGGSGGGGSGGGGSGGGGSGG GGSDHCPLGPGRCCRLHTVRASLED LGWADWVLSPREVQVTMCIGACPSQ FRAANMHAQIKTSLHRLKPDTVPAP CCVPASYNPMVLIQKTDTGVSLQTY DDLLAKDCHCI | 67 |

TABLE 6-continued

GLP1-GDF15 fusion proteins

| GLP1-GDF15 fusion proteins | Protein Sequence | SEQ ID NO: |
|---|---|---|
| 36 | HGEGTFTSDLSKQMEEEAVRLFIEW LKNGGPSSGAPPPSASAPAPAPA PGSDAHKSEVAHRFKDLGEENFKAL VLIAFAQYLQQSPFEDHVKLVNEVT EFAKTCVADESAENCDKSLHTLFGD KLCTVATLRETYGEMADCCAKQEPE RNECFLQHKDDNPNLPRLVRPEVDV MCTAFHDNEETFLKKYLYEIARRHP YFYAPELLFFAKRYKAAFTECCQAA DKAACLLPKLDELRDEGKASSAKQR LKCASLQKFGERAFKAWAVARLSQR FPKAEFAEVSKLVTDLTKVHTECCH GDLLECADDRADLAKYICENQDSIS SKLKECCEKPLLEKSHCIAEVENDE MPADLPSLAADFVESKDVCKNYAEA KDVFLGMFLYEYARRHPDYSVVLLL RLAKTYETTLEKCCAAADPHECYAK VFDEFKPLVEEPQNLIKQNCELFEQ LGEYKFQNALLVRYTKKVPQVSTPT LVEVSRNLGKVGSKCCKHPEAKRMP CAEDYLSVVLNQLCVLHEKTPVSDR VTKCCTESLVNRRPCFSALEVDETY VPKEFNAETFTFHADICTLSEKERQ IKKQTALVELVKHKPKATKEQLKAV MDDFAAFVEKCCKADDKETCFAEEG KKLVAASQAALGLGSGGGGSGGGGS GGGGSGGGGSGGGGSGGGGSGGGGS GGGGSDHCPLGPGRCCRLHTVRASL EDLGWADWVLSPREVQVTMCIGACP SQFRAANMHAQIKTSLHRLKPDTVP APCCVPASYNPMVLIQKTDTGVSLQ TYDDLLAKDCHCI | 68 |
| 37 | HGEGTFTSDVSSYLEEQAAKEFIAW LVKGGASGGGGSGGGGSDAHKSEVA HRFKDLGEENFKALVLIAFAQYLQQ SPFEDHVKLVNEVTEFAKTCVADES AENCDKSLHTLFGDKLCTVATLRET YGEMADCCAKQEPERNECFLQHKDD NPNLPRLVRPEVDVMCTAFHDNEET FLKKYLYEIARRHPYFYAPELLFFA KRYKAAFTECCQAADKAACLLPKLD ELRDEGKASSAKQRLKCASLQKFGE RAFKAWAVARLSQRFPKAEFAEVSK LVTDLTKVHTECCHGDLLECADDRA DLAKYICENQDSISSKLKECCEKPL LEKSHCIAEVENDEMPADLPSLAAD FVESKDVCKNYAEAKDVFLGMFLYE YARRHPDYSVVLLLRLAKTYETTLE KCCAAADPHECYAKVFDEFKPLVEE PQNLIKQNCELFEQLGEYKFQNALL VRYTKKVPQVSTPTLVEVSRNLGKV GSKCCKHPEAKRMPCAEDYLSVVLN QLCVLHEKTPVSDRVTKCCTESLVN RRPCFSALEVDETYVPKEFNAETFT FHADICTLSEKERQIKKQTALVELV KHKPKATKEQLKAVMDDFAAFVEKC CKADDKETCFAEEGKKLVAASQAAL GLGSGGGGSGGGGSGGGGSGGGGSG GGGSGGGGSGGGGSGGGGSDHCPLG PGRCCRLHTVRASLEDLGWADWVLS PREVQVTMCIGACPSQFRAANMHAQ IKTSLHRLKPDTVPAPCCVPASYNP MVLIQKTDTGVSLQTYDDLLAKDCH CI | 69 |
| 38 | HGEGTFTSDVSSYLEEQAAKEFIAW LVKGGASAPAPAPAPAPAPGSDAHKSE VAHRFKDLGEENFKALVLIAFAQYL QQSPFEDHVKLVNEVTEFAKTCVAD ESAENCDKSLHTLFGDKLCTVATLR ETYGEMADCCAKQEPERNECFLQHK DDNPNLPRLVRPEVDVMCTAFHDNE ETFLKKYLYEIARRHPYFYAPELLF FAKRYKAAFTECCQAADKAACLLPK LDELRDEGKASSAKQRLKCASLQKF GERAFKAWAVARLSQRFPKAEFAEV SKLVTDLTKVHTECCHGDLLECADD RADLAKYICENQDSISSKLKECCEK PLLEKSHCIAEVENDEMPADLPSLA ADFVESKDVCKNYAEAKDVFLGMFL YEYARRHPDYSVVLLLRLAKTYETT LEKCCAAADPHECYAKVFDEFKPLV EEPQNLIKQNCELFEQLGEYKFQNA LLVRYTKKVPQVSTPTLVEVSRNLG KVGSKCCKHPEAKRMPCAEDYLSVV LNQLCVLHEKTPVSDRVTKCCTESL VNRRPCFSALEVDETYVPKEFNAET FTFHADICTLSEKERQIKKQTALVE LVKHKPKATKEQLKAVMDDFAAFV EKCCKADDKETCFAEEGKKLVAASQA ALGLGSGGGGSGGGGSGGGGSGGGG SGGGGSGGGGSGGGGSGGGGSDHCP LGPGRCCRLHTVRASLEDLGWADWV LSPREVQVTMCIGACPSQFRAANMH AQIKTSLHRLKPDTVPAPCCVPASY NPMVLIQKTDTGVSLQTYDDLLAKD CHCI | 70 |
| 39 | HSEGTFTSDVSSYLEGQAAKEFIEW LVKGRGGGGSGGGGSGGGGSDAHKS EVAHRFKDLGEENFKALVLIAFAQY LQQSPFEDHVKLVNEVTEFAKTCVA DESAENCDKSLHTLFGDKLCTVATL RETYGEMADCCAKQEPERNECFLQH KDDNPNLPRLVRPEVDVMCTAFHDN EETFLKKYLYEIARRHPYFYAPELL FFAKRYKAAFTECCQAADKAACLLP KLDELRDEGKASSAKQRLKCASLQK FGERAFKAWAVARLSQRFPKAEFAE VSKLVTDLTKVHTECCHGDLLECAD DRADLAKYICENQDSISSKLKECCE KPLLEKSHCIAEVENDEMPADLPSL AADFVESKDVCKNYAEAKDVFLGMF LYEYARRHPDYSVVLLLRLAKTYET TLEKCCAAADPHECYAKVFDEFKPL VEEPQNLIKQNCELFEQLGEYKFQN ALLVRYTKKVPQVSTPTLVEVSRNL GKVGSKCCKHPEAKRMPCAEDYLSV VLNQLCVLHEKTPVSDRVTKCCTES LVNRRPCFSALEVDETYVPKEFNAE TFTFHADICTLSEKERQIKKQTALV ELVKHKPKATKEQLKAVMDDFAAFV EKCCKADDKETCFAEEGKKLVAASQ AALGLGSGGGGSGGGGSGGGGSGGG GSGGGGSGGGGSGGGGSGGGGSDHC PLGPGRCCRLHTVRASLEDLGWADW VLSPREVQVTMCIGACPSQFRAANM HAQIKTSLHRLKPDTVPAPCCVPAS YNPMVLIQKTDTGVSLQTYDDLLAK DCHCI | 71 |
| 40 | HGEGTFTSDVSSYLEEQAAKEFIAW LVKGGGGGSGGGGSGGGGSDAHKS EVAHRFKDLGEETFKALVLIAFAQY LQQSPFEDHVKLVNEVTEFAKTCVA DESAENCDKSLHTLFGDKLCTVATL RETYGEMADCCAKQEPERNECFLQH KDDNPNLPRLVRPEVDVMCTAFHDN EETFLKKYLYEIARRHPYFYAPELL FFAARYKAAFTECCQAADKAACLLP KLDELRDEGKASSAKQRLKCASLQK FGERAFKAWAVARLSQRFPKAEFAE VSKLVTDLTKVHTECCHGDLLECAD DRADLAKYICENQDSISSKLKECCE | 12 |

TABLE 6-continued

GLP1-GDF15 fusion proteins

| GLP1-GDF15 fusion proteins | Protein Sequence | SEQ ID NO: |
|---|---|---|
| | KPLLEKSHCLAEVENDEMPADLPSL AADFVESKDVCKNYAEAKDVFLGMF LYEYARRHPDYSVVLLLRLAKTYET TLEKCCAAADPHECYAKVFDEFKPL VEEPQNLIKQNCELFEQLGEYKFQN ALLVRYTKKVPQVSTPTLVEVSRNL GKVGSKCCKHPEAKRMPCAEDYLSV VLNQLCVLHEKTPVSDRVTKCCTES LVNRRPCFSALEVDETYVPKEFNAE TFTFHADICTLSEKERQIKKQTALA ELVKHKPKATKEQLKTVMDDFAAFV EKCCKADDKETCFAEEGKKLVAASQ AALGLGSGGGSGGGGSGGGGSGGG GSGGGSGGGGSGGGGSGGGGSDHC PLGPGRCCRLHTVRASLEDLGWADW VLSPREVQVTMCIGACPSQFRAANM HAQIKTSLHRLKPDTVPAPCCVPAS YNPMVLIQKTDTGVSLQTYDDLLAK DCHCI | |
| 41 | HGEGTFTSDVSSYLEEQAAKEFIAW LVKGGGGGSGGGGSGGGGSDAHKS EVAHRFKDLGEETFKALVLVAFAQY LQQSPFEDHVKLVNEVTEFAKTCVA DESAENCDKSLHTLFGDKLCTVATL RETYGEMADCCAKQEPERNECFLQH KDDNPNLPRLVRPEVDVMCTAFHDN EETFLKKYLYEIARRHPYFYAPELL FFAARYKAAFTECCQAADKAACLLP KLDELRDEGKASSAKQRLKCASLQK FGERAFKAWAVARLSQRFPKAEFAE VSKLVTDLTKVHTECCHGDLLECAD DRADLAKYICENQDSISSKLKECCE KPLLEKSHCLAEVENDEMPADLPSL AADFVESKDVCKNYAEAKDVFLGMF LYEYARRHPDYSVVLLLRLAKTYET TLEKCCAAADPHECYAKVFDEFKPL VEEPQNLIKQNCELFEQLGEYKFQN ALLVRYTKKVPQVSTPTLVEVSRNL GKVGSKCCKHPEAKRMPCAEDYLSV VLNQLCVLHEKTPVSDRVTKCCTES LVNRRPCFSALEVDETYVPKEFNAE TFTFHADICTLSEKERQIKKQTALA ELVKHKPKATKEQLKTVMDDFAAFV EKCCKADDKETCFAEEGKKLVAASQ AALGLGSGGGSGGGGSGGGGSGGG GSGGGSGGGGSGGGGSGGGGSDHC PLGPGRCCRLHTVRASLEDLGWADW VLSPREVQVTMCIGACPSQFRAANM HAQIKTSLHRLKPDTVPAPCCVPAS YNPMVLRQKTDTGVSLQTYDDLLAK DCHCI | 73 |
| 42 | EGTFTSDVSSYLEEQAAKEFIAWLV KGGGGGSGGGGSGGGGSDAHKSEV AHRFKDLGEETFKALVLVAFAQYLQ QSPFEDHVKLVNEVTEFAKTCVADE SAENCDKSLHTLFGDKLCTVATLRE TYGEMADCCAKQEPERNECFLQHKD DNPNLPRLVRPEVDVMCTAFHDNEE TFLKKYLYEIARRHPYFYAPELLFF AARYKAAFTECCQAADKAACLLPKL DELRDEGKASSAKQRLKCASLQKFG ERAFKAWAVARLSQRFPKAEFAEVS KLVTDLTKVHTECCHGDLLECADDR ADLAKYICENQDSISSKLKECCEKP LLEKSHCLAEVENDEMPADLPSLAA DFVESKDVCKNYAEAKDVFLGMFLY EYARRHPDYSVVLLLRLAKTYETTL EKCCAAADPHECYAKVFDEFKPLVE EPQNLIKQNCELFEQLGEYKFQNAL LVRYTKKVPQVSTPTLVEVSRNLGK VGSKCCKHPEAKRMPCAEDYLSVVL NQLCVLHEKTPVSDRVTKCCTESLV NRRPCFSALEVDETYVPKEFNAETF TFHADICTLSEKERQIKKQTALAEL VKHKPKATKEQLKTVMDDFAAFVEK CCKADDKETCFAEEGKKLVAASQAA LGLGSGGGSGGGGSGGGGSGGGGS GGGGSGGGGSGGGGSGGGGSDHCPL GPGRCCRLHTVRASLEDLGWADWVL SPREVQVTMCIGACPSQFRAANMHA QIKTSLHRLKPDTVPAPCCVPASYN PMVLIQKTDTGVSLQTYDDLLAKDC HCI | 74 |

GLP1-GDF15 Fusion Polynucleotides and Vectors

In another general aspect, the invention relates to an isolated nucleic acid encoding the GLP1-GDF15 fusion proteins of the invention. It will be appreciated by those skilled in the art that the coding sequence of a protein can be changed (e.g., replaced, deleted, inserted, etc.) without changing the amino acid sequence of the protein. Accordingly, it will be understood by those skilled in the art that nucleic acid sequences encoding the fusion proteins of the invention can be altered without changing the amino acid sequences of the proteins.

In another general aspect, the invention relates to a vector comprising an isolated nucleic acid encoding a fusion protein of the invention. Any vector known to those skilled in the art in view of the present disclosure can be used, such as a plasmid, a cosmid, a phage vector or a viral vector. In some embodiments, the vector is a recombinant expression vector such as a plasmid. The vector can include any element to establish a conventional function of an expression vector, for example, a promoter, ribosome binding element, terminator, enhancer, selection marker, and origin of replication. The promoter can be a constitutive, inducible or repressible promoter. A number of expression vectors capable of delivering nucleic acids to a cell are known in the art and can be used herein for production of a fusion protein in the cell. Conventional cloning techniques or artificial gene synthesis can be used to generate a recombinant expression vector according to embodiments of the invention.

In another general aspect, the invention relates to a host cell comprising an isolated nucleic acid encoding a fusion protein of the invention. Any host cell known to those skilled in the art in view of the present disclosure can be used for recombinant expression of fusion proteins of the invention. In some embodiments, the host cells are *E. coli* TG1 or BL21 cells, CHO-DG44 or CHO-K1 cells or HEK293 cells. According to particular embodiments, the recombinant expression vector is transformed into host cells by conventional methods such as chemical transfection, heat shock, or electroporation, where it is stably integrated into the host cell genome such that the recombinant nucleic acid is effectively expressed.

In another general aspect, the invention relates to a method of producing a fusion protein of the invention, comprising culturing a cell comprising a nucleic acid encoding the fusion protein under conditions to produce a fusion protein of the invention, and recovering the fusion protein from the cell or cell culture (e.g., from the supernatant). Expressed fusion proteins can be harvested from the cells and purified according to conventional techniques known in the art and as described herein.

Pharmaceutical Compositions

In another general aspect, the invention relates to a pharmaceutical composition, comprising the GLP1-GDF15 fusion proteins and/or GLP1-GDF15 fusion polynucleotides of the invention and a pharmaceutically acceptable carrier. The term "pharmaceutical composition" as used herein means a product comprising a GLP1-GDF15 fusion proteins and/or GLP1-GDF15 fusion polynucleotides of the invention together with a pharmaceutically acceptable carrier. GLP1-GDF15 fusion proteins and/or GLP1-GDF15 fusion polynucleotides of the invention and compositions comprising them are also useful in the manufacture of a medicament for therapeutic applications mentioned herein.

As used herein, the term "carrier" refers to any excipient, diluent, filler, salt, buffer, stabilizer, solubilizer, oil, lipid, lipid containing vesicle, microsphere, liposomal encapsulation, or other material well known in the art for use in pharmaceutical formulations. It will be understood that the characteristics of the carrier, excipient or diluent will depend on the route of administration for a particular application. As used herein, the term "pharmaceutically acceptable carrier" refers to a non-toxic material that does not interfere with the effectiveness of a composition according to the invention or the biological activity of a composition according to the invention. According to particular embodiments, in view of the present disclosure, any pharmaceutically acceptable carrier suitable for use in a peptide pharmaceutical composition can be used in the invention.

Pharmaceutically acceptable acidic/anionic salts for use in the invention include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate and triethiodide. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid.

Pharmaceutically acceptable basic/cationic salts include, and are not limited to aluminum, 2-amino-2-hydroxymethyl-propane-1,3-diol (also known as tris(hydroxymethyl) aminomethane, tromethane or "TRIS"), ammonia, benzathine, t-butylamine, calcium, chloroprocaine, choline, cyclohexylamine, diethanolamine, ethylenediamine, lithium, L-lysine, magnesium, meglumine, N-methyl-D-glucamine, piperidine, potassium, procaine, quinine, sodium, triethanolamine, or zinc.

In some embodiments of the invention, pharmaceutical formulations are provided comprising the GLP1-GDF15 fusion proteins and/or GLP1-GDF15 fusion polynucleotides of the invention in an amount from about 0.001 mg/ml to about 100 mg/ml, from about 0.01 mg/ml to about 50 mg/ml, or from about 0.1 mg/ml to about 25 mg/ml. The pharmaceutical formulation can have a pH from about 3.0 to about 10, for example from about 3 to about 7, or from about 5 to about 9. The formulation can further comprise at least one ingredient selected from the group consisting of a buffer system, preservative(s), tonicity agent(s), chelating agent(s), stabilizer(s) and surfactant(s).

The formulation of pharmaceutically active ingredients with pharmaceutically acceptable carriers is known in the art, e.g., Remington: The Science and Practice of Pharmacy (e.g. 21st edition (2005), and any later editions). Non-limiting examples of additional ingredients include: buffers, diluents, solvents, tonicity regulating agents, preservatives, stabilizers, and chelating agents. One or more pharmaceutically acceptable carriers can be used in formulating the pharmaceutical compositions of the invention.

In one embodiment of the invention, the pharmaceutical composition is a liquid formulation. A preferred example of a liquid formulation is an aqueous formulation, i.e., a formulation comprising water. The liquid formulation can comprise a solution, a suspension, an emulsion, a microemulsion, a gel, and the like. An aqueous formulation typically comprises at least 50% w/w water, or at least 60%, 70%, 75%, 80%, 85%, 90%, or at least 95% w/w of water.

In one embodiment, the pharmaceutical composition can be formulated as an injectable which can be injected, for example, via an injection device (e.g., a syringe or an infusion pump). The injection can be delivered subcutaneously, intramuscularly, intraperitoneally, or intravenously, for example.

In another embodiment, the pharmaceutical composition is a solid formulation, e.g., a freeze-dried or spray-dried composition, which can be used as is, or whereto the physician or the patient adds solvents, and/or diluents prior to use. Solid dosage forms can include tablets, such as compressed tablets, and/or coated tablets, and capsules (e.g., hard or soft gelatin capsules). The pharmaceutical composition can also be in the form of sachets, dragees, powders, granules, lozenges, or powders for reconstitution, for example.

The dosage forms can be immediate release, in which case they can comprise a water-soluble or dispersible carrier, or they can be delayed release, sustained release, or modified release, in which case they can comprise water-insoluble polymers that regulate the rate of dissolution of the dosage form in the gastrointestinal tract.

In other embodiments, the pharmaceutical composition can be delivered intranasally, intrabuccally, or sublingually.

The pH in an aqueous formulation can be between pH 3 and pH 10. In one embodiment of the invention, the pH of the formulation is from about 7.0 to about 9.5. In another embodiment of the invention, the pH of the formulation is from about 3.0 to about 7.0.

In another embodiment of the invention, the pharmaceutical composition comprises a buffer. Non-limiting examples of buffers include: arginine, aspartic acid, bicine, citrate, disodium hydrogen phosphate, fumaric acid, glycine, glycylglycine, histidine, lysine, maleic acid, malic acid, sodium acetate, sodium carbonate, sodium dihydrogen phosphate, sodium phosphate, succinate, tartaric acid, tricine, and tris(hydroxymethyl)-aminomethane, and mixtures thereof. The buffer can be present individually or in the aggregate, in a concentration from about 0.01 mg/ml to about 50 mg/ml, for example from about 0.1 mg/ml to about 20 mg/ml. Pharmaceutical compositions comprising each one of these specific buffers constitute alternative embodiments of the invention.

In another embodiment of the invention, the pharmaceutical composition comprises a preservative. Non-limiting examples of preservatives include: benzethonium chloride, benzoic acid, benzyl alcohol, bronopol, butyl 4-hydroxy-benzoate, chlorobutanol, chlorocresol, chlorhexidine, chlorphenesin, o-cresol, m-cresol, p-cresol, ethyl 4-hydroxybenzoate, imidurea, methyl 4-hydroxybenzoate, phenol, 2-phenoxyethanol, 2-phenylethanol, propyl 4-hydroxybenzoate, sodium dehydroacetate, thiomerosal, and mixtures thereof. The preservative can be present individually or in the aggregate, in a concentration from about 0.01 mg/ml to about 50 mg/ml, for example from about 0.1 mg/ml to about 20 mg/ml. Pharmaceutical compositions comprising each one of these specific preservatives constitute alternative embodiments of the invention.

In another embodiment of the invention, the pharmaceutical composition comprises an isotonic agent. Non-limiting examples of the embodiment include a salt (such as sodium chloride), an amino acid (such as glycine, histidine, arginine, lysine, isoleucine, aspartic acid, tryptophan, and threonine), an alditol (such as glycerol, 1,2-propanediol propyleneglycol), 1,3-propanediol, and 1,3-butanediol), polyethyleneglycol (e.g. PEG400), and mixtures thereof. Another example of an isotonic agent includes a sugar. Non-limiting examples of sugars may be mono-, di-, or polysaccharides, or water-soluble glucans, including for example fructose, glucose, mannose, sorbose, xylose, maltose, lactose, sucrose, trehalose, dextran, pullulan, dextrin, cyclodextrin, alpha and beta-HPCD, soluble starch, hydroxyethyl starch, and sodium carboxymethylcellulose. Another example of an isotonic agent is a sugar alcohol, wherein the term "sugar alcohol" is defined as a C(4-8) hydrocarbon having at least one —OH group. Non-limiting examples of sugar alcohols include mannitol, sorbitol, inositol, galactitol, dulcitol, xylitol, and arabitol. Pharmaceutical compositions comprising each isotonic agent listed in this paragraph constitute alternative embodiments of the invention. The isotonic agent can be present individually or in the aggregate, in a concentration from about 0.01 mg/ml to about 50 mg/ml, for example from about 0.1 mg/ml to about 20 mg/ml. Pharmaceutical compositions comprising each one of these specific isotonic agents constitute alternative embodiments of the invention.

In another embodiment of the invention, the pharmaceutical composition comprises a chelating agent. Non-limiting examples of chelating agents include citric acid, aspartic acid, salts of ethylenediaminetetraacetic acid (EDTA), and mixtures thereof. The chelating agent can be present individually or in the aggregate, in a concentration from about 0.01 mg/ml to about 50 mg/ml, for example from about 0.1 mg/ml to about 20 mg/ml. Pharmaceutical compositions comprising each one of these specific chelating agents constitute alternative embodiments of the invention.

In another embodiment of the invention, the pharmaceutical composition comprises a stabilizer. Non-limiting examples of stabilizers include one or more aggregation inhibitors, one or more oxidation inhibitors, one or more surfactants, and/or one or more protease inhibitors.

In another embodiment of the invention, the pharmaceutical composition comprises a stabilizer, wherein said stabilizer is carboxy-/hydroxycellulose and derivates thereof (such as HPC, HPC-SL, HPC-L and HPMC), cyclodextrins, 2-methylthioethanol, polyethylene glycol (such as PEG 3350), polyvinyl alcohol (PVA), polyvinyl pyrrolidone, salts (such as sodium chloride), sulphur-containing substances such as monothioglycerol), or thioglycolic acid. The stabilizer can be present individually or in the aggregate, in a concentration from about 0.01 mg/ml to about 50 mg/ml, for example from about 0.1 mg/ml to about 20 mg/ml. Pharmaceutical compositions comprising each one of these specific stabilizers constitute alternative embodiments of the invention.

In further embodiments of the invention, the pharmaceutical composition comprises one or more surfactants, preferably a surfactant, at least one surfactant, or two different surfactants. The term "surfactant" refers to any molecules or ions that are comprised of a water-soluble (hydrophilic) part, and a fat-soluble (lipophilic) part. The surfactant can, for example, be selected from the group consisting of anionic surfactants, cationic surfactants, nonionic surfactants, and/or zwitterionic surfactants. The surfactant can be present individually or in the aggregate, in a concentration from about 0.1 mg/ml to about 20 mg/ml. Pharmaceutical compositions comprising each one of these specific surfactants constitute alternative embodiments of the invention.

In a further embodiment of the invention, the pharmaceutical composition comprises one or more protease inhibitors, such as, e.g., EDTA, and/or benzamidine hydrochloric acid (HCl). The protease inhibitor can be present individually or in the aggregate, in a concentration from about 0.1 mg/ml to about 20 mg/ml. Pharmaceutical compositions comprising each one of these specific protease inhibitors constitute alternative embodiments of the invention.

The pharmaceutical composition of the invention can comprise an amount of an amino acid base sufficient to decrease aggregate formation of the polypeptide during storage of the composition. The term "amino acid base" refers to one or more amino acids (such as methionine, histidine, imidazole, arginine, lysine, isoleucine, aspartic acid, tryptophan, threonine), or analogues thereof. Any amino acid can be present either in its free base form or in its salt form. Any stereoisomer (i.e., L, D, or a mixture thereof) of the amino acid base can be present. The amino acid base can be present individually or in the combination with other amino acid bases, in a concentration from about 0.01 mg/ml to about 50 mg/ml, for example from about 0.1 mg/ml to about 20 mg/ml. Pharmaceutical compositions comprising each one of these specific amino acid bases constitute alternative embodiments of the invention.

The pharmaceutically-acceptable salts of the GLP1-GDF15 fusion proteins and/or GLP1-GDF15 fusion polynucleotides of the invention include the conventional non-toxic salts or the quaternary ammonium salts which are formed from inorganic or organic acids or bases. Examples of such acid addition salts include acetate, adipate, benzoate, benzenesulfonate, citrate, camphorate, dodecylsulfate, hydrochloride, hydrobromide, lactate, maleate, methanesulfonate, nitrate, oxalate, pivalate, propionate, succinate, sulfate and tartrate. Base salts include ammonium salts, alkali metal salts such as sodium and potassium salts, alkaline earth metal salts such as calcium and magnesium salts, salts with organic bases such as dicyclohexylamino salts and salts with amino acids such as arginine. Also, the basic nitrogen-containing groups can be quaternized with, for example, alkyl halides.

The pharmaceutical compositions of the invention can be administered by any means that accomplish their intended purpose. Examples include administration by parenteral, subcutaneous, intravenous, intramuscular, intraperitoneal, transdermal, buccal or ocular routes. Administration can be by the oral route. Suitable formulations for parenteral administration include aqueous solutions of the active conjugates in water-soluble form, for example, water-soluble salts, acidic solutions, alkaline solutions, dextrose-water solutions, isotonic carbohydrate solutions and cyclodextrin inclusion complexes.

The present invention also encompasses a method of making a pharmaceutical composition comprising mixing a pharmaceutically acceptable carrier with any of the GLP1-

GDF15 fusion proteins and/or GLP1-GDF15 fusion polynucleotides of the present invention. Additionally, the present invention includes pharmaceutical compositions made by mixing one or more pharmaceutically acceptable carriers with any of the GLP1-GDF15 fusion proteins and/or GLP1-GDF15 polynucleotides of the present invention.

Furthermore, the GLP1-GDF15 fusion proteins and/or GLP1-GDF15 fusion polynucleotides of the present invention can have one or more polymorph or amorphous crystalline forms and as such are intended to be included in the scope of the invention. In addition, the GLP1-GDF15 fusion proteins and/or GLP1-GDF15 fusion polynucleotides can form solvates, for example with water (i.e., hydrates) or common organic solvents. As used herein, the term "solvate" means a physical association of the GLP1-GDF15 fusion proteins and/or GLP1-GDF15 fusion polynucleotides of the present invention with one or more solvent molecules. This physical association involves varying degrees of ionic and covalent bonding, including hydrogen bonding. In certain instances, the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include ethanolates, methanolates, and the like.

It is intended that the present invention include within its scope polymorphs and solvates of the GLP1-GDF15 fusion proteins and/or GLP1-GDF15 fusion polynucleotides of the present invention. Thus, in the methods of treatment of the present invention, the term "administering" shall encompass the means for treating, ameliorating or preventing a syndrome, disorder or disease described herein with the GLP1-GDF15 fusion proteins and/or GLP1-GDF15 fusion polynucleotides of the present invention or a polymorph or solvate thereof, which would obviously be included within the scope of the invention albeit not specifically disclosed.

In another embodiment, the invention relates to the GLP1-GDF15 fusion proteins and/or GLP1-GDF15 fusion polynucleotides of the invention for use as a medicament.

The present invention includes within its scope prodrugs of the GLP1-GDF15 fusion proteins and/or GLP1-GDF15 fusion polynucleotides of this invention. In general, such prodrugs will be functional derivatives of the GLP1-GDF15 fusion proteins and/or GLP1-GDF15 fusion polynucleotides, which are readily convertible in vivo into the required GLP1-GDF15 fusion proteins and/or GLP1-GDF15 fusion polynucleotides. Thus, in the methods of treatment of the present invention, the term "administering" shall encompass the treatment of the various disorders described with the GLP1-GDF15 fusion proteins and/or GLP1-GDF15 fusion polynucleotides specifically disclosed or with a GLP1-GDF15 fusion proteins and/or GLP1-GDF15 fusion polynucleotides, which may not be specifically disclosed, but which converts to the specified GLP1-GDF15 fusion proteins and/or GLP1-GDF15 fusion polynucleotides in vivo after administration to the patient. Conventional procedures for the selection and preparation of suitable prodrug derivatives are described, for example, in "Design of Prodrugs", Ed. H. Bundgaard, Elsevier, 1985.

During any of the processes for preparation of the GLP1-GDF15 fusion proteins and/or GLP1-GDF15 fusion polynucleotides of the present invention, it can be necessary and/or desirable to protect sensitive or reactive groups on any of the molecules concerned. This can be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991, each of which is herein incorporated by reference in its entirety for all purposes. The protecting groups can be removed at a convenient subsequent stage using methods known from the art.

Methods of Use

The present invention is directed to a method for preventing, treating or ameliorating a GDF15 receptor (GDF15R, GFRAL) mediated syndrome and/or a GLP1 receptor mediated syndrome, disorder or disease in a subject in need thereof comprising administering to the subject in need thereof an effective amount of a GLP1-GDF15 fusion protein, GLP1-GDF15 fusion polynucleotide, and/or pharmaceutical composition of the invention.

The present invention also provides a method for preventing, treating, delaying the onset of, or ameliorating a disorder, disease, or condition or any one or more symptoms of said disorder, disease, or condition in a subject in need thereof, comprising administering to the subject in need thereof an effective amount of a GLP1-GDF15 fusion protein, GLP1-GDF15 fusion polynucleotide, and/or pharmaceutical composition of the invention.

According to particular embodiments, the disease disorder, or condition is selected from the group consisting of obesity, type I or II diabetes, metabolic syndrome (i.e., Syndrome X), insulin resistance, impaired glucose tolerance (e.g., glucose intolerance), hyperglycemia, hyperinsulinemia, hypertriglyceridemia, hypoglycemia due to congenital hyperinsulinism (CHI), dyslipidemia, atherosclerosis, diabetic nephropathy, and other cardiovascular risk factors such as hypertension and cardiovascular risk factors related to unmanaged cholesterol and/or lipid levels, osteoporosis, inflammation, non-alcoholic fatty liver disease (NAFLD), non-alcoholic steatohepatitis (NASH), renal disease, eczema, sleep apnea, osteoarthritis, polycystic ovarian syndrome, chronic kidney syndrome, depression, and/or cancer.

According to particular embodiments, a therapeutically effective amount refers to the amount of therapy which is sufficient to achieve one, two, three, four, or more of the following effects: (i) reduce or ameliorate the severity of the disease, disorder, or condition to be treated or a symptom associated therewith; (ii) reduce the duration of the disease, disorder or condition to be treated, or a symptom associated therewith; (iii) prevent the progression of the disease, disorder or condition to be treated, or a symptom associated therewith; (iv) cause regression of the disease, disorder or condition to be treated, or a symptom associated therewith; (v) prevent the development or onset of the disease, disorder or condition to be treated, or a symptom associated therewith; (vi) prevent the recurrence of the disease, disorder or condition to be treated, or a symptom associated therewith; (vii) reduce hospitalization of a subject having the disease, disorder or condition to be treated, or a symptom associated therewith; (viii) reduce hospitalization length of a subject having the disease, disorder or condition to be treated, or a symptom associated therewith; (ix) increase the survival of a subject with the disease, disorder or condition to be treated, or a symptom associated therewith; (xi) inhibit or reduce the disease, disorder or condition to be treated, or a symptom associated therewith in a subject; (xii) enhance or improve the prophylactic or therapeutic effect(s) of another therapy; and/or (xiii) improve quality of life of a subject with the disease, disorder or condition to be treated.

The therapeutically effective amount or dosage can vary according to various factors, such as the disease, disorder or condition to be treated, the means of administration, the target site, the physiological state of the subject (including, e.g., age, body weight, health), whether the subject is a human or an animal, other medications administered, and whether the treatment is prophylactic or therapeutic. Treatment dosages are optimally titrated to optimize safety and efficacy.

As used herein, the terms "treat," "treating," and "treatment" are all intended to refer to an amelioration or reversal of at least one measurable physical parameter related the disease, disorder, or condition, which is not necessarily discernible in the subject, but can be discernible in the subject. The terms "treat," "treating," and "treatment," can also refer to causing regression, preventing the progression, or at least slowing down the progression of the disease, disorder, or condition. In a particular embodiment, "treat," "treating," and "treatment" refer to an alleviation, prevention of the development or onset, or reduction in the duration of one or more symptoms associated with the disease, disorder, or condition. In a particular embodiment, "treat," "treating," and "treatment" refer to prevention of the recurrence of the disease, disorder, or condition. In a particular embodiment, "treat," "treating," and "treatment" refer to an increase in the survival of a subject having the disease, disorder, or condition. In a particular embodiment, "treat," "treating," and "treatment" refer to elimination of the disease, disorder, or condition in the subject.

In one embodiment, the invention provides a method for preventing, treating, delaying the onset of, or ameliorating obesity, or any one or more symptoms of obesity in a subject in need thereof, the method comprising administering to the subject in need thereof an effective amount of a GLP1-GDF15 fusion protein, GLP1-GDF15 fusion polynucleotide, and/or pharmaceutical composition of the invention. In some embodiments, the body weight of a subject is reduced, for example, by between about 0.01% to about 0.1%, between about 0.1% to about 0.5%, between about 0.5% to about 1%, between about 1% to about 5%, between about 2% to about 3%, between about 5% to about 10%, between about 10% to about 15%, between about 15% to about 20%, between about 20% to about 25%, between about 25% to about 30%, between about 30% to about 35%, between about 35% to about 40%, between about 40% to about 45%, or between about 45% to about 50%, relative to the body weight of a subject prior to administration of any of the GLP1-GDF15 fusion proteins, GLP1-GDF15 fusion polynucleotides, pharmaceutical compositions, forms, or medicaments of the invention described herein, or compared to control subjects not receiving any of the GLP1-GDF15 fusion proteins, GLP1-GDF15 fusion polynucleotides, compositions, forms, medicaments, or combinations of the invention described herein.

In some embodiments, the reduction in body weight is maintained for about 1 week, for about 2 weeks, for about 3 weeks, for about 1 month, for about 2 months, for about 3 months, for about 4 months, for about 5 months, for about 6 months, for about 7 months, for about 8 months, for about 9 months, for about 10 months, for about 11 months, for about 1 year, for about 1.5 years, for about 2 years, for about 2.5 years, for about 3 years, for about 3.5 years, for about 4 years, for about 4.5 years, for about 5 years, for about 6 years, for about 7 years, for about 8 years, for about 9 years, for about 10 years, for about 15 years, or for about 20 years, for example.

The present invention provides a method of preventing, treating, delaying the onset of, or ameliorating a syndrome, disorder or disease, or any one or more symptoms of said syndrome, disorder, or disease in a subject in need thereof, wherein said syndrome, disorder or disease is selected from the group consisting of obesity, type I or type II diabetes, metabolic syndrome (i.e., Syndrome X), insulin resistance, impaired glucose tolerance (e.g., glucose intolerance), hyperglycemia, hyperinsulinemia, hypertriglyceridemia, hypoglycemia due to congenital hyperinsulinism (CHI), dyslipidemia, atherosclerosis, diabetic nephropathy, and other cardiovascular risk factors such as hypertension and cardiovascular risk factors related to unmanaged cholesterol and/or lipid levels, osteoporosis, inflammation, non-alcoholic fatty liver disease (NAFLD), non-alcoholic steatohepatitis (NASH), renal disease, and eczema, comprising administering to the subject in need thereof an effective amount of a GLP1-GDF15 fusion protein, GLP1-GDF15 fusion polynucleotide, and/or pharmaceutical composition of the invention.

As used herein, metabolic syndrome refers to a subject having any one or more of the following: high blood sugar (e.g., high fasting blood sugar), high blood pressure, abnormal cholesterol levels (e.g., low HDL levels), abnormal triglyceride levels (e.g., high triglycerides), a large waistline (i.e., waist circumference), increased fat in the abdominal area, insulin resistance, glucose intolerance, elevated C-reactive protein levels (i.e., a proinflammatory state), and increased plasma plasminogen activator inhibitor-1 and fibrinogen levels (i.e., a prothrombotic state).

The present invention provides a method of reducing food intake in a subject in need thereof, the method comprising administering to the subject in need thereof an effective amount of a GLP1-GDF15 fusion protein, GLP1-GDF15 fusion polynucleotide, and/or pharmaceutical composition of the invention. In some embodiments, food intake of a subject is reduced, for example, by between about 0.01% to about 0.1%, between about 0.1% to about 0.5%, between about 0.5% to about 1%, between about 1% to about 5%, between about 2% to about 3%, between about 5% to about 10%, between about 10% to about 15%, between about 15% to about 20%, between about 20% to about 25%, between about 25% to about 30%, between about 30% to about 35%, between about 35% to about 40%, between about 40% to about 45%, or between about 45% to about 50%, relative to food intake of a subject prior to administration of any of the GLP1-GDF15 fusion proteins, GLP1-GDF15 fusion polynucleotides, compositions, forms, medicaments, or combinations of the invention described herein, or compared to control subjects not receiving any of the GLP1-GDF15 fusion proteins, GLP1-GDF15 fusion polynucleotides, compositions, forms, medicaments, or combinations of the invention described herein.

In some embodiments, the reduction in food intake is maintained for about 1 week, for about 2 weeks, for about 3 weeks, for about 1 month, for about 2 months, for about 3 months, for about 4 months, for about 5 months, for about 6 months, for about 7 months, for about 8 months, for about 9 months, for about 10 months, for about 11 months, for about 1 year, for about 1.5 years, for about 2 years, for about 2.5 years, for about 3 years, for about 3.5 years, for about 4 years, for about 4.5 years, for about 5 years, for about 6 years, for about 7 years, for about 8 years, for about 9 years, for about 10 years, for about 15 years, or for about 20 years, for example.

The present invention provides a method of reducing glycated hemoglobin (A1C) in a subject in need thereof, the method comprising administering to the subject in need thereof an effective amount of a GLP1-GDF15 fusion protein, GLP1-GDF15 fusion polynucleotide, and/or pharmaceutical composition of the invention. In some embodiments, A1C of a subject is reduced, for example, by between about 0.001% and about 0.01%, between about 0.01% and about 0.1%, between about 0.1% and about 0.2%, between about 0.2% and about 0.3%, between about 0.3% and about 0.4%, between about 0.4% and about 0.5%, between about 0.5% and about 1%, between about 1% and about 1.5%, between about 1.5% and about 2%, between about 2% and about 2.5%, between about 2.5% and about 3%, between about 3% and about 4%, between about 4% and about 5%, between about 5% and about 6%, between about 6% and about 7%, between about 7% and about 8%, between about 8% and about 9%, or between about 9% and about 10% relative to the A1C of a subject prior to administration of any of the GLP1-GDF15 fusion proteins, GLP1-GDF15 fusion polynucleotides, compositions, forms, medicaments, or combinations of the invention described herein, or compared to control subjects not receiving any of the GLP1-GDF15 fusion proteins, GLP1-GDF15 fusion polynucleotides, compositions, forms, medicaments, or combinations of the invention described herein.

In other embodiments, methods are provided for reducing fasting blood glucose levels in a subject in need thereof, the methods comprising administering to the subject in need thereof an effective amount of a GLP1-GDF15 fusion protein, GLP1-GDF15 fusion polynucleotide, and/or pharmaceutical composition of the invention. Fasting blood glucose levels may be reduced to less than about 140 to about 150 mg/dL, less than about 140 to about 130 mg/dL, less than about 130 to about 120 mg/dL, less than about 120 to about 110 mg/dL, less than about 110 to about 100 mg/dL, less than about 100 to about 90 mg/dL, or less than about 90 to about 80 mg/dL, relative to the fasting blood glucose levels of a subject prior to administration of any of the GLP1-GDF15 fusion proteins, GLP1-GDF15 fusion polynucleotides, compositions, forms, medicaments, or combinations of the invention described herein, or compared to control subjects not receiving any of the GLP1-GDF15 fusion proteins, GLP1-GDF15 fusion polynucleotides, compositions, forms, medicaments, or combinations of the invention described herein.

The present invention provides a method of modulating GLP1 receptor activity and GDF15 receptor activity in a subject in need thereof, the method comprising administering to the subject in need thereof an effective amount of a GLP1-GDF15 fusion protein, GLP1-GDF15 fusion polynucleotide, and/or pharmaceutical composition of the invention. As used herein, "modulating" refers to increasing or decreasing receptor activity.

In some embodiments, an effective amount of a GLP1-GDF15 fusion protein and/or GLP1-GDF15 fusion polynucleotide of the invention or a form, composition or medicament thereof is administered to a subject in need thereof once daily, twice daily, three times daily, four times daily, five times daily, six times daily, seven times daily, or eight times daily. In other embodiments, an effective amount of a GLP1-GDF15 fusion protein and/or GLP1-GDF15 fusion polynucleotide of the invention or a form, composition or medicament thereof is administered to a subject in need thereof once every other day, once per week, twice per week, three times per week, four times per week, five times per week, six times per week, two times per month, three times per month, or four times per month.

Another embodiment of the invention comprises a method of preventing, treating, delaying the onset of, or ameliorating a disease, disorder or syndrome, or one or more symptoms of any of said diseases, disorders, or syndromes in a subject in need thereof, the method comprising administering to the subject in need thereof an effective amount of a GLP1-GDF15 fusion protein, GLP1-GDF15 fusion polynucleotide, and/or pharmaceutical composition of the invention in a combination therapy. In certain embodiments, the combination therapy is a second therapeutic agent. In certain embodiments, the combination therapy is a surgical therapy.

As used herein, the term "in combination," in the context of the administration of two or more therapies to a subject, refers to the use of more than one therapy.

As used herein, combination therapy refers to administering to a subject in need thereof one or more additional therapeutic agents, or one or more surgical therapies, concurrently with an effective amount of a GLP1-GDF15 fusion protein and/or GLP1-GDF15 fusion polynucleotide of the invention or a form, composition or medicament thereof. In some embodiments, the one or more additional therapeutic agents or surgical therapies can be administered on the same day as an effective amount of a GLP1-GDF15 fusion protein and/or GLP1-GDF15 fusion polynucleotide of the invention, and in other embodiments, the one or more additional therapeutic agents or surgical therapies may be administered in the same week or the same month as an effective amount of a GLP1-GDF15 fusion protein and/or GLP1-GDF15 fusion polynucleotide of the invention.

The present invention also contemplates preventing, treating, delaying the onset of, or ameliorating any of the diseases, disorders, syndromes, or symptoms described herein in a subject in need thereof with a combination therapy that comprises administering to the subject in need thereof an effective amount of a GLP1-GDF15 fusion protein, GLP1-GDF15 fusion polynucleotide, and/or pharmaceutical composition of the invention, in combination with any one or more of the following therapeutic agents: a dipeptidyl peptidase-4 (DPP-4) inhibitor (e.g., sitagliptin, saxagliptin, linagliptin, alogliptin, etc.); a GLP1 receptor agonist (e.g., short-acting GLP1 receptor agonists such as exenatide and lixisenatide; intermediate-acting GLP1 receptor agonists such as liraglutide; long-acting GLP1 receptor agonists such as exenatide extended-release, albiglutide, dulaglutide); a sodium-glucose co-transporter-2 (SGLT-2) inhibitors (e.g., canaglifozin, dapaglifozin, empaglifozin, etc.); bile acid sequestrants (e.g., colesevelam, etc.); dopamine receptor agonists (e.g., bromocriptine quick-release); biguanides (e.g., metformin, etc.); insulin; oxyntomodulin; sulfonylureas (e.g., chlorpropamide, glimepiride, glipizide, glyburide, glibenclamide, glibornuride, glisoxepide, glyclopyramide, tolazamide, tolbutamide, acetohexamide, carbutamide, etc.); and thiazolidinediones (e.g; pioglitazone, rosiglitazone, lobeglitazone, ciglitazone, darglitazone, englitazone, netoglitazone, rivoglitazone, troglitazone, etc.). In some embodiments, the dose of the additional therapeutic agent(s) is reduced when given in combination with a GLP1-GDF15 fusion protein and/or GLP1-GDF15 fusion polynucleotide of the invention. In some embodiments, when used in combination with a GLP1-GDF15 fusion protein and/or GLP1-GDF15 fusion polynucleotide of the invention, the additional therapeutic agent(s) may be used in lower doses than when each is used singly.

The present invention contemplates preventing, treating, delaying the onset of, or ameliorating any of the diseases, disorders, syndromes, or symptoms described herein in a subject in need thereof, with a combination therapy that comprises administering to the subject in need thereof an effective amount of a GLP1-GDF15 fusion protein, GLP1-GDF15 fusion polynucleotide, and/or pharmaceutical composition of the invention in combination with a surgical therapy. In certain embodiments, the surgical therapy can be bariatric surgery (e.g., gastric bypass surgery, such as Rouxen-Y gastric bypass surgery; sleeve gastrectomy; adjustable gastric band surgery; biliopancreatic diversion with duodenal switch; intragastric balloon; gastric plication; and combinations thereof).

In embodiments in which the one or more additional therapeutic agents or surgical therapies is administered on the same day as an effective amount of a GLP1-GDF15 fusion protein and/or GLP1-GDF15 fusion polynucleotide of the invention, the GLP1-GDF15 fusion protein and/or GLP1-GDF15 fusion polynucleotide of the invention may be administered prior to, after, or simultaneously with the additional therapeutic agent or surgical therapy. The use of the term "in combination" does not restrict the order in which therapies are administered to a subject. For example, a first therapy (e.g., a composition described herein) can be administered prior to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

EMBODIMENTS

The invention provides also the following non-limiting embodiments.

Embodiment 1 is a glucagon-like peptide-1 (GLP1)/growth differentiation factor 15 (GDF15) fusion protein, wherein the GLP1-GDF15 fusion protein comprises a GLP1 peptide, a first linker peptide, a serum albumin protein, a second linker peptide, and a GDF15 protein.

Embodiment 2 is the GLP1-GDF15 fusion protein of embodiment 1, wherein GLP1 peptide comprises an amino acid sequence selected from the group consisting of SEQ ID NOs:1-4.

Embodiment 3 is the GLP1-GDF15 fusion protein of embodiment 1 or 2, wherein the first linker peptide comprises an amino acid sequence selected from the group consisting of SEQ ID NOs:5-25.

Embodiment 4 is the GLP1-GDF15 fusion protein of any one of embodiments 1-3, wherein the serum albumin protein comprises an amino acid sequence selected from SEQ ID NO:26 or SEQ ID NO:27.

Embodiment 5 is the GLP1-GDF15 fusion protein of any one of embodiments 1-4, wherein the second linker peptide comprises an amino acid sequence selected from the group consisting of SEQ ID NOs:28-30.

Embodiment 6 is the GLP1-GDF15 fusion protein of any one of embodiments 1-5, wherein the GDF15 protein comprises an amino acid sequence selected from SEQ ID NO:31 or SEQ ID NO:32.

Embodiment 7 is a GLP1-GDF15 fusion protein, wherein the GLP1-GDF15 fusion protein comprises an amino acid sequence selected from the group consisting of SEQ ID NOs:33-74 and 84.

Embodiment 8 is an isolated nucleic acid encoding the GLP1-GDF15 fusion protein of any one of embodiments 1-7.

Embodiment 9 is a vector comprising the isolated nucleic acid of embodiment 8.

Embodiment 10 is a host cell comprising the isolated nucleic acid of embodiment 8 or the vector of claim 9.

Embodiment 11 is a pharmaceutical composition comprising the GLP1-GDF15 fusion protein of any one of embodiments 1-7 and a pharmaceutically acceptable carrier.

Embodiment 12 is a method for treating or preventing obesity in a subject in need thereof, comprising administering to the subject in need thereof an effective amount of the pharmaceutical composition of embodiment 11.

Embodiment 13 is the method of embodiment 12, wherein administration of the effective amount of the pharmaceutical composition to the subject in need thereof results in a reduction in body weight of about 5% to about 10%, about 10% to about 15%, about 15% to about 20%, or about 20% to about 25% as compared to the body weight of the subject prior to administration of the pharmaceutical composition.

Embodiment 14 is a method for treating or preventing a disease or disorder in a subject in need thereof, wherein said disease or disorder is selected from the group consisting of obesity, type I or type II diabetes, metabolic syndrome, insulin resistance, impaired glucose tolerance, hyperglycemia, hyperinsulinemia, hypertriglyceridemia, hypoglycemia due to congenital hyperinsulinism (CHI), dyslipidemia, atherosclerosis, diabetic nephropathy, and other cardiovascular risk factors such as hypertension and cardiovascular risk factors related to unmanaged cholesterol and/or lipid levels, osteoporosis, inflammation, non-alcoholic fatty liver disease (NAFLD), non-alcoholic steatohepatitis (NASH), renal disease, and eczema, the method comprising administering to the subject in need thereof an effective amount of the pharmaceutical composition of embodiment 11.

Embodiment 15 is the method of embodiment 14, wherein said disease or disorder is obesity.

Embodiment 16 is the method of embodiment 14, wherein said disease or disorder is type I diabetes.

Embodiment 17 is the method of embodiment 14, wherein said disease or disorder is type II diabetes.

Embodiment 18 is the method of embodiment 14, wherein said disease or disorder is a metabolic syndrome.

Embodiment 19 is the method of embodiment 14, wherein said disease or disorder is a renal disease.

Embodiment 20 is the method of embodiment 14, wherein said disease or disorder is non-alcoholic steatohepatitis (NASH).

Embodiment 21 is the method of embodiment 14, wherein said disease or disorder is non-alcoholic fatty liver disease (NAFLD).

Embodiment 22 is a method of reducing food intake in a subject in need thereof, the method comprising administering to the subject in need thereof an effective amount of the pharmaceutical composition of embodiment 11.

Embodiment 23 is the method of embodiment 22, wherein administration of the effective amount of the pharmaceutical composition to the subject in need thereof results in a reduction in food intake of about 5% to about 10%, about 10% to about 15%, about 15% to about 20%, about 20% to about 25%, about 25% to about 30%, about 30% to about 35%, about 35% to about 40%, about 40% to about 45%, or about 45% to about 50% as compared to the food intake of the subject prior to administration of the pharmaceutical composition.

Embodiment 24 is a method of modulating GLP1 receptor activity in a subject in need thereof, the method comprising administering to the subject in need thereof an effective amount of the pharmaceutical composition of embodiment 11.

Embodiment 25 is a method of modulating GDF15 receptor activity in a subject in need thereof, the method comprising administering to the subject in need thereof an effective amount of the pharmaceutical composition of embodiment 11.

Embodiment 26 is the method of any one of embodiments 11-25, wherein the pharmaceutical composition is administered via an injection.

Embodiment 27 is the method of embodiment 26, wherein the injection is delivered subcutaneously, intramuscularly, intraperitoneally, or intravenously.

Embodiment 28 is the method of any one of embodiments 11-27, wherein the pharmaceutical composition is administered in combination with a second therapeutic agent.

Embodiment 29 is the method of any one of embodiments 11-28, wherein the pharmaceutical composition is administered daily, weekly, or monthly to the subject in need thereof.

Embodiment 30 is the method of embodiment 29, wherein the pharmaceutical composition is administered once, twice, three, four, five, or six times per day.

Embodiment 31 is the method of embodiment 29, wherein the pharmaceutical composition is administered once, twice, three, four, five, or six times per week.

Embodiment 32 is the method of embodiment 29, wherein the pharmaceutical composition is administered once, twice, three, or four times per month.

Embodiment 33 is a kit comprising the GLP1-GDF15 fusion protein of any one of embodiments 1-7, the isolated nucleic acid of embodiment 8, and/or the vector of embodiment 9.

Embodiment 34 is the kit of embodiment 33, wherein the kit further comprises a device for injection.

Embodiment 35 is a method of producing a pharmaceutical composition comprising the GLP1-GDF15 fusion protein of any one of embodiments 1-7, comprising combining the GLP1-GDF15 fusion protein with a pharmaceutically acceptable carrier to obtain the pharmaceutical composition.

Embodiment 36 is a method of producing the GLP1-GDF15 fusion protein of any one of embodiments 1-7, comprising culturing a cell comprising a nucleic acid encoding the GLP1-GDF15 fusion protein under conditions to produce the GLP1-GDF15 fusion protein, and recovering the GLP1-GDF15 fusion protein from the cell or culture.

EXAMPLES

Example 1: Combination of GLP1 and GDF15 Agonists

The potential additive weight loss effects of combining GLP1 and GDF15 agonists were tested in diet induced obese (DIO) mice. Liraglutide, a GLP1 agonist, was administered alone or in combination with an HSA-GDF15 (SEQ ID NO:81) molecule for 8 days. Liraglutide was subcutaneously administered daily while HSA-GDF15 was given every two days. Body weight loss was greater in the animals receiving both agonists compared to either single agent demonstrating the potential for additivity when combining these independent mechanisms (FIG. 1).

Example 2: Design of the GLP1-GDF15 Fusion Proteins

Figure 3:
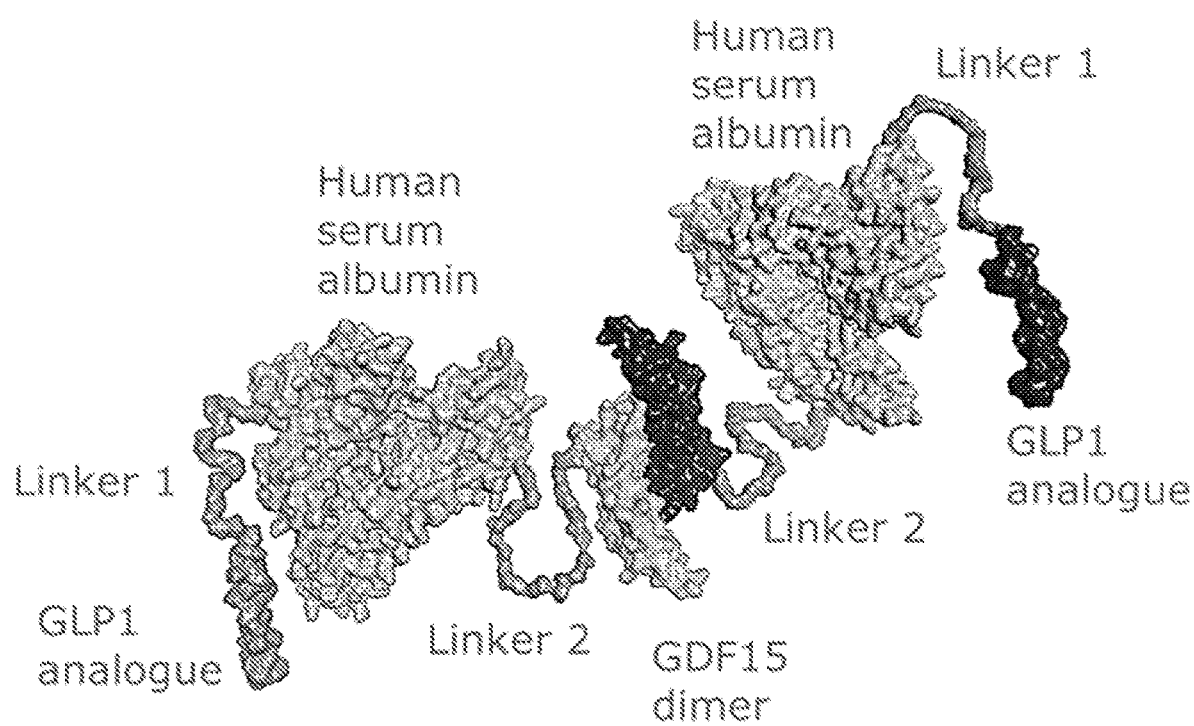
FIG. 3 shows a schematic of a GLP1-GDF15 fusion protein.

Recombinant fusion proteins comprised of a GLP1 peptide or GLP1 variant peptide, serum albumin protein, and GDF15 protein or GDF15 variant protein were designed as follows: GLP1 peptide or GLP1 variant peptides were connected via a first linker peptide at the C-terminus of the GLP1 peptide or GLP1 variant peptide to the N-terminus of human serum albumin. The human serum albumin is connected at the C-terminus to the N-terminus of the GDF15 protein or GDF15 protein variant via a second linker peptide. The design aims to leave the GDF15 dimerization interface unperturbed and allow for formation of the native inter-chain disulfide, resulting in a homodimer of approximately 170 KDa. The entire molecules were designed to be made recombinantly, needing only one gene (FIG. 3).

GLP1 peptides or GLP1 variant peptides include either human GLP1(7-36) peptide with mutations or Exendin 4(9-39) peptide, a venom peptide from Gila monster that agonizes the human GLP1 receptor. SEQ ID NO:1 contains (A8S, A30E) mutations (numbering for mutation positions refer to GLP1 peptide mutations in Table 1, not from the starting of fusion protein) and SEQ ID NO:2 contains (A8G, G22E, R36G) mutations from human GLP1 peptide (UniProtKB—P01275 98-127). SEQ ID NO:3 contains the Exendin 4 peptide (UniProtKB—P26349 48-86).

Native human serum albumin (UniProtKB—P02768 25-609) contains 35 cysteine (Cys, C) residues which form 17 intramolecular disulfide bonds, leaving Cys-34 as the only free cysteine. This free Cys-34 has been shown to function as a free radical scavenger, by trapping multiple reactive oxygen species (ROS) and reactive nitrogen species (RNS) (Taverna et. al, Ann Intensive Care, 3:4 (2013)). This free Cys was therefore mutated to Ser to create SEQ ID NO:26 to minimize chemical reactivity and the risk of heterogeneity due to oxidation.

The N terminus of mature GDF15 (UniProtKB—Q99988 197-308) contains a proteolytic liability site (R198) and a deamidation liability site (N199). Therefore, the fusion proteins contain GDF15(201-308) (SEQ ID NO:31) with those liability sites deleted.

Example 3: Expression and Purification Methods

GLP1-GDF15 fusion proteins, GLP1-first linker-serum albumin (e.g., HSA, GSA) proteins, serum albumin (e.g., HSA, GSA)-second linker-GDF15 proteins, and/or GDF15 proteins utilized in the examples above were expressed either in HEK Expi293F™ (ThermoFisher Scientific, Cat #A14527) or ExpiCHO-S™ (ThermoFisher Scientific, Cat #A29127; Waltham, MA). For expression in HEK Expi293F™, a plasmid encoding the GLP1-GDF15 fusion protein was transfected into cells by transient transfection following the manufacturer's recommendations. Briefly, Expi293F cells were maintained in suspension in Expi293™ expression medium (ThermoFisher Scientific) in a shaking incubator set at 37° C., 8% $CO_2$ and 125 RPM. The cells were passaged so that on the day of transfection, dilution down to $2.5 \times 10^6$ cells per ml could be achieved, maintaining cell viability at 95% or better. Transient transfections were performed using the ExpiFectamine™ 293 transfection kit (ThermoFisher Scientific). For each ml of diluted cells to be transfected, one microgram of plasmid DNA was diluted into OptiMEM™ SFM complexation medium. ExpiFectamine™ 293 reagent was used at a 1:2.6 ratio (v/v, DNA:reagent) and also diluted into OptiMEM™ and allowed to incubate for 5 minutes at room temperature. The diluted DNA and transfection reagent were combined for twenty minutes, allowing DNA/lipid complex formation, and then added to the cells. After overnight incubation, Expi293™ feed and ExpiFectamine™ 293 enhancer were added to the cells. Cells were cultured with shaking at 37° C. for four days prior to harvesting the culture supernatants.

ExpiCHO-S™ cells were maintained in suspension in ExpiCHO™ expression medium (ThermoFisher Scientific)

in a shaking incubator set at 37° C., 8% $CO_2$ and 125 RPM. The cells were passaged so that on the day of transfection, dilution down to $6.0 \times 10^6$ cells per ml could be achieved, maintaining cell viability at 98% or better. Transient transfections were done using the ExpiFectamine™ CHO transfection kit (ThermoFisher Scientific). For each ml of diluted cells to be transfected, one microgram of plasmid DNA is diluted into OptiPRO™ SFM complexation medium. ExpiFectamine™ CHO reagent is used at a 1:3 ratio (v/v, DNA:reagent) and also diluted into OptiPRO™. The diluted DNA and transfection reagent were combined for one minute, allowing DNA/lipid complex formation, and then added to the cells. After overnight incubation, ExpiCHO™ feed and ExpiFectamine™ CHO enhancer were added to the cells. Cells were cultured with shaking at 32° C. for five days prior to harvesting the culture supernatants.

GLP1-GDF15 fusion proteins were purified from harvested culture supernatant either by single-step affinity capture or a two-step process using affinity capture followed by a preparative size exclusion chromatography (SEC) polishing step. Cell supernatants from transiently transfected ExpiCHO™ cells were loaded onto a pre-equilibrated (dPBS, pH 7.2) HSA CaptureSelect column (CaptureSelect Human Albumin Affinity Matrix from ThermoFisher Scientific) at an approximate capacity of 10 mg protein per ml of resin. After loading, unbound proteins and impurities were removed by washing the column with up to 12 column volumes (CV) of dPBS pH 7.2 followed by 3 CV of 1M NaCl in 50 mM Sodium phosphate, pH 7.4. The GLP1-GDF15 fusion protein which bound to the column was eluted with up to 10 CV of 0.1M Sodium Acetate, pH 3.5, into fraction tubes containing 10 percent (by volume) of 1M Tris (untitrated). Peak fractions were pooled and filtered over a 0.2 μm membrane, then either buffer exchanged into dPBS pH 7.2 or continued to SEC step at 4° C.

For SEC step, the protein from the capture step was concentrated to an appropriate volume before loading onto a 26/60 superdex 200 column (GE Healthcare; Little Chalfont, United Kingdom). Protein fractions eluted from SEC column with high purity (determined by SDS-PAGE) were pooled. The concentration of protein (from either method) was determined by the absorbance at 280 nm on a BioTek Synergy HT™ spectrophotometer. The quality of the purified proteins was assessed by SDS-PAGE and analytical size exclusion HPLC (SE-HPLC, Dionex HPLC system). Endotoxin levels were measured using a LAL assay (Pyrotell®-T, Associates of Cape Cod; East Falmouth, MA).

Figure 2:
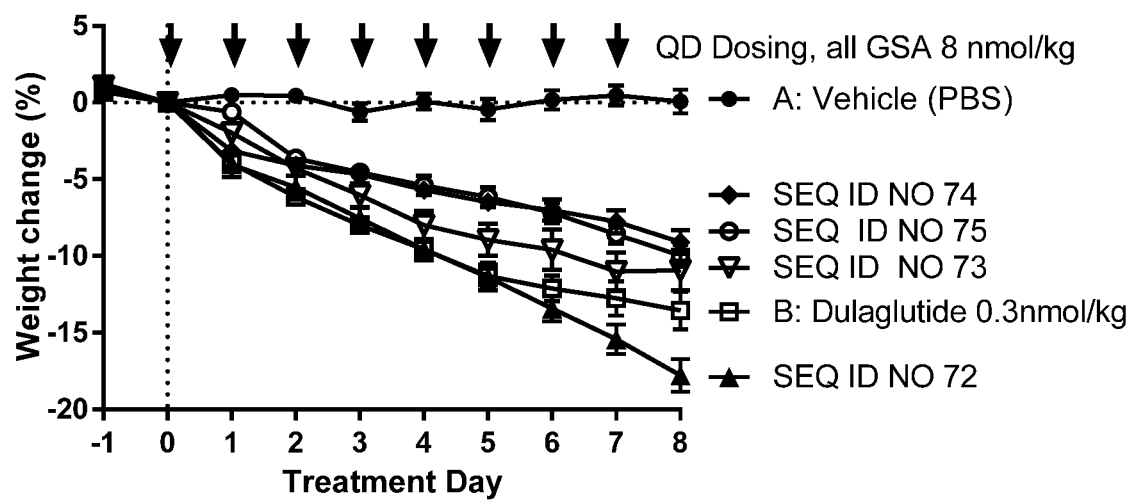
FIG. 2 shows a graph demonstrating average percent weight change (from day 0) in DIO mice receiving daily administration of GLP1-GSA-GDF15 (SEQ ID NO:72), GLP1-GSA-GDF15(I89R) (SEQ ID NO:73, I89R mutation abolishes GDF15 activity), GLP1(9-39)-GSA-GDF15 (SEQ ID NO:74, abolishes GLP1 activity), or GSA-GDF15 (SEQ ID NO:75). Dulaglutide treatment served as a positive control, while vehicle treatment served as a negative control. ±SEM, n=8.

Example 4: Dual Target Engagement and Additive Effects with Delivery of Both GLP1 and GDF15 Agonists on One Molecule The potential to achieve additive effects through delivering both GLP1 and GDF15 agonists on one molecule was tested by assessing weight loss in DIO mice over eight days of treatment with fusions of the agonists with gorilla serum albumin (GSA). GSA was used as a surrogate for HSA in these tool molecules. Mice received subcutaneous administration of 8 nmol/kg of GLP1-GSA-GDF15 (SEQ ID NO:72), GLP1-GSA-GDF15(I89R) (SEQ ID NO:73, I89R mutation abolishes GDF15 activity), GLP1(9-36)-GSA-GDF15 (SEQ ID NO:74, or GSA-GDF15 (SEQ ID NO:75), the latter two both designed to represent degraded GLP1. Two additional groups of animals served as controls and references, one receiving vehicle alone or another that was administered the GLP1 agonist dulaglutide. Mice treated with GLP1-GSA-GDF15 (SEQ ID NO:72) had greater weight loss than those treated with GLP1(9-36)-GSA-GDF15 (SEQ ID NO:74), GLP1-GSA-GDF15(I89R) (SEQ ID NO:73), and GSA-GDF15 (SEQ ID NO:75), providing proof of concept that both GLP1R and GFRAL can be agonized with a single molecule resulting in additive efficacy (FIG. 2).

Example 5: Effect of GLP1 Peptide or GLP1 Peptide Variants and First Linker Peptides on In Vitro Human GLP1R Potency, Ex Vivo Human, and In Vivo Mouse Plasma Stability Different GLP1 peptide or GLP1 peptide variants and different first linker peptides have different effects on in vitro hGLP1 receptor potency in an assay measuring cyclic adenosine monophosphate (cAMP) levels in hGLP1-overexpressing HEK cells. Fusions were screened for in vitro GLP1R potency in cell-based assays measuring intracellular cAMP production using the Lance competitive cAMP immunoassay (Perkin Elmer, Waltham, MA) according to the kit instructions. Clonal HEK293 cells stably expressing mouse or human GLP1R were used in the assays. Resulting data was used to calculate compound ECso values using Prism statistical software (GraphPad Software, San Diego, CA). In general, GLP1 variant (SEQ ID NO:1) is less potent than the other two GLP1 variants (SEQ ID NO:2 and SEQ ID NO:3) in the in vitro hGLP1R assay.

Ex vivo stability in human plasma was assessed. In brief, fresh, non-frozen human plasma was generated from heparinized blood by centrifugation. Fusion proteins were incubated in this matrix at 37° C. with gentle mixing for 0, 4, 24, 48, 72, and 96 hours. The stability of the GLP1 region of the fusion molecules over time in human plasma was monitored by immuno-affinity capture-trypsin digestion-LC-MS/MS analysis. Selected tryptic peptides, namely HSE (HSEGTFTSDVSSYLEGQAAK) (SEQ ID NO:76), HGE-1 (HGEGTFTSDVSSYLEEQAAK) (SEQ ID NO:77), and HGE-2 (HGEGTFTSDLSK) (SEQ ID NO:78), are located at the N-terminus of the GLP1 peptide or GLP1 variant peptides (SEQ ID NOs:1, 2, and 3), respectively. These selected tryptic peptides were monitored by LC-MS/MS after anti-GDF15 immuno-affinity capture and trypsin digestion which served as a surrogate measure of the concentration of fusion molecule with an intact GLP1 containing N-terminus. With this methodology, all the molecules tested demonstrated reasonable GLP1 stability over time in human plasma.

In vivo stability in mice was assessed. The fusion proteins were subcutaneously administered to male C57Bl/6 mice at a dose of 2 mg/kg in PBS, pH 7. Blood samples were collected into K3E Sarstedt blood collection tubes with protease inhibitors at 0, 4, 24 and 48 hours post administration. Plasma was prepared by centrifugation. The stability of the GLP1 region of the fusion proteins over time in vivo in mice was monitored by immuno-affinity capture-trypsin digestion-LC-MS/MS analysis. Selected tryptic peptides, namely HSE (HSEGTFTSDVSSYLEGQAAK) (SEQ ID NO:76), HGE-1 (HGEGTFTSDVSSYLEEQAAK) (SEQ ID NO:77), and HGE-2 (HGEGTFTSDLSK) (SEQ ID NO:78), are located at the N-terminus of SEQ ID NOs:1, 2, and 3 containing fusion proteins, respectively. These selected tryptic peptides were monitored by LC-MS/MS after anti-GDF15 immuno-affinity capture and trypsin digestion which served as a surrogate measure of the concentration of fusion protein with an intact GLP1 containing N-terminus. With this methodology, all the molecules tested demonstrated reasonable GLP1 stability over time in vivo in mice.

Table 7 provides results for in vitro GLP1 receptor potency measuring cAMP levels of GLP1R over-expressing cells, ex vivo human plasma stability and in vivo mouse plasma stability, both assessed by mass spectrometry, for the indicated GLP1-GDF15 fusion proteins.

A top 2 data dependent experiment was performed with the precursor scan set to Orbitrap detection, 70,000 resolution, mass range 150-2000 m/z, AGC Target 1.0e6, maximum injection time 50 ms, 1 microscan, positive polarity. The precursor decision criteria were monoisotopic precursor selection—peptides, charge state: 2-7, dynamic exclusion: 6.0 seconds and precursor intensity threshold of 5e4. Precursor peptides were isolated by the quadrupole with an

TABLE 7

In vitro hGLP1R potency, ex vivo human, and in vivo mouse plasma stability of GLP1-GDF15 fusion proteins

| Molecule | | | In vitro | | Ex vivo human plasma | | | | | In vivo mouse plasma stability | | |
|---|---|---|---|---|---|---|---|---|---|---|---|---|
| | First Linker | | hGLP1R potency | | stability by MS | | | | | by MS (% intact GLP1 relative to | | |
| | GLP1 (SEQ | Peptide (SEQ | | +/− | (% intact GLP1 relative to t = 0) | | | | | HSA on the same molecule) | | |
| Seq ID | ID NO) | ID NO) | (nM) | error | 4 h | 24 h | 48 h | 72 h | 96 h | 4 h | 24 h | 48 h |
| 68 | 3 | 1-7 (11) | 0.09 | 0.04 | 90.8 | 94 | 89.5 | 74.4 | 70.1 | 93.4 | 57.6 | 81.5 |
| 60 | 3 | 1-6 (10) | 0.09 | 0.03 | | | Not tested | | | | Not tested | |
| 59 | 3 | 1-9 (13) | 0.1 | 0.05 | | | | | | | | |
| 64 | 3 | 1-19 (23) | 0.12 | 0.03 | 87.4 | 80 | 75.7 | 62.2 | 56.9 | 80.3 | 51.7 | 32.9 |
| 67 | 3 | 1-8 (12) | 0.13 | 0.02 | 86.5 | 89.8 | 76 | 68.2 | 64.7 | 88.8 | 55 | 34.1 |
| 70 | 2 | 1-7 (11) | 0.26 | 0.1 | 122.7 | 125.8 | 122.1 | 102.9 | 99.5 | 93.1 | 71.2 | 44.8 |
| 62 | 1 | 1-9 (13) | 0.35 | 0.1 | | | | | | | Not tested | |
| 69 | 2 | 1-8 (12) | 0.38 | 0.03 | 102.3 | 100.1 | 102.7 | 84.7 | 91.3 | 81.5 | 69.6 | 64.9 |
| 63 | 2 | 1-19 (23) | 0.39 | 0.15 | 92.5 | 88.7 | 82.2 | 77.8 | 77.3 | 109 | 95 | 74.6 |
| 61 | 1 | 1-6 (10) | 0.39 | 0.09 | | | Not tested | | | | Not tested | |
| 66 | 1 | 1-7 (11) | 0.6 | 0.14 | 107.5 | 99 | 91.2 | 80.5 | 70.7 | 112 | 55.9 | 37.3 |
| 71 | 1 | 1-19 (23) | 1.5 | 0.13 | 100.2 | 93.6 | 84.9 | 62.6 | 60.6 | 87 | 52 | 30 |
| 65 | 1 | 1-8 (12) | 2.98 | 0.74 | 100.7 | 84.9 | 84.8 | 69.4 | 165.4 | 102 | 59.3 | 45.8 |

Example 6: Removing O-Linked Xylosylation by Eliminating Serine Residues in First and Second Linker Peptides Molecules containing glycine-serine linkers were tested for O-linked xylose levels since xylose glycans were reported to attach to glycine-serine linkers (Spahr et. al, mAbs 6 (4): 904-914). Briefly, samples were prepared by dilution into Guanidine-HCl buffered at pH 8.0 for denaturation, followed by adding DTT for reduction and incubating for 1 hour at 37° C. After reduction, the samples were alkylated using freshly prepared iodoacetamide for 60 minutes at room temperature in the dark. Then, DTT was added to the sample to chelate unreacted iodoacetamide. Next, samples were desalted using Zeba Spin Desalting columns according to the manufacturer's protocol in 50 mM Tris, 1 mM $CaCl_2$, pH 8.0 and digested with trypsin (Promega) for 4 hr at 37° C. Following digestion, TFA was added to each sample in order to quench the digestion reaction. Digested samples were kept at 4° C. and injected into LC/MS within 24 hours.

Digested samples were injected into an Agilent AdvanceBio Peptide Map Micro Bore Rapid Resolution Column using an Agilent Infinity 1290 UHPLC (Agilent Technologies) at a flow rate of 0.1 mL/min. The column temperature was maintained at 65° C. Mass spectrometry grade HPLC solvents (0.1% Formic acid and B: 100% ACN in 0.1% Formic acid) were purchased from VWR. The proteolytic peptides were eluted from the column using a 50 min gradient of 2 to 40% ACN in 0.1% FA. The column effluent was introduced into a Thermo Orbitrap Q-Exactive Mass spectrometer via heated electrospray ionization probe (HESI) using a spray voltage of 3.5 kV, sheath gas 20, aux gas 7, ion transfer tube at 299° C. and vaporizer at 100° C.

isolation window of 1.6 m/z and sent to the collision cell. A collision energy of 28 resulted in high energy collisional dissociation (HCD) of the peptide. These fragments were then transferred to the orbitrap for mass measurement. The orbitrap settings were 17,500 resolution, 200-2000 m/z range, AGC target 5e5, maximum injection time 100 ms, 1 microscan, and spectra acquired in centroid mode.

Peptide mapping data is processed using Byonic (Protein Metrics Inc) search algorithm. Custom library of core xylose glycosoaminoglycans and their monoisotopic mass was added to the search parameters as a Ser specific modification. Byonic search results were imported into Byologic (Protein Metrics Inc) for quantification based on extracted ion chromatograms (XIC) areas of the modified and unmodified peptide species.

GLP1-GDF15 fusion proteins containing $G_4S$ first and second linker peptides showed various levels of O-linked xylosylation on the serine residues of the first and second linker peptides. Table 8 shows the results of three such molecules expressed transiently from ExpiCHO cells. The level of xylose was protein context-dependent and ranged from 'not detected' to 1% in first linker peptides, which connect the GLP1 peptide or GLP1 peptide variants to the HSA protein, and from 11.61% to 56.2% in second linker peptides, which connect the HSA protein to the GDF15 protein or GDF15 protein variant. To avoid potential O-linked xylosylation risk on linker peptides, GLP1-GDF15 fusion proteins that do not contain serine residues in the first and/or second linker peptides were designed and generated. These GLP1-GDF15 fusion proteins contained linkers that comprise AP repeats, $G_4A$ repeats or poly-glycine repeats.

TABLE 8

Levels of xylose detected on serine residues in first or second linker peptide of GLP1-GDF15 fusion proteins comprising G$_4$S linker peptides.

| Sequence ID | Linker motif | | Total Xyl % relative abundance by peptide mapping |
|---|---|---|---|
| 64 | Frist linker peptide (1-9) connecting GLP1 to HSA | SEQ ID NO: 13 AS-8x(G$_4$S) | Not detected |
|  | Second linker peptide (2-3) connecting HSA to GDF15 | SEQ ID NO: 30 GS-8x(G$_4$S) | 11.61 |
| 67 | Frist linker peptide (1-8) connecting GLP1 to HSA | SEQ ID NO: 12 AS-2x(G$_4$S) | 1.0 |
|  | Second linker peptide (2-3) connecting HSA to GDF15 | SEQ ID NO: 30 GS-8x(G$_4$S) | 56.2 |
| 63 | Frist linker peptide (1-19) connecting GLP1 to HSA | SEQ ID NO: 23 3x(G$_4$S) | 0.5 |
|  | Second linker peptide (2-3) connecting HSA to GDF15 | SEQ ID NO: 30 GS-8x(G$_4$S) | 23.1 |

Example 7: In Vitro Potency on GLP1R and GDF15R

In vitro activity of GLP1-GDF15 fusion proteins were tested for both GLP1R and GDF15R potency in cell based assays. GDF15R (GFRAL) activity was determined by measuring phospho-AKT (Ser473) level in SK-N-AS human neuroblastoma cells stably transfected to overexpress either human or cynomolgus monkey GFRAL. Phosphorylation of AKT after treating the GFRAL expressing cells with various concentrations of fusion molecules was measured using the Phospho-AKT (Ser473) Assay kit (Cisbio, Beford, MA) according to manufacturer's instructions. Resulting data was used to calculate compound EC$_{50}$ values using Prism statistical software (GraphPad Software San Diego). GLP1-GDF15 fusion proteins tested in Table 9 have similar GDF15R potency, with EC$_{50}$ in the 4.6-6.9 nM range.

GLP1R potency of the fusions was determined by measuring cAMP levels in clonal HEK293 cells stably transfected to overexpress human, mouse, or cynomolgus monkey GLP1R. Intracellular cAMP production after treating the cells with varying concentrations of the fusion molecules was measured using the Lance competitive cAMP immunoassay (Perkin Elmer, Waltham, Massachusetts) according to the kit instructions. Resulting data was used to calculate compound EC$_{50}$ values using Prism statistical software (GraphPad Software San Diego).

When serine residues in the first linker peptide, which connects the GLP1 peptide or GLP1 peptide variant to the HSA protein, were replaced with alanine or removed (switching from G$_4$S to G$_4$A or poly-G linker with similar length), GLP1 activity was not impacted when tested in a human or mouse GLP1R assay. In addition, changing the second linker peptide, which connects the HSA protein to the GDF15 protein or GDF15 protein variant, from GS-8x (G$_4$S) to GA-8x(G$_4$A) or 10x(AP) did not impact GLP1R potency. In addition, fusion proteins with increasing numbers of repeats in first linker (5X(G$_4$A), 8X(G$_4$A), 5X(AP), 10X(AP), 20X(AP), 25X(AP) were made and tested in the human GLP1R assay. Results demonstrated that these fusion proteins activated GLP1R signaling with varying potency.

TABLE 9 in vitro potency of GLP1-GDF15 fusion proteins on GLP1R and GDF15R

| | cAMP induction | | | | | | | | |
|---|---|---|---|---|---|---|---|---|---|
| | hGLP1R | | | mGLP1R | | | CGLP1R | | |
| SEQ ID NO: | EC50 (nM) | STD | n | EC50 (nM) | STD | n | EC50 (nM) | STD | n |
| 45 | 0.070 | 0.012 | 2 | 0.023 | 0.003 | 2 | 0.155 | 0.125 | 4 |
| 47 | 0.081 | 0.038 | 2 | 0.029 | 0.007 | 2 | 0.156 | 0.074 | 4 |
| 48 | 0.092 | 0.040 | 2 | 0.037 | 0.006 | 2 | 0.163 | 0.038 | 4 |
| 49 | 0.127 | 0.058 | 2 | 0.040 | 0.001 | 2 | 0.170 | 0.031 | 4 |
| 50 | 0.095 | 0.050 | 2 | 0.029 | 0.004 | 2 | 0.154 | 0.029 | 4 |
| 33 | 0.120 | 0.051 | 2 | 0.034 | 0.000 | 2 | 0.190 | 0.140 | 4 |
| 46 | 0.065 | 0.008 | 2 | 0.030 | 0.001 | 2 | 0.117 | 0.003 | 2 |
| 44 | 0.076 | 0.037 | 2 | 0.032 | 0.004 | 2 | 0.109 | 0.039 | 2 |
| GLP1 | 0.011 | 0.004 | 25 | 0.012 | 0.004 | 21 | 0.013 | 0.003 | 8 |
| Dulaglutide | 0.038 | 0.010 | 27 | 0.020 | 0.004 | 23 | 0.045 | 0.014 | 8 |
| Liraglutide | 0.057 | 0.025 | 18 | 0.052 | 0.022 | 14 | 0.079 | 0.022 | 2 |
| Albiglutide | 0.981 | 0.438 | 23 | 1.486 | 0.624 | 19 | 1.759 | 0.735 | 6 |

| | Phosphor-AKT (Ser473) | | | | | |
|---|---|---|---|---|---|---|
| | hGDF15R | | | cGDF15R | | |
| SEQ ID NO: | EC50 (nM) | 95% CI | n | EC50 (nM) | 95% CI | n |
| 45 | 4.561 | 3.975-5.258 | 1 | 1.031 | 0.6679-1.4 | 1 |
| 47 | 5.899 | 5.146-6.813 | 1 | 0.937 | 0.7413-1.137 | 1 |
| 48 | 6.283 | 5.479-7.281 | 1 | 1.585 | 1.374-1.819 | 1 |
| 49 | 4.825 | 4.11-5.726 | 1 | 1.157 | 0.7357-1.62 | 1 |
| 50 | 5.983 | 5.333-6.731 | 1 | 1.225 | 0.9865-1.473 | 1 |
| 33 | 5.251 | 4.523-6.113 | 1 | 1.004 | 0.7745-1.243 | 1 |
| 46 | 6.917 | 6.3-7.623 | 1 | 1.521 | 1.267-1.805 | 1 |
| 44 | 4.945 | 4.393-5.572 | 1 | 1.350 | 1.102-1.614 | 1 |

Example 8: Effect of First and Second Linker Peptides on Protein Purity and Stability Size exclusion high-performance liquid chromatography (SE-HPLC) was used to examine the purity and stability of the molecules by quantifying the percentage of main species as well as both high molecular weight (HMW) species that represent aggregates and low molecular weight (LMW) species that represent fragments. Briefly, to determine protein purity, 20 µg of protein was injected onto Tosoh TSKgel BioAssist G3SWXL (Cat #20026) column with a 1×DPBS, pH7.2 (Gibco Cat #14190-136) mobile phase. The protein species were eluted at a flow rate of 1 mL/min at room temperature, and the UV-280 nm absorbance values were monitored using a Dionex Ultimate3000 HPLC system equipped with a variable wavelength detector. To determine protein stability, 100 µg of protein was injected onto Tosoh TSKgel BioAssist G3SWXL (Cat #20026) column with a 0.2 M sodium phosphate pH 7.0 mobile phase. The protein species were eluted at a flow rate of 0.7 mL/min at room temperature, and the UV-280 nm absorbance values were monitored using a Dionex Ultimate3000 HPLC system equipped with a variable wavelength detector. Data is analyzed using Chromeleon software.

When GLP1-GDF15 fusion proteins were made from transient expression in ExpiCHO cells and purified by affinity capture following the methods described in Example 2, the GLP1-GDF15 fusion proteins with 10x(AP) second linker peptides (SEQ ID NO:28) (connecting the HSA protein to the GDF15 protein or GDF15 protein variant) consistently resulted in a lower percentage of low molecular weight (LMW) species compared with molecules containing GA-8x($G_4$A) second linker peptides (SEQ ID NO:29) (Table 10). The LMW species were removed by polishing steps during purification and the resulting final GLP1-GDF15 fusion proteins were greater than 97% pure by SE-HPLC.

These GLP1-GDF15 fusion proteins were tested for stability under defined stressed conditions. To force chemical induced oxidation stress, the samples were exposed to a final concentration of 0.1% hydrogen peroxide and incubated for 6 hours in the dark prior to adding catalase to stop the reaction. In the metal induced oxidation condition, a final concentration of 30 µM ferrous iron was added to the samples. After incubation for two weeks in the dark, EDTA was added to stop the reaction. To test stability at low pH, the samples were dialyzed into 50 mM acetate pH 3.5 buffer, kept for 6 hours and dialyzed back to 0.1M sodium phosphate pH 7.4. To test sample stability under thermal stress, they were concentrated to approximately 10 mg/ml using ultra centrifugal filter with a molecular weight cut-off of 30 KDal and were held at 40° C. for two weeks in PBS. These samples that undergo the abovementioned chemical- or metal-induced oxidation, as well as low pH condition or thermal stress condition were analyzed under analytical size-exclusion chromatography (TOSOH column) with flow rate of 1 ml/min for a 20-minute run at room temperature. Signals are collected for UV-280 nm (Agilent 1100 LC system) and data analysis is done with Chemstation (Agilent).

Table 11 shows the influence of second linker on the stability of GLP1-GDF15 fusion proteins under thermal stress (40° C. for 2 weeks). The GLP1-GDF15 fusion proteins that contained a 10x(AP) second linker peptide (SEQ ID NO:28) resulted in a lower level of LMW species formed compared with GLP1-GDF15 fusion proteins containing a GA-8x($G_4$A) second linker peptide (SEQ ID NO:29), indicating that a AP second linker peptide is more thermally stable compared with a $G_4$A second linker peptide. Under other tested stress conditions (low pH, metal- or chemical-induced oxidation), the level of LMW species of the samples remain at minimal levels, similar to the non-stressed samples.

Differential Scanning Calorimetry (DSC) was performed to determine the thermal stability of the GLP1-HSA-GDF15 proteins. Samples were evaluated at approximately 0.5-1 mg/ml in PBS pH7.4 buffer using an automated MicroCal VP-Capillary DSC instrument. The thermal scans span from 25° C. to 95° C. at a linear rate of 1° C./min. A pre-scan time of 15 minutes and a filtering period of 10 seconds were used for each run. The data were processed using non-2 state fitting function in Origin7 software package. DSC results demonstrated that these GLP1-GDF15 fusion proteins have melting temperature ($T_m$) in the 63-72° C. range (Table 12), similar to an HSA-GDF15 fusion protein that does not contain a GLP1 peptide or GLP1 peptide variant.

TABLE 10

GLP1-GDF15 fusion proteins with different first and second linker peptides show various levels of low molecular weight species by SE-HPLC after affinity purification.

| SEQ ID NO: | First linker peptide (SEQ ID NO) | Second linker peptide (SEQ ID NO) | SE-HPLC after affinity purification | | |
|---|---|---|---|---|---|
| | | | % HMW | % main | % LMW |
| 45 | 10x(AP) (6) | 10x(AP) (28) | 0-1.32 | 98.68-100 | 0 |
| 33 | 5x($G_4$A) (18) | 10x(AP) (28) | 0 | 100 | 0 |
| 44 | 15x(AP) (5) | 10x(AP) (28) | 0 | 100 | 0 |
| 47 | 25x(G) (22) | GA-8x($G_4$A) (29) | 2.3 | 86.64 | 11.06 |
| 48 | 20x(G) (21) | GA-8x($G_4$A) (29) | 5.56 | 83.77 | 10.67 |
| 49 | 4x($G_4$A) (17) | GA-8x($G_4$A) (29) | 2.93 | 94.64 | 2.43 |
| 46 | 5x(AP) (5) | GA-8x($G_4$A) (29) | 0 | 92.33 | 7.67 |
| 50 | 5x($G_4$A) (18) | GA-8x($G_4$A) (29) | 0.77-3 | 89.71-91.00 | 7.29-8.22 |

TABLE 11

GLP1-GDF15 fusion proteins with different first
and second linker peptides show various levels of low
molecular weight species under thermal stress (40° C. for 2 weeks).

| SEQ ID NO: | GLP1 peptide or GLP1 peptide variant | First linker peptide (SEQ ID NO:) | Second linker peptide (SEQ ID NO:) | SE-HPLC after all-step purification % main | SE-HPLC after 40° C. for 2 weeks | | |
|---|---|---|---|---|---|---|---|
| | | | | | % HMW | % main | % LMW |
| 45 | GLP1-based | 10x(AP) (6) | 10x(AP) (28) | 98.68-100 | 5.32 | 92.6 | 2.13 |
| 33 | GLP1-based | 5x(G$_4$A) (18) | 10x(AP) (28) | 100 | 2.5 | 95.4 | 2.1 |
| 44 | Exendin4-based | 5x(AP) (5) | 10x(AP) (28) | 100 | 7.3 | 90.8 | 2.6 |
| 47 | GLP1-based | 25x(G) (22) | GA-8x(G$_4$A) (29) | 100 | 0.91 | 93.9 | 5.19 |
| 48 | GLP1-based | 20x(G) (21) | GA-8x(G$_4$A) (29) | 97.13 | 5.22 | 86.97 | 7.81 |
| 49 | GLP1-based | 4x(G$_4$A) (17) | GA-8x(G$_4$A) (29) | 100 | 0.42 | 93.56 | 6.02 |
| 50 | GLP1-based | 5x(G$_4$A) (18) | GA-8x(G$_4$A) (29) | 100 | 0.49 | 92.17 | 7.34 |
| 46 | Exendin4-based | 5x(AP) (5) | GA-8x(G$_4$A) (29) | 100 | 5.9 | 74.5 | 19.6 |

TABLE 12

Tm for GLP1-GDF15 fusion proteins by differential
scanning calorimetry (DSC).

| SEQ ID NO: | GLP1 peptide or GLP1 peptide variant | First linker peptide (SEQ ID NO:) | Second linker peptide (SEQ ID NO:) | Tm by DSC (° C.) | | | |
|---|---|---|---|---|---|---|---|
| | | | | Tm1 | Tm2 | Tm3 | Tm4 |
| 45 | GLP1-based | 10x(AP) (6) | 10x(AP) (28) | 64.88 | 68.79 | 73.38 | 76.59 |
| 33 | GLP1-based | 5x(G$_4$A) (18) | 10x(AP) (28) | 63.96 | 68.38 | 73.37 | 76.44 |
| 47 | GLP1-based | 25x(G) (22) | GA-8x(G$_4$A) (29) | 68.31 | 74.55 | 77.98 | na |
| 48 | GLP1-based | 20x(G) (21) | GA-8x(G$_4$A) (29) | 64.74 | 69.28 | 74.27 | 77.15 |
| 49 | GLP1-based | 4x(G$_4$A) (17) | GA-8x(G$_4$A) (29) | 64.64 | 69.58 | 74.29 | 77.04 |
| 50 | GLP1-based | 5x(G$_4$A) (18) | GA-8x(G$_4$A) (29) | 63.39 | 67.78 | 72.8 | 75.99 |
| 46 | Exendin4-based | 5x(AP) (5) | GA-8x(G$_4$A) (29) | 72.07 | 74.81 | 77.02 | na |
| 44 | Exendin4-based | 5x(AP) (5) | 10x(AP) (29) | 69.79 | 73.82 | 76.23 | na |

Example 9: Ex Vivo Human Plasma Study

The stability of the GLP1-GDF15 fusion proteins was assessed ex vivo in human plasma. In brief, fresh, non-frozen human plasma was generated from heparinized blood by centrifugation. Fusion proteins were incubated in this matrix at 37° C. with gentle mixing for 0, 4, 24, 48, 72 and 96 hours. The concentration of the fusion molecules over time in human plasma was monitored by immuno-affinity capture with an anti-GDF15 antibody and immuno-detection with either an anti-HSA antibody ("total format") or anti-GLP1 N-terminal specific antibody ("GLP1 active format"). Table 13 and 14 demonstrate the results from these two immunoassays.

TABLE 13 ex vivo human plasma stability by immunoassay measured by an anti-GDF15 capture antibody and an anti-HSA detection antibody.

| Time point (hr) | Concentration (µg/mL) | | | | | | | Normalized % recovery to 0 hr | | | | | | |
|---|---|---|---|---|---|---|---|---|---|---|---|---|---|---|
| | SEQ ID: 50 | SEQ ID: 33 | SEQ ID: 49 | SEQ ID: 48 | SEQ ID: 47 | SEQ ID: 45 | SEQ ID: 44 | SEQ ID: 50 | SEQ ID: 33 | SEQ ID: 49 | SEQ ID: 48 | SEQ ID: 47 | SEQ ID: 45 | SEQ ID: 44 |
| 0 | 13.69 | 13.13 | 13.14 | 12.69 | 13.32 | 12.79 | 13.77 | 100.0 | 100.0 | 100.0 | 100.0 | 100.0 | 100.0 | 100.0 |
| 4 | 14.14 | 13.56 | 12.83 | 13.20 | 12.53 | 12.89 | 13.30 | 103.3 | 103.3 | 97.6 | 104.0 | 94.0 | 100.8 | 96.6 |
| 24 | 13.84 | 13.49 | 12.16 | 13.21 | 13.3 | 12.76 | 12.53 | 101.1 | 102.8 | 92.5 | 104.0 | 99.9 | 99.8 | 91.0 |
| 48 | 12.84 | 13.57 | 12.21 | 12.56 | 12.48 | 11.88 | 11.55 | 93.8 | 103.4 | 92.9 | 98.9 | 93.7 | 92.9 | 83.9 |
| 72 | 13.18 | 14.00 | 11.21 | 12.12 | 12.35 | 12.18 | 12.93 | 96.3 | 106.7 | 85.3 | 95.5 | 92.7 | 95.2 | 93.9 |
| 96 | 12.92 | 13.01 | 11.23 | 12.09 | 12.16 | 12.32 | 12.34 | 94.4 | 99.1 | 85.4 | 95.2 | 91.3 | 96.3 | 89.6 |

TABLE 14 ex vivo human plasma stability by immunoassay by an anti-GDF15 capture
antibody and an anti-GLP1 detection antibody (recognizing the
N-terminal GLP1, specific to the active form of GLP1).

| Time point (hr) | Concentration (μg/mL) | | | | | | | Normalized % recovery to 0 hr | | | | | | |
|---|---|---|---|---|---|---|---|---|---|---|---|---|---|---|
| | SEQ ID: 50 | SEQ ID: 33 | SEQ ID: 49 | SEQ ID: 48 | SEQ ID: 47 | SEQ ID: 45 | SEQ ID: 44 | SEQ ID: 50 | SEQ ID: 33 | SEQ ID: 49 | SEQ ID: 48 | SEQ ID: 47 | SEQ ID: 45 | SEQ ID: 44 |
| 0 | 11.45 | 10.93 | 11.28 | 11.54 | 11.50 | 11.99 | 12.04 | 100.0 | 100.0 | 100.0 | 100.0 | 100.0 | 100.0 | 100.0 |
| 4 | 11.60 | 10.86 | 10.85 | 11.44 | 11.00 | 11.35 | 10.88 | 101.3 | 99.4 | 96.2 | 99.1 | 95.7 | 94.6 | 90.4 |
| 24 | 10.32 | 10.50 | 10.17 | 10.43 | 10.08 | 10.64 | 9.73 | 90.2 | 96.1 | 90.2 | 90.4 | 87.7 | 88.7 | 80.8 |
| 48 | 9.07 | 9.66 | 9.47 | 9.40 | 8.28 | 10.26 | 8.95 | 79.2 | 88.4 | 83.9 | 81.5 | 72.0 | 85.6 | 74.3 |
| 72 | 8.68 | 9.22 | 8.71 | 8.76 | 6.30 | 9.17 | 9.13 | 75.8 | 84.4 | 77.3 | 75.9 | 54.8 | 76.4 | 75.9 |
| 96 | 8.37 | 9.71 | 7.94 | 8.24 | 6.62 | 9.14 | 8.21 | 73.1 | 88.8 | 70.4 | 71.4 | 57.6 | 76.2 | 68.2 |

Example 10: Multispecies Pharmacokinetics

Mouse Pharmacokinetics

GLP1-GDF15 fusion proteins derived from SEQ ID NOs: 50, 45, 46, and 44 were administered to female C57Bl/6 mice at a dose of 5 mg/kg IV and SC in PBS, pH 7. Blood samples were collected, plasma was processed and drug concentrations were measured up to 4 days following both routes of administration. The concentration of analytes in plasma after IV and SC administration was measured by immuno-affinity capture-trypsin digestion-LC-MS/MS analysis. Selected tryptic peptides, namely, ALV (ALVLIA-FAQYLQQSPFEDHVK) (SEQ ID NO:79), HGE-1 (HGEGTFTSDVSSYLEEQAAK) (SEQ ID NO:77), and HGE-2 (HGEGTFTSDLSK) (SEQ ID NO:78), and TDT (TDTGVSLQTYDDLLAK) (SEQ ID NO:80), which are located near the N-terminus of the HSA protein, the N-terminus of the GLP1 peptide or GLP1 peptide variant, and the C-terminus of the GDF15 protein or GDF15 protein variant, respectively. Monitoring these surrogate peptides enabled pharmacokinetic assessment of each region (GLP1, HSA, GDF15) of the GLP1-GDF15 fusion proteins. The plasma drug concentration-time profiles are summarized in Tables 15-22.

Table 15: Plasma concentration (μg/mL) and standard error of the mean (SEM, n=3) of SEQ ID NO:50 over time following a single subcutaneous (SC) administration in C57BL/6 female mice.

| SC Time (h) | Concentration (μg/mL) | | | SEM | | |
|---|---|---|---|---|---|---|
| | HGE (GLP1) | ALV (HSA) | TDT (GDF15) | HGE (GLP1) | ALV (HSA) | TDT (GDF15) |
| 2 | 14.780 | 15.140 | 16.360 | 0.905 | 1.014 | 1.063 |
| 6 | 26.700 | 37.300 | 30.180 | 1.248 | 5.012 | 1.563 |
| 24 | 19.980 | 36.780 | 28.880 | 0.691 | 2.956 | 0.944 |
| 48 | 10.716 | 22.940 | 19.640 | 0.330 | 1.677 | 0.458 |
| 72 | 5.034 | 10.790 | 12.960 | 0.286 | 0.525 | 0.631 |
| 96 | 2.450 | 7.218 | 8.444 | 0.244 | 0.844 | 0.699 |

TABLE 16

Plasma concentration (μg/mL) and standard error of the mean (SEM, n = 3)
of SEQ ID NO: 50 over time following a single intravenous
(IV) administration in C57BL/6 female mice.

| IV Time (h) | Concentration (μg/mL) | | | SEM | | |
|---|---|---|---|---|---|---|
| | HGE (GLP1) | ALV (HSA) | TDT (GDF15) | HGE (GLP1) | ALV (HSA) | TDT (GDF15) |
| 0.5 | 68.320 | 71.760 | 82.860 | 4.188 | 6.659 | 5.408 |
| 6 | 45.020 | 48.560 | 60.660 | 1.427 | 1.487 | 1.707 |
| 24 | 16.900 | 23.820 | 28.340 | 0.991 | 0.913 | 1.646 |
| 48 | 9.472 | 20.620 | 20.540 | 0.510 | 0.843 | 1.365 |
| 72 | 5.048 | 12.118 | 14.440 | 0.303 | 0.996 | 0.842 |
| 96 | 2.144 | 5.404 | 7.926 | 0.103 | 0.365 | 0.445 |

TABLE 17

Plasma concentration (μg/mL) and standard error of the mean (SEM, n = 3)
of SEQ ID NO: 45 over time following a single subcutaneous
(SC) administration in C57BL/6 female mice.

| SC Time (h) | Concentration (μg/mL) | | | SEM | | |
|---|---|---|---|---|---|---|
| | HGE (GLP1) | ALV (HSA) | TDT (GDF15) | HGE (GLP1) | ALV (HSA) | TDT (GDF15) |
| 2 | 13.536 | 12.032 | 12.512 | 3.674 | 3.373 | 3.499 |
| 6 | 21.780 | 20.540 | 22.120 | 3.155 | 2.770 | 3.161 |
| 24 | 18.020 | 27.580 | 26.520 | 1.712 | 3.014 | 2.732 |

TABLE 17-continued

Plasma concentration (μg/mL) and standard error of the mean (SEM, n = 3) of SEQ ID NO: 45 over time following a single subcutaneous (SC) administration in C57BL/6 female mice.

| SC Time (h) | Concentration (μg/mL) | | | SEM | | |
|---|---|---|---|---|---|---|
| | HGE (GLP1) | ALV (HSA) | TDT (GDF15) | HGE (GLP1) | ALV (HSA) | TDT (GDF15) |
| 48 | 8.856 | 20.060 | 18.980 | 0.469 | 1.183 | 1.248 |
| 72 | 4.348 | 18.180 | 15.260 | 0.329 | 1.697 | 1.065 |
| 96 | 1.786 | 9.866 | 9.676 | 0.164 | 0.907 | 0.854 |

TABLE 18

Plasma concentration (μg/mL) and standard error of the mean (SEM, n = 3) of SEQ ID NO: 45 over time following a single intravenous (IV) administration in C57BL/6 female mice.

| IV Time (h) | Concentration (μg/mL) | | | SEM | | |
|---|---|---|---|---|---|---|
| | HGE (GLP1) | ALV (HSA) | TDT (GDF15) | HGE (GLP1) | ALV (HSA) | TDT (GDF15) |
| 0.5 | 76.800 | 69.080 | 69.560 | 7.469 | 7.052 | 7.981 |
| 6 | 56.180 | 57.040 | 59.460 | 5.162 | 5.781 | 5.527 |
| 24 | 21.120 | 30.860 | 30.680 | 1.668 | 2.444 | 2.480 |
| 48 | 10.398 | 22.560 | 21.500 | 0.855 | 2.104 | 2.152 |
| 72 | 4.794 | 18.800 | 16.180 | 0.368 | 1.880 | 1.030 |
| 96 | 1.986 | 10.854 | 10.284 | 0.134 | 0.837 | 0.707 |

TABLE 19

Plasma concentration (μg/mL) and standard error of the mean (SEM, n = 3) of SEQ ID NO: 46 over time following a single subcutaneous (SC) administration in C57BL/6 female mice.

| SC Time (h) | Concentration (μg/mL) | | | SEM | | |
|---|---|---|---|---|---|---|
| | HGE (GLP1) | ALV (HSA) | TDT (GDF15) | HGE (GLP1) | ALV (HSA) | TDT (GDF15) |
| 2 | 3.420 | 2.850 | 3.720 | 0.376 | 0.311 | 0.337 |
| 6 | 5.718 | 6.522 | 7.516 | 0.730 | 0.704 | 0.609 |
| 24 | 4.792 | 8.504 | 9.154 | 0.398 | 0.708 | 0.858 |
| 48 | 2.146 | 5.766 | 6.910 | 0.389 | 0.541 | 0.455 |
| 72 | 0.689 | 2.818 | 3.286 | 0.061 | 0.260 | 0.336 |
| 96 | 0.205 | 1.270 | 1.516 | 0.026 | 0.137 | 0.186 |

TABLE 20

Plasma concentration (μg/mL) and standard error of the mean (SEM, n = 3) of SEQ ID NO: 46 following a single intravenous (IV) administration in C57BL/6 female mice.

| IV Time (h) | Concentration (μg/mL) | | | SEM | | |
|---|---|---|---|---|---|---|
| | HGE (GLP1) | ALV (HSA) | TDT (GDF15) | HGE (GLP1) | ALV (HSA) | TDT (GDF15) |
| 0.5 | 55.525 | 42.525 | 57.875 | 15.521 | 10.592 | 15.368 |
| 6 | 27.125 | 24.750 | 34.950 | 5.185 | 4.660 | 6.461 |
| 24 | 4.933 | 9.423 | 11.280 | 0.255 | 0.893 | 0.879 |
| 48 | 1.355 | 5.023 | 5.893 | 0.125 | 0.278 | 0.702 |
| 72 | 0.510 | 2.623 | 2.968 | 0.049 | 0.269 | 0.329 |
| 96 | 0.196 | 1.345 | 1.593 | 0.020 | 0.155 | 0.171 |

TABLE 21

Plasma concentration (μg/mL) and standard error of the mean (SEM, n = 3) of SEQ ID NO: 44 following a single subcutaneous (SC) administration in C57BL/6 female mice.

| SC Time (h) | Concentration (μg/mL) | | | SEM | | |
|---|---|---|---|---|---|---|
| | HGE (GLP1) | ALV (HSA) | TDT (GDF15) | HGE (GLP1) | ALV (HSA) | TDT (GDF15) |
| 2 | 6.340 | 6.124 | 6.792 | 2.029 | 1.845 | 2.289 |
| 6 | 8.534 | 10.310 | 10.672 | 1.697 | 1.721 | 1.876 |
| 24 | 4.646 | 10.098 | 10.018 | 0.969 | 1.801 | 1.874 |
| 48 | 1.879 | 6.264 | 6.480 | 0.486 | 1.171 | 1.162 |
| 72 | 0.691 | 3.678 | 3.694 | 0.153 | 0.766 | 0.760 |
| 96 | 0.194 | 1.758 | 1.860 | 0.048 | 0.304 | 0.331 |

TABLE 22

Plasma concentration (μg/mL) and standard error of the mean (SEM, n = 3) of SEQ ID NO: 44 following a single intravenous (IV) administration in C57BL/6 female mice.

| IV Time (h) | Concentration (mg/mL) | | | SEM | | |
|---|---|---|---|---|---|---|
| | HGE (GLP1) | ALV (HSA) | TDT (GDF15) | HGE (GLP1) | ALV (HSA) | TDT (GDF15) |
| 0.5 | 57.920 | 53.300 | 60.760 | 4.648 | 3.971 | 4.489 |
| 6 | 29.560 | 33.360 | 37.400 | 2.266 | 2.199 | 2.176 |
| 24 | 4.564 | 10.420 | 10.684 | 0.424 | 0.393 | 0.560 |
| 48 | 1.300 | 6.276 | 6.022 | 0.217 | 0.312 | 0.250 |
| 72 | 0.540 | 3.396 | 3.562 | 0.040 | 0.257 | 0.195 |
| 96 | 0.159 | 1.784 | 1.804 | 0.025 | 0.180 | 0.123 |

Noncompartmental pharmacokinetic analysis (NCA) using the data in Tables 15-22 revealed a terminal half-life of 14-23 hours for the GLP1 peptide or GLP1 peptide variant, 22-49 hours for the GDF15 protein or GDF15 protein variant, and 22-47 hours for the HSA protein following SC and IV administration of the four GLP1-GDF15 fusion proteins tested in C57BL/6 mice (Table 23).

TABLE 23

Estimated terminal half-life of GLP1-GDF15 fusion proteins upon 5 mg/kg IV and SC administration in female C57BL/6 mice.

| SEQ ID NO: | Region | Half-life (hour) NCA SC Dosing | Half-life (hour) NCA IV Dosing |
|---|---|---|---|
| 50 | GDF15 | 39.4 | 39.8 |
| 50 | GLP1 | 22.5 | 24.4 |
| 50 | HSA | 29.5 | 24.8 |
| 45 | GDF15 | 49.4 | 46.7 |
| 45 | GLP1 | 21.8 | 20.1 |
| 45 | HSA | 46.9 | 38.3 |
| 46 | GDF15 | 21.9 | 25.4 |
| 46 | GLP1 | 14.2 | 17.2 |
| 46 | HSA | 22.0 | 25.3 |
| 44 | GDF15 | 26.7 | 28.4 |
| 44 | GLP1 | 15.8 | 15.2 |
| 44 | HSA | 28.8 | 26.5 |

Monkey Pharmacokinetics

GLP-GDF15 fusion proteins derived from SEQ ID NOs: 33, 50, 45, 46, and 44 were administered to naïve male cynomolgus monkeys (*Macaca fascicularis*) at a dose of 0.5 mg/kg SC in PBS, pH 7. Blood samples were collected, plasma was processed and drug concentrations were measured up to 21 days using immunoassay bioanalysis. Immunoassay strategy included an anti-GDF15 capture antibody and detection with either an antibody recognizing intact GLP1 ("Active") or an antibody recognizing HSA ("Total"). The plasma drug concentration-time profile is summarized in Tables 24 and 25.

TABLE 24

Average (Avg, n = 3) plasma concentration (ng/ml) of active SEQ ID NOs: 33, 50, 45, 46, and 44 over time following a single SC administration in cynomolgus monkeys as determined by immunoassay.

| | Time point | SEQ ID NO: 46 | SEQ ID NO: 44 | SEQ ID NO: 45 | SEQ ID NO: 50 | SEQ ID NO: 33 |
|---|---|---|---|---|---|---|
| Active GLP1 (ng/mL) | Predose | <2.50 | <2.50 | <2.50 | <2.50 | <1.25 |
| | 6-hr | 1747.72 | 2530.81 | 2457.83 | 1667.36 | 1880.02 |
| | 24-hr | 3057.60 | 3492.18 | 3946.41 | 3191.24 | 3151.63 |
| | 48-hr | 3177.96 | 3416.86 | 3655.95 | 3643.12 | 3448.62 |
| | 72-hr | 2689.49 | 3013.14 | 3015.11 | 2991.62 | 2949.14 |
| | 120-hr | 1501.85 | 1669.39 | 1402.39 | 2029.62 | 1991.88 |
| | 168-hr | 813.84 | 1020.04 | 725.75 | 1208.07 | 1246.28 |
| | 240-hr | 378.81 | 471.08 | 265.28 | 564.57 | 583.56 |
| | 336-hr | 137.73 | 192.90 | 81.18 | 197.74 | 211.92 |

TABLE 24-continued

Average (Avg, n = 3) plasma concentration (ng/ml) of active SEQ ID
NOs: 33, 50, 45, 46, and 44 over time following a single SC
administration in cynomolgus monkeys as determined by immunoassay.

| Time point | SEQ ID NO: 46 | SEQ ID NO: 44 | SEQ ID NO: 45 | SEQ ID NO: 50 | SEQ ID NO: 33 |
|---|---|---|---|---|---|
| 432-hr | 53.16 | 61.11 | 25.47 | 70.28 | 79.78 |
| 528-hr | 23.10 | 35.96 | 10.60 | 25.70 | 36.59 |

TABLE 25

Average (Avg, n = 3) plasma concentration (ng/ml) of Total SEQ ID
NOs: 33, 50, 45, 46, and 44 over time following a single SC
administration in cynomolgus monkeys as determined by immunoassay.

| | Time point | SEQ ID NO: 46 | SEQ ID NO: 44 | SEQ ID NO: 45 | SEQ ID NO: 50 | SEQ ID NO: 33 |
|---|---|---|---|---|---|---|
| Total (ng/mL) | Predose | <5.00 | <5.00 | <5.00 | <5.00 | <5.00 |
| | 6-hr | 1628.27 | 2299.98 | 2139.00 | 1427.28 | 1726.39 |
| | 24-hr | 3350.99 | 3873.18 | 4639.00 | 3430.23 | 3451.14 |
| | 48-hr | 3956.92 | 4427.70 | 5607.40 | 4892.71 | 4542.34 |
| | 72-hr | 3672.20 | 4399.17 | 5310.44 | 4303.43 | 4514.28 |
| | 120-hr | 2699.22 | 3612.21 | 4616.56 | 4133.96 | 4114.96 |
| | 168-hr | 1930.94 | 2745.57 | 3902.73 | 3237.20 | 3431.95 |
| | 240-hr | 1261.95 | 1964.84 | 2820.20 | 2353.01 | 2504.95 |
| | 336-hr | 719.72 | 1357.09 | 2005.69 | 1597.70 | 1682.87 |
| | 432-hr | 442.57 | 806.98 | 1399.11 | 964.85 | 1096.51 |
| | 528-hr | 328.35 | 532.75 | 961.88 | 708.00 | 879.52 |

Pharmacokinetic analysis of the data in Tables 24 and 25 revealed a terminal half-life of 2-3 days for the active molecule and 5-8 days for the total molecule in cynomolgus monkeys following SC administration (Table 26).

TABLE 26

Terminal half-life of SEQ ID NOs: 50, 33,
45, 46, and 44 following 0.5 mg/kg SC
administration in cynomolgus monkeys.

| SEQ ID NO: | Detection | half-life (d) |
|---|---|---|
| 44 | Active | 3.2 |
| | Total | 6.6 |
| 46 | Active | 2.6 |
| | Total | 4.6 |
| 50 | Active | 2.9 |
| | Total | 6.6 |
| 45 | Active | 2.3 |
| | Total | 7.6 |
| 33 | Active | 3.0 |
| | Total | 7.8 |

Example 11: In Vivo Potency of GLP1-GDF15 Fusion Proteins

Figure 4:
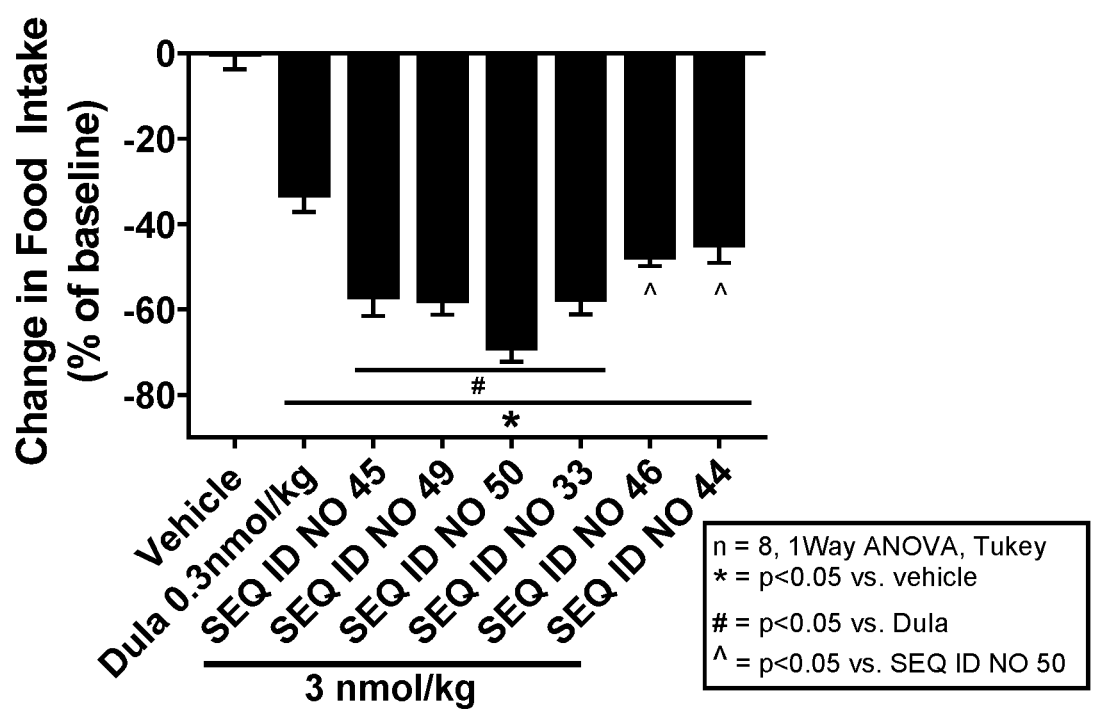
FIG. 4 shows a graph demonstrating the effects of subcutaneous administration of SEQ ID NOs:45, 49, 50, 33, 46, and 44 on food intake in C57BL/6 mice. Data is presented as percent change in food intake as compared to food intake prior to treatment at 24 hours.
Figure 5:
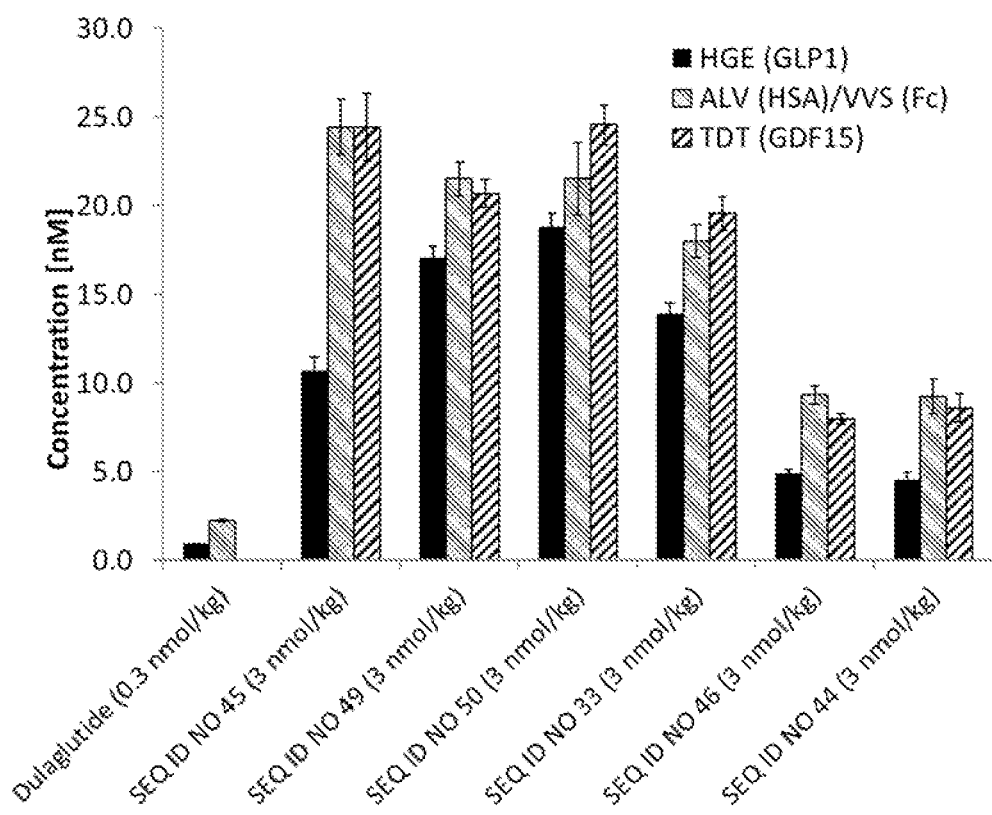
FIG. 5 shows a graph demonstrating the plasma concentration of GLP1-GDF15 fusion proteins (SEQ ID NOs:45, 49, 50, 33, 46, and 44) at 24 hours after administration in mice as determined by immune-affinity capture-trypsin digestion-LC-MS/MS analysis.

Assessment of food intake in C57BL/6 male mice: The purpose of this experiment was to demonstrate the in vivo pharmacodynamic effect of molecules corresponding to SEQ ID NOs:50, 33, 49, 45, 46, and 44 on the inhibition of food intake in C57BL/6 mice. 24-hour food intake was measured before and after subcutaneous administration of GLP1-GDF15 fusion proteins (test articles) or controls (PBS vehicle or dulaglutide) between 4:00 and 5:00 pm. The change in food weight for each cage was recorded every 24 hours. The results are expressed as the percent change in food intake compared to the 24 hours prior to treatment and are partially dependent on the circulating concentration of each test article used in the study (FIG. 4). Circulating concentration of test articles was determined 24 hours after administration by immuno-affinity capture-trypsin digestion-LC-MS/MS analysis. Selected tryptic peptides were monitored, namely, ALV (ALVLIA-FAQYLQQSPFEDHVK) (SEQ ID NO:79), HGE-1 (HGEGTFTSDVSSYLEEQAAK) (SEQ ID NO:77), and HGE-2 (HGEGTFTSDLSK) (SEQ ID NO:78), and TDT (TDTGVSLQTYDDLLAK) (SEQ ID NO:80), which are located near the N-terminus of the HSA protein, the N-terminus of the GLP1 peptide or GLP1 peptide variant, and the C-terminus of the GDF15 protein or GDF15 protein variant, respectively. The VVS peptide (VVSVLTVLHQDWLNGK) (SEQ ID NO:82) is located in the Fc portion of dulaglutide. Monitoring these surrogate peptides enabled pharmacokinetic assessment of each region (GLP1, HSA, GDF15) of the GLP1-GDF15 fusion proteins. The plasma drug concentrations are shown in FIG. 5. The results indicated that subcutaneous administration of SEQ ID NOs:50, 33, 49, 45, 46, and 44 to C57BL/6 mice significantly inhibited food intake relative to vehicle-treated animals.

Figure 6:
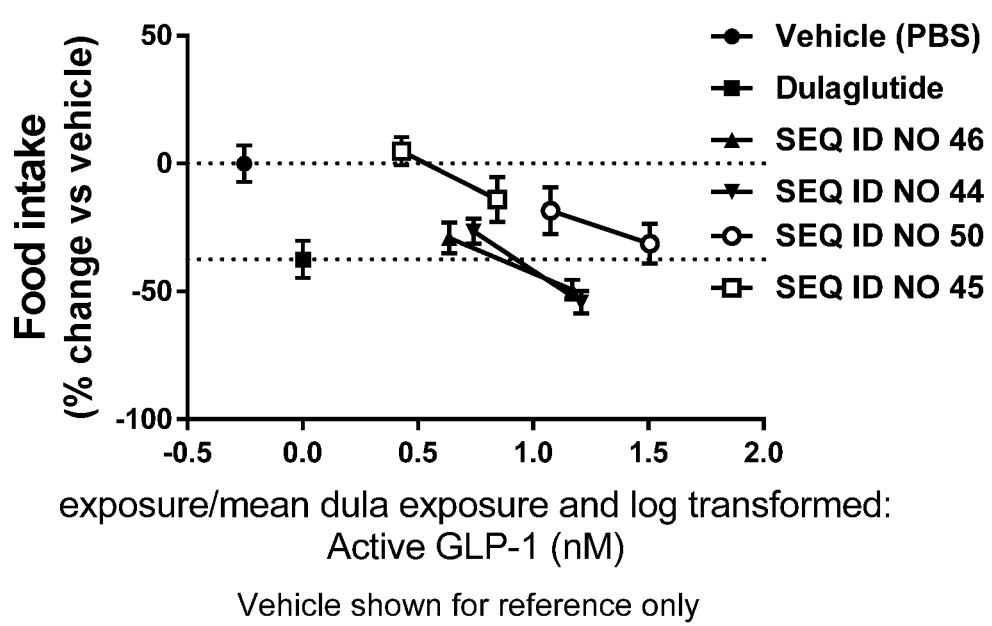
FIG. 6 shows a graph demonstrating the effects of subcutaneous administration of SEQ ID NOs:45, 50, 46, and 44 on food intake in GFRAL-deficient mice. Data is presented as percent change in food intake (compared to vehicle treatment) versus the plasma concentration of the test article with intact GLP1 arms at 24 hours.
Figure 7:
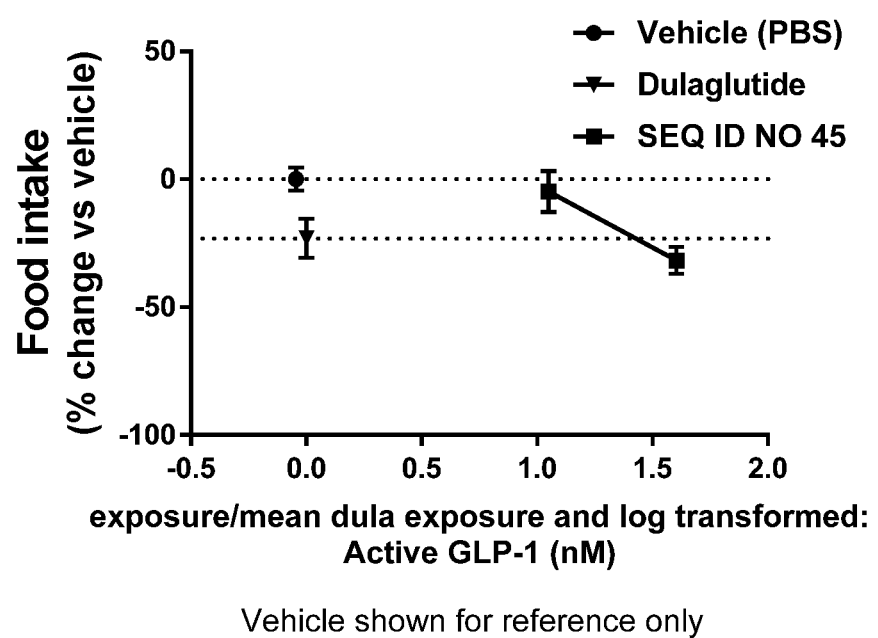
FIG. 7 shows a graph demonstrating the effects of subcutaneous administration of SEQ ID NO:45 on food intake in GFRAL-deficient mice. Data is presented as percent change in food intake (compared to vehicle treatment) versus the plasma concentration of the test article with intact GLP1 arms at 24 hours.
Figure 8:
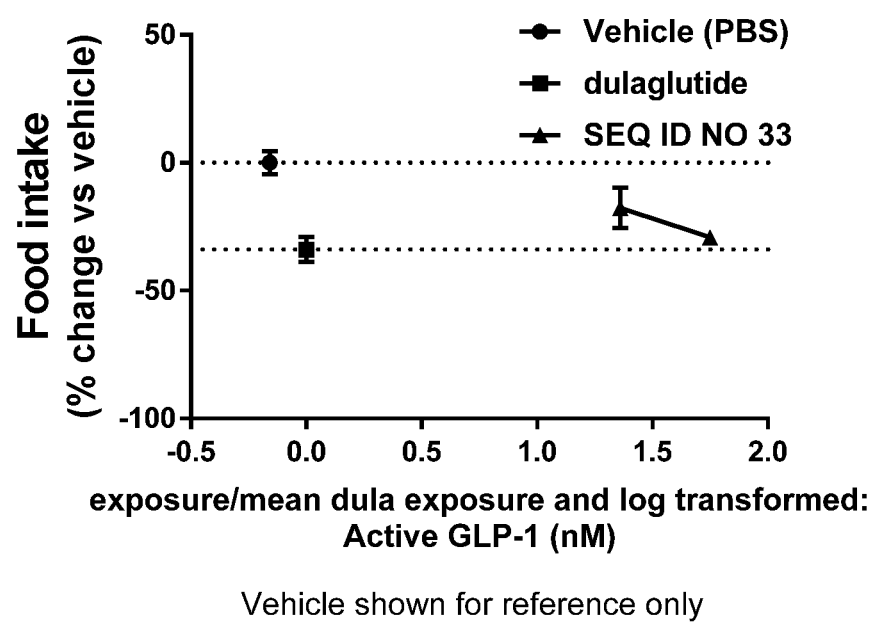
FIG. 8 shows a graph demonstrating the effects of subcutaneous administration of SEQ ID NO:33 on food intake in GFRAL-deficient mice. Data is presented as percent change in food intake (compared to vehicle treatment) versus the plasma concentration of the test article with intact GLP1 arms at 24 hours.
Figure 9:
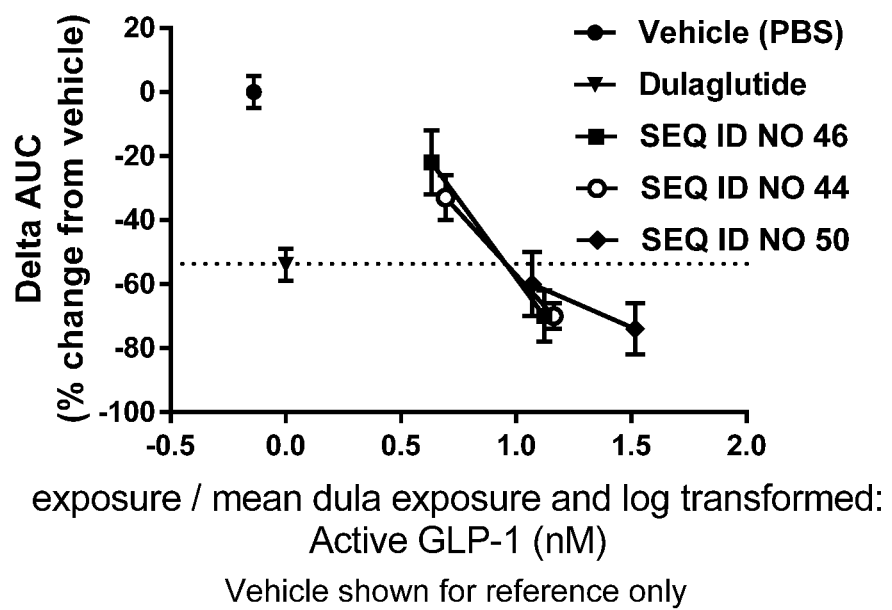
FIG. 9 shows a graph demonstrating the effects of subcutaneous administration of SEQ ID NOs:50, 46, and 44 on glucose tolerance in mice. Data is presented as percent change in delta AUC compared to vehicle treatment versus the plasma concentration of the GLP1-GDF15 fusion proteins with intact GLP1 peptides or GLP1 peptide variants.
Figure 10:
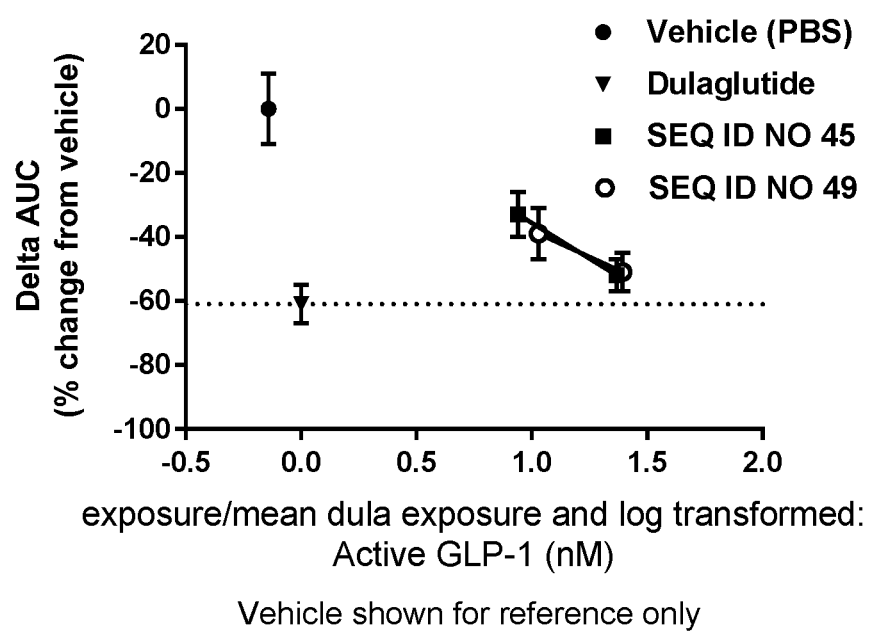
FIG. 10 shows a graph demonstrating the effects of subcutaneous administration of SEQ ID NOs:45 and 49 on glucose tolerance in mice. Data is presented as percent change in delta AUC compared to vehicle treatment versus the plasma concentration of the GLP1-GDF15 fusion proteins with intact GLP1 peptides or GLP1 peptide variants.
Figure 11:
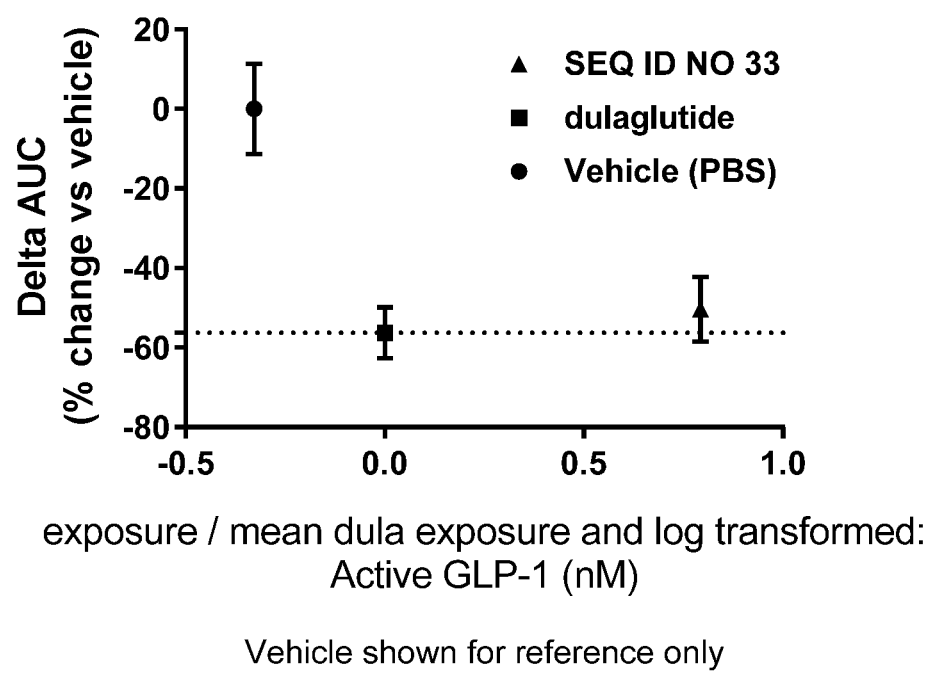
FIG. 11 shows a graph demonstrating the effects of subcutaneous administration of SEQ ID NO:33 on glucose tolerance in mice. Data is presented as percent change in delta AUC compared to vehicle treatment versus the plasma concentration of the GLP1-GDF15 fusion proteins with intact GLP1 peptides or GLP1 peptide variants.
Figure 12:
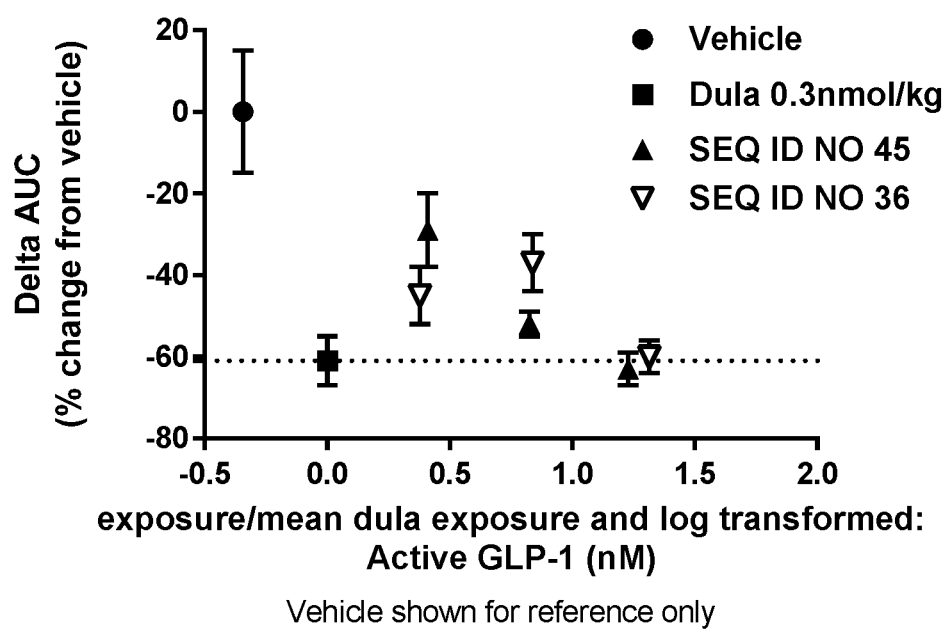
FIG. 12 shows a graph demonstrating the effects of subcutaneous administration of SEQ ID NO:45 and SEQ ID NO:36 on glucose tolerance in mice. Data is presented as percent change in delta AUC compared to vehicle treatment versus the plasma concentration of the GLP1-GDF15 fusion proteins with intact GLP1 peptides or GLP1 peptide variants.

Assessment of GLP1R mediated food intake effects in GFRAL KO mice: Inhibition of food intake in C57BL/6 mice is a result of both GLP1R and GDF15R (GFRAL) engagement. To determine the GLP1R specific effects of SEQ ID NOs:50, 33, 45, 46, and 44 on food intake, mice lacking GFRAL were used. The objective of these experiments was to determine the extent of GLP1R engagement by the fusion proteins when they were administered at a dose predicted to be efficacious for HSA-GDF15 fusions in mice (FIGS. 1 and 2 and US20170327560A1). 24-hour food intake was measured before and after subcutaneous administration of GLP1-GDF15 fusion proteins (test articles: 3 and 10 nmol/kg) or controls (PBS vehicle or dulaglutide) between 4:00 and 5:00 pm. The change in food weight for each cage was recorded every 24 hours. Circulating concentration of fusion molecules containing intact GLP1 peptide or GLP1 peptide variants was determined 24 hours after administration by immuno-affinity capture-trypsin digestion-LC-MS/MS analysis and selective monitoring of tryptic peptides, HGE-1 (HGEGTFTSDVSSYLEEQAAK) (SEQ ID NO:77) or HGE-2 (HGEGTFTSDLSK) (SEQ ID NO:78) which are located near the N-terminus of the GLP1 peptide or GLP1 peptide variant. The results are graphed as the percent change in food intake versus the plasma concentration of the HGE peptide (intact GLP1 peptide or GLP1 peptide variant) (FIGS. 6, 7, and 8). The results indicated that delivery of fusion proteins having SEQ ID NOs: 50, 33, 45, 46, and 44 resulted in GLP1R engagement at doses that were previously demonstrated to be efficacious for HSA-GDF15. Surprisingly, GLP1R engagement elicited a desired pharmacodynamic response similar to the Fc-GLP1 agonist dulaglutide despite having a GLP1 moiety exposure 10-30 times greater than dulaglutide. Had the GLP1 component of the fusion protein been as potent as dulaglutide in vivo, GLP1R engagement would have been much higher than desired, potentially causing predicted adverse events in humans such as nausea and emesis. Therefore, delivery of GLP1 peptides as fusions with HSA-GDF15 impacts in vivo potency at the GLP1R in a way that enables the desired balance of the two agonists.

Assessment of GLP1R mediated glucose tolerance in fasted DIO mice: GLP1R agonism in the pancreas results in enhanced insulin secretion and increased glucose uptake and can be measured using an intraperitoneal glucose tolerance test in diet-induced obese mice. The objective of these experiments was to determine the extent of GLP1R engagement by the fusion proteins when they were administered at a dose predicted to be efficacious for HSA-GDF15 fusions in mice (FIGS. 1 and 2 and US20170327560A1). Male C57BL/6 mice were maintained on Research Diet D12492 from 6 weeks of age until the initiation of dosing at 20 weeks of age to induce obesity. Fed blood glucose and body weight measurements were used to randomize the mice into treatment groups. At 4:00 pm, mice were transferred to clean cages with access to water; food was withheld for the duration of the study. Control (PBS vehicle and dulaglutide) and test articles (SEQ ID NOs:33, 50, 49, 45, 46, 44, and 36) (1, 3, and 10 nmol/kg) were administered subcutaneously at the time of food removal. 17 hours after administration, baseline glucose was collected and 1 g of glucose was administered interperitoneally per kg of body weight. Blood glucose was measured at 10, 30, 60 and 120 minutes following the glucose bolus. Circulating plasma concentration of fusion molecules containing intact GLP1 peptide or GLP1 peptide variants was determined immediately after the 120 minute time point by immuno-affinity capture-trypsin digestion-LC-MS/MS analysis and selective monitoring of tryptic peptides, HGE-1 (HGEGTFTSDVSSYLEEQAAK) (SEQ ID NO:77) or HGE-2 (HGEGTFTSDLSK) (SEQ ID NO:78) which are located near the N-terminus of the GLP1 peptide or GLP1 peptide variant. Glucose was graphed as a function of time and the area under the curve after normalizing to baseline glucose levels (Delta AUC) was calculated for each animal. The results are graphed as the percent change in Delta AUC (compared to vehicle treatment) versus the plasma concentration of the HGE peptide (intact GLP1 agonist) (FIGS. 9, 10, 11, and 12). The results indicated that delivery of fusion proteins having SEQ ID NOs:33, 50, 49, 45, 46, 44, and 36 resulted in GLP1R engagement at doses that were previously demonstrated to be efficacious for HSA-GDF15. Surprisingly, GLP1R engagement elicited a desired pharmacodynamics response similar to the Fc-GLP1 agonist dulaglutide despite having a GLP1 moiety exposure 10-30 times greater than dulaglutide. Had the GLP1 component of the fusion protein been as potent as dulaglutide in vivo, GLP1R engagement would have been much higher than desired, potentially causing predicted adverse events in humans such as nausea and emesis. Therefore, delivery of GLP1 peptides as fusions with HSA-GDF15 impacts in vivo potency at the GLP1R in a way that enables the desired balance of the two agonists.

Figure 13:
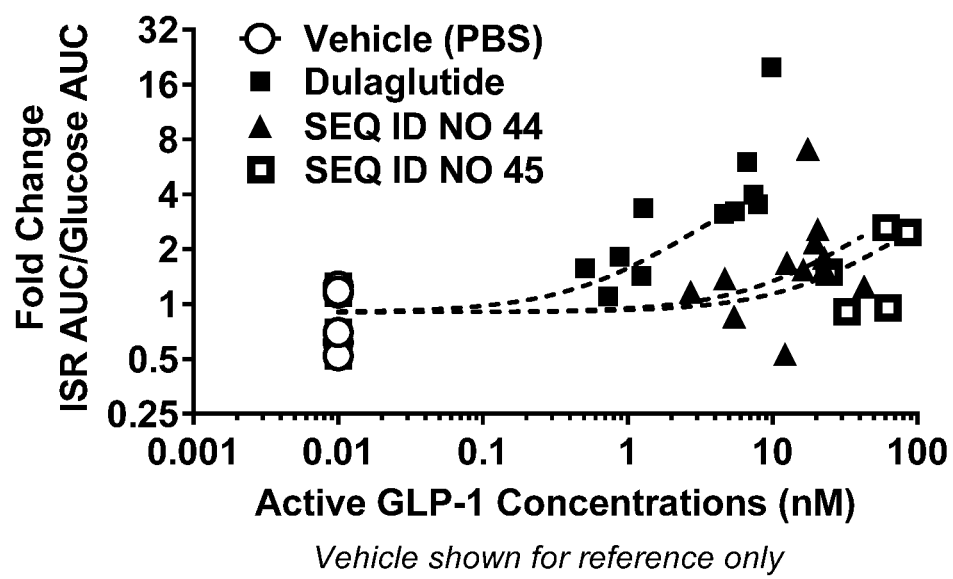
FIG. 13 shows a graph demonstrating the effects of subcutaneous administration of SEQ ID NOs:45 and 44 on insulin secretion during a graded glucose infusion in cynomolgus monkeys. Data is presented as fold change in ISR AUC normalized to glucose AUC (compared to baseline) versus the plasma concentration of the GLP1-GDF15 fusion proteins with intact GLP1 peptides or GLP1 peptide variants.

Assessment of GLP1R engagement in primates with a graded glucose infusion: Insulin secretion upon intravenous graded glucose infusion (GGI) in Non-Human Primates was used to assess GLP1R engagement of SEQ ID NOs:45 and 44. The objective of these experiments was to determine the extent of GLP1R engagement by the fusion proteins when the fusion proteins were administered at a dose predicted to be efficacious for HSA-GDF15 fusions in non-human primates (Mullican et al., 2017 and US20170327560A1). GGI procedures were conducted in sedated cynomolgus monkeys following a 16-hr overnight fast to compare the baseline and treatment responses with a 14-day recovery period between the two GGI procedures. On day 1, animals were dosed with vehicle immediately following food removal. On day 2, animals were anesthetized, and baseline was established with two blood samples collected 10 min apart. GGI1 was initiated at 0 minutes with a glucose infusion rate of 8 mg/kg/min, followed by infusions of 12, 16 and 24 mg/kg/min. Each infusion rate was administered for a period of 40 minutes. Blood samples were taken at 20-minute intervals for measurement of glucose, insulin, and C-peptide, results were graphed as a function of time and area under the curve (AUC) was determined for each analyte measured in each animal. Animals were then randomized into test article treatment groups based on their baseline insulin secretion rate (ISR) from GGI1. On day 15 animals were dosed with the test article at varying dose concentrations (0.1 to 1.1 mg/kg of fusion proteins and 0.016 to 0.1 dulaglutide) prior to fasting overnight. The second GGI (GGI2) was performed on day 16 as described for day 2. Compound exposure was assessed on plasma samples collected at timepoint 0 prior to glucose infusion by immunoassay specifically designed to monitor test articles with intact GLP1 peptide or peptide variants. Data in FIG. 13 is reported as the treatment induced fold change in ISR AUC normalized to glucose AUC compared to baseline versus the plasma concentration of test article with intact GLP1. Dulaglutide was used as a Fc-GLP1 agonist reference. The results indicated that delivery of fusion proteins having SEQ ID NOs:45 and 44 resulted in GLP1R engagement at doses that were previously demonstrated to be efficacious for HSA-GDF15. Surprisingly, GLP1R engagement elicited a desired pharmacodynamic response similar to Fc-GLP1 agonist dulaglutide despite having a GLP1 moiety exposure 10-30 times greater than dulaglutide. Had the GLP1 component of the fusion protein been as potent as dulaglutide in vivo, GLP1R engagement would have been much higher than desired, potentially causing predicted adverse events in humans such as nausea and emesis. Therefore, delivery of GLP1 peptides as fusions with HSA-GDF15 impacts in vivo potency at the GLP1R in a way that enables the desired balance of the two agonists.

The results shown in FIGS. 6-13 demonstrate that GLP1 in vivo activity or potency in preclinical species is reduced in the homodimeric GLP1-GDF15 dual agonists compared with the Fc fused GLP1 peptide of dulaglutide. This enables balance of both agonists (GLP1 peptide or GLP1 peptide variant and GDF15 protein or GDF15 protein variant) on one molecule; therefore, allowing delivery of a GLP1 peptide or GLP1 peptide variant at an efficacious concentration that also achieves GDF15 protein or GDF15 protein variant exposure within the predicted therapeutic range.

Figure 14:
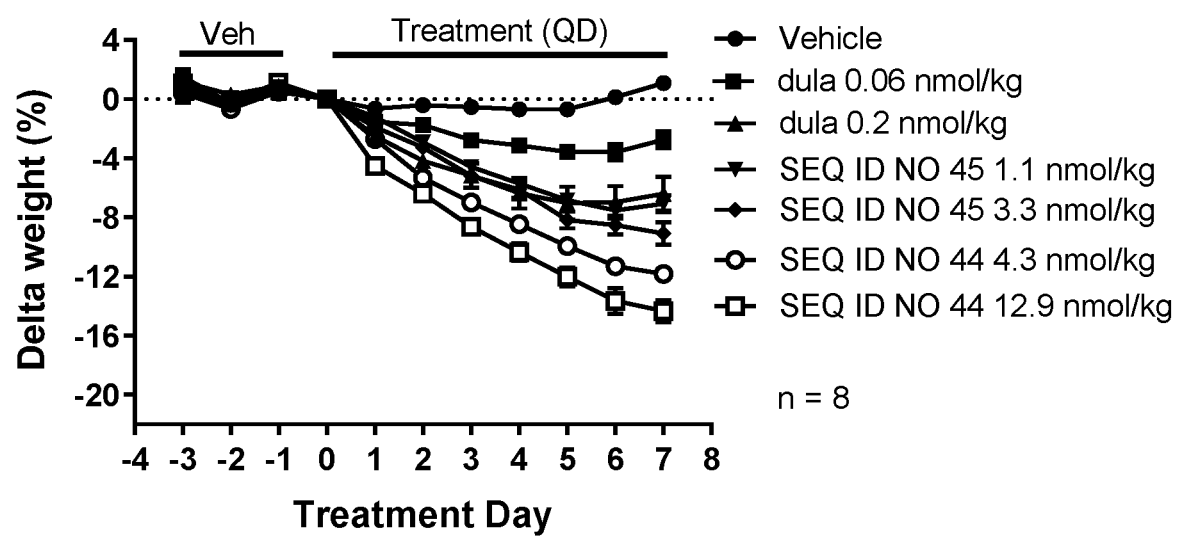
FIG. 14 shows a graph demonstrating the weight loss efficacy of daily subcutaneous administration of GLP1-GDF15 fusion proteins (SEQ ID NOs:45 and 44) in diet induced obese mice. Data is presented as percent change in body weight from Day 0.
Figure 15:
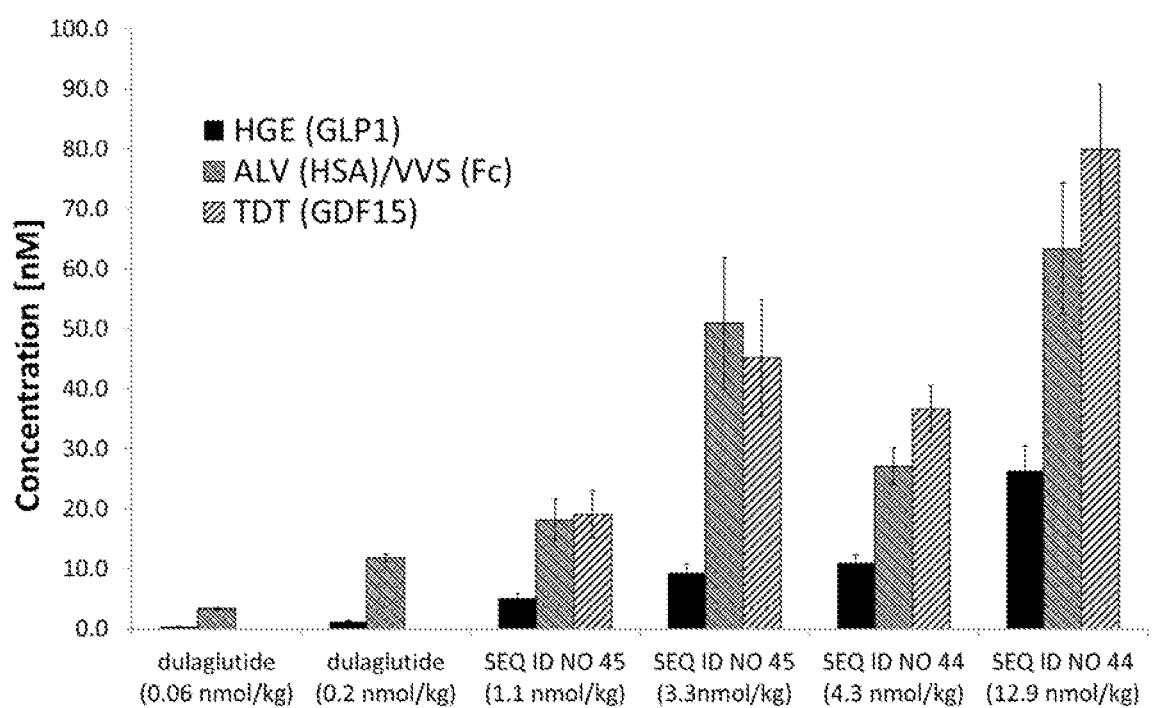
FIG. 15 shows a graph demonstrating the plasma concentration of GLP1-GDF15 fusion proteins (SEQ ID NOs:45 and 44) after 7 days of daily administration in diet induced obese mice as determined by immuno-affinity capture-trypsin digestion-LC-MS/MS analysis.

Assessment of weight loss efficacy of GLP1-GDF15 fusion proteins after repeat dosing in mice: The ability of GLP1-GDF15 fusion proteins to cause weight loss was tested in diet induced obese mice. Mice were subcutaneously administered varying concentrations of test articles (SEQ ID NOS:45 and 44), dulaglutide or a vehicle control daily for seven days. Body weight was monitored throughout the study and FIG. 14 shows the percent change in body weight over time relative to Day 0 (just prior to the first dose). Circulating concentration of test articles was determined after seven days of treatment by immuno-affinity capture-trypsin digestion-LC-MS/MS analysis. Selected tryptic peptides were monitored, namely, ALV (ALVLIAFAQYLQQSPFEDHVK) (SEQ ID NO:79), HGE-1 (HGEGTFTSDVSSYLEEQAAK) (SEQ ID NO:77), and HGE-2 (HGEGTFTSDLSK) (SEQ ID NO:78), and TDT (TDTGVSLQTYDDLLAK) (SEQ ID NO:80), which are located near the N-terminus of the HSA protein, the N-terminus of the GLP1 peptide or GLP1 peptide variant, and the C-terminus of the GDF15 protein or GDF15 protein variant, respectively. The VVS peptide (VVSVLTVLHQDWLNGK) (SEQ ID NO:82) is located in the Fc portion of dulaglutide. Monitoring these surrogate peptides enabled pharmacokinetic assessment of each region (GLP1, HSA, GDF15) of the GLP1-GDF15 fusion proteins. The plasma drug concentrations are shown in FIG. 15. The results indicated that repeat administration of SEQ ID NOs: 45 and 44 leads to weight loss in diet induced obese mice in a concentration dependent manner.

Assessment of Food Intake Effects of GLP1-GDF15 Fusion Proteins in Nonhuman Primates.

Figure 16:
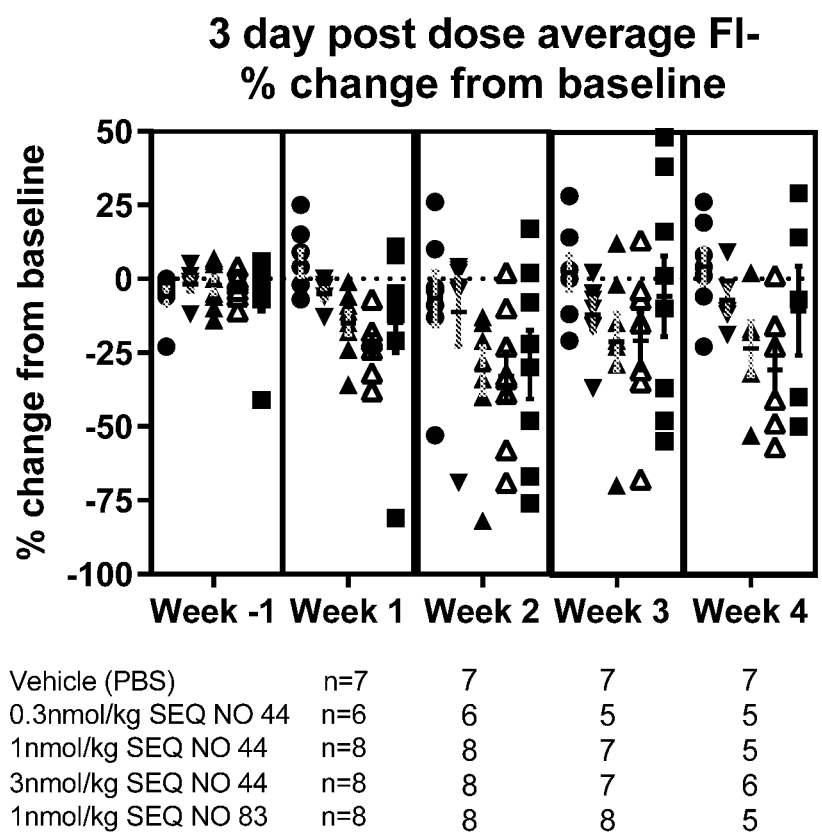
FIG. 16 shows a graph demonstrating the 3-day percent change in food intake at baseline and after each QW subcutaneous administration of GLP1-GDF15 fusion proteins (SEQ ID NOs: 44 and 83) over 4 weeks in spontaneously obese nonhuman primates. Data is presented for individual subjects and those without detectable level of test article in their plasma are not included in the figure as outlined below the x-axis.
Figure 17:
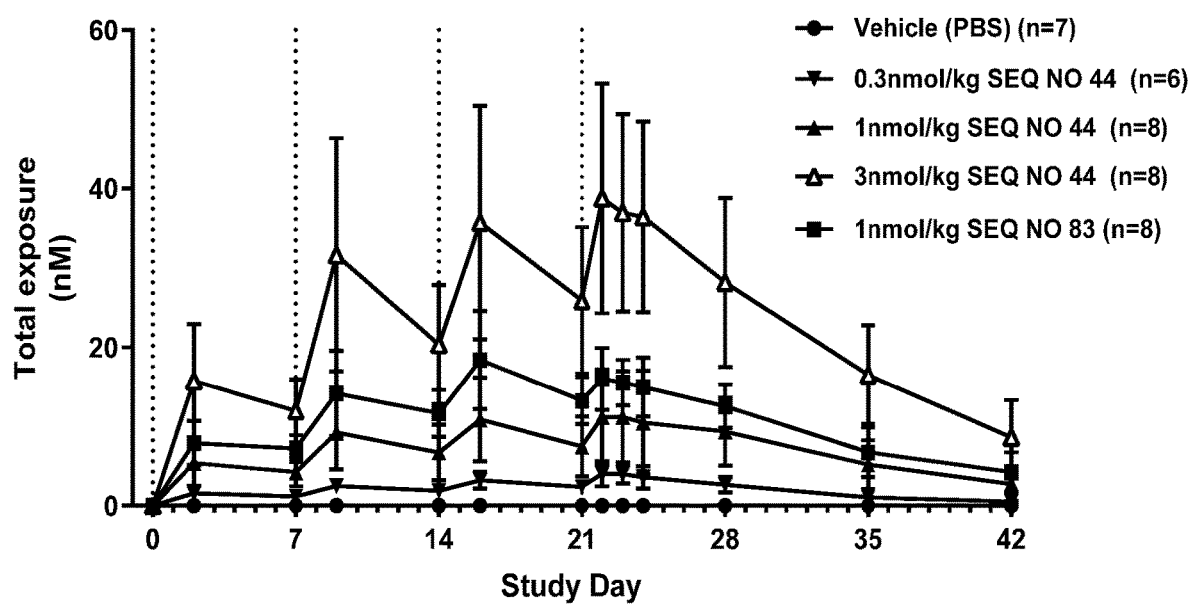
FIG. 17 shows a graph demonstrating the plasma concentration of total test article during a 4-week treatment with varying concentrations of GLP1-GDF15 fusion proteins (SEQ ID NOs: 44 and 83) administered QW in spontaneously obese nonhuman primates as determined by immunoassay. Data is presented as the average (±SEM).
Figure 18:
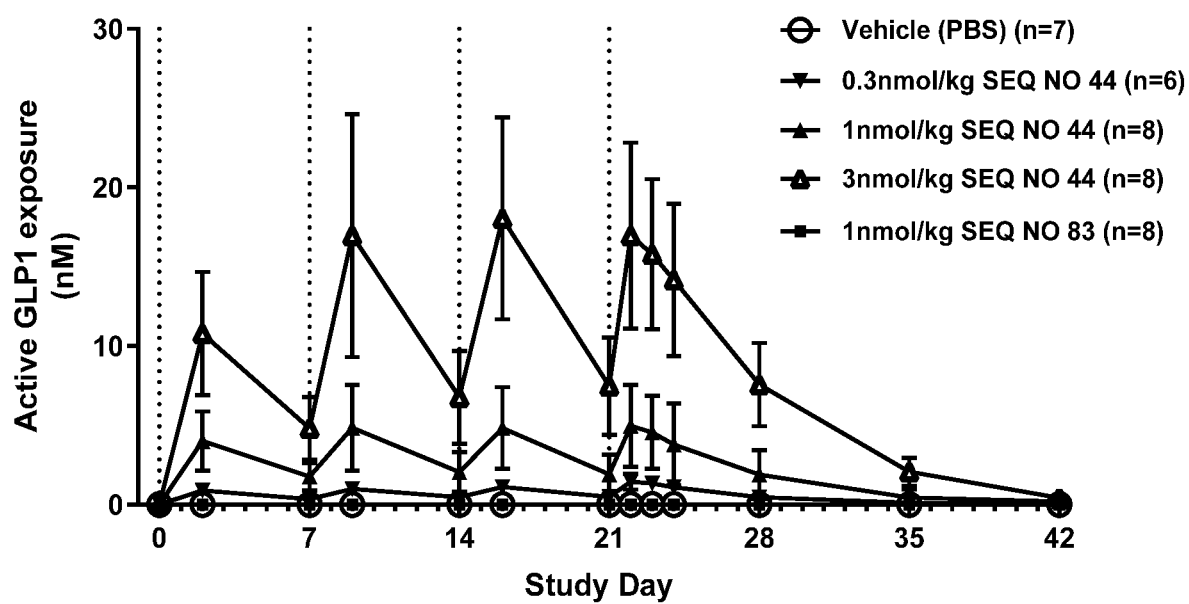
FIG. 18 shows a graph demonstrating the plasma concentration of GLP1 moiety containing test article during a 4-week treatment with varying concentrations of GLP1-GDF15 fusion protein (SEQ ID NO. 44) administered QW in spontaneously obese nonhuman primates as determined by immunoassay. Data is presented as the average (±SEM).

The ability of GLP1-GDF15 fusion proteins to decrease food intake was tested in spontaneously obese cynomolgus monkeys. Subjects were subcutaneously administered varying concentrations of test articles with and without an active GLP1 moiety (SEQ ID NOS: 44 and 83, respectively; SEQ ID NO:83, which comprises a HSA peptide fused to an AP10 linker fused to a GDF15 peptide, was previously disclosed in U.S. Pat. No. 10,336,812) or vehicle QW for a period of 4 weeks. Food intake was monitored prior to dosing and throughout the study. The 3-day percent change in food intake at baseline and after each administration of test article is shown in FIG. 16. The concentration of SEQ ID NOs: 44 and 83 in cynomolgus monkey plasma during the study was determined using two separate immunoassay methods to detect the "total" molecule (HSA detection) and the "active" GLP1 moiety (N-terminal GLP1 peptide detection). The plasma drug concentrations are shown in FIGS. 17 and 18. The results indicated that administration of SEQ ID NOs: 44 and 83 reduces food intake in spontaneously obese nonhuman primates.

Assessment of Food Intake and Body Weight Effects of GLP1-GDF15 Fusion Proteins after a 21-Day Dose Escalation in Nonhuman Primates.

Figure 19:
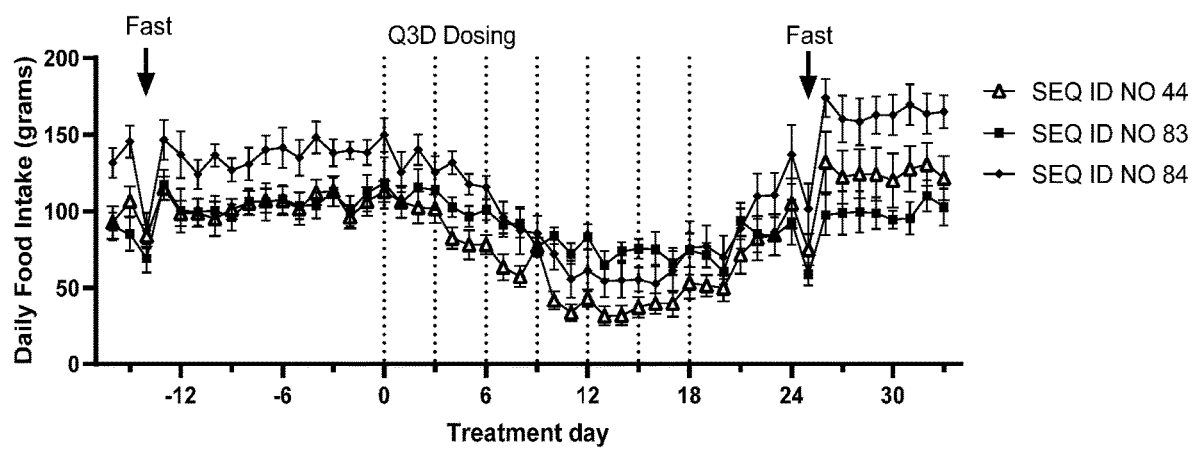
FIG. 19 shows a graph demonstrating the absolute daily food intake before, during and after a 21-day treatment with escalating concentrations of GLP1-GDF15 fusion proteins (SEQ ID NOs: 44, 83 and 84) administered Q3D in spontaneously obese nonhuman primates. Data is presented as the average (±SEM) of ten subjects per group.
Figure 20:
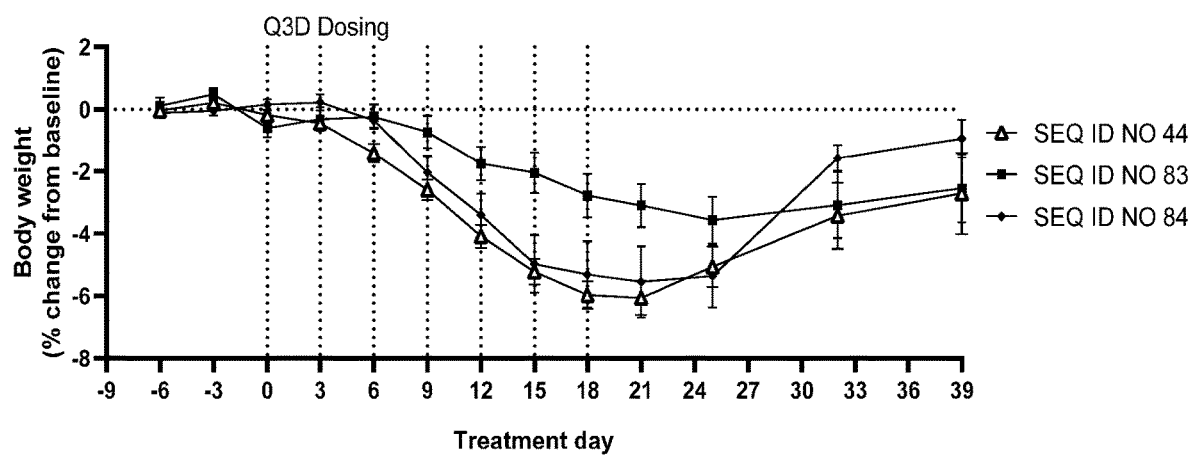
FIG. 20 shows a graph demonstrating body weight change (relative to baseline) after a 21-day treatment with escalating concentrations of GLP1-GDF15 fusion proteins (SEQ ID NOs: 44, 83 and 84) administered Q3D in spontaneously obese nonhuman primates. Data is presented as the average (±SEM) of ten subjects per group.
Figure 21:
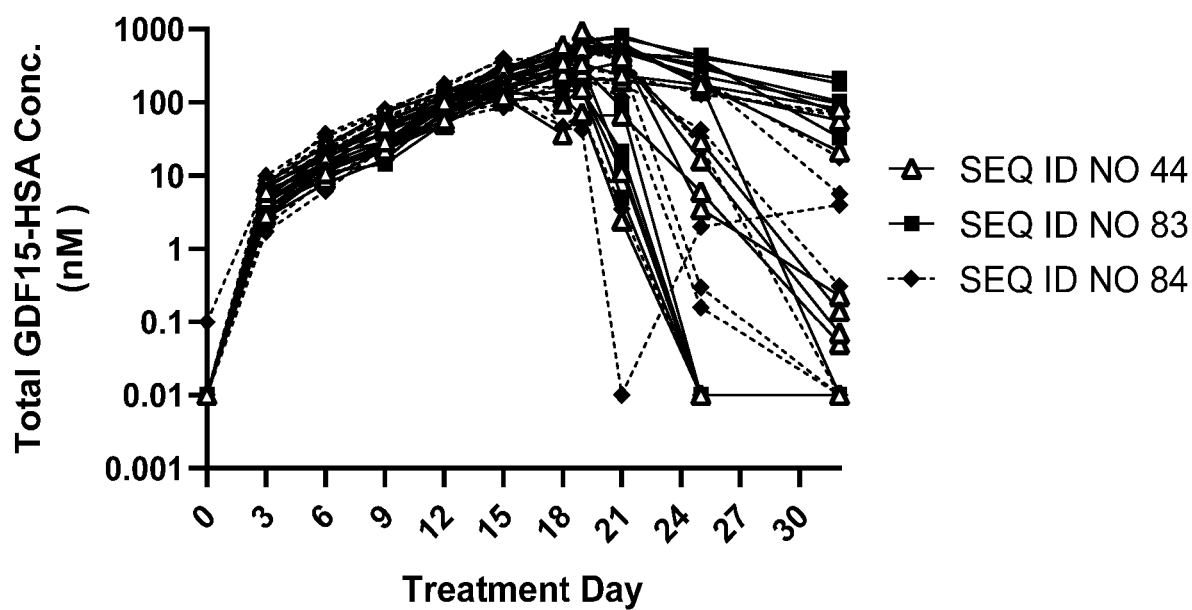
FIG. 21 shows a graph demonstrating the plasma concentration of total test article during and after a 21-day treatment with escalating concentrations of GLP1-GDF15 fusion proteins (SEQ ID NOs: 44, 83 and 84) administered Q3D in spontaneously obese nonhuman primates as determined by immunoassay. Data is presented for individual subjects.
Figure 22:
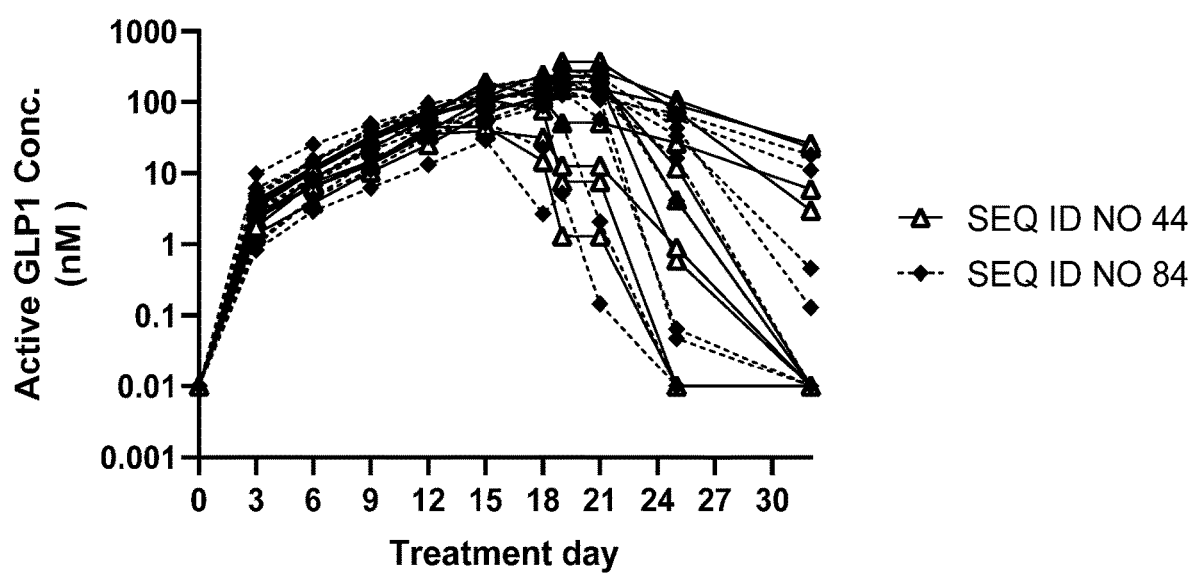
FIG. 22 shows a graph demonstrating the plasma concentration of GLP1 moiety containing test article during and after a 21-day treatment with escalating concentrations of GLP1-GDF15 fusion proteins (SEQ ID NOs: 44 and 84) administered Q3D in spontaneously obese nonhuman primates as determined by immunoassay. Data is presented for individual subjects.

The ability of GLP1-GDF15 fusion proteins to decrease food intake and cause weight loss was tested in spontaneously obese cynomolgus monkeys. Subjects were subcutaneously administered test articles containing both active GDF15 and GLP1, only active GDF15, or only active GLP1 moieties (SEQ ID NOS: 44, 83, 84, respectively; SEQ ID NO:84 comprises a GLP1 peptide fused to an AP5 linker peptide fused to a HSA peptide fused to an AP10 linker peptide fused to a GDF15 peptide with an I89R mutation; the GDF15 peptide with an I89R mutation was previously disclosed in U.S. Pat. No. 10,336,812) every three days for a period of 21 days. The initial dose given at Day 0 was 0.7 nmol/kg and was escalated upon each administration up to 20 nmol/kg. Daily food intake prior to dosing, during the 21-day treatment period and during test article washout is shown in FIG. 19. Body weight was monitored throughout the study and FIG. 20 shows the percent change in body weight over time relative to baseline. The concentration of test articles in cynomolgus monkey plasma during the study was determined using two separate immunoassay methods to detect the "total" molecule (HSA detection; SEQ ID NOS: 44, 83, 84) and the "active" GLP1 moiety (N-terminal GLP1 peptide detection; for SEQ ID NOS: 44 and 84 only). The plasma drug concentrations are shown in FIGS. 21 and 22. The results indicated that repeat administration of SEQ ID NOs: 44, 83, 84 leads to a reduction in food intake and subsequent weight loss in spontaneously obese nonhuman primates.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

All documents cited herein are incorporated by reference.

It is claimed:

1. A method for treating obesity, the method comprising administering to the subject an effective amount of a glucagon-like peptide-1 (GLP-1)/growth differentiation factor 15 (GDF 15) fusion protein, wherein the GLP-1-GDF 15 fusion protein comprises a GLP-1 peptide, a first linker peptide, a serum albumin protein, a second linker peptide, and a GDF 15 protein, wherein the GLP-1 peptide comprises an amino acid sequence selected from the group consisting of SEQ ID NOs: 1-4, and wherein the GDF15 protein comprises an amino acid sequence selected from SEQ ID NO: 31 or SEQ ID NO: 32.

2. The method of claim 1, wherein the first linker peptide comprises an amino acid sequence selected from the group consisting of SEQ ID NOs: 5-25.

3. The method of claim 1, wherein the serum albumin protein comprises an amino acid sequence selected from SEQ ID NO: 26 or SEQ ID NO: 27.

4. The method of claim 1, wherein the second linker peptide comprises an amino acid sequence selected from the group consisting of SEQ ID NOs: 28-30.

5. The method of claim 1, wherein the GLP-1-GDF15 fusion protein comprises an amino acid sequence selected from the group consisting of SEQ ID NOs: 33-74 and 84.

6. A method of reducing food intake in a subject in need thereof, the method comprising administering to the subject an effective amount of a glucagon-like peptide-1 (GLP-1)/growth differentiation factor 15 (GDF 15) fusion protein, wherein the GLP-1-GDF 15 fusion protein comprises a GLP-1 peptide, a first linker peptide, a serum albumin protein, a second linker peptide, and a GDF 15 protein, wherein the GLP-1 peptide comprises an amino acid sequence selected from the group consisting of SEQ ID NOs: 1-4, and wherein the GDF15 protein comprises an amino acid sequence selected from SEQ ID NO: 31 or SEQ ID NO: 32.

7. The method of claim 6, wherein the first linker peptide comprises an amino acid sequence selected from the group consisting of SEQ ID NOs: 5-25.

8. The method of claim 6, wherein the serum albumin protein comprises an amino acid sequence selected from SEQ ID NO: 26 or SEQ ID NO: 27.

9. The method of claim 6, wherein the second linker peptide comprises an amino acid sequence selected from the group consisting of SEQ ID NOs: 28-30.

10. The method of claim 6, wherein the GLP-1-GDF15 fusion protein comprises an amino acid sequence selected from the group consisting of SEQ ID NOs: 33-74 and 84.

11. A method of modulating GLP-1 receptor activity or GDF15 receptor (GFRAL) activity in a subject in need thereof, the method comprising administering to the subject an effective amount of a glucagon-like peptide-1 (GLP-1)/growth differentiation factor 15 (GDF 15) fusion protein, wherein the GLP-1-GDF 15 fusion protein comprises a GLP-1 peptide, a first linker peptide, a serum albumin protein, a second linker peptide, and a GDF 15 protein, wherein the GLP-1 peptide comprises an amino acid sequence selected from the group consisting of SEQ ID NOs: 1-4, and wherein the GDF15 protein comprises an amino acid sequence selected from SEQ ID NO: 31 or SEQ ID NO: 32.

12. The method of claim 11, wherein the first linker peptide comprises an amino acid sequence selected from the group consisting of SEQ ID NOs: 5-25.

13. The method of claim 11, wherein the serum albumin protein comprises an amino acid sequence selected from SEQ ID NO: 26 or SEQ ID NO: 27.

14. The method of claim 11, wherein the second linker peptide comprises an amino acid sequence selected from the group consisting of SEQ ID NOs: 28-30.

15. The method of claim 11, wherein the GLP-1-GDF15 fusion protein comprises an amino acid sequence selected from the group consisting of SEQ ID NOs: 33-74 and 84.

* * * * *